US011473082B2

(12) United States Patent
Ostertag et al.

(10) Patent No.: US 11,473,082 B2
(45) Date of Patent: Oct. 18, 2022

(54) COMPOSITIONS AND METHODS FOR DIRECTING PROTEINS TO SPECIFIC LOCI IN THE GENOME

(71) Applicant: Poseida Therapeutics, Inc., San Diego, CA (US)

(72) Inventors: Eric Ostertag, San Diego, CA (US); Tseten Yeshi, San Diego, CA (US); Xianghong Li, San Diego, CA (US)

(73) Assignee: Poseida Therapeutics, Inc., San Diego, CA (US)

( * ) Notice: Subject to any disclaimer, the term of this patent is extended or adjusted under 35 U.S.C. 154(b) by 504 days.

(21) Appl. No.: 15/580,675

(22) PCT Filed: Jun. 16, 2016

(86) PCT No.: PCT/US2016/037922
§ 371 (c)(1),
(2) Date: Dec. 7, 2017

(87) PCT Pub. No.: WO2016/205554
PCT Pub. Date: Dec. 22, 2016

(65) Prior Publication Data
US 2018/0187185 A1   Jul. 5, 2018

Related U.S. Application Data

(60) Provisional application No. 62/181,162, filed on Jun. 17, 2015.

(51) Int. Cl.
C12N 15/11    (2006.01)
C12N 9/22     (2006.01)
C12N 9/16     (2006.01)
A61K 48/00    (2006.01)

(52) U.S. Cl.
CPC .......... *C12N 15/11* (2013.01); *C12N 9/16* (2013.01); *C12N 9/22* (2013.01); *A61K 48/00* (2013.01); *C07K 2319/80* (2013.01); *C12N 2310/20* (2017.05)

(58) Field of Classification Search
CPC . C12N 15/11; C12N 9/16; C12N 9/22; C12N 2310/20; A61K 48/00; C07K 2319/80
USPC .................... 435/455, 69.7, 199; 530/350
See application file for complete search history.

(56) References Cited

U.S. PATENT DOCUMENTS

| | | |
|---|---|---|
| 4,554,101 A | 11/1985 | Hopp |
| 4,873,192 A | 10/1989 | Kunkel |
| 5,240,846 A | 8/1993 | Collins et al. |
| 5,380,831 A | 1/1995 | Adang et al. |
| 5,399,346 A | 3/1995 | Anderson et al. |
| 5,436,146 A | 7/1995 | Shenk et al. |
| 5,436,391 A | 7/1995 | Fujimoto et al. |
| 5,529,774 A | 6/1996 | Barba et al. |
| 5,547,932 A | 8/1996 | Curiel et al. |
| 5,639,642 A | 6/1997 | Kjeldsen et al. |
| 5,645,829 A | 7/1997 | Shockely et al. |
| 5,656,465 A | 8/1997 | Panicali et al. |
| 5,670,488 A | 9/1997 | Gregory et al. |
| 5,672,344 A | 9/1997 | Kelley et al. |
| 5,741,486 A | 4/1998 | Pathak et al. |
| 5,817,492 A | 10/1998 | Saito et al. |
| 5,830,880 A | 11/1998 | Sedlacek et al. |
| 5,854,019 A | 12/1998 | Sedlacek et al. |
| 5,869,040 A | 2/1999 | Qin et al. |
| 5,910,488 A | 6/1999 | Nabel et al. |
| 5,911,983 A | 6/1999 | Barranger et al. |
| 5,928,214 A | 7/1999 | Rubinstein et al. |
| 5,928,914 A | 7/1999 | Leboulch et al. |
| 6,596,509 B1 | 7/2003 | Bauer et al. |
| 6,824,978 B1 | 11/2004 | Cox et al. |
| 6,933,113 B2 | 8/2005 | Case et al. |
| 6,979,539 B2 | 12/2005 | Cox et al. |
| 7,001,768 B2 | 2/2006 | Wolffe |
| 7,013,219 B2 | 3/2006 | Case et al. |
| 7,070,934 B2 | 7/2006 | Cox et al. |
| 7,163,824 B2 | 1/2007 | Cox et al. |
| 7,220,719 B2 | 5/2007 | Case et al. |
| 7,262,054 B2 | 8/2007 | Jamieson et al. |

(Continued)

FOREIGN PATENT DOCUMENTS

| | | |
|---|---|---|
| CA | 2246005 | 4/2000 |
| CN | 104450785 A | 3/2015 |

(Continued)

OTHER PUBLICATIONS

Guilinger et al. (2014) Nat. Biotech., vol. 32(6), 577-583, published online Apr. 25, 2014.*
Tsai et al. (2014) Nat. Biotech., vol. 32(6), 569-577, published online on Apr. 25, 2014.*
Addgene, "TALEN Expression Vectors for REAL, REAL-Fast and FLASH" [online]. Retrieved from the Internet: www.addgene.org/talengineering/expressionvectors/, Retrieved on Aug. 22, 2018; 1 page.
Allison, R. et al. "The nucleotide sequence of the coding region of tobacco etch virus genomic RNA: evidence for the synthesis of a single polyprotein", (1986), Virology 154, 9-20.
An, G. et al. "Transformation of Tobacco, Tomato, Potato, and *Arabidopsis thaliana* Using a Binary Ti Vector System", (1986) Plant Pysiol., 81:301-305.

(Continued)

*Primary Examiner* — Anne Marie S Wehbe
(74) *Attorney, Agent, or Firm* — Cooley LLP; Ivor Elrifi; Matthew Pavao

(57) ABSTRACT

Disclosed are compositions and methods for directing proteins to specific loci in the genome and uses thereof. In one aspect, the disclosed methods allow for directing proteins to specific loci in the genome of an organism, including the steps of providing a fusion protein comprising a DNA localization component and an effector molecule. Preferred embodiments of the disclosure include, but are not limited to, the following fusion proteins: dSaCas9-Clo051, dCas9-Clo051, *Xanthomonas*-TALE-Clo051, and *Ralstonia*-TALE-Clo051.

28 Claims, 12 Drawing Sheets

Specification includes a Sequence Listing.

(56) References Cited

U.S. PATENT DOCUMENTS

| | | | |
|---|---|---|---|
| 7,273,923 | B2 | 9/2007 | Jamieson et al. |
| 7,285,416 | B2 | 10/2007 | Choo et al. |
| 7,361,635 | B2 | 4/2008 | Miller et al. |
| 7,521,241 | B2 | 4/2009 | Choo et al. |
| 7,790,379 | B2 | 9/2010 | Laemmli et al. |
| 8,586,526 | B2 | 11/2013 | Gregory et al. |
| 9,410,134 | B2* | 8/2016 | Kuhn ................ C12N 15/8509 |
| 9,499,592 | B2 | 11/2016 | Zhang |
| 10,415,024 | B2 | 9/2019 | Ostertag et al. |
| 10,844,361 | B2 | 11/2020 | Ostertag et al. |
| 2003/0138850 | A1 | 7/2003 | Mossner et al. |
| 2005/0272107 | A1 | 12/2005 | Rabbitts et al. |
| 2006/0099654 | A1 | 5/2006 | Huster |
| 2006/0252140 | A1 | 11/2006 | Yant et al. |
| 2009/0305402 | A1 | 12/2009 | Liljedahl et al. |
| 2010/0261177 | A1 | 10/2010 | Weiner et al. |
| 2011/0059502 | A1 | 3/2011 | Chalasani |
| 2011/0117625 | A1 | 5/2011 | Lippow et al. |
| 2012/0270273 | A1 | 10/2012 | Zhang et al. |
| 2013/0117869 | A1 | 5/2013 | Duchateau et al. |
| 2014/0068797 | A1* | 3/2014 | Doudna ................ C12N 15/63 800/18 |
| 2014/0087426 | A1* | 3/2014 | Liu .......................... C12N 9/22 435/91.3 |
| 2014/0186958 | A1 | 7/2014 | Zhang et al. |
| 2014/0298505 | A1 | 10/2014 | Kuhn |
| 2014/0304847 | A1 | 10/2014 | Kuhn |
| 2015/0044772 | A1 | 2/2015 | Zhao |
| 2016/0060610 | A1 | 3/2016 | Ostertag et al. |
| 2017/0107541 | A1 | 4/2017 | Ostertag et al. |
| 2017/0114149 | A1 | 4/2017 | Ostertag et al. |
| 2020/0199553 | A1 | 6/2020 | Ostertag et al. |
| 2021/0062170 | A1 | 3/2021 | Ostertag et al. |

FOREIGN PATENT DOCUMENTS

| | | | |
|---|---|---|---|
| EP | 2 522 726 A1 | | 11/2012 |
| JP | 2007-159512 A | | 6/2007 |
| JP | 2010-209068 A | | 9/2010 |
| JP | 6206893 B2 | | 9/2017 |
| WO | WO 2000/071702 A1 | | 11/2000 |
| WO | WO 2004/046185 A2 | | 6/2004 |
| WO | WO 2007/060495 | | 5/2007 |
| WO | WO 2007/122511 A2 | | 11/2007 |
| WO | WO 2009/095793 | | 8/2009 |
| WO | WO 2010/097385 A1 | | 9/2010 |
| WO | WO 2011/146121 A1 | | 11/2011 |
| WO | WO 2012/092970 A1 | | 7/2012 |
| WO | WO 2012/093833 A2 | | 7/2012 |
| WO | WO 2012/138927 A2 | | 10/2012 |
| WO | WO 2012/158986 A2 | | 11/2012 |
| WO | WO 2012/168304 A1 | | 12/2012 |
| WO | WO 2013/088446 A1 | | 6/2013 |
| WO | WO 2013/152220 A2 | | 10/2013 |
| WO | WO 2013/177231 A1 | | 11/2013 |
| WO | WO 2014/064277 A1 | | 5/2014 |
| WO | WO 2014/089290 A1 | | 6/2014 |
| WO | WO 2015/195798 A1 | | 12/2015 |

OTHER PUBLICATIONS

Arora et al. "Residues 1-254 of Anthrax Toxin Lethal Factor are Sufficient to Cause Cellular Uptake of Fused Polypeptides", (1993) J. Biol. Chem 268:3334 3341.

Asano, et al. "Transgenic plants of Agrostis alba obtained by electroporation-mediated direct gene transfer into protoplasts", (1994) Plant Cell Reports 13:243-246.

Ayeres, N.M. and Park, W.D. "Genetic Transformation of Rice", (1994) Critical Reviews in Plant Science, 13:219-239.

Baim et al. "A chimeric mammalian transactivator based on the lac repressor that is regulated by temperature and isopropyl (8-D-thiogalactopyranoside", (1991) Proc. Natl. Acad. Sci. USA 88:5072-5076.

Ballas et al. "Effi'cient functioning of plant promoters and poly(A) sites in Xenopus oocytes", (1989) Nucleic Acids Res. 17:7891-7903.

Barcelo, et al. "Transgenic cereal (tritordeum) plants obtained at high efficiency by microprojectile bombardment of inflorescence tissue", (1994) Plant Journal 5:583-592.

Barkley et al. "Repressor Recognition of Operator and Effectors", (1980) The Operon, p. 177-220.

Becker, et al. "Fertile transgenic wheat from microprojectile bombardment of scutellar tissue", (1994) Plant. Journal 5:299-307.

Bibikova et al. "Enhancing Gene Targeting with Designed Zinc Finger Nucleases", (2003) Science 300, 764.

Block, M. "Genotype-independent leaf disc transformation of potato (*Solarium tuberosum*) using *Agrobacterium tumefaciens*", (1988) Theor. Appl Genet. 76:767-774.

Bolte et al. "The N-myristoylated Rab-GTPase m-Rabmc is involved in post-Golgi trafficking events to the lytic vacuole in plant cells", (2004) Journal of Cell Science 117:943-54.

Borkowska et al. "Transformation of diploid potato with an *Agrobacterium tumefaciens* binary vector system: I. Methodological approach" (1994) Acta. Physiol Plant. 16:225-230.

Brown et al. "kc Repressor Can Regulate Expression from a Hybrid SV40 Early Promoter Containing a lac Operator in Animal Cells", (1987) Cell 49:603-612.

Campbell and Gowri "Codon Usage in Higher Plants, Green Algae, and Cyanobacteria", (1990) Plant Physiol. 92: 1-11.

Carbonetti et al. (1995) "Use of Perussis toxin Vaccine Molecule PT9K/129G to Deliver Peptide Epitopes for Stimulation of a Cytotoxic T Lymphocyte Response" Abstr. Annu. Meet. Am Soc. Microbiol. 95:295, Abstract E-86 . . . .

Casas et al. "Transgenic sorghum plants via microprojectile bombardment", (1993) Proc. Nat. Acad Sci. USA 90:11212-11216.

Chee, P.P. and Slightom, J.L. "Transformation of cucumber tissues by identification of plants containing functional genes", (1992) Gene, 118:255-260.

Chevalier et al. "Design, Activity, and Structure of a Highly Specific Artificial Endonuclease", (2002) Molecular Cell 10:895-905.

Christou et al. "The development of a variety-independent gene-transfer method for rice", (1992) Trends in Biotechnol. 10:239-246.

Christou, P. "Genetic ingeenering of crop legumes and cereals: current status and recent advances", (1994) Agro. Food. Ind. Hi Tech. 5: 17-27.

Christou, P. "Philosophy andpractive of variety-independent gene transfer into recalcitrant crops", (1993) In Vitro Cell. Dev. Biol.-Plant, 29P:119-124.

Christopherson et al. "Ecdysteroid-dependent regulation of genes in mammalian cells by a *Drosophila ecdysone* receptor and chimeric transactivators", (1992) Proc. Natl. Acad. Sci. USA 89:6314-6318.

Cousins, et al. "Transformation of an Australian Cotton Cultivar: Prospects for Cotton Improvement through Genetic Engineering", (1991) Aust. J. Plant Physiol. 18:481-494.

Davies et al. "Transformation of peas", (1993) Plant Cell Rep. 12:180-183.

Degenkolb et al. "Structural Requirements of Tetracycline-Tet Repressor Interaction: Determination of Equilibrium Binding Constants for Tetracycline Analogs with the Tet Repressor" (1991) Antimicrob. Agents Chemother. 35:1591-1595.

Della-Cioppa et al. "Protein Trafficking in Plant Cells", (1987) Plant Physiol. 84:965-968.

Derossi et al. "The Third Helix of the Antennapedia Homeodornain Translocates through Biological Embranes", (1994) J. Biol. Chem 269: 10444-10450.

Deuschle et al. "Regulated expression of foreign genes in mammalian cells under the control of coliphage T3 RNA polymerase and lac repressor", (1989) Proc. Natl. Acad. Aci. USA 86:5400-5404.

Deuschle et al. "RNA Polymerase II Transcription Blocked by *Escherichia coli* Lac Repressor" (1990) Science 248:480-483.

D'Halluin, et al. "Transformation of Sugarbeet (*Beta vulgaris* I.) and evaluation of herbicide resistance in transgenic plants", (1992) Bio/Technol. 10:309-314.

Dhir et al. "Regeneration of Transgenic Soybean (*Glycine max*) Plants from Electroporated Protoplasts", (1992) Plant Physiol. 99:81-88.

(56) References Cited

OTHER PUBLICATIONS

Dong, J. A. and Mchughen, A. "Transgenic flax plants from *Agrobacterium* mediated transformation incidence of chimeric regenerants and inheritance of transgenic plants", (1993) Plant Sci. 91:139-148.
Donnelly et al. "Targeted delivery of peptide epitopes to class I major histocompatibility molecules by a modified Pseudomonas exotoxin" (1993) Proc. Nad. Acad. Sci. USA 90:3530-3534.
Eapen et al. "Agrobacterium tumefaciens mediated gene transfer in peanut (*Arachis hypogaea* L.)", (1994) Plant Cell Rep. 13:582-586.
Elliot and O'Hare "Intercellular Trafficking and Protein Delivery by a Herpesvirus Structural Protein", (1997) Cell 88:223-233.
Elroy-Stein et al. "Cap-independent translation of mRNA conferred by encephalomyocarditis virus 5' sequence improves the performance of the vaccinia virus/bacteriophage T7 hybrid expression system", (1989) *Proc. Natl. Acad. Sci. USA* 86:6126-6130.
Fahraeus et al. "Inhibition of pRb phosphorylation and cell-cyde progression by a 20-residue peptide derived from p1&CDKN211NK4A", (1996) Current Biology 6:84-91.
Fajardo-Sanchez et al. "Computer design of obligate heterodimer meganucleases allows efficient cutting of custom DNA sequences", (2008) Nucleic Acids Res. 36:2163-2173.
Fetter et al. "Interactions between Plasma Membrane Aquaporins Modulate Their Water Channel Activity", (2004) Plant Cell 16:215-228.
Figge et al. "Stringent Regulation of Stably Integrated Chloramphenicol Acetyl Transferase Genes by *E. coli* lac Repressor in Monkey Cells", (1988) Cell 52:713-722.
Franklin, C. I. and Trieu, T. N. "Transformation of the forage grass Caucasian bluestem via biolistic bombardment-mediated DNA transfer", (1993) Plant. Physiol. 102:167.
Fry, J. et al. "Transformation of *Brassica napus* with *A grobacterium tumefaciens* based vectors", (1987) Plant Cell Rep. 6:321-325.
Fuerst et al. "Transfer of the inducible lac repressor/operator system from *Escherichia coli* to a vaccinia virus expression vector", (1989) Proc. Natl. Acad. Sci. USA 86:2549-2553.
Gallie et al. "The tobacco etch viral 5' leader and poly (A) tail are functionally synergistic regulators of translation", (1995) Gene 165(2):233-238.
Gallie et al. "Eukaryotic viral 5'-leader sequences act as translational enhancers in eukaryotes and prokaryotes", (1989) in Molecular Biology of RNA, pp. 237-256.
Gilbert, L. et al. "CRISPR-Mediated Modular RNA-Guided Regulation of Transcription in Eukaryotes", CELL, vol. 154, No. 2, 2013, pp. 442-S5.
Gill et al. "Negative effect of the transcriptional activator GAL4", (1988) Nature 334:721-724.
Golovkin M. et al. "Production of transgenic maize plants by direct DNA uptake into embryogenic protoplasts", (1993) Plant Science, 90:41-52.
Gossen et al. "Tight control of gene expression in mammalian cells by tetracycline-responsive promoters", (1992) Proc. Natl. Acad. Sci. USA 89:5547-5551.
Guerineau et al. "Effect of deletions in the cauliflower mosaic virus polyadenylation sequence on the choice of the polyadenylation sites in tobacco protoplasts", (1991) Mol. Gen. Genet. 262: 141-144.
Guo et al. "Transgenic Plants Obtained From Wheat Protoplasts Transformed by PEGmediated Direct Gene Transfer", Chinese Science Bulletin, 38(24):2072-2078.
Hartman, et al. "Herbicide resistant turfgrass (*Agrostis palustris* Huds.) by biolistic transformation", (1994) Bio-Technology 12: 919-923.
Hillen and Wissman "Tet repressor-tel operator interaction", (1989) Topics Mol. Struc. Biol. 10:143-162.
Hinchee, et al. "Transformation and regeneration of non-solanaceous crop plants", (1990) Stadler. Genet. Symp., p. 203-212.
Hu et al. "The Inducible lac Operator-Repressor System is Functional in Mammalian Cells", (1987) Cell 48:555-566.

Jobling et al. "Ethanced translation of chimaeric messenger RNAs containing a plant viral untranslated leader sequence", (1987) Nature 325:622-625.
Joshi et al. "Putative polyadenylation signals in nuclear genes of higher plants: a compilation and analysis", (1987) Nucleic Acids Res. 15:9627-9639.
Kato et al. "Spectral Profiling for the Simultaneous Observation of Four Distinct Fluorescent Proteins and Detection of Protein-Protein Interaction via Fluorescence Resonance Energy Transfer in Tobacco Leaf Nuclei", (2002) Plant Physiology, 129:913-42.
Kleinschmidt et al. "Dynamics of Repressor-Operator Recognition: The Tn10-Encoded Tetracycline Resistance Control", (1988) Biochemistry 27:1094-1104.
Klimpel et al. "Anthrax toxin protective antigen is activated by a cell surface protease with the sequence specificity and catalytic properties of furin", (1992) Proc. Natl. Acad. Sci. USA 89:10277 10281.
Kulinski et al. "CEL I Enzymatic Mutation Detection Assay", BioTechniques (2000), 29(1):44-48.
Kyte et al. "A Simple Method for Displaying the Hydropathic Character of a Protein", J. Mol. Biol. (1982), 157:105-132.
Labow et al. "Conversion of the lac Repressor into an Allosterically Regulated Transcriptional Activator for Mammalian Cells", (1990) Molecular and Cellular Biology 10:3343-3356.
Lehninger, "The amino acid building blocks of proteins", Biochemistry, Second Edition, (1975), p. 71-77.
Lommel et al. "Identification of the Maize Chlorotic Mottle Virus Capsid Protein Cistron and Characterization of its Subgenomic Messenger RNA", (1991) Virology 81:382-385.
Macejak et al. "Internal initiation of translation mediated by the 5' leader of a cellular mRNA", (1991) Nature 353:90-94.
Mali, L. et al. "RNA-Guided Human Genome Engineering via Cas9", Science, vol. 339, No. 6121, 2013, pp. 823-826.
Miller, J.C. et al. "A TALE nuclease architecture for efficient genome editing", Nature Biotechnology (2011), 29:143-148.
Mogen et al. "Upstream Sequences Other than AAUAAA Are Required for Efficient Messenger RNA 3'-End Formation in Plants", (1990) Plant Cell 2:1261-1272.
Munroe et al. "Tales of poly (A): a review", (1990) Gene 91:151-158.
Murray et al. "Codon usage in plant genes", (1989) Nucleic Acids Research, 17:477-498.
Novak et al. "Functional Characterization of Protease-treated *Bacillus anthracis* Protective Antigen", Journal of Biological Chemistry (1992), 267:17186-17193.
Oliva et al. "Evidence that Tetracycline Analogs Whose Primary Target is Not the Bacterial Ribosome Cause Lysis of *Escherichia coli*", Antimicrobial Agents and Chemotherapy (1992), 36:913-919.
Perelle et al. "Characterization of Clostridium perfringens Iota-Toxin Genes and Expression in *Eschenichia coli*", (1993) Infection and Immunity, 61:5147-5156.
PROUDFOOT "Poly(A) Signals", (1991) Cell 64:671-674.
Reines et al. "Elongation factor Sil-dependent transcription by RNA polymerase II through a sequence-specific DNA-binding protein", (1993) Proc. Natl. Acad. Sci. USA 90:1917-1921.
Reyon et al. "FLASH assembly of TALENs for high-throughput genome editing" Nature Biotechnology (2012), 30(5):460-465.
Reznikoff "The lactose operon-controlling elements: a complex paradigm", (1992) Molecular Microbiology (1992), 6:2419-2422.
Ritala et al. "Fertile transgenic barley by particle bombardment of immature embryos", (1994) Plant. Mol. Biol. 24:317-325.
Sanfacon et al. "A dissection of the cauliflower mosaic virus polyadenylation signal", Genes and Development (1991), 5:141-149.
Sebo et al. "Cell-Invasive Activity of Epitope-Tagged Adenylate Cyclase of *Bordetella pertussis* Allows In Vitro Presentation of a Foreign Epitope to CD8+ Cytotoxic T Cells", Infection and Immunity (1995) 63:3851-3857.
Stenmark et al. "Peptides Fused to the Amino-Terminal End of Diphtheria Toxin are Translocated to the Cytosol", (1991) J. Cell Biol. 113: 1025 1032.

(56) References Cited

OTHER PUBLICATIONS

Su et al. "High-Level Secretion of Functional Green Fluorescent Protein From Transgenic Tobacco Cell Cultures: Characterization and Sensing", (2004) Biotechnol Bioeng 85:610-619.
Tatusova and Madden, "BLAST 2 SEQUENCES, a new tool for comparing protein andnucleotide sequences", FEMS Microbiology Letters (1999), 174:247-250.
Urnov et al. "Highly efficient endogenous human gene correction using designed zinc-finger nucleases", (2005) Nature 435: 646-651.
Wan, Y. C. and Lemaux, P. G. "Generation of Large Numbers of Independently Transformed Fertile Barley Plants", (1994) Plant Physiol. 104:37-48.
Wright et al. "High-frequency homologous recombination in plants mediated by zinc-finger nucleases" (2005) The Plant Journal 44:693-705.
Yao et al. "*Drosophila* ultraspiracle modulates ecdysone receptor function via heterodimer formation", (1992) Cell 71:63-72.
Yarranton "Inducible vectors for expression in mammalian cells", (1992) Curr. Opin. Biotech. 3:506-511.
Zambretti et al. "A mutant p53 protein is required for maintenance of the transformed phenotype in cells transformed with p53 plus ras cDNAs", (1992) Proc. Natl Acad. Sci. USA 89:3952-3956.
Wyborski et al. "Analysis of inducers of the *E.coli lac* repressor system in mammalian cells and whole animals", (1991) Nucleic Acids Res. 19:4647-4653.
Abe, R. et al. (Apr. 1, 20141) "Ultra Q-bodies: quench-based antibody probes that utilize dye-dye interactions with enhanced antigen-dependent fluorescence" *Scientific Reports*, 4:4640; DOI: 10.1038/srep04640, 9 pages.
Auf Der Maur, A. et al. (2002) "Direct in vivo screening of intrabody libraries constructed on a highly stable single-chain framework", *Journal of Biological Chemistry*, vol. 277, No. 47, pp. 45075-45085.
Banta, S. et al. (2013) "Replacing Antibodies: Engineering New Binding Proteins" Annual Reviews Biomedical Engineering, 15:93-113.
Barlos, K. et al. (1989) "Darstellung geschützter peptid-fragmente unter einsatz substituierter triphenylmethyl-harze" *Tetrahedron Lett*, 30(30):3943-3946. German with English Summary on p. 3943.
Biocca, S. (2011) "Intrabody Expression in Mammalian Cells" in *Antibody Expression and Production. Cell Engineering*, vol. 7. Mohamed Al-Rubeai (Ed.) New York: Springer Science+Business Media; pp. 179-195.
Bochtler, M. (Oct. 2012) "Structural basis of the TAL effector-DNA interaction" *Biol. Chem*, 393(10):1055-1066.
Brooks, A.I. et al. (1998) "Reproducible and efficient murine CNS gene delivery using a microprocessor-controlled injector" *J. Neurosci. Methods*, 80:137-147.
Choulika, A. et al. (1995) "Induction of homologous recombination in mammalian chromosomes by using the I-SceI system of *Saccharomyces cerevisiae*" *Mol Cell Biol*, 15(4):1968-1973.
Christian, M. et al. (Oct. 2010) "Targeting DNA Double-Strand Breaks with TAL Effector Nucleases" *Genetics*, 186(2):757-761 (with Supporting Information, 8 pages).
Cong, L. et al. (Feb. 15, 2013) "Multiplex Genome Engineering Using CRISPR/Cas Systems", Science, 339(6121):819-823.
De Lange, O. et al. (May 2013) "Breaking the DNA-binding code of *Ralstonia solanacearum* TAL effectors provides new possibilities to generate plant resistance genes against bacterial wilt disease" *New Phytologist*, 199(3):773-786 (with Supplementary Information, 47 pages).
Fields, S. and O-k Song (Jul. 1989) "A Novel Genetic System to Detect Protein-Protein Interactions" *Nature*, vol. 340, No. 6230, pp. 245-246.
Galán, J.E. and A. Collmer (May 21, 1999) "Type III Secretion Machines: Bacterial Devices for Protein Delivery into Host Cells" *Science*, 284:1322-1328.
GenBank Accession No. AAA25728 (Jul. 2, 19936) "avirulence protein [Pseudomonas syringae]" National Center for Biotechnology Information (NCBI).gov [online]. Retrieved from: http://www.ncbi.nlm.nih.gov/protein/AAA25728; retrieved on Feb. 15, 2019; 1 page.
GenBank Accession No. AAA26525 (Apr. 26, 1993) "IpaA protein, partial [Shigella flexneri]" National Center for Biotechnology Information (NCBI).gov [online]. Retrieved from: http://www.ncbi.nlm.nih.gov/protein/AAA26525; retrieved on Feb. 15, 2019; 1 page.
GenBank Accession No. AAC02071 (Oct. 4, 1999) "SopE [*Salmonella enterica* subsp. enterica serovar Typhimurium str. SL1344]" National Center for Biotechnology Information (NCBI).gov [online]. Retrieved from: http://www.ncbi.nlm.nih.gov/protein/AAC02071; retrieved on Feb. 15, 2019; 1 page.
GenBank Accession No. AAC44349 (Sep. 4, 1996) "protein tyrosine phosphatase SptP [*Salmonella enterica* subsp. enterica serovar Typhimurium str. SL1344]" National Center for Biotechnology Information (NCBI).gov [online]. Retrieved from: http://www.ncbi.nlm.nih.gov/protein/AAC44349; retrieved on Feb. 15, 2019; 2 pages.
GenBank Accession No. AAC69765 (Jul. 26, 2016) "secreted protein kinase (plasmid) [Yersinia pestis]" National Center for Biotechnology Information (NCBI).gov [online]. Retrieved from: http://www.ncbi.nlm.nih.gov/protein/AAC69765; retrieved on Feb. 15, 2019; 2 pages.
GenBank Accession No. AAC69766 (Jul. 26, 2016) "targeted effector protein (plasmid) [Yersinia pestis]" National Center for Biotechnology Information (NCBI).gov [online]. Retrieved from: http://www.ncbi.nlm.nih.gov/protein/AAC69766; retrieved on Feb. 15, 2019; 1 page.
GenBank Accession No. AAC69768 (Jul. 26, 2016) "targeted effector protein (plasmid) [Yersinia pestis]" National Center for Biotechnology Information (NCBI).gov [online]. Retrieved from: http://www.ncbi.nlm.nih.gov/protein/AAC69768; retrieved on Feb. 15, 2019; 2 pages.
GenBank Accession No. AAD11434 (Feb. 1, 1999) "avirulence protein AvrBs2 [Xanthomonas euvesicatoria]" National Center for Biotechnology Information (NCBI).gov [online]. Retrieved from: http://www.ncbi.nlm.nih.gov/protein/AAD11434; retrieved on Feb. 21, 2019; 2 pages.
GenBank Accession No. AAF21057 (Dec. 29, 1999) "invasion protein D, partial [*Salmonella typhimurium*]" National Center for Biotechnology Information (NCBI).gov [online]. Retrieved from: http://www.ncbi.nlm.nih.gov/protein/AAF21057.1; retrieved on Feb. 21, 2019; 1 page.
GenBank Accession No. AAF71481.1 (May 23, 2000) "type III effector protein [Pseudomonas syringae pv. syringae]" National Center for Biotechnology Information (NCBI).gov [online]. Retrieved from: http://www.ncbi.nlm.nih.gov/protein/AAF71481.1; retrieved on Feb. 21, 2019; 1 page.
GenBank Accession No. AAG03434 (Jan. 31, 2014) "exoenzyme T [Pseudomonas aeruginosa PAO1]" National Center for Biotechnology Information (NCBI).gov [online]. Retrieved from: http://www.ncbi.nlm.nih.gov/protein/AAG03434; retrieved on Feb. 15, 2019; 2 pages.
GenBank Accession No. AAG05579 (Jan. 31, 2014) "adenylate cyclase ExoY [Pseudomonas aeruginosa PAO1]" National Center for Biotechnology Information (NCBI).gov [online]. Retrieved from: http://www.ncbi.nlm.nih.gov/protein/AAG05579; retrieved on Feb. 15, 2019; 2 pages.
GenBank Accession No. AAG07228 (Jan. 31, 2014) "exoenzyme S [Pseudomonas aeruginosa PAO1]" National Center for Biotechnology Information (NCBI).gov [online]. Retrieved from: http://www.ncbi.nlm.nih.gov/protein/AAG07228; retrieved on Feb. 15, 2019; 2 pages.
GenBank AccessionNo. AF232006 (May 23, 2000) "Pseudomonas syringae pv. tomato strainDC3000 AvrE (avrE), HrpW (hrpW), and GstA (gstA) genes, complete cds; and unknown genes" National Center for Biotechnology Information (NCBI).gov [online]. Retrieved from: http://www.ncbi.nlm.nih.gov/protein/AF232006,1; retrieved on Feb. 21, 2019; 8 pages.
GenBank Accession No. BAA96815 (Jun. 2, 2000) "Tir [*Escherichia coli*]" National Center for Biotechnology Information (NCBI).gov [online]. Retrieved from: http://www.ncbi.nlm.nih.gov/protein/BAA96815; retrieved on Feb. 15, 2019; 2 pages.

(56) References Cited

OTHER PUBLICATIONS

GenBank Accession No. CAA34257 (Jul. 26, 2016) "avirulence protein avrBs3 (plasmid) [Xanthomonas vesicatoria]" National Center for Biotechnology Information (NCBI).gov [online]. Retrieved from: http://www.ncbi.nlm.nih.gov/protein/CAA34257; retrieved on Feb. 15, 2019; 2 pages.
GenBank Accession No. CAA63302 (Jul. 23, 2016) "sipA, partial [*Salmonella enterica* subsp. enterica serovar Typhi str. Ty2]" National Center for Biotechnology Information (NCBI).gov [online]. Retrieved from: http://www.ncbi.nlm.nih.gov/protein/CAA63302; retrieved on Feb. 15, 2019; 1 page.
GenBank Accession No. EFW82095 (Jan. 28, 2011) "chemotaxis-specific methylesterase [Pseudomonas savastanoi pv. glycinea str. B076]" National Center for Biotechnology Information (NCBI).gov [online], Retrieved from: http://www.ncbi.nlm.nih.gov/protein/EFW82095; retrieved on Feb. 15, 2019; 2 pages.
GenBank Accession No. EFW86187 (Jan. 28, 2011) "chemotaxis-specific methylesterase [Pseudomonas savastanoi pv. glycinea str. race 4]" National Center for Biotechnology Information (NCBI).gov [online], Retrieved from: http://www.ncbi.nlm.nih.gov/protein/EFW86187; retrieved on Feb. 15, 2019; 2 pages.
GenBank Accession No. EGH06695 (May 22, 2012) "chemotaxis-specific methylesterase [Pseudomonas amygdali pv. morspmnomm str. M302280]" National Center for Biotechnology Information (NCBI).gov [online]. Retrieved from: http://www.ncbi.nlm.nih.gov/protein/EGH06695; retrieved on Feb. 15, 2019; 2 pages.
GenBank Accession No. EGH23390 (Apr. 28, 2011) "chemotaxis-specific methylesterase [Pseudomonas amygdali pv. mori str. 301020]" National Center for Biotechnology Information (NCBI).gov [online], Retrieved from: http://www.ncbi.nlm.nih.gov/protein/EGH23390; retrieved on Feb. 15, 2019; 2 pages.
GenBank Accession No. EGH31878 (May 22, 2011) "chemotaxis-specific methylesterase, partial [Pseudomonas syringae pv. japonica str. M301072]" National Center for Biotechnology Information (NCBI).gov [online]. Retrieved from: http://www.ncbi.nlm.nih.gov/protein/EGH31878; retrieved on Feb. 15, 2019; 2 pages.
GenBank Accession No. EGH48032 (Apr. 28, 2011) "chemotaxis-specific methylesterase, partial [Pseudomonas syringae pv. pisi str. 1704B]" National Center for Biotechnology Information (NCBI).gov [online]. Retrieved from: http://www.ncbi.nlm.nih.gov/protein/EGH48032; retrieved on Feb. 15, 2019; 2 pages.
GenBank Accession No. EGH54563 (Apr. 28, 20118) "chemotaxis-specific methylesterase [Pseudomonas syringae Cit 7]" National Center for Biotechnology Information (NCBI).gov [online]. Retrieved from: http://www.ncbi.nlm.nih.gov/protein/EGH54563; retrieved on Feb. 15, 2019; 2 pages.
GenBank Accession No. EGH56182 (Apr. 28, 2011) "amino acid adenylation, partial [Pseudomonas syringae Cit 7]" National Center for Biotechnology Information (NCBI).gov [online]. Retrieved from: http://www.ncbi.nlm.nih.gov/protein/EGH51682; retrieved on Feb. 15, 2019; 1 page.
GenBank Accession No. EGH61007 (Apr. 28, 2011) "chemotaxis-specific methylesterase [Pseudomonas syringae pv. maculicola str. ES4326]" National Center for Biotechnology Information (NCBI).gov [online], Retrieved from: http://www.ncbi.nlm.nih.gov/protein/EGH61007; retrieved on Feb. 15, 2019; 2 pages.
GenBank Accession No. EGH66597 (Apr. 28, 2011) "chemotaxis-specific methylesterase [Pseudomonas syringae pv. actinidiae str. M302091]" National Center for Biotechnology Information (NCBI).gov [online], Retrieved from: http://www.ncbi.nlm.nih.gov/protein/EGH66597; retrieved on Feb. 15, 2019; 2 pages.
GenBank Accession No. EGH71924 (Apr. 28, 2011) "chemotaxis-specific methylesterase, partial [Pseudomonas syringae pv. aceris str. M302273]" National Center for Biotechnology Information (NCBI).gov [online], Retrieved from: http://www.ncbi.nlm.nih.gov/protein/EGH71924; retrieved on Feb. 15, 2019; 2 pages.
GenBank Accession No. EGH77388 (Apr. 28, 2011) "chemotaxis-specific methylesterase [Pseudomonas syringae pv. aptata str. DSM 50252]" National Center for Biotechnology Information (NCBI).gov [online], Retrieved from: http://www.ncbi.nlm.nih.gov/protein/EGH77388; retrieved on Feb. 15, 2019; 2 pages.
GenBank Accession No. EJ092907 (Aug. 13, 2012) "response regulator receiver modulated CheB methylesterase [Pseudomonas mendocina DLHK]" National Center for Biotechnology Information (NCBI).gov [online]. Retrieved from: http://www.ncbi.nlm.nih.gov/protein/EJ092907; retrieved on Feb. 15, 2019; 2 pages.
GenBank Accession No. EKE17764 (Sep. 26, 2012) "hypothetical protein ACD_10C00285G0003 [uncultured bacterium]" National Center for Biotechnology Information (NCBI).gov [online]. Retrieved from: http://www.ncbi.nlm.nih.gov/protein/EKE17764; retrieved on Feb. 15, 2019; 1 page.
GenBank Accession No. J04623 (Apr. 26, 1993) "F.okeanokoites methylase (MFokI) and endonuclease (RFokI) genes, complete cds" National Center for Biotechnology Information (NCBI).gov [online]. Retrieved from: https://www.ncbi.nlm.nih.gov/nuccore/J04623.1; retrieved on Feb. 21, 2019, 2 pages.
GenBank Accession No. M28828 (Apr. 26, 1993) "F.okeanokoites fokIR and fokIM genes encoding endonuclease and methyltransferase, complete cds" National Center for Biotechnology Information (NCBI).gov [online]. Retrieved from: https://www.ncbi.nlm.nih.gov/nuccore/M28828.1/; retrieved on Feb. 21, 2019, 3 pages.
GenPept Accession No. A34965 (Jul. 16, 1999) "62K membrane antigen ipaB—Shigella flexneri plasmid" National Center for Biotechnology Information (NCBI).gov [online]. Retrieved from: http://www.ncbi.nlm.nih.gov/protein/A34965; retrieved on Feb. 21, 2019; 2 pages.
GenPept Accession No. NP_790747 (Aug. 6, 2012) "protein-glutamate methylesterase CheB [Pseudomonas syringae pv. tomato str. DC3000]" National Center for Biotechnology Information (NCBI).gov [online], Retrieved from: http://www.ncbi.nlm.nih.gov/protein/NP_790747; retrieved on Feb. 20, 2019, 2 pages.
GenPept Accession No. S14242 (Oct. 8, 1999) "yopE protein—Yersinia enterocolitica virulence plasmid pYVe439-80" National Center for Biotechnology Information (NCBI).gov [online]. Retrieved from: https://www.ncbi.nlm.nih.gov/protein/96986?report-genpept; retrieved on Feb. 21, 2019, 2 pages.
GenPept Accession No. S15579 (Aug. 26, 1999) "ipaD protein—Shigella dysenteriae" National Center for Biotechnology Information (NCBI).gov [online]. Retrieved from: https://www.ncbi.nlm.nih.gov/protein/96907?report-genpept; retrieved on Feb. 21, 2019, 1 page.
GenPept Accession No. YP_001187060 (Sep. 27, 2012) "response regulator receiver modulated CheB methylesterase [Pseudomonas mendocina ymp]" National Center for Biotechnology Information (NCBI).gov [online]. Retrieved from: http://www.ncbi.nlm.nih.gov/protein/YP_001187060; retrieved on Feb. 20, 2019; 2 pages.
GenPept Accession No. YP_001792820 (Jan. 25, 2012) "chemotaxis-specific methylesterase [Leptothrix cholodnii SP-6]" National Center for Biotechnology Information (NCBI).gov [online]. Retrieved from: http://www.ncbi.nlm.nih.gov/protein/YP_001792820; retrieved on Feb. 20, 2019; 2 pages.
GenPept AccessionNo. YP_003847734 (Jan. 25, 2012) "response regulator receiver modulated CheB methylesterase [Gallionella capsiferriformans ES-2]" National Center for Biotechnology Information (NCBI).gov [online]. Retrieved from: http://www.ncbi.nlm.nih.gov/protein/YP_003847734; retrieved on Feb. 20, 2019; 2 pages.
GenPept Accession No. YP_003907367 (Jun. 18, 2012) "response regulator receiver modulated CheB methylesterase [*Burkholderia* sp. CCGE1003]" National Center for Biotechnology Information (NCBI).gov [online]. Retrieved from: http://www.ncbi.nlm.nih.gov/protein/YP_003907367; retrieved on Feb. 20, 2019; 2 pages.
GenPept Accession No. YP_004030667 (Apr. 25, 2011) "hypothetical protein RBRH_01777 (plasmid) [Burkholderia rhizoxinica HKI 454]" National Center for Biotechnology Information (NCBI).gov [online], Retrieved from: http://www.ncbi.nlm.nih.gov/protein/YP_004030667; retrieved on Feb. 20, 2019; 1 page.
GenPept Accession No. YP_004846745 (Sep. 28, 2012) "response regulator receiver modulated CheB methylesterase [*Pseudogulbenkiania* sp. NH8B]" National Center for Biotechnology Information (NCBI).gov [online]. Retrieved from: http://www.ncbi.nlm.nih.gov/protein/YP_004846745; retrieved on Feb. 20, 2019; 2 pages.

(56) References Cited

OTHER PUBLICATIONS

GenPept Accession No. YP_005027668 (Jun. 25, 2012) "chemotaxis response regulator containing a CheY-like receiver domain and a methylesterase domain [Dechlorosoma suillum PS]" National Center for Biotechnology Information (NCBI).gov [online]. Retrieved from: http://www.ncbi.nlm.nih.gov/protein/YP_005027668; retrieved on Feb. 20, 2019; 2 pages.
GenPept Accession No. YP_233877 (Sep. 27, 2012) "chemotaxis-specific methylesterase [Pseudomonas syringae pv. syringae B728a]" National Center for Biotechnology Information (NCBI).gov [online]. Retrieved from: http://www.ncbi.nlm.nih.gov/protein/YP_233877; retrieved on Feb. 20, 2019; 2 pages.
GenPept Accession No. YP_273082 (Sep. 27, 2012) "chemotaxis-specific methylesterase [Pseudomonas syringae pv. phaseolicola 1448A]" National Center for Biotechnology Information (NCBI).gov [online], Retrieved from: http://www.ncbi.nlm.nih.gov/protein/YP_273082; retrieved on Feb. 20, 2019; 2 pages.
GenPept Accession No. ZP_03698248 (Nov. 9, 2010) "response regulator receiver modulated CheB methylesterase [Pseudogulbenkiania ferrooxidans 2002]" National Center for Biotechnology Information (NCBI).gov [online]. Retrieved from: http://www.ncbi.nlm.nih.gov/protein/ZP_03698248; retrieved on Feb. 20, 2019; 2 pages.
GenPept Accession No. ZP_04590480 (Nov. 14, 2012) "chemotaxis-specific methylesterase [Pseudomonas syringae pv. oryzae str. 1 6]" National Center for Biotechnology Information (NCBI).gov [online]. Retrieved from: http://www.ncbi.nlm.nih.gov/protein/ZP_04590480; retrieved on Feb. 20, 2019; 1 page.
GenPept Accession No. ZP_05638023 (Nov. 14, 2012) "chemotaxis-specific methylesterase [Pseudomonas syringae pv. tabaci str. ATCC 11528]" National Center for Biotechnology Information (NCBI).gov [online], Retrieved from: http://www.ncbi.nlm.nih.gov/protein/ZP_05638023; retrieved on Feb. 20, 2019; 1 page.
GenPept Accession No. ZP_06457223 (Nov. 14, 2012) "chemotaxis-specific methylesterase [Pseudomonas syringae pv. aesculi str. NCPPB 3681]" National Center for Biotechnology Information (NCBI).gov [online], Retrieved from: http://www.ncbi.nlm.nih.gov/protein/ZP_06457223; retrieved on Feb. 20, 2019; 1 page.
GenPept Accession No. ZP_06495900 (Nov. 14, 2012) "chemotaxis-specific methylesterase, partial [Pseudomonas syringae pv. syringae FF5]" National Center for Biotechnology Information (NCBI).gov [online]. Retrieved from: http://www.ncbi.nlm.nih.gov/protein/ZP_06495900; retrieved on Feb. 20, 2019; 1 page.
GenPept Accession No. ZP_07003572 (Jun. 22, 2010) "Chemotaxis response regulator protein-glutamate methylesterase CheB [Pseudomonas savastanoi pv. savastanoi NCPPB 3335]" National Center for Biotechnology Information (NCBI).gov [online]. Retrieved from: http://www.ncbi.nlm.nih.gov/protein/ZP_07003572; retrieved on Feb. 20, 2019; 1 page.
GenPept Accession No. ZP_07251539 (Dec. 10, 2010) "chemotaxis-specific methylesterase [Pseudomonas syringae pv. tomato K40]" National Center for Biotechnology Information (NCBI).gov [online]. Retrieved from: http://www.ncbi.nlm.nih.gov/protein/ZP_07251539; retrieved on Feb. 20, 2019; 2 pages.
GenPept Accession No. ZP_07265841 (Dec. 10, 2010) "chemotaxis-specific methylesterase [Pseudomonas syringae pv. syringae 642]" National Center for Biotechnology Information (NCBI).gov [online]. Retrieved from: http://www.ncbi.nlm.nih.gov/protein/ZP_07265841; retrieved on Feb. 20, 2019; 2 pages.
GenPept Accession No. ZP_08780698 (Nov. 15, 2011) "response regulator receiver modulated CheB methylesterase [Methylobacter tundripaludum SV96]" National Center for Biotechnology Information (NCBI).gov [online]. Retrieved from: http://www.ncbi.nlm.nih.gov/protein/ZP_08780698; retrieved on Feb. 20, 2019; 2 pages.
GenPept Accession No. ZP_10381001 (Jul. 11, 2012) "chemotaxis-specific methylesterase [Sulfuricella denitrificans skB26]" National Center for Biotechnology Information (NCBI).gov [online]. Retrieved from: http://www.ncbi.nlm.nih.gov/protein/ZP_10381001; retrieved on Feb. 20, 2019; 1 page.
GenPept Accession No. ZP_10442431 (Jul. 11, 2012) "response regulator receiver modulated cheb methylesterase [Janthinobacterium lividum PAMC 25724]" National Center for Biotechnology Information (NCBI).gov [online]. Retrieved from: http://www.ncbi.nlm.nih.gov/protein/ZP_10442431; retrieved on Feb. 20, 2019; 2 pages.
GenPept AccessionNo. ZP_10991552 (Nov. 14, 2012) "chemotaxis-specific protein-glutamate methyltransferase [Pseudomonas fuscovaginae UPB0736]" National Center for Biotechnology Information (NCBI).gov [online]. Retrieved from: http://www.ncbi.nlm.nih.gov/protein/ZP_10991552; retrieved on Feb. 20, 2019; 2 pages.
GenPept Accession No. ZP_10995147 (Sep. 13, 2012) "response regulator receiver modulated CheB methylesterase [Pseudomonas fuscovaginae UPB0736]" National Center for Biotechnology Information (NCBI).gov [online]. Retrieved from: http://www.ncbi.nlm.nih.gov/protein/ZP_10995147; retrieved on Feb. 20, 2019; 2 pages.
Guglielmi, L. et al. (2011) "Selection for intrabody solubility in mammalian cells using GFP fusions" *Protein Engineering, Design & Selection*, 24(12):873-881.
Guilinger, J.P. et al. (Jun. 2014) "Fusion of catalytically inactive Cas9 to FokI nuclease improves the specificity of genome modification" *Nature Biotechnology*, vol. 32, No. 6, pp. 577-582.
Hassanzadeh-Ghassabeh, G. et al. (2013) "Nanobodies and their potential applications" *Nanomedicine*, 8(6):1013-1026.
Holliger, P. and P. J. Hudson (Sep. 2005) "Engineered antibody fragments and the rise of single domains" *Nature Biotechnology*, 23(9):1126-1136.
Kim, Y-G. et al. (1996) "Hybird restriction enzymes: Zinc finger fusions to *Fok* I cleavage domain" *Proc Natl Acad Sci*, 93(3):1156-1160.
Kunkel, T. (Jan. 1985) "Rapid and efficient site-specific mutagenesis without phenotypic selection" *Proc Natl Acad Sci*, 82(2):488-492.
Kunkel, T.A. et al. (1987) "Rapid and Efficient Site-Specific Mutagenesis without Phenotypic Selection" *Methods in Enzymol*, 154:367-382.
Li, L. et al. (May 1992) "Functional domains in *Fok* I restriction endonuclease" *Proc Natl Acad Sci USA*, 89(10):4275-4279.
Li, L. et al. (Jul. 2013) "Characterization and DNA-Binding Specificities of *Ralstonia* TAL-Like Effectors" *Mol Plant*, 6(4):1318-1330.
Li, Y. et al. (Aug. 2011) "Molecular recognition code between pathogenic bacterial TAL-effectors and host target genes: a review" *Chinese Journal of Biotechnology*, 27(8):1132-1141 (English Abstract and Figure Legends included).
Li, Y. et al. (Nov. 28, 2012) "Transcription activator-like effector hybrids for conditional control and rewiring of chromosomal transgene expression", *Scientific Reports*, vol. 2, No. 897, DOI: 10.1038/srep00897; 7 pages.
Luo, Y. et al. (1997) "Mammalian Two-Hybrid System: A Complementary Approach to the Yeast Two-Hybrid System" *Biotechniques*, vol. 22, No. 2, pp. 350-352.
Mali, P. et al. (Sep. 2013) "CAS9 transcriptional activators for target specificity screening and paired nickases for cooperative genome engineering", *Nature Biotechnology*, vol. 31, No. 9, p. 833-840.
Maynard, J. and G. Georgiou et al. (2000) "Antibody Engineering" *Annual Reviews Biomedical Engineering*, 02:339-376.
Mino, T. et al. (2009) "Efficient double-stranded DNA cleavage by artificial zinc-finger nucleases composed of one zinc-finger protein and a single-chain FokI dimer" *J. Biotechnol.*, 140:156-161.
Mössner, E. et al. (2001) "Fast selection of antibodies without antigen purification: adaptation of the protein fragment complementation assay to select antigen-antibody pairs" *Journal of Molecular Biology*, vol. 308, No. 2, pp. 115-122.
Muramatsu, T. et al. (Jan. 1998) "In vivo electroporation: a powerful and convenient means of nonviral gene transfer to tissues of living animals (Review)" *Int. J. Mol. Med.*, 1:55-62.
Phelan, A. et al. (May 1998) "Intercellular Delivery of Functional p53 by the Herpesvirus Protein VP22" *Nat. Biotechnol.*, 16:440-443.
Puchta, H. et al. (1993) "Homologous recombination in plant cells is enhanced by in vivo induction of double strand breaks into DNA by a site-specific endonuclease" *Nucleic Acids Res*, 21(22):5034-5040.
Remement, B. et al. (2010) "Genomes of three tomato pathogens within the *Ralstonia solanacearum* species complex reveal significant evolutionary divergence" *BMC Genomics*, 11:379, 16 pages.

(56) References Cited

OTHER PUBLICATIONS

Remenant, B. et al. (2012) "Sequencing of K60, Type Strain of the Major Plant Pathogen *Ralstonia solanacearum*" *J Bacterial*, 194(10):2742-2743.

Salanoubat, M. et al. (Jan. 2002) "Genome sequence of the plant pathogen *Ralstonia solanacearum*" *Nature*, 415:497-502.

Schandry, N. et al. (Aug. 17, 2016) "TALE-Like Effectors are an Ancestral Feature of the *Ralstonia solanacearum* Species Complex and Converge in DNA Targeting Specificity" *Frontiers in Plant Science*, 7:Article 1225, doi:10.3389/fpls.2016.01225, 16 pages.

Schwarze, S.R. et al. (Jul. 2000) "ProteinTransduction: Unrestricted Delivery Into all Cells?" *Trends Cell Biol*, 10:290-295.

Secco, P. et al. (2009) "Antibody library selection by the β-lactamase protein fragment complementation assay", *Protein Engineering, Design and Selection*, vol. 22, No. 3, pp. 149-158.

Segal, D.J. and D. Carroll (Jan. 1995) "Endonuclease-induced, targeted homologous extrachromosomal recombination in *Xenopus* oocytes" *Proc Natl Acad Sci USA*, 92(3):806-810.

Shulka, V.K. et al. (2009) "Precise genome modification in the crop species *Zea mays* using zinc-finger nucleases" *Nature*, 459:437-441.

Smolarek, D. et al. (2010) "A recombinant dromedary antibody fragment (VHH or nanobody) directed against human Duffy antigen receptor for chemokines" Cell Mol Life Sci, 67(19):3371-3387. Author Manuscript, HAL Archives Ouvertes—France [online]. Retrieved from: https://www.ncbi.nlm.nih.gov/pmc/articles/PMC2966875/?report=printable; retreived on Jun. 18, 2018, 30 pages.

Tanenbaum, M. et al. (Oct. 2014) "A Protein-Tagging System for Signal Amplification in Gene Expression and Fluorescence Imaging" *Cell*, vol. 159, No. 3, pp. 635-646.

Thierry, A. et al. (1991) "Cleavage of yeast and bacteriophage T7 genomes at a single site using the rare cutter endonuclease I-*Sce* I" *Nucleic Acids Res*, 9(1):189-190.

Townsend, J.A. et al. (May 21, 2009) "High-frequency modification of plant genes using engineered zinc-finger nucleases" *Nature*, 459:442-445.

Tsai, S. et al. (Jun. 2014) "Dimeric CRISPR RNA-guided FokI nucleases for highly specific genome editing", *Nature Biotechnology*, vol. 32, No. 6, p. 569-577.

UniProtKB Sequence Accession No. D8N2L9 (Jun. 7, 2017) "Type III effector AvrBs3 family" [online]. Retrieved from: www.uniprot.org/uniprot/D8N2L9.txt?version=27, on Apr. 9, 2019, 1 page.

Vannocci, T. et al. (2014) "Nuclease-stimulated homologous recombination at the human beta-globin gene", *The Journal of Gene Medicine*, vol. 16, No. 1-2, p. 1-10.

Vielemeyer, O. et al. (2010) "Characterization of single chain antibody targets through yeast two hybrid" *BMC Biotechnology*, 10:59, 13 pages.

Visintin, M. et al. (Oct. 1999) "Selection of antibodies for intracellular function using a two-hybrid in vivo system", *Proceedings of the National Academy of Sciences, USA*, vol. 96, No. 21, pp. 11723-11728.

Lippow, S.M. et al. (2009) "Creation of a type IIS restriction endonuclease with a long recognition sequence" Nucleic Acids Research, 37(9):3061-3073.

\* cited by examiner

Lane1: Xanthomonas TALEN transfected sample
Lane2: Ralstonia TALEN transfected sample
Lane3: WT sample
Lane4: DNA Ladder Cell Assay with TALE-Clo51

Test of TAL-Bfil and TAL-Bmrl in HEK293 cells

AAVS1 XTN F/R + indicator: pictures 3 days post transfection

COMPOSITIONS AND METHODS FOR DIRECTING PROTEINS TO SPECIFIC LOCI IN THE GENOME

RELATED APPLICATIONS

This application is a National Stage Application, filed under 35 U.S.C. § 371, of International Application No. PCT/US2016/037922, filed on Jun. 16, 2016, which claims priority to, and the benefit of provisional application U.S. Ser. No. 62/181,162, filed Jun. 17, 2015, the contents of which are herein incorporated by reference in their entirety.

INCORPORATION OF SEQUENCE LISTING

The contents of the text file named "POTH-003/001WO_SeqList.txt," which was created on Jun. 16, 2016 and is 205 KB in size, are hereby incorporated by reference in their entirety.

FIELD OF THE DISCLOSURE

The present invention is directed to compositions and methods for targeted gene modification.

BACKGROUND

There are many instances in which it would be desirable to localize a protein to a specific locus in the genome of an organism in order for the protein to carry out a specific function. One instance in which it is desirable to localize a protein to a specific location in the genome is in the case of gene editing. In such examples of gene editing tools, a DNA binding domain is fused to a nuclease domain through a covalent linkage via a peptide bond. The instant disclosure provides compositions and methods for fusion proteins for gene editing with superior efficacy.

SUMMARY

The disclosure provides compositions and methods for directing a protein to a specific locus or loci in a genome of an organism. Upon contact of the genome with a composition or polypeptide of the disclosure, one or more strand of the double-stranded DNA may be cut. If the cut is made in the presence of one or more DNA repair pathways or components thereof, may either interrupt gene expression or provide modification of the genomic sequence by insertion, deletion, or substitution of one or more base pairs. Compositions and methods of the disclosure provide superior and unexpectedly efficient nuclease activity at a target locus or loci in a genome.

The disclosure provides a fusion protein comprising, consisting essentially of or consisting of a DNA localization component and an effector molecule.

In certain embodiments of the fusion proteins of the disclosure, the DNA localization component may comprise, consist essentially of or consist of, at least one guide RNA (gRNA). In certain aspects of these embodiments, the DNA localization component may comprise, consist essentially of or consist of, two guide RNAs (gRNAs), wherein a first gRNA specifically binds to a first strand of a double-stranded DNA target sequence and a second gRNA specifically binds to a second strand of the double-stranded DNA target sequence.

In certain embodiments of the disclosure the DNA localization component may comprise, consist essentially of or consist of, at least one guide RNA (gRNA) and the effector molecule may comprise, consist essentially of or consist of a Cas9, a Cas9 nuclease domain or a fragment thereof. In certain embodiments of the disclosure the DNA localization component may comprise, consist essentially of or consist of, at least one guide RNA (gRNA) and the effector molecule may comprise, consist essentially of or consist of an inactivated Cas9 (dCas9) or an inactivated nuclease domain. In certain embodiments of the disclosure the DNA localization component may comprise, consist essentially of or consist of, at least one guide RNA (gRNA) and the effector molecule may comprise, consist essentially of or consist of an inactivated small Cas9 (dSaCas9). In each of these embodiments, the effector molecule may comprise, consist essentially of or consist of a Cas9, dCas9, dSaCas9, or nuclease domain thereof and a second endonuclease. The second endonuclease may comprise, consist essentially of or consist of a Type IIS endonuclease. The second endonuclease may comprise, consist essentially of or consist of a Type IIS endonuclease, including, but not limited to, one or more of AciI, MnlI, AlwI, BbvI, BccI, BceAI, BsmAI, BsmFI, BspCNI, BsrI, BtsCI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, FokI or Clo051. In certain embodiments, the effector molecule may comprise, consist essentially of or consist of dCas9 or a nuclease domain thereof and a Type IIS endonuclease. The second endonuclease may comprise, consist essentially of or consist of a Type IIS endonuclease, including, but not limited to, one or more of AciI, MnlI, AlwI, BbvI, BccI, BceAI, BsmAI, BsmFI, BspCNI, BsrI, BtsCI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, or Clo051. In certain embodiments, the effector molecule may comprise, consist essentially of or consist of dCas9 or a nuclease domain thereof and not comprise, consist essentially of or consist of FokI. In certain embodiments, the effector molecule may comprise, consist essentially of or consist of a homodimer of a type IIS endonuclease, including, but not limited to, AciI, MnlI, AlwI, BbvI, BccI, BceAI, BsmAI, BsmFI, BspCNI, BsrI, BtsCI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, or Clo051. In certain embodiments, the effector molecule may comprise, consist essentially of or consist of a heterodimer of a type IIS endonuclease, including, but not limited to, one or more of AciI, MnlI, AlwI, BbvI, BccI, BceAI, BsmAI, BsmFI, BspCNI, BsrI, BtsCI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, or Clo051.

In certain embodiments of the fusion proteins of the disclosure, the DNA localization component may comprise, consist essentially of or consist of, a DNA-binding domain of a transcription activator-like effector nuclease (TALEN). In certain embodiments of the fusion proteins of the disclosure, the DNA localization component may comprise, consist essentially of or consist of, a DNA-binding domain of a TALEN (also referred to as a TAL protein) and the effector molecule may comprise an endonuclease. The DNA binding domain, or TAL protein, may be derived from *Xanthomonas*. The DNA binding domain, or TAL protein, may be derived from *Ralstonia*.

In certain embodiments of the fusion proteins of the disclosure, the DNA localization component may comprise, consist essentially of or consist of, a DNA-binding domain of a TALEN, or TAL protein, derived from *Xanthomonas* and the effector molecule may comprise, consist essentially of or consist of, a Type IIS endonuclease. The effector molecule may comprise, consist essentially of or consist of a Type IIS endonuclease, including, but not limited to, one or more of AciI, MnlI, AlwI, BbvI, BccI, BceAI, BsmAI, BsmFI, BspCNI, BsrI, BtsCI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I or Clo051. In certain embodiments of the fusion proteins of the disclosure, the DNA localization component may comprise, consist essentially of or consist of, a DNA-binding domain of a TALEN, or TAL protein, derived from *Xanthomonas* and the effector molecule may not comprise, consist essentially of or consist of FokI. In certain embodiments of the fusion proteins of the disclosure, the DNA localization component may comprise, consist essentially of or consist of, a DNA-binding domain of a TALEN, or TAL protein, derived from *Xanthomonas* and the effector molecule may not comprise, consist essentially of or consist of Clo051. In certain embodiments, the effector molecule may comprise, consist essentially of or consist of a homodimer of a type IIS endonuclease, including, but not limited to, AciI, MnlI, AlwI, BbvI, BccI, BceAI, BsmAI, BsmFI, BspCNI, BsrI, BtsCI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, or Clo051. In certain embodiments, the effector molecule may comprise, consist essentially of or consist of a heterodimer of a type IIS endonuclease, including, but not limited to, one or more of AciI, MnlI, AlwI, BbvI, BccI, BceAI, BsmAI, BsmFI, BspCNI, BsrI, BtsCI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, or Clo051.

In certain embodiments of the fusion proteins of the disclosure, the DNA localization component may comprise, consist essentially of or consist of, a DNA-binding domain of a TALEN, or TAL protein, derived from *Ralstonia* and the effector molecule may comprise, consist essentially of or consist of, a Type IIS endonuclease. The effector molecule may comprise, consist essentially of or consist of a Type IIS endonuclease, including, but not limited to, one or more of AciI, MnlI, AlwI, BbvI, BccI, BceAI, BsmAI, BsmFI, BspCNI, BsrI, BtsCI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I or Clo051. In certain embodiments of the fusion proteins of the disclosure, the DNA localization component may comprise, consist essentially of or consist of, a DNA-binding domain of a TALEN, or TAL protein, derived from *Ralstonia* and the effector molecule may not comprise, consist essentially of or consist of FokI. In certain embodiments, the effector molecule may comprise, consist essentially of or consist of a homodimer of a type IIS endonuclease, including, but not limited to, AciI, MnlI, AlwI, BbvI, BccI, BceAI, BsmAI, BsmFI, BspCNI, BsrI, BtsCI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, or Clo051. In certain embodiments, the effector molecule may comprise, consist essentially of or consist of a heterodimer of a type IIS endonuclease, including, but not limited to, one or more of AciI, MnlI, AlwI, BbvI, BccI, BceAI, BsmAI, BsmFI, BspCNI, BsrI, BtsCI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, or Clo051.

In certain embodiments of the fusion proteins of the disclosure, the effector molecule may comprise, consist essentially of or consist of, a heterodimer.

In certain embodiments of the fusion proteins of the disclosure, the effector molecule may comprise, consist essentially of or consist of, a homodimer. In certain embodiments of the fusion proteins of the disclosure, the effector molecule may comprise, consist essentially of or consist of, a homodimer of a type IIS endonuclease.

Effector molecules of the disclosure, including heterodimers and homodimers of the disclosure, may comprise, consist essentially of or consist of a nuclease or endonuclease. Effector molecules of the disclosure, including heterodimers and homodimers of the disclosure, may comprise, consist essentially of or consist of a Cas9, a Cas9 nuclease domain or a fragment thereof. The Cas9 may be or may comprise, consist essentially of or consist of an inactivated Cas9 (dCas9) or an inactivated nuclease domain. The Cas9 may be or may comprise, consist essentially of or consist of an inactivated small Cas9 (dSaCas9).

In certain embodiments of the disclosure, the effector molecule may comprise, consist essentially of or consist of a dCas9 or an inactivated nuclease domain thereof and a type IIS endonuclease. In certain embodiments of the disclosure, the effector molecule may comprise, consist essentially of or consist of a dCas9 or an inactivated nuclease domain thereof and a type IIS endonuclease, including, but not limited to, AciI, MnlI, AlwI, BbvI, BccI, BceAI, BsmAI, BsmFI, BspCNI, BsrI, BtsCI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I or Clo051. In certain embodiments of the disclosure, the effector molecule may comprise, consist essentially of or consist of a dCas9 or an inactivated nuclease domain thereof and not may not comprise, consist essentially of or consist of FokI.

In certain embodiments of the disclosure, the effector molecule may comprise, consist essentially of or consist of a dSaCas9 or an inactivated nuclease domain thereof and a type IIS endonuclease. In certain embodiments of the disclosure, the effector molecule may comprise, consist essentially of or consist of a dSaCas9 or an inactivated nuclease domain thereof and a type IIS endonuclease, including, but not limited to, AciI, MnlI, AwI, BbvI, BccI, BceAI, BsmAI, BsmFI, BspCNI, BsrI, BtsCI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, FokI or Clo051.

In certain embodiments of the disclosure, the effector molecule may comprise, consist essentially of or consist of a heterodimer of one or more type IIS endonucleases. In certain embodiments of the disclosure, the effector molecule may comprise, consist essentially of or consist of a heterodimer of one or more type IIS endonucleases, including, but not limited to, AciI, MnlI, AlwI, BbvI, BccI, BceAI, BsmAI, BsmFI, BspCNI, BsrI, BtsCI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, FokI or Clo051.

In certain embodiments of the fusion proteins of the disclosure, the effector molecule may comprise, consist essentially of or consist of, a homodimer of type IIS endonucleases. In certain embodiments of the disclosure, the effector molecule may comprise, consist essentially of or consist of a homodimer of type IIS endonucleases, including, but not limited to, AciI, MnlI, AlwI, BbvI, BccI, BceAI, BsmAI, BsmFI, BspCNI, BsrI, BtsCI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, FokI or Clo051.

Effector molecules of the disclosure, including heterodimers and homodimers of the disclosure, may comprise, consist essentially of or consist of a DNA cleavage domain of a TALEN. The TALEN may be derived from *Xanthomonas* or *Ralstonia*.

In certain embodiments of the disclosure, the effector molecule may comprise, consist essentially of or consist of a DNA cleavage domain of a TALEN, wherein the TALEN is derived from Xanthomonus, and a type IIS endonuclease. In certain embodiments of the disclosure, the effector molecule may comprise, consist essentially of or consist of a DNA cleavage domain of a TALEN, wherein the TALEN is derived from Xanthomonus, and a type IIS endonuclease, including, but not limited to, AciI, MnlI, AlwI, BbvI, BccI, BceAI, BsmAI, BsmFI, BspCNI, BsrI, BtsCI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I or Clo051. In certain embodiments of the disclosure, the effector molecule may comprise, consist essentially of or consist of a DNA cleavage domain of a TALEN, wherein the TALEN is derived from Xanthomonus, and not may not comprise, consist essentially of or consist of FokI. In certain embodiments of the disclosure, the effector molecule may comprise, consist essentially of or consist of a DNA cleavage domain of a TALEN, wherein the TALEN is derived from Xanthomonus, and not may not comprise, consist essentially of or consist of Clo051.

In certain embodiments of the disclosure, the effector molecule may comprise, consist essentially of or consist of a DNA cleavage domain of a TALEN, wherein the TALEN is derived from *Ralstonia*, and a type IIS endonuclease. In certain embodiments of the disclosure, the effector molecule may comprise, consist essentially of or consist of a DNA cleavage domain of a TALEN, wherein the TALEN is derived from *Ralstonia*, and a type IIS endonuclease, including but not limited to, AciI, MnlI, AlwI, BbvI, BccI, BceAI, BsmAI, BsmFI, BspCNI, BsrI, BtsCI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, or Clo051.

Effector molecules of the disclosure, including heterodimers and homodimers of the disclosure, may comprise, consist essentially of or consist of AciI, MnlI, AlwI, BbvI, BccI, BceAI, BsmAI, BsmFI, BspCNI, BsrI, BtsCI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I or Clo051. In certain embodiments, the effector molecule may comprise, consist essentially of or consist of Clo051, BfiI or BmrI. In certain embodiments, the effector molecule may comprise, consist essentially of or consist of Clo051.

The disclosure provides a nucleic acid encoding a fusion protein of the disclosure.

The disclosure provides a vector comprising, consisting essentially of or consisting of, a nucleic acid of the disclosure. Preferably, the disclosure provides a vector comprising, consisting essentially of or consisting of, a nucleic acid encoding a fusion protein of the disclosure.

The disclosure provides a cell comprising a fusion protein, a nucleic acid, a vector or a composition of the disclosure. The cell may be in vivo, ex vivo or in vitro. The cell may be a unicellular or single-celled organism, including, for example, bacteria, archaea, protozoa, unicellular algae and/or unicellular fungi.

The disclosure provides a composition comprising a fusion protein, a nucleic acid, a vector or a cell of the disclosure. Compositions of the disclosure may further comprise, consist essentially of or consist of pharmaceutically-acceptable carrier.

The disclosure provides a multicellular organism comprising, consisting essentially of or consisting of, a fusion protein, a nucleic acid, a vector, a cell, or a composition of the disclosure. The multicellular organism may be a plant. The multicellular organism may be an animal. In certain embodiments, the animal is not a human or a human embryo or is not derived from either a human or a human embryo.

The disclosure provides a method for directing proteins to specific loci in a genome of an organism comprising providing to a genomic DNA sequence a fusion protein, a nucleic acid, a vector, a cell or a composition of the disclosure. In certain embodiments of this method, the fusion protein, the nucleic acid, the vector, the cell or the composition contacts the genomic DNA sequence in vivo, ex vivo, or in vitro. In certain embodiments of this method, the genomic DNA sequence is not a human genomic DNA sequence.

The disclosure provides a composition comprising, consisting essentially of or consisting of, a DNA localization component and an effector molecule, wherein the DNA localization component and the effector molecule are capable of operatively linking via a non-covalent linkage.

DNA localization components of the disclosure may comprise, consist essentially of or consist of, at least one guide RNA (gRNA). In certain embodiments of the compositions and methods of the disclosure, DNA localization components may comprise, consist essentially of or consist of, two (2) guide RNAs (gRNAs), wherein a first gRNA specifically binds to a first strand of a double-stranded DNA target sequence and a second gRNA specifically binds to a second strand of the double-stranded DNA target sequence. Alternatively, DNA localization components of the disclosure may comprise a DNA binding domain of a transcription activator-like effector nuclease (TALEN). Exemplary DNA binding domains of TALEN of the disclosure may be derived from *Xanthomonas* or *Ralstonia*.

Effector molecules of the disclosure may comprise, consist essentially of or consist of, a homodimer or a heterodimer. Effector molecules, including those effector molecules comprising a homodimer or a heterodimer, may comprise, consist essentially of or consist of, a nuclease. In preferred embodiments, the nuclease is an endonuclease. Effector molecules, including those effector molecules comprising a homodimer or a heterodimer, may comprise, consist essentially of or consist of, a Cas9, a Cas9 nuclease domain or a fragment thereof In certain embodiments, the Cas9 is a catalytically inactive or "inactivated" Cas9 (dCas9). In certain embodiments, the Cas9 is a catalytically inactive or "inactivated" nuclease domain of Cas9. In preferred embodiments, the dCas9 is encoded by a shorter sequence that is derived from a full length, catalytically inactivated, Cas9, referred to herein as a "small" dCas9 or dSaCas9.

Effector molecules, including those effector molecules comprising a homodimer or a heterodimer, may comprise, consist essentially of or consist of Clo051, BfiI or BmrI. In preferred embodiments, effector molecules, including those effector molecules comprising a homodimer or a heterodimer, may comprise, consist essentially of or consist of Clo051.

Effector molecules, including those effector molecules comprising a heterodimer, may comprise, consist essentially of or consist of a Cas9, a Cas9 nuclease domain or a fragment thereof that forms a heterodimer with Clo051, BfiI or BmrI. In certain embodiments, effector molecules, including those effector molecules comprising a heterodimer, may comprise, consist essentially of or consist of a Cas9, a Cas9 nuclease domain or a fragment thereof that forms a heterodimer with Clo051.

Effector molecules, including those effector molecules comprising a heterodimer, may comprise, consist essentially of or consist of a dCas9 or inactivated nuclease domain thereof that forms a heterodimer with Clo051, BfiI or BmrI. In preferred embodiments, effector molecules, including those effector molecules comprising a heterodimer, may comprise, consist essentially of or consist of a dCas9 or inactivated nuclease domain thereof that forms a heterodimer with Clo051.

Effector molecules, including those effector molecules comprising a heterodimer, may comprise, consist essentially of or consist of a dSaCas9 that forms a heterodimer with Clo051, BfiI or BmrI. In preferred embodiments, effector molecules, including those effector molecules comprising a heterodimer, may comprise, consist essentially of or consist of a dSaCas9 that forms a heterodimer with Clo051.

Effector molecules, including those effector molecules comprising a homodimer, may comprise, consist essentially of or consist of a catalytically-inactive form of Cas9 (e.g. dCas9 or dSaCas9) or a fragment thereof and a homodimer comprising, consisting essentially of or consisting of Clo051, BfiI or BmrI. In certain embodiments, effector molecules, including those effector molecules comprising a homodimer, may comprise, consist essentially of or consist of a catalytically-inactive form of Cas9 (e.g. dCas9 or dSaCas9) or a fragment thereof and a homodimer comprising, consisting essentially of or consisting of Clo051.

Effector molecules, including those effector molecules comprising a homodimer or a heterodimer, may comprise, consist essentially of or consist of a DNA cleavage domain of a TALEN. Exemplary DNA cleavage domains of TALENs of the disclosure may be derived from *Xanthomonas* or *Ralstonia*.

Effector molecules, including those effector molecules comprising a heterodimer, may comprise, consist essentially of or consist of a DNA cleavage domain of a *Xanthomonas* TALEN that forms a heterodimer with Clo051, BfiI or BmrI. In preferred embodiments, effector molecules, including those effector molecules comprising a heterodimer, may comprise, consist essentially of or consist of a DNA cleavage domain of a *Xanthomonas* TALEN that forms a heterodimer with Clo051.

Effector molecules, including those effector molecules comprising a homodimer, may comprise, consist essentially of or consist of a DNA cleavage domain of a *Xanthomonas* TALEN and a homodimer comprising, consisting essentially of or consisting of Clo051, BfiI or BmrI. In certain embodiments, effector molecules, including those effector molecules comprising a homodimer, may comprise, consist essentially of or consist of a DNA cleavage domain of a *Xanthomonas* TALEN and a homodimer comprising, consisting essentially of or consisting of Clo051.

Effector molecules, including those effector molecules comprising a heterodimer, may comprise, consist essentially of or consist of a DNA cleavage domain of a *Ralstonia* TALEN that forms a heterodimer with Clo051, BfiI or BmrI. In preferred embodiments, effector molecules, including those effector molecules comprising a heterodimer, may comprise, consist essentially of or consist of a DNA cleavage domain of a *Ralstonia* TALEN that forms a heterodimer with Clo051.

Effector molecules, including those effector molecules comprising a homodimer, may comprise, consist essentially of or consist of a DNA cleavage domain of a *Ralstonia* TALEN and a homodimer comprising, consisting essentially of or consisting of Clo051, BfiI or BmrI. In certain embodiments, effector molecules, including those effector molecules comprising a homodimer, may comprise, consist essentially of or consist of a DNA cleavage domain of a *Ralstonia* TALEN and a homodimer comprising, consisting essentially of or consisting of Clo051.

Non-covalent linkages of the disclosure may comprise, consist essentially of or consist of an antibody fragment covalently attached to the effector molecule and which non-covalently binds directly to the DNA localization component. Non-covalent linkages of the disclosure may comprise, consist essentially of or consist of an antibody fragment covalently attached to the DNA localization component and which non-covalently binds directly to the effector component. Non-covalent linkages of the disclosure may comprise, consist essentially of or consist of an antibody fragment covalently attached to either the effector molecule or the DNA localization component and which non-covalently binds to an epitope tag covalently attached to the opposite component. Antibody fragments of the disclosure may comprise or consist of a single-chain variable fragment (scFv), a single domain antibody (sdAB), a small modular immunopharmaceutical (SMIP) molecule, or a nanobody.

Non-covalent linkages of the disclosure may comprise, consist essentially of or consist of a protein binding domain covalently attached to either the effector molecule or the DNA localization component and which non-covalently binds to the opposite component.

Non-covalent linkages of the disclosure may comprise, consist essentially of or consist of a protein covalently attached to either the effector molecule or the DNA localization component capable of binding to a protein covalently attached to the opposite component.

Non-covalent linkages of the disclosure may comprise, consist essentially of or consist of a small molecule covalently attached either to the effector molecule or the DNA localization component and which non-covalently binds to a protein or other small molecule covalently attached to the opposite component.

Non-covalent linkages of the disclosure may comprise, consist essentially of or consist of an antibody mimetic. Exemplary antibody mimetics of the disclosure comprise or consist of an organic compound that specifically binds a target sequence and has a structure distinct from a naturally-occurring antibody. Antibody mimetics may comprise or consist of a protein, a nucleic acid, or a small molecule. Antibody mimetics may comprise or consist of an affibody, an afflilin, an affimer, an affitin, an alphabody, an anticalin, and avimer, a DARPin, a Fynomer, a Kunitz domain peptide, or a monobody.

The disclosure provides a vector comprising a nucleic acid sequence that encodes for a DNA localization component, an effector molecule, and/or noncovalent-linkage of the disclosure.

The disclosure provides a polypeptide encoded by a vector of the disclosure. The disclosure provides a composition comprising a polypeptide encoded by a vector of the disclosure.

The disclosure provides a polypeptide comprising a DNA localization component and an effector molecule, wherein the DNA localization component and the effector molecule are capable of operatively linking via a non-covalent linkage. The disclosure provides a composition comprising a DNA localization component and an effector molecule, wherein the DNA localization component and the effector molecule are capable of operatively linking via a non-covalent linkage.

Compositions of the disclosure may comprise a pharmaceutically-acceptable carrier.

The disclosure provides a cell comprising a nucleic acid, a vector, a polypeptide, or a composition of the disclosure. The cell may be in situ, in vivo, ex vivo, or in vitro. Cells comprising a vector of the disclosure include single-celled organisms, including bacteria and archaea.

The disclosure provides a multicellular organism comprising a cell comprising a vector, polypeptide or composition of the disclosure. Exemplary multicellular organisms include, but are not limited to, a plant or an animal. In certain embodiments of the disclosure, an animal comprising a cell comprising a vector, polypeptide or composition of the disclosure is not a human. In certain embodiments of the disclosure, an animal comprising a cell comprising a vector, polypeptide or composition of the disclosure is not a human embryo.

The disclosure provides a method for directing proteins to specific loci in a genome of an organism comprising providing a composition, a nucleic acid, a vector, or a polypeptide of the disclosure to the genome. In certain embodiments of this method, composition, the nucleic acid, the vector, or the polypeptide are contact a genomic DNA sequence in vivo, ex vivo, or in vitro. In certain embodiments of this method, the genome is not a human genome.

The disclosure provides a method for modifying a genome of an organism comprising providing to a genomic DNA sequence or base pair a fusion protein, a nucleic acid, a vector, a cell or a composition according to the disclosure. In certain embodiments, the step of providing comprises bringing into contact a genomic sequence or base pair and at least one of the fusion protein, the nucleic acid, the vector, the cell or the composition. In certain aspects, contact between a genomic sequence or base pair and at least one of the fusion protein, the nucleic acid, the vector, the cell or the composition may be achieved through fluid communication.

According to this method, the modification of the genomic sequence or base pair may comprise a separation of a sequence and/or base pairs by an activity of an endonuclease. Alternatively, or in addition, the modification of the genomic sequence or base pair may comprise, consist essentially of or consist of a deletion, an insertion, a substitution, an inversion, and/or a relocation of a sequence or base pair. In certain embodiments, a DNA repair mechanism induces the deletion, insertion, substitution, inversion, and/or relocation. For example, when the DNA repair mechanism includes the Non-Homologous End Joining (NHEJ) DNA repair pathway, the NHEJ pathway may induce an insertions or deletions (InDels) at the target site, resulting in frameshifts and/or premature stop codons. Thus, when the DNA repair mechanism includes the Non-Homologous End Joining (NHEJ) DNA repair pathway, the NHEJ pathway may disrupt the open reading frame (ORF) of a target gene or genomic sequence. Disruption of the ORF of the target gene or genomic sequence may silence expression of the target gene or genomic sequence. For example, when the DNA repair mechanism includes the Homology Directed Repair (HDR) pathway, a repair template may be used to reconnect a single or double strand break in the genomic sequence. Repair templates of the disclosure may be used to insert desired sequences into the genome at the site of endonuclease activity. Exemplary repair templates of the disclosure may comprise an exogenous, artificial, and/or heterologous sequence.

Regardless of the mechanism or DNA repair pathway, inserted sequences of the disclosure may comprise an exogenous, artificial, and/or heterologous sequence. In certain embodiments, the genomic sequence comprising the insertion is non-naturally occurring. For example, when an insertion comprises an exogenous, artificial, and/or heterologous sequence, the resultant genomic sequence is non-naturally occurring.

The disclosure provides a genomic sequence modified according to a method of the disclosure.

The disclosure provides a cell comprising the genomic sequence of claim 47.

The disclosure provides a cell comprising a modification resulting from a method of the disclosure. Modification of the cell or a genomic sequence thereof may be performed in vivo, ex vivo or in vitro. For example, a cell may be modified ex vivo or in vitro and administered to a subject. In certain embodiments, the modified cell or modified genomic sequence of the disclosure is neither a human cell nor a human genomic sequence. In certain embodiments, the modified cell or modified genomic sequence of the disclosure is neither a human embryonic cell nor a human embryonic genomic sequence.

DETAILED DESCRIPTION

Figure 1:
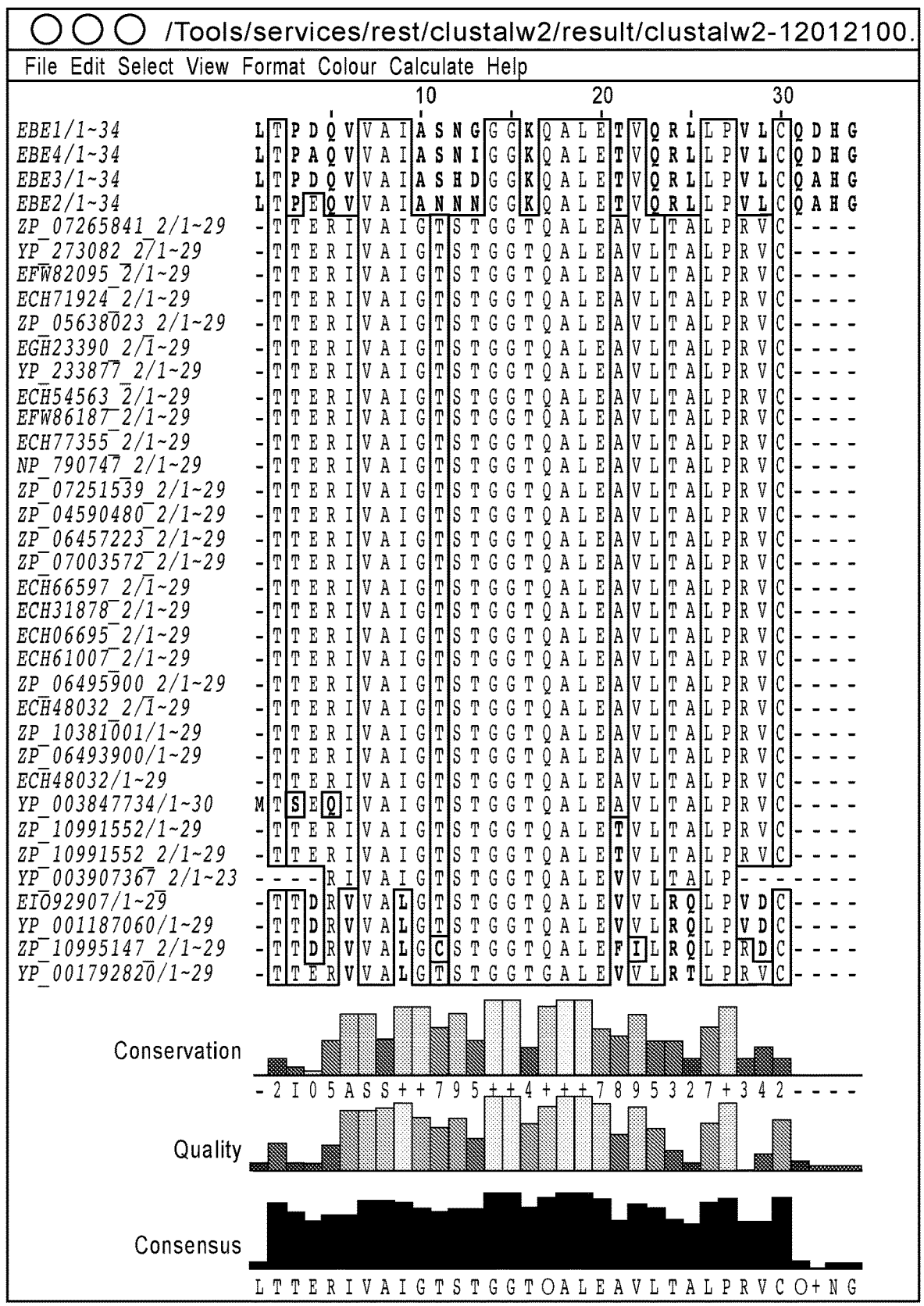
FIG. 1 is an alignment depicting a consensus sequence of a DNA-binding protein from *Xanthamonas* aligned via BLAST to methyltransferase sequences from bacterial strains. Based upon sequence alignment, the DNA binding function of the sequences are demonstrated. From top to bottom, SEQ ID Nos: 248 to 283 are shown, the consensus sequence TTERIVAIGTSTGGTOALEAVLTALPRVC (SEQ ID NO: 284).
Figure 2:
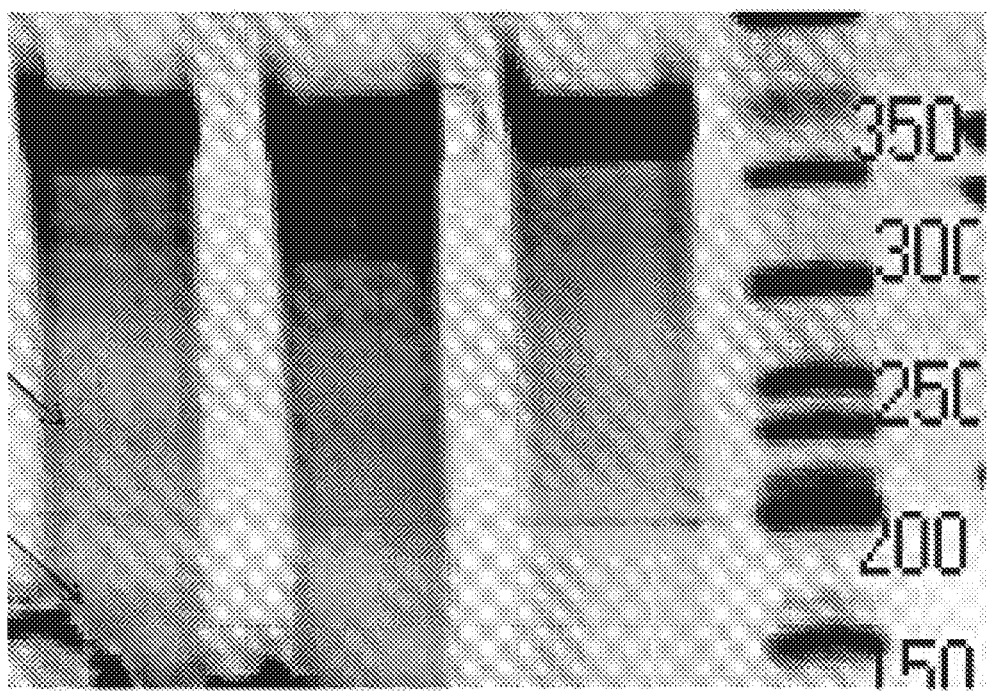
FIG. 2 is a photograph of a gel electrophoresis demonstrating RTN functionality.

Disclosed are compositions and methods for directing proteins to specific loci in the genome and uses thereof. In one aspect, the disclosed methods allow for directing proteins to specific loci in the genome of an organism, including the steps of providing a fusion protein comprising a DNA localization component and an effector molecule. Alternatively, the disclosed methods allow for directing proteins to specific loci in the genome of an organism, including the steps of providing a DNA localization component and an effector molecule, wherein the DNA localization component and the effector molecule are capable of being operatively linked via a non-covalent linkage. In certain embodiments of this method, the DNA localization component is capable of binding a specific DNA sequence.

DNA Localization Components

DNA localization components of the disclosure may be capable of binding a specific DNA sequence. The DNA localization component may be selected from, for example, a DNA-binding oligonucleotide, a DNA-binding protein, a DNA binding protein complex, and combinations thereof. Other suitable DNA binding components will be recognized by one of ordinary skill in the art.

DNA localization components may comprise an oligonucleotide directed to a specific locus or loci in the genome. The oligonucleotide may be selected from DNA, RNA, DNA/RNA hybrids, and combinations thereof.

DNA localization components may comprise a nucleotide binding protein or protein complex that binds an oligonucleotide when bound to a target DNA. The protein or protein complex may be capable of recognizing a feature selected from RNA-DNA heteroduplexes, R-loops, or combinations thereof. In one aspect, the DNA localization component may comprise a protein or protein complex capable of recognizing an R-loop selected from Cas9, Cascade complex, RecA, RNase H, RNA polymerase, DNA polymerase, or a combination thereof.

DNA localization components may comprise an engineered protein capable of binding to target DNA. In this aspect, the DNA localization component may comprise a protein capable of binding a DNA sequence selected from meganuclease, zinc finger array, transcription activator-like (TAL) array, and combinations thereof.

DNA localization components may comprise a protein that contains a naturally occurring DNA binding domain.

The DNA localization component may comprise, for example, a protein comprising a naturally occurring DNA binding domain is selected from a bZIP domain, a Helix-loop-helix, a Helix-turn-helix, a HMG-box, a Leucine zipper, a Zinc finger, or a combination thereof.

Exemplary DNA localization components of the disclosure include, but are not limited to, a DNA-binding oligonucleotide, a DNA-binding protein, a DNA binding protein complex, and any combination thereof.

DNA localization components of the disclosure may comprise an oligonucleotide directed to a specific locus in the genome. Exemplary oligonucleotides include, but are not limited to, DNA, RNA, DNA/RNA hybrids, and any combination thereof.

DNA localization components of the disclosure may comprise a protein or a protein complex capable of recognizing a feature selected from RNA-DNA heteroduplexes, R-loops, and any combination thereof. Exemplary proteins or protein complexes capable of recognizing an R-loop include, but are not limited to, Cas9, Cascade complex, RecA, RNase H, RNA polymerase, DNA polymerase, and any combination thereof. In certain embodiments of the methods of the disclosure, the protein or protein complex capable of recognizing an R-loop comprises Cas9.

DNA localization components of the disclosure may comprise a protein capable of binding a DNA sequence selected from meganuclease, Zinc Finger array, TAL array, and any combination thereof.

DNA localization components of the disclosure may comprise a protein comprising a naturally occurring DNA binding domain. Exemplary naturally occurring DNA binding domains include, but are not limited to, a bZIP domain, a Helix-loop-helix, a Helix-turn-helix, a HMG-box, a Leucine zipper, a Zinc finger, and any combination thereof.

DNA localization components of the disclosure may comprise an oligonucleotide directed to a target location in a genome and a protein capable of binding to a target DNA sequence.

Effector Molecules

Methods of the disclosure comprise providing an effector molecule.

Exemplary effector molecules of the disclosure are capable of a predetermined effect at a specific locus in the genome.

Exemplary effector molecules of the disclosure include, but are not limited to, a transcription factor (activator or repressor), chromatin remodeling factor, nuclease, exonuclease, endonuclease, transposase, methytransferase, demethylase, acetyltransferase, deacetylase, kinase, phosphatase, integrase, recombinase, ligase, topoisomerase, gyrase, helicase, fluorophore, or any combination thereof.

Exemplary effector molecules of the disclosure may comprise a transposase. In other aspects, the effector molecule may comprise a PB transposase (PBase).

Exemplary effector molecules of the disclosure comprise a nuclease. Non-limiting examples of nucleases include restriction endonucleases, homing endonucleases, S1 Nuclease, mung bean nuclease, pancreatic DNase I, micrococcal nuclease, yeast HO endonuclease, or any combination thereof. In certain embodiments, the effector molecule comprises a restriction endonuclease. In certain embodiments, the effector molecule comprises a Type IIS restriction endonuclease.

Exemplary effector molecules of the disclosure may comprise an endonuclease. Non-limiting examples of the endonuclease include AciI, MnlI, AlwI, BbvI, BccI, BceAI, BsmAI, BsmFI, BspCNI, BsrI, BtsCI, HgaI, HphI, HpyAV, MboII, MylI, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I and Clo051. In certain embodiments, the effector molecule comprises BmrI, BfiI, or Clo051. The effector molecule may comprise BmrI. The effector molecule may comprise BfiI. The effector molecule may comprise Clo051.

Linkages

The disclosure provides a fusion protein comprising, consisting essentially of or consisting of a DNA localization component and an effector molecule. When the polypeptides of the disclosure are fusion proteins, the nucleic acid sequences encoding one or more components of the fusion protein may be operably linked, for example, in an expression vector. Fusion proteins of the disclosure may be chimeric proteins. Fusion proteins of the disclosure may also include proteins encoded by one or more recombinant nucleic acid sequences. Fusion proteins may also include a linker region to operatively-link two components of the fusion protein. For example, the disclosure provides a fusion protein comprising, consisting essentially of or consisting of a DNA localization component and an effector molecule, operatively-linked by a linker region. In this embodiment, the DNA localization component, the linker region, and the effector molecule may be encoded by one or more nucleic acid sequences inserted into an expression cassette and/or expression vector such that translation of the nucleic acid sequence results in the fusion protein.

Polypeptides and compositions of the disclosure may comprise a non-covalent linkage between the DNA localization component and the effector molecule. The non-covalent linkage may comprise an antibody, an antibody fragment, an antibody mimetic, or a scaffold protein.

Exemplary non-covalent linkages of the disclosure may comprise an antibody fragment covalently attached to an effector molecule, which non-covalently binds directly to a DNA localization component.

Exemplary non-covalent linkages of the disclosure may comprise an antibody fragment covalently attached to a DNA localization component, non-covalently binds directly to an effector component.

Exemplary non-covalent linkages of the disclosure may comprise an antibody fragment covalently attached to either an effector molecule or a DNA localization component, which non-covalently binds to an epitope tag covalently attached to the opposite component. In certain embodiments of the disclosure, antibody fragments may comprise or consist of a single-chain variable fragment (scFv), a single domain antibody (sdAB), a small modular immunopharmaceutical (SMIP) molecule, or a nanobody.

Exemplary non-covalent linkages of the disclosure may comprise a protein binding domain covalently attached to either an effector molecule or a DNA localization component, which non-covalently binds to the opposite component Exemplary non-covalent linkages of the disclosure may comprise a protein covalently attached to either an effector molecule or a DNA localization component capable of binding to a protein covalently attached to the opposite component.

Non-covalent linkages of the disclosure may comprise or consist of an antibody mimetic. Exemplary antibody mimetics include, but are not limited to, an organic compound that specifically binds a target sequence and has a structure distinct from a naturally-occurring antibody. Moreover, Exemplary antibody mimetics include, but are not limited to, a protein, a nucleic acid, or a small molecule. In certain embodiments of the disclosure, the antibody mimetic comprises or consists of an affibody, an afflilin, an affimer, an affitin, an alphabody, an anticalin, and avimer, a DARPin, a Fynomer, a Kunitz domain peptide, or a monobody.

Exemplary non-covalent linkages of the disclosure may comprise a small molecule covalently attached either to an effector molecule or a DNA localization component, which non-covalently binds to a protein or other small molecule covalently attached to the opposite component.

Antibodies and fragments thereof, include, but are not limited to, single-chain variable fragment (scFv), single domain antibodies (sdAB), monobodies, and nanobodies. For example, the non-covalent linkage may comprise, a single-chain variable fragment (scFv) or a single domain antibody (sdAB) covalently attached to one or more effector molecules, and which is capable of a non-covalent association to the DNA localization component. In a further aspect, the non-covalent linkage may comprise a single-chain variable fragment (scFv) covalently attached to the DNA localization component and which non-covalently binds directly to the effector component. In a further aspect, the non-covalent linkage may comprise a single-chain variable fragment (scFv) covalently attached to either the effector molecule or the DNA localization component. The scFV may then non-covalently bind to an epitope tag covalently attached to the opposite component (i.e., to the DNA localization component or the effector molecule).

The non-covalent linkage may comprise, for example, an antibody mimetic. As used herein, the term "antibody mimetic" is intended to describe an organic compound that specifically binds a target sequence and has a structure distinct from a naturally-occurring antibody. Antibody mimetics may comprise a protein, a nucleic acid, or a small molecule. The target sequence to which an antibody mimetic of the disclosure specifically binds may be an antigen. Antibody mimetics may provide superior properties over antibodies including, but not limited to, superior solubility, tissue penetration, stability towards heat and enzymes (e.g. resistance to enzymatic degradation), and lower production costs. Exemplary antibody mimetics include, but are not limited to, an affibody, an afflilin, an affimer, an affitin, an alphabody, an anticalin, and avimer (also known as avidity multimer), a DARPin (Designed Ankyrin Repeat Protein), a Fynomer, a Kunitz domain peptide, and a monobody.

Affibody molecules of the disclosure comprise a protein scaffold comprising or consisting of one or more alpha helix without any disulfide bridges. Preferably, affibody molecules of the disclosure comprise or consist of three alpha helices. For example, an affibody molecule of the disclosure may comprise an immunoglobulin binding domain. An affibody molecule of the disclosure may comprise the Z domain of protein A.

Affilin molecules of the disclosure comprise a protein scaffold produced by modification of exposed amino acids of, for example, either gamma-B crystallin or ubiquitin. Affilin molecules functionally mimic an antibody's affinity to antigen, but do not structurally mimic an antibody. In any protein scaffold used to make an affilin, those amino acids that are accessible to solvent or possible binding partners in a properly-folded protein molecule are considered exposed amino acids. Any one or more of these exposed amino acids may be modified to specifically bind to a target sequence or antigen.

Affimer molecules of the disclosure comprise a protein scaffold comprising a highly stable protein engineered to display peptide loops that provide a high affinity binding site for a specific target sequence. Exemplary affimer molecules of the disclosure comprise a protein scaffold based upon a cystatin protein or tertiary structure thereof. Exemplary affimer molecules of the disclosure may share a common tertiary structure of comprising an alpha-helix lying on top of an anti-parallel beta-sheet.

Affitin molecules of the disclosure comprise an artificial protein scaffold, the structure of which may be derived, for example, from a DNA binding protein (e.g. the DNA binding protein Sac7d). Affitins of the disclosure selectively bind a target sequence, which may be the entirety or part of an antigen. Exemplary affitins of the disclosure are manufactured by randomizing one or more amino acid sequences on the binding surface of a DNA binding protein and subjecting the resultant protein to ribosome display and selection. Target sequences of affitins of the disclosure may be found, for example, in the genome or on the surface of a peptide, protein, virus, or bacteria. In certain embodiments of the disclosure, an affitin molecule may be used as a specific inhibitor of an enzyme. Affitin molecules of the disclosure may include heat-resistant proteins or derivatives thereof.

Alphabody molecules of the disclosure may also be referred to as Cell-Penetrating Alphabodies (CPAB). Alphabody molecules of the disclosure comprise small proteins (typically of less than 10 kDa) that bind to a variety of target sequences (including antigens). Alphabody molecules are capable of reaching and binding to intracellular target sequences. Structurally, alphabody molecules of the disclosure comprise an artificial sequence forming single chain alpha helix (similar to naturally occurring coiled-coil structures). Alphabody molecules of the disclosure may comprise a protein scaffold comprising one or more amino acids that are modified to specifically bind target proteins. Regardless of the binding specificity of the molecule, alphabody molecules of the disclosure maintain correct folding and thermostability.

Anticalin molecules of the disclosure comprise artificial proteins that bind to target sequences or sites in either proteins or small molecules. Anticalin molecules of the disclosure may comprise an artificial protein derived from a human lipocalin. Anticalin molecules of the disclosure may be used in place of, for example, monoclonal antibodies or fragments thereof. Anticalin molecules may demonstrate superior tissue penetration and thermostability than monoclonal antibodies or fragments thereof. Exemplary anticalin molecules of the disclosure may comprise about 180 amino acids, having a mass of approximately 20 kDa. Structurally, anticalin molecules of the disclosure comprise a barrel structure comprising antiparallel beta-strands pairwise connected by loops and an attached alpha helix. In preferred embodiments, anticalin molecules of the disclosure comprise a barrel structure comprising eight antiparallel beta-strands pairwise connected by loops and an attached alpha helix.

Avimer molecules of the disclosure comprise an artificial protein that specifically binds to a target sequence (which may also be an antigen). Avimers of the disclosure may recognize multiple binding sites within the same target or within distinct targets. When an avimer of the disclosure recognize more than one target, the avimer mimics function of a bi-specific antibody. The artificial protein avimer may comprise two or more peptide sequences of approximately 30-35 amino acids each. These peptides may be connected via one or more linker peptides. Amino acid sequences of one or more of the peptides of the avimer may be derived from an A domain of a membrane receptor. Avimers have a rigid structure that may optionally comprise disulfide bonds and/or calcium. Avimers of the disclosure may demonstrate greater heat stability compared to an antibody.

DARPins (Designed Ankyrin Repeat Proteins) of the disclosure comprise genetically-engineered, recombinant, or chimeric proteins having high specificity and high affinity for a target sequence. In certain embodiments, DARPins of the disclosure are derived from ankyrin proteins and, optionally, comprise at least three repeat motifs (also referred to as repetitive structural units) of the ankyrin protein. Ankyrin proteins mediate high-affinity protein-protein interactions. DARPins of the disclosure comprise a large target interaction surface.

Fynomers of the disclosure comprise small binding proteins (about 7 kDa) derived from the human Fyn SH3 domain and engineered to bind to target sequences and molecules with equal affinity and equal specificity as an antibody.

Kunitz domain peptides of the disclosure comprise a protein scaffold comprising a Kunitz domain. Kunitz domains comprise an active site for inhibiting protease activity. Structurally, Kunitz domains of the disclosure comprise a disulfide-rich alpha+beta fold. This structure is exemplified by the bovine pancreatic trypsin inhibitor. Kunitz domain peptides recognize specific protein structures and serve as competitive protease inhibitors. Kunitz domains of the disclosure may comprise Ecallantide (derived from a human lipoprotein-associated coagulation inhibitor (LACI)).

Monobodies of the disclosure are small proteins (comprising about 94 amino acids and having a mass of about 10 kDa) comparable in size to a single chain antibody. These genetically engineered proteins specifically bind target sequences including antigens. Monobodies of the disclosure may specifically target one or more distinct proteins or target sequences. In preferred embodiments, monobodies of the disclosure comprise a protein scaffold mimicking the structure of human fibronectin, and more preferably, mimicking the structure of the tenth extracellular type III domain of fibronectin. The tenth extracellular type III domain of fibronectin, as well as a monobody mimetic thereof, contains seven beta sheets forming a barrel and three exposed loops on each side corresponding to the three complementarity determining regions (CDRs) of an antibody. In contrast to the structure of the variable domain of an antibody, a monobody lacks any binding site for metal ions as well as a central disulfide bond. Multispecific monobodies may be optimized by modifying the loops BC and FG. Monobodies of the disclosure may comprise an adnectin.

The non-covalent linkage may comprise, for example, a scaffold protein. Scaffold proteins of the disclosure include, for example, antibody mimetics of the disclosure. Scaffold proteins of the disclosure further include, for example, small modular immunopharmaceutical (SMIP) molecules, a domain antibody, and a nanobody.

SMIP molecules of the disclosure are artificial proteins comprising one or more sequences or portions of an immunoglobulin (antibody) that are monospecific for a target sequence or antigen. SMIPs of the disclosure may substitute for the use of a monoclonal antibody. Structurally, SMIPs are single chain proteins comprising a binding region, a hinge region (i.e. a connector), and an effector domain. The binding region of a SMIP may comprise a modified single-chain variable fragment (scFv). SMIPs may be produced from genetically-modified cells as dimers.

Domain antibodies of the disclosure comprise a single monomeric variable antibody domain (i.e. either heavy or light variable domain). Domain antibodies of the disclosure demonstrate the same antigen specificity as a whole and intact antibody. Domain antibodies of the disclosure may be manufactured, at least in part, by immunization of dromedaries, camels, llamas, alpacas or sharks with the desired antigen and subsequent isolation of the mRNA coding for heavy-chain antibodies.

Nanobodies of the disclosure comprise a VHH single domain antibody. Nanobodies of the disclosure may comprise single domain antibodies of the disclosure.

Non-covalent linkages may comprise a protein binding domain covalently attached to either the effector molecule or the DNA localization component and which is capable of a non-covalent interaction with the opposite component. Non-limiting examples of protein binding domains include, for example, SH2, SH3, PTB, LIM, SAM, PDZ, FERM, CH, Pleckstin, WW, WS×WS, and the E3 ligase domain.

Non-covalent linkages may comprise a protein covalently attached to either the effector molecule or the DNA localization component that is capable of binding to a protein covalently attached to the opposite component. Non-limiting examples include any two proteins that interact non-covalently. Such proteins are readily identified via the Database of Interacting Proteins (DIP), STRING, BioGRID, MIPS, or the like.

Non-covalent linkage may comprise a small molecule covalently attached either to an effector molecule or a DNA localization component, and is capable of forming a non-covalent bond to a protein or other small molecule covalently attached to the opposite component. One such example would include biotin attached to an oligonucleotide and avidin covalently linked to an effector molecule.

The above described methods and compositions may be used, for example, in situations in which a particular protein may have several functions. Transposase proteins, for example, must perform several steps to achieve the desired function, including transposon recognition, cleavage of DNA to excise a transposon, movement of a transposon sequence to a new genomic location, recognition of a new target site, and cleavage of DNA to integrate the transposon at a new locus. In certain aspects, it may be desirable to direct a transposase to integrate a transposon at a particular site in the genome. In these aspects, this could be carried out by, for example, adding a heterologous protein with site-specific DNA binding activity. However, the heterologous protein with site-specific DNA binding activity would only be required during the target site recognition step, and the presence of this protein at earlier stages in the process described above may be detrimental to the other steps. As such, in this aspect, a temporary association of the heterologous protein with site-specific DNA binding activity with the transposase would allow the transposase to be directed to the genomic site of interest while allowing for the other steps of the process to be carried out with limited interference of the protein due to the non-covalent binding.

As another example, it may be desirable to have an enzymatic protein, such as a nuclease, methylase, deacetylase, etc. to temporarily interact with a specific DNA binding domain so that its activity occurs at a specific location in the genome. For example, it may be desired to cause a Clo051 restriction nuclease to temporarily interact with a Cas9 protein that is catalytically inactive for DNA cleavage.

In one aspect, the linker comprises a non-covalent linkage between the DNA binding element and the effector. For example, in one aspect, phage display (PhD) may be used to produce single-chain variable fragment (scFv) antibodies or single domain antibodies (sdAbs) against a particular target. PhD may be used to identify a scFv antibody against an effector, for example piggyBBac (PB) transposase that provides a linkage. A large diversity in scFv affinity may be obtained by limiting the stringency of the affinity selection process. In one aspect, the linkage may be between PB transposase (PBase) and a modular DNA binding domain such as a polydactyl zinc finger, a TAL array, or a dCas9 protein (with associated guide RNA). In some aspects, a scFv antibody with a faster off-rate may provide permissive "breathing" of the complex. In other aspects, conformation and/or flexibility of an effector and DNA binding element may be critical. Non-covalent linkages may provide conformational pliability to the disclosed gene editing compositions. Alternatively, slower off-rates (and a higher Kd) of an scFv that binds particular epitopes of an effector may provide an optimal stability and conformation of the gene editing complex that would not otherwise be obtainable through traditional peptide linkage. A near-exhaustive search among scFv antibodies allows one to select from among a large diversity of possible conformations of a gene editing complex. A PhD strategy creates such diversity through the generation of unique monovalent scFvs against multiple unique epitopes.

Furthermore, a non-covalent linkage method, such as that achieved through the use of a scFv antibody, may employ an unmodified and native effector (e.g., PB). This provides a reversible associate between the effector and the DNA binding element, which may circumvent any permanent interference with the activity of an effector that may occur when it is subjected to covalent linkage. Certain non-covalent associations could introduce steric hindrances that compromise the effector reaction. As several activities may be involved (site recognition, strand cleavage, transposon binding and integration) it is likely that each separate step may be differentially affected by a particular steric hindrance. For example, if transposase association with the DNA transposon (during transposon mobilization from one genomic site to another) has a very slow off-rate, then it would be detrimental to have a very high affinity association between a DNA binding element-scFv and the PBase that disrupts this association. However, if the DNA binding element-scFv protein binds with a lower, but significant affinity, it could be temporarily displaced during transposon mobilization. It is possible that such an early step could involve temporary dissociation of DNA binding factor-scFv with the PBase, with subsequent reassembly of the complex at later steps to create a fully functional and DNA binding factor-enabled site-specific transposase.

Dual Reporter Plasmid

Polypeptides of the disclosure may be introduced into a dual reporter plasmid to validate the efficiency of polypeptides comprising a nuclease to cut DNA at the targeted site.

Figure 5:
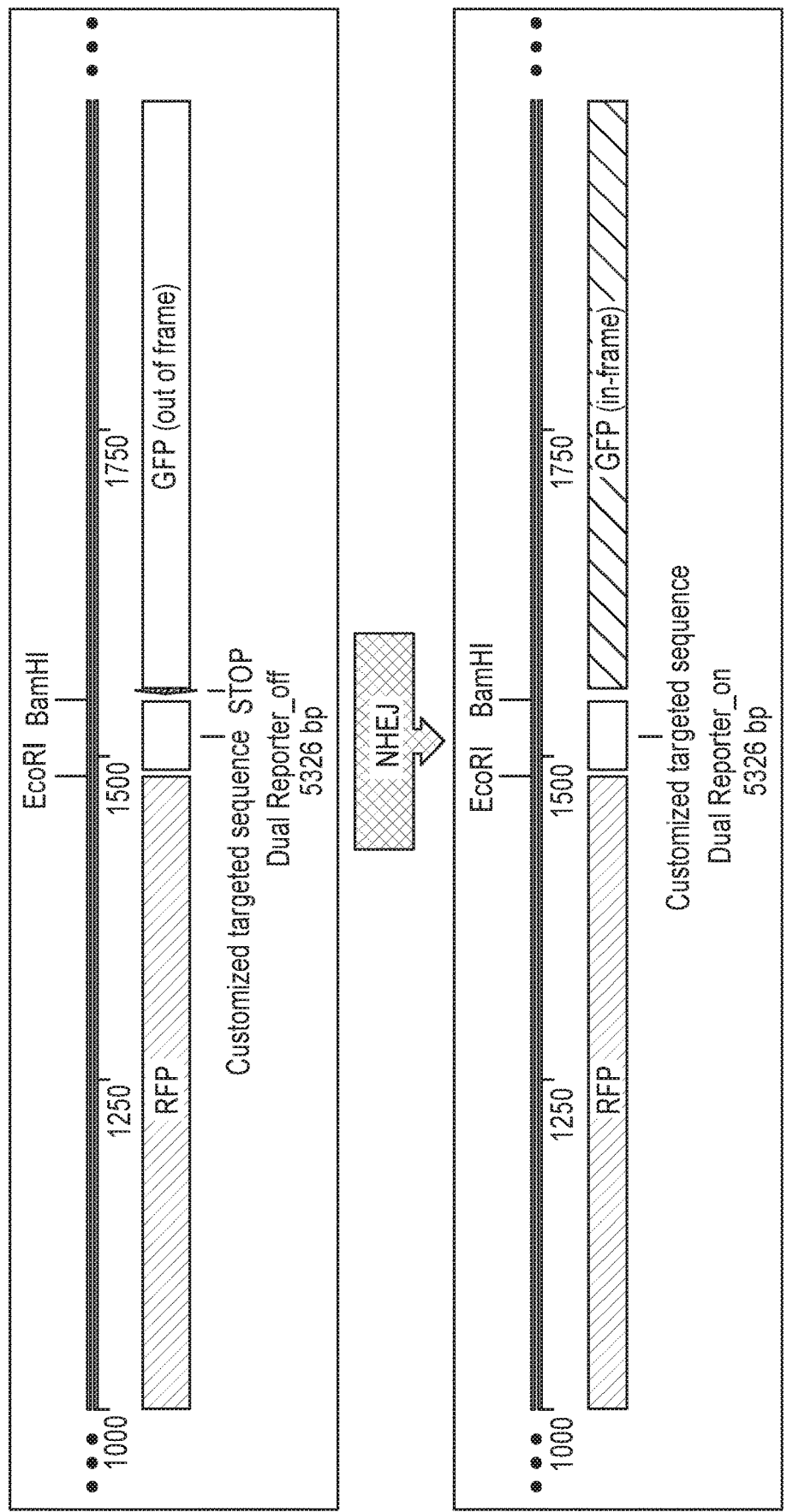
FIG. 5 is a schematic depicting of the use of a dual-reporter plasmid for validating efficiency of specific binding and endonuclease activity for polypeptide constructs of the disclosure.

FIG. 5 depicts a use of an exemplary dual reporter plasmid of the disclosure that may be used to validate the efficiency of polypeptide specific binding to a target sequence and subsequent endonuclease activity at that site. According to the plasmid depicted in FIG. 5 and further described in Example 8, expression of the red fluorescent protein (RFP) under the control of a constitutive reporter illustrates transfection efficiency of the plasmid. According to the plasmid depicted in FIG. 5 and further described in Example 8, expression of the green fluorescent protein (GFP) under the control of a promoter, the activity of which is induced by a targeted double-strand break and subsequent repair by non-homologous end joining (NHEJ) repair, illustrates the efficacy of the nuclease activity of the polypeptide of the disclosure that specifically targets the customized target sequence of the plasmid.

Figure 6:
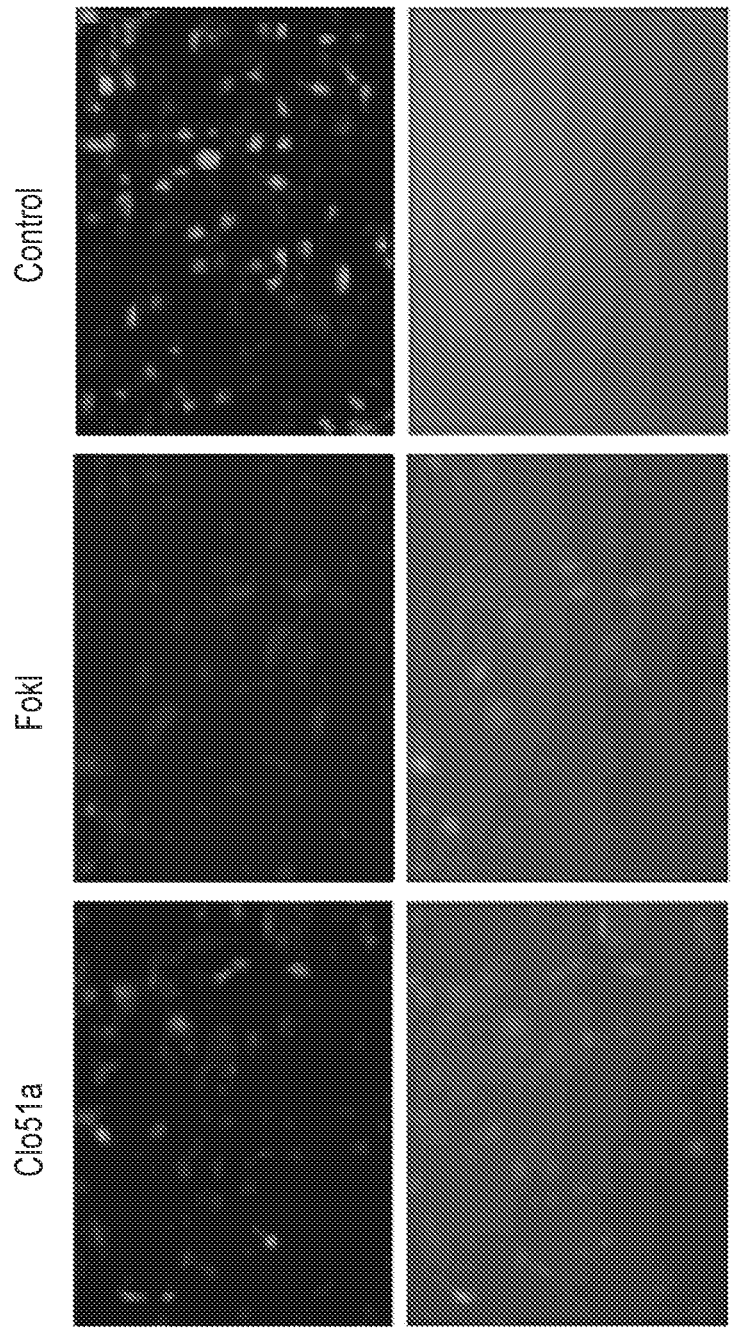
FIG. 6 is a series of photographs depicting the endonuclease activity of an AAVS1 (adeno-associated virus integration site 1) vector indicator 22 hours post-transfection. AAVS1 is an exemplary dual-reporter plasmid of the disclosure that is also depicted in FIG. 5. Endonuclease activity of Clo051 and FokI are shown relative to an endonuclease-free control.

FIG. 6 demonstrates the endonuclease activity of an AAVS1 vector containing at least a nuclease domain of either Clo051 or FokI relative to an endonuclease-free control. Among the photographs in the top row, expression of the red fluorescent protein (RFP) under the control of a constitutive reporter illustrates transfection efficiency of the plasmid. Compared to the positive control, the vector containing Clo051 demonstrates superior transfection efficiency compared to the vector containing FokI. Among the photographs in the bottom row, expression of the green fluorescent protein (GFP) under the control of a promoter, the activity of which is induced by a targeted double-strand break and subsequent repair by non-homologous end joining (NHEJ) repair, illustrates the efficacy of the nuclease activity of either Clo051 or FokI compared to the negative control lacking an endonuclease domain. Compared to the negative control, the vector containing Clo051 demonstrates greater nuclease activity compared to the vector containing FokI.

Cas9 Constructs

Polypeptides of the disclosure include a DNA localization component and an effector molecule. In some embodiments, the polypeptide is a fusion protein comprising, consisting essentially of or consisting of a DNA localization component and an effector molecule. Alternatively, the polypeptide may comprise, consist essentially of or consist of a DNA localization component and an effector molecule, wherein the DNA localization component and the effector molecule are capable of operatively linking via a covalent or non-covalent linkage.

In certain embodiments of the compositions of the disclosure, the DNA localization component comprises one or more guide RNAs (gRNAs) and the effector comprises a type IIS endonuclease. In certain embodiments, effectors of the disclosure may comprise an endonuclease homodimer or heterodimer. In certain embodiments, the effector may comprise an endonuclease homodimer or heterodimer comprising, consisting essentially or consisting of a catalytic domain of a form of Cas9 and a type IIS endonuclease or, alternatively, two distinct type II endonucleases. In certain embodiments, the effector may comprise an endonuclease homodimer comprising, consisting essentially or consisting of two identical type II endonucleases.

Exemplary Cas9 constructs may include a catalytically inactive Cas9 (dCas9) and an effector. For example, Cas9 construct of the disclosure may include an effector comprising a type IIS endonuclease including, but not limited to, AciI, MnlI, AlwI, BbvI, BccI, BceAI, BsmAI, BsmFI, BspCNI, BsrI, BtsCI, HgaI, HphI, HpyAV, MboII, MyII, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I or Clo051. In certain embodiments, the effector molecule comprises BmrI, BfiI, or Clo051. In certain embodiments, the effector comprises a homodimer comprising a type IIS endonuclease including, but not limited to, AciI, MnlI, AlwI, BbvI, BccI, BceAI, BsmAI, BsmFI, BspCNI, BsrI, BtsCI, HgaI, HphI, HpyAV, MboII, MyII, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I or Clo051.

Exemplary Cas9 constructs may include a catalytically inactive small Cas9 (dSaCas9) and an effector. For example, Cas9 construct of the disclosure may include an effector comprising a type IIS endonuclease including, but not limited to, AciI, MnlI, AlwI, BbvI, BccI, BceAI, BsmAI, BsmFI, BspCNI, BsrI, BtsCI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I or Clo051. In certain embodiments, the effector molecule comprises BmrI, BfiI, or Clo051. In certain embodiments, the effector comprises a homodimer comprising a type IIS endonuclease including, but not limited to, AciI, MnlI, AlwI, BbvI, BccI, BceAI, BsmAI, BsmFI, BspCNI, BsrI, BtsCI, HgaI, HphI, HpyAV, MboII, MlyI, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I or Clo051.

Alignment of the small *Staphylococcus aureus* Cas9 (SaCas9) (SEQ ID NO: 20) aligned to a full-length *Staphylococcus pyogenes* Cas9 (SpCas9) (SEQ ID NO: 21)

```
SpCas9  MDKKYSIGLDIGTNSVGWAVITDEYKVPSKKFKVLGNTDRHSIKKNLIGALLFDSG--ET
SaCas9  mkrnyilgldigitsvgygiidyetrdvid----------------agvrlfkeanven
        *.::* :*****.***:.*  *  :         .        *. **... *.

SpCas9  AEATRLKRTARRRYTRRKNRICYLQEIFSNEMAKVDDSFFHRLEESFLVEEDKKHERHPI
SaCas9  negrrskrgarrlkrrrrhriqrvkkllfdyn-------------lltdhselsginp-
        *. * ** ***   **:.**  :::::  :                :*.:..:    .*

SpCas9  FGNIVDEVAYHEKYPTIYHLRKKLVDSTDKADLRLIYLALAHMIKFRGHFLIEGDLNPDN
SaCas9  ---------year---vkglsqklse-------eefsaallhlakrrgvhnvn-------
                 *. :    *  :** :        . :  ** *: * ** . ::

SpCas9  SDVDKLFIQLVQTYNQLFEENPINASGVDAKAILSARLSKSRRLENLIAQLPGEKKNGLF
SaCas9  ------------------------------------------------------------

SpCas9  GNLIALSLGLTPNFKSNFDLAEDAKLQLSKDTYDDDLDNLLAQIGDQYADLFLAAKNLSD
SaCas9  -----------------eveed--------------------tgn--------------
                         :: **                     *:

SpCas9  AILLSDILRVNTEITKAPLSASMIKRYDEHHQDLTLLKALVR--QQLPEKYKEIFFDQSK
SaCas9  ---------------------------------elstkeqisrnskaleekyvae-----
                                         .*:   :  : *  : * ***

SpCas9  NGYAGYIDGGASQEEFYKFIKPILEKMDGTEELLVKLNREDLLRKQRTFDNGSIPHQIHL
SaCas9  --------------------lqlerlkkdgevrgsin---------rfkts-----dyv
                             **::. *: ..:*         *...      ..

SpCas9  GELHAILRRQEDFYPFLKDNREKIEKILTFRIPYYVGPLARGNSRFAWMTRKSEETITPW
SaCas9  keakqllkvqkayhqldqsfidtyidlletrrtyyegpge--gspfgwkdik------ew
        *  : :*: *: :: :  :.   :.  ..:* *  ** **    * *.*  *       *

SpCas9  NFEEVVDKGASAQSFIERMTNFDKNLPNEKVLPKHSLLYEYFTVYNELTKVKYVTEGMRK
SaCas9  yeml----------mghctyfpeelrsvk----yaynadlynalndlnnlvitrden--
         :  * * ::* . *     ::    : :..  *:*.:: .  :

SpCas9  PAFLSGEQKKAIVDLLFKTNRKVTVKQLKEDYFKKIECFDSVEISGVEDRFNASLGTYHD
SaCas9  -ekleyyekfqiienvfkqkkkpptlkqiakeilvneedikgyrvtstgkpeftnlkvyhd
        *.  :*  *::  :**  ::* *:**:  ::  :  *  :.. .:.:..   :.* .***

SpCas9  LLKIIKDKDFLDNEENEDILEDIVLTLTLFEDREMIEERLKTYAHLFDDKVMK-QLKRRR
SaCas9  ikditarkeiiena---elldqiakiltiyqssediqeeltnlnseltqeeieqisnlkg
        : .*   *:::*     ::*::*. **:::. * *:*.*..       :  ::    : :

SpCas9  YTGWGRLSRKLINGIRDKQSGKTILDFLKSDGFANRNFMQLIHDDSLTFKEDIQKAQVSG
SaCas9  ytgthnlslkainlildelwh------------tndnqiaifnrl----klvpkkvdlsq
        *** .** ** ** *:             :* * : ::.       *  :*.::*

SpCas9  QGDSLHEHIANLAGSPAIKKGILQTVKVVDELVKVMGRHKPENIVIEMARENQTTQKG--
SaCas9  qkeipttivddfilspvvkrsfiqsikvinaiikkygl--pndiiielareknskdaqkm SpCas9  ----QKNSRERMKRIEEGIKELGSQILKEHPVENTQLQNEKLYLYYLQNGRDMYVDQELD
SaCas9  inemqkrnrqtnerieeiirt--------tgkenakyliekiklhdmqegkclysleaip
            **..*:  :**** *:          **::  **: *: :*:*: :*   :  :

SpCas9  ----INRLSDYDVDHIVPQSFLKDDSIDNKVLTRSDKNRGKSDNVPSEEVVKKM-----K
SaCas9  ledllnnpfnyevdhiiprsvsfdnsfnnkvlvkqeenskkgnrtpfqylsssdskisye
        :.*.  :*:****:*:*.  *:*::****.::*  *.:..:*   :. *  : ..    :

SpCas9  NYWRQLLNAKL----ITQRKFDNLTKAERGGLSELDKAGFIKRQLVETRQITKHVAQILD
SaCas9  tfkkhilnlakgkgrisktkkeyl-leerdinrfsvqkdfinrnlvdtryatrglmnllr
        .:  :::**      *::  * :  *  **           : **:*:**:** *:  :*

SpCas9  SRMNTKYDENDKLIREVKVITLKSKLVSDFRKDFQFYKVREINNYHHAHDAYLNAVVGTA
SaCas9  syfrvn-------nldvkvksinggftsflrrkwkfkkernkgykhhaedaliian----
        *  :..:        :*** :::. :.*  :*:..:* * *:    ***.**  :  *
```

```
SpCas9  LIKKYPKLESEFVYGDYKVYDVRKMIAKSEQEIGKATAKYFFYSNIMNFFKTEITLANGE
SaCas9  ---------adfifkewkkldkakkvmenqmf----------------------eekq
              ::*::  ::*   *  *   : :.:                         :  :

SpCas9  IRKRPLIETNGETGEIVWDK--------GRDFATVRKVLSMPQVNIVKKTEVQ-------
SaCas9  aesmpeieteqeykeifitphqikhikdfkdykyshrvdkkpnrelindtlystrkddkg
        .. * ***: *  **.              :*:   ::* . *: ::::.* *

SpCas9  --------TGGFSKES----ILPKRNSDKLIARKKDWDPK---------KYGGFDSPTV
SaCas9  ntlivnninglydkdndkikklinkspekl;my--hhdpqtyqkiklimeqygdeknply
                 .* :.*:.      * ::.:**:   . **.        :** ..*

SpCas9  AYSVLVV------AKVEKGK-SKKLKSVKELLGITIMERSSFEKNPIDFLEAKGYKEVKK
SaCas9  kyyeetgnyltkyskkdngpvikkikyygnklnahl-----------di--tddypnsrn
          *    .    :* ::*   **:*    :  *   :          *:  :. * :.

SpCas9  DL-IIKLPKYSL-FELENGRKRMLASA--GELQKGNELALPSKYVNFLYLASHYEKLKGS
SaCas9  kvvklslkpyrfdvyldngvykfvtvknldvikkenyyevn---------skcyeeakkl
        .:  :.*   *  : . *:**   ::::     ::*  *   :          :. **: *

SpCas9  PEDNEQKQLFVEQHKHYLDEIIEQISEFSKRVI------------LADANLDKVLSAYNK
saCas9  kkisnqae-fia--sfynndlikingelyrvigvnndllnrievnmidityreylenmnd
        : ..:*  :  *:   ..* :::*:  .*:  : :               : *  .: *.  *.

SpCas9  HRDKPIREQAENIIHLFTLTNLGAPAAFKYFDTTIDRKRYTSTKEVLDATLIHQSITGLY
SaCas9  krpp-------riiktia----sktqsikkystdi--------------------lgnly
        :*           .**: ::    .  ::*: * *                       :  **

SpCas9  ETRID----LSQLGGD
SaCas9  evkskkhpqiikkg--
        *.: .      : : *
```

Small Cas9 (SaCas9)

The disclosure provides compositions comprising a small, Cas9 (Cas9) operatively-linked to an effector. In certain embodiments, the disclosure provides a fusion protein comprising, consisting essentially of or consisting of a DNA localization component and an effector molecule, wherein the effector comprises a small, Cas9 (Cas9). In certain embodiments, a small Cas9 construct of the disclosure may comprise an effector comprising a type IIS endonuclease.

Amino acid sequence of *Staphylococcus aureus* Cas9 with an active catalytic site.

(SEQ ID NO: 22)

```
   1  mkrnyilgld igitsvgygi idyetrdvid agvrlfkean vennegrrsk rgarrlkrrr
  61  rhriqrvkkl lfdynlltdh selsginpye arvkglsqkl seeefsaall hlakrrgvhn
 121  vneveedtgn elstkeqisr nskaleekyv aelqlerlkk dgevrgsinr fktsdyvkea
 181  kqllkvqkay hqldqsfidt yidlletrrt yyegpgegsp fgwkdikewy emlmghctyf
 241  peelrsvkya ynadlynaln dlnnlvitrd enekleyyek fqiienvfkq kkkptlkqia
 301  keilvneedi kgyrvtstgk peftnlkvyh dikditarke iienaelldq iakiltiyqs
 361  sediqeeltn lnseltqeei eqisnlkgyt gthnlslkai nlildelwht ndnqiaifnr
 421  lklvpkkvdl sqqkeipttl vddfilspvv krsfiqsikv inaiikkygl pndiiielar
 481  eknskdaqkm inemqkrnrq tnerieeiir ttgkenakyl iekiklhdmq egkclyslea
 541  ipledllnnp fnyevdhiip rsvsfdnsfn nkvlvkqeen skkgnrtpfq ylsssdskis
 601  yetfkkhiln lakgkgrisk tkkeylleer dinrfsvqkd finrnlvdtr yatrglmnll
 661  rsyfrvnnld vkvksinggf tsflrrkwkf kkernkgykh haedaliian adfifkewkk
 721  ldkakkvmen qmfeekqaes mpeieteqey keifitphqi khikdfkdyk yshrvdkkpn
 781  relindtlys trkddkgntl ivnnlnglyd kdndklkkli nkspekllmy hhdpqtyqkl
 841  klimeqygde knplykyyee tgnyltkysk kdngpvikki kyygnklnah lditddypns
 901  rnkvvklslk pyrfdvyldn gvykfvtvkn ldvikkenyy evnskcyeea kklkkisnqa
 961  efiasfynnd likingelyr vigvnndlln rievnmidit yreylenmnd krppriikti
1021  asktqsikky stdilgnlye vkskkhpqii kkg
```

Inactivated, Small Cas9 (dSaCas9)

The disclosure provides compositions comprising an inactivated, small, Cas9 (dSaCas9) operatively-linked to an effector. In certain embodiments, the disclosure provides a fusion protein comprising, consisting essentially of or consisting of a DNA localization component and an effector molecule, wherein the effector comprises a small, inactivated Cas9 (dSaCas9). In certain embodiments, a small, inactivated Cas9 (dSaCas9) construct of the disclosure may comprise an effector comprising a type IIS endonuclease.

dSaCas9 Sequence: D10A and N580A mutations (bold, capitalized, and underlined) inactivate the catalytic site.

(SEQ ID NO: 23)

```
   1  mkrnyilglA igitsvgygi idyetrdvid agvrlfkean vennegrrsk rgarrlkrrr
  61  rhriqrvkkl lfdynlltdh selsginpye arvkglsqkl seeefsaall hlakrrgvhn
 121  vneveedtgn elstkeqisr nskaleekyv aelqlerlkk dgevrgsinr fktsdyvkea
 181  kqllkvqkay hqldqsfidt yidlletrrt yyegpgegsp fgwkdikewy emlmghctyf
 241  peelrsvkya ynadlynaln dlnnlvitrd enekleyyek fqiienvfkq kkkptlkqia
 301  keilvneedi kgyrvtstgk peftnlkvyh dikditarke iienaelldq iakiltiyqs
 361  sediqeeltn lnseltqeei eqisnlkgyt gthnlslkai nlildelwht ndnqiaifnr
 421  lklvpkkvdl sqqkeipttl vddfilspvv krsfiqsikv inaiikkygl pndiiielar
 481  eknskdaqkm inemqkrnrq tnerieeiir ttgkenakyl iekiklhdmq egkclyslea
 541  ipledllnnp fnyevdhiip rsvsfdnsfn nkvlvkqeeA skkgnrtpfq ylsssdskis
 601  yetfkkhiln lakgkgrisk tkkeylleer dinrfsvqkd finrnlvdtr yatrglmnll
 661  rsyfrvnnld vkvksinggf tsflrrkwkf kkernkgykh haedaliian adfifkewkk
 721  ldkakkvmen qmfeekqaes mpeieteqey keifitphqi khikdfkdyk yshrvdkkpn
 781  relindtlys trkddkgntl ivnnlnglyd kdndklkkli nkspekllmy hhdpqtyqkl
 841  klimeqygde knplykyyee tgnyltkysk kdngpvikki kyygnklnah lditddypns
 901  rnkvvklslk pyrfdvyldn gvykfvtvkn ldvikkenyy evnskcyeea kklkkisnqa
 961  efiasfynnd likingelyr vigvnndlln rievnmidit yreylenmnd krppriikti
1021  asktqsikky stdilgnlye vkskkhpqii kkg
```

Figure 9:
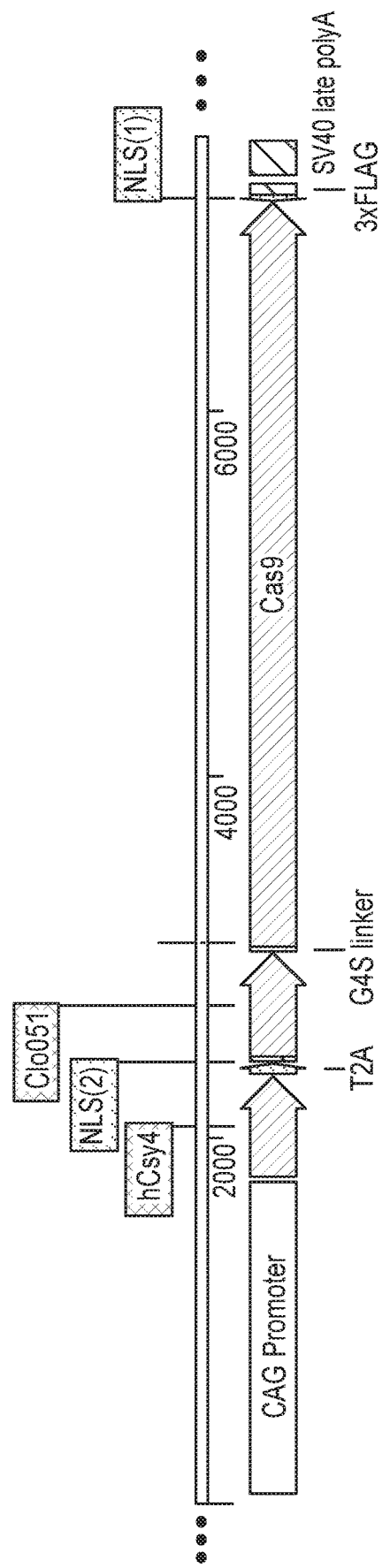
FIG. 9 is a schematic depiction of the Csy4-T2A-Clo051-G4Slinker-dCas9 construct map.

Exemplary Cas9 constructs of the disclosure include, but are not limited to, Clo051-Cas9. FIG. 9 provides a construct map for an exemplary vector of the disclosure, Csy4-T2A-Clo051-G4Slinker-dCas9. The corresponding amino acid sequence for this construct is provided below:

(SEQ ID NO: 24)
MGDHYLDIRLRPDPEFPPAQLMSVLFGKLHQALVAQGGDRIGVSFPDLDE
SRSRLGERLRIHASADDLRALLARPWLEGLRDHLQFGEPAVVPHPTPYRQ
VSRVQAKSNPERLRRRLMRRHDLSEEEARKRIPDTVARALDLPFVTLRSQ
STGQHFRLFIRHGPLQVTAEEGGFTCYGLSKGGFVPWFGTEGRGSLLTCG
DVEENPGPMPKKKRKVEGIKSNISLLKDELRGQISHISHEYLSLIDLAFD
SKQNRLFEMKVLELLVNEYGFKGRHLGGSRKPDGIVYSTTLEDNFGIIVD
TKAYSEGYSLPISQADEMERYVRENSNRDEEVNPNKWWENFSEEVKKYYF
VFISGSFKGKFEEQLRRLSMTTGVNGSAVNVVNLLLGAEKIRSGEMTIEE
LERAMFNNSEFILKYGGGGSDKKYSIGLAIGTNSVGWAVITDEYKVPSKK
FKVLGNTDRHSIKKNLIGALLFDSGETAEATRLKRTARRRYTRRKNRICY
LQEIFSNEMAKVDDSFFHRLEESFLVEEDKKHERHPIFGNIVDEVAYHEK
YPTIYHLRKKLVDSTDKADLRLIYLALAHMIKFRGHFLIEGDLNPDNSDV
DKLFIQLVQTYNQLFEENPINASGVDAKAILSARLSKSRRLENLIAQLPG
EKKNGLFGNLIALSLGLTPNFKSNFDLAEDAKLQLSKDTYDDDLDNLLAQ
IGDQYADLFLAAKNLSDAILLSDILRVNTEITKAPLSASMIKRYDEHHQD
LTLLKALVRQQLPEKYKEIFFDQSKNGYAGYIDGGASQEEFYKFIKPILE
KMDGTEELLVKLNREDLLRKQRTFDNGSIPHQIHLGELHAILRRQEDFYP
FLKDNREKIEKILTFRIPYYVGPLARGNSRFAWMTRKSEETITPWNFEEV
VDKGASAQSFIERMTNFDKNLPNEKVLPKHSLLYEYFTVYNELTKVKYVT
EGMRKPAFLSGEQKKAIVDLLFKTNRKVTVKQLKEDYFKKIECFDSVEIS
GVEDRFNASLGTYHDLLKIIKDKDFLDNEENEDILEDIVLTLTLFEDREM
IEERLKTYAHLFDDKVMKQLKRRRYTGWGRLSRKLINGIRDKQSGKTILD
FLKSDGFANRNFMQLIHDDSLTFKEDIQKAQVSGQGDSLHEHIANLAGSP
AIKKGILQTVKVVDELVKVMGRHKPENIVIEMARENQTTQKGQKNSRERM
KRIEEGIKELGSQILKEHPVENTQLQNKLYLYYLQNGRDMYVDQELDINR
LSDYDVDAIVPQSFLKDDSIDNKVLTRSDKNRGKSDNVPSEEVVKKMKNY
WRQLLNAKLITQRKFDNLTKAERGGLSELDKAGFIKRQLVETRQITKHVA
QILDSRMNTKYDENDKLIREVKVITLKSKLVSDFRKDFQFYKVREINNYH
HAHDAYLNAVVGTALIKKYPKLESEFVYGDYKVYDVRKMIAKSEQEIGKA
TAKYFFYSNIMNFFKTEITLANGEIRKRPLIETNGETGEIVWDKGRDFAT

-continued

```
VRKVLSMPQVNIVKKTEVQTGGFSKESILPKRNSDKLIARKKDWDPKKYG

GFDSPTVAYSVLVVAKVEKGKSKKLKSVKELLGITIMERSSFEKNPIDFL

EAKGYKEVKKDLIIKLPKYSLFELENGRKRMLASAGELQKGNELALPSKY

VNFLYLASHYEKLKGSPEDNEQKQLFVEQHKHYLDEIIEQISEFSKRVIL

ADANLDKVLSAYNKHRDKPIREQAENIIHLFTLTNLGAPAAFKYFDTTID

RKRYTSTKEVLDATLIHQSITGLYETRIDLSQLGGD
```

Figure 10:
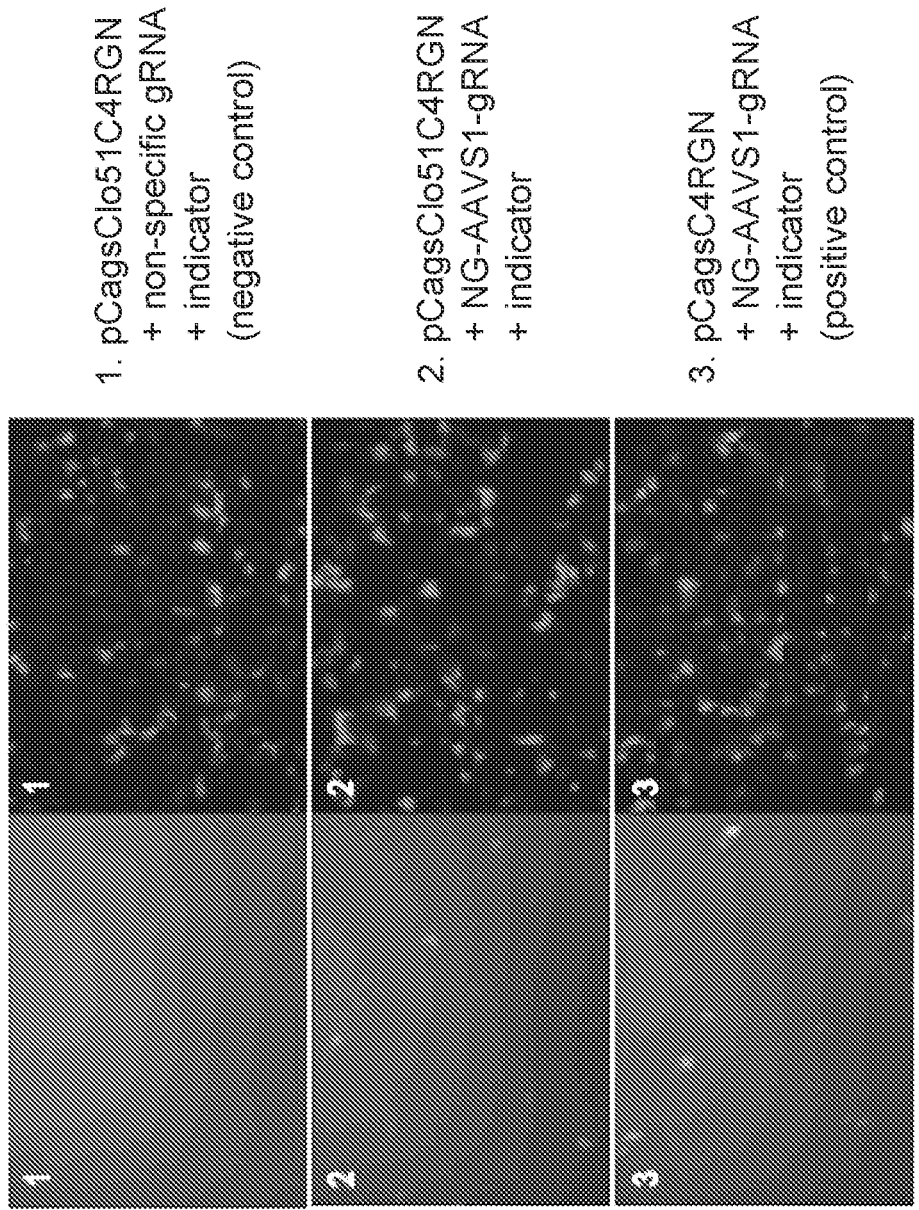
FIG. 10 is a series of photographs depicting Clo051-Cas9 activity. Condition (1) shows the pCagsClo051C4RGN plasmid (that encodes for Clo051-dCas9) transfected with a non-specific guide RNA (gRNA) and an indicator, the combination of which serve as a negative control for this experiment. Condition (2) shows the pCagsClo051C4RGN plasmid (that encodes for CLo051-dCas9) transfected with NG-AAVS1-gRNA and an indicator. Condition (3) shows the pCagsC4RGN plasmid (that encodes for FokI-dCas9) transfected with NG-AAVS1-gRNA and an indicator, the combination of which serve as a positive control in this experiment.

FIG. 10 demonstrates that an exemplary Clo051-Cas9 construct, including the Csy4-T2A-Clo051-G4Slinker-dCas9 construct, of the disclosure is active.

Cas9 may be combined with any nuclease, including but not limited to Clo051, BfiI and BmrI. Exemplary sequences for the nuclease domains of Clo051, BfiI and BmrI are provided below.

An exemplary Clo051 nuclease domain may comprise, consist essentially of or consist of, the amino acid sequence of:

```
                                          (SEQ ID NO: 25)
EGIKSNISLLKDELRGQISHISHEYLSLIDLAFDSKQNRLFEMKVLELLV

NEYGFKGRHLGGSRKPDGIVYSTTLEDNFGIIVDTKAYSEGYSLPISQAD

EMERYVRENSNRDEEVNPNKWWENFSEEVKKYYFVFISGSFKGKFEEQLR

RLSMTTGVNGSAVNVVNLLLGAEKIRSGEMTIEELERAMFNNSEFILKY.
```

An exemplary BfiI nuclease domain may comprise, consist essentially of or consist of, the amino acid sequence below wherein the catalytic residues include H105, K107, N125, and E136:

```
                                          (SEQ ID NO: 26)
MNFFSLHPNVYATGRPKGLIGMLENVWVSNHTPGEGTLYLISGFSNYNGG

VRFYETFTEHINQGGRVIAILGGSTSQRLSSRQVVEELLNRGVEVHIINR

KRILHAKLYGTSNNLGESLVVSSGNFTGPGMSQNIEASLLLDNNTTQSMG

FSWNDMISEMLNQNWHIHNMTNATDASPGWNLLYDERTTNLTL
```

An exemplary BmrI nuclease domain may comprise, consist essentially of or consist of, the amino acid sequence below wherein the catalytic residues include H105, K107, N125, and E136:

```
                                          (SEQ ID NO: 27)
MNYFSLHPNVYATGRPKGLINMLESVWISNQKPGDGTMYLISGFANYNGG

IRFYETFTEHINHGGKVIAILGGSTSQRLSSKQVVAELVSRGVDVYIINR

KRLLHAKLYGSSSNSGESLVVSSGNFTGPGMSQNVEASLLLDNNTTSSMG

FSWNGMVNSMLDQKWQIHNLSNSNPTSPSWNLLYDERTTNLTL
```

Transcriptional Activator-Like (TAL) Proteins

Transcription factors with programmable DNA binding domains provide a means to create an exogenous biological circuit in an endogenous system and create designer proteins that bind to pre-determined DNA sequences or individual nucleic acids. Modular DNA binding domains have been identified in transcriptional activator-like (TAL) proteins, or, more specifically, transcriptional activator-like effector nucleases (TALENs), thereby allowing for the de novo creation of synthetic transcription factors that bind to DNA sequences of interest and, if desirable, also allowing a second domain present on the protein or polypeptide to perform an activity related to DNA. TAL proteins have been derived from the organisms *Xanthomonas* and *Ralstonia*.

*Xanthomonas*

The disclosure provides polypeptides derived from *Xanthomonas* amino acid sequences or amino acid sequences related thereto, nucleic acids encoding the same, compositions comprising the same, kits comprising the same, non-human transgenic animals comprising the same, and methods of using the same.

As described herein, effector proteins derived from *Xanthomonas*, including TAL proteins, may be used as part of a larger targeted chimeric protein (i.e. a component of a chimeric protein). Chimeric effector proteins of the disclosure, including those comprising or consisting of a TAL protein, or any component thereof, may demonstrate accessory activities related to nucleic acids such as nuclease activity. For instance, in some embodiments, a polypeptide or pronucleases that can facilitate homologous recombination in genome engineering may be used as a component of a chimeric protein. In certain embodiments, a transcription factor may be used as a component of a chimeric protein, making the resultant chimeric protein particularly useful for therapeutic compositions and uses thereof requiring a very high level of specificity (including therapeutic compositions and uses thereof directed against pathogens (e.g., viruses)).

Polypeptides or proteins of the disclosure may be derived from polypeptides or proteins found in *Xanthomonas*. Polypeptides or proteins of the disclosure may contain one or more sequences that are neither identical to any polypeptide or protein found in *Xanthomonas* nor naturally-occurring in *Xanthomonas*.

Polypeptides or proteins of the disclosure may comprise at least a first domain and a second domain, wherein the first domain comprises at least one coding sequence for a nucleic acid recognition element and the second domain comprises at least one coding sequence for a nucleic acid effector element.

The disclosure provides a preferred *Xanthomonas*-TALE-Clo051 (XTC) polypeptide. This polypeptide comprises a TAL DNA-binding domain derived from *Xanthomonas* fused to the Clo051 endonuclease.

Figure 3:
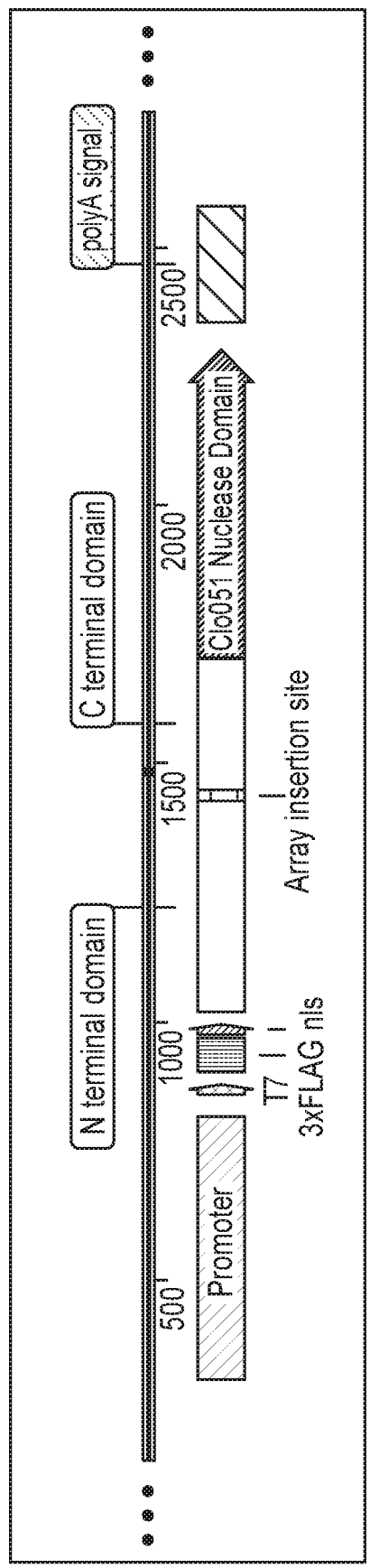
FIG. 3 is a construct map depicting an exemplary *Xanthomonas*-TALE-Clo051 (XTC) Empty Backbone of the disclosure.
Figure 4:
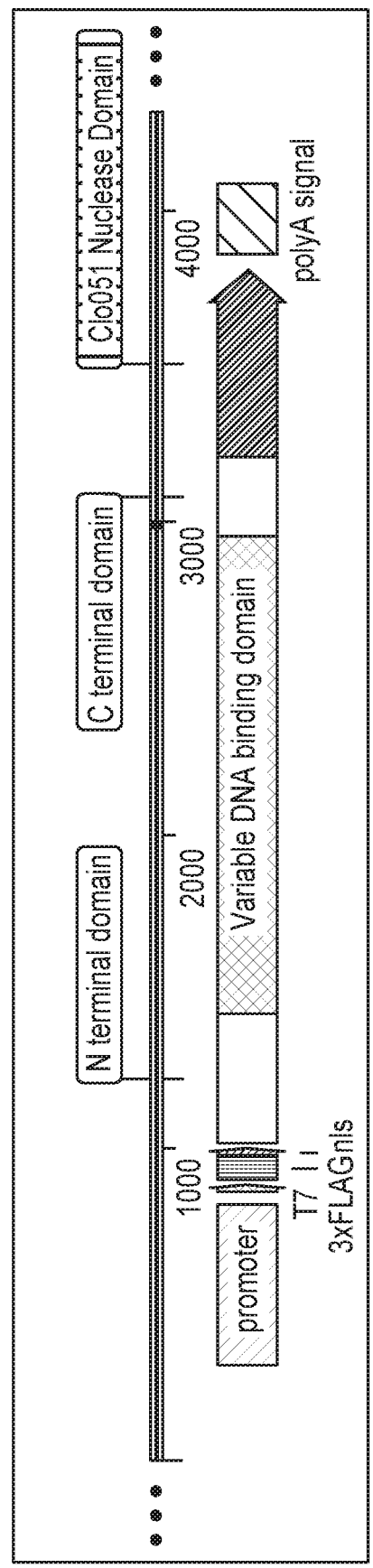
FIG. 4 is a construct map depicting an exemplary XTC cloned DNA binding domain of the disclosure. Customized TALE arrays can be cloned into the XTC backbone to target 16-20 bp specific DNA sequences.

FIGS. 3 and 4 provide a construct map corresponding to an exemplary empty backbone and cloned DNA binding domain for the XTC polypeptide.

In certain embodiments of the XTC polypeptide, the N-terminal domain sequence comprises a T7 promotor and a nuclear localization signal (NLS) in a 3×FLAG® System Expression Vector. The amino acid sequence encoding a *Xanthomonas* TAL DNA-binding domain comprises:

```
                                          (SEQ ID NO: 28)
"MDYKDHDGDYKDHDIDYKDDDDK

MAPKKKRKVGIHRGVPMVDLRTLGYSQQQQEKIKPKVRSTVAQHHEALV

GHGFTHAHIVALSQHPAALGTVAVKYQDMIAALPEATHEAIVGVGKQWS

GARALEALLTVAGELRGPPLQLDTGQLLKIAKRGGVTAVEAVHAWRNAL

TGAPLN",
``` wherein the sequence "MDYKDHDGDYKDHDI-DYKDDDDK" (SEQ ID NO: 29) is a 3×FLAG® epitope tag and the *Xanthomonas* TAL DNA-binding domain is encoded by the sequence (SEQ ID NO: 30)
"MAPKKKRKVGIHRGVPMVDLRTLGYSQQQQEKIKPKVRSTVAQHHEAL
VGHGFTHAHIVALSQHPAALGTVAVKYQDMIAALPEATHEAIVGVGKQW
SGARALEALLTVAGELRGPPLQLDTGQLLKIAKRGGVTAVEAVHAWRNA
LTGAPLN".

The C-terminal Domain sequence of the XTC polypeptide may comprise one of four potential sequences. Variable amino acid positions are denoted by the letter "X". The consensus sequence of the XTC C-terminal Domain comprises "LTPEQVVAIAXXXGGRPALESIVAQLSRPDPA-LAALTNDHLVALACLGGRPALDAV KKGLPHAPA-LIKRTNRRIPERTSHRVAGS" (SEQ ID NO: 31) wherein the bolded "XXX" positions are variable.

In a first embodiment of the sequence of the XTC C-terminal Domain, the XXX variable amino acids are "NNN" and specify a glycine (G). The complete sequence for this first embodiment of the sequence of the XTC C-terminal Domain is (SEQ ID NO: 32)
"LTPEQVVAIANNNGGRPALESIVAQLSRPDPALAALTNDHLVALACLGG
RPALDAVKKGLPHAPALIKRTNRRIPERTSHRVAGS".

In a second embodiment of the sequence of the XTC C-terminal Domain, the XXX variable amino acids are "SNG" and specify a threonine (T). The complete sequence for this second embodiment of the sequence of the XTC C-terminal Domain is (SEQ ID NO: 33)
"LTPEQVVAIASNGGGRPALESIVAQLSRPDPALAALTNDHLVALACLGG
RPALDAVKKGLPHAPALIKRTNRRIPERTSHRVAGS".

In a third embodiment of the sequence of the XTC C-terminal Domain, the XXX variable amino acids are "SHD" and specify a cysteine (C). The complete sequence for this third embodiment of the sequence of the XTC C-terminal Domain is (SEQ ID NO: 34)
"LTPEQVVAIASHDGGRPALESIVAQLSRPDPALAALTNDHLVALACLGG
RPALDAVKKGLPHAPALIKRTNRRIPERTSHRVAGS".

In a fourth embodiment of the sequence of the XTC C-terminal Domain, the XXX variable amino acids are "SNI" and specify an alanine (A). The complete sequence for this fourth embodiment of the sequence of the XTC C-terminal Domain is (SEQ ID NO: 35)
"LTPEQVVAIASNIGGRPALESIVAQLSRPDPALAALTNDHLVALACLGG
RPALDAVKKGLPHAPALIKRTNRRIPERTSHRVAGS".

Preferred *Xanthomonas*-TALE-Clo051 (XTC) polypeptides of the disclosure comprise a Clo051 nuclease domain comprising, consisting essentially of or consisting of the amino acid sequence of (SEQ ID NO: 36)
"EGIKSNISLLKDELRGQISHISHEYLSLIDLAFDSKQNRLFEMKVLELL
VNEYGFKGRHLGGSRKPDGIVYSTTLEDNFGIIVDTKAYSEGYSLPISQA
DEMERYVRENSNRDEEVNPNKWWENFSEEVKKYYFVFISGSFKGKFEEQL
RRLSMTTGVNGSAVNVVNLLLGAEKIRSGEMTIEELERAMFNNSEFILK
Y".

Figure 7:
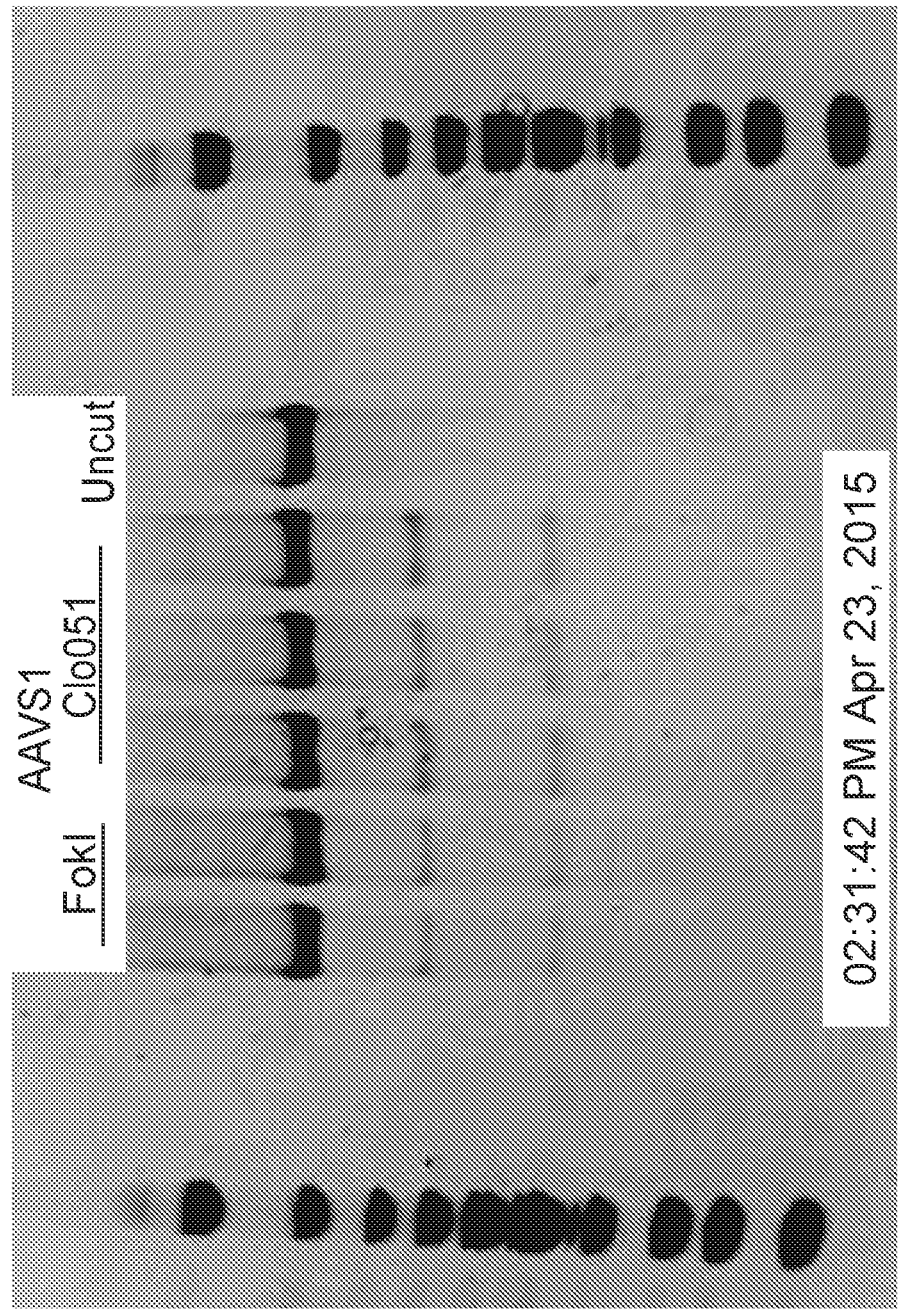
FIG. 7 is a photograph of a gel depicting the results of a Cell Assay with TALE-Clo051. Cutting efficiency of TALE-Clo051 (average cutting efficiency of replicates of 8.1%) was compared to the cutting efficiency of TALE-FokI. Average cutting efficiency of replicates of TALE-Clo051 was 8.1% compared to the average cutting efficiency of replicates of TALE-FokI, which was 7.1%. Thus, TALE-Clo051 has a superior cutting efficiency to TALE-FokI.

As shown in FIG. 7, for example, *Xanthomonas*-TALE-Clo051 (XTC) polypeptides of the disclosure, including TALE-Clo051, demonstrate superior cutting efficiency compared to TALE-FokI. In this experiment, endonuclease activity (cutting efficiency) was determined in a CEL I mismatch endonuclease assay using either TALE-Clo051 or TALE-FokI. Cell assays are described in greater detail in Kulinski et al. The CEL I Enzymatic Mutation Detection Assay, BioTechniques 29(1):44-48 (July 2000) (the contents of which are herein incorporated by reference). Moreover, FIG. 8 depicts another comparison of endonuclease activity, also demonstrated by CEL I assay, between XTN TALEN compositions of the disclosure and alternative TALEN constructs that are not encompassed by the disclosure.

Figure 8:
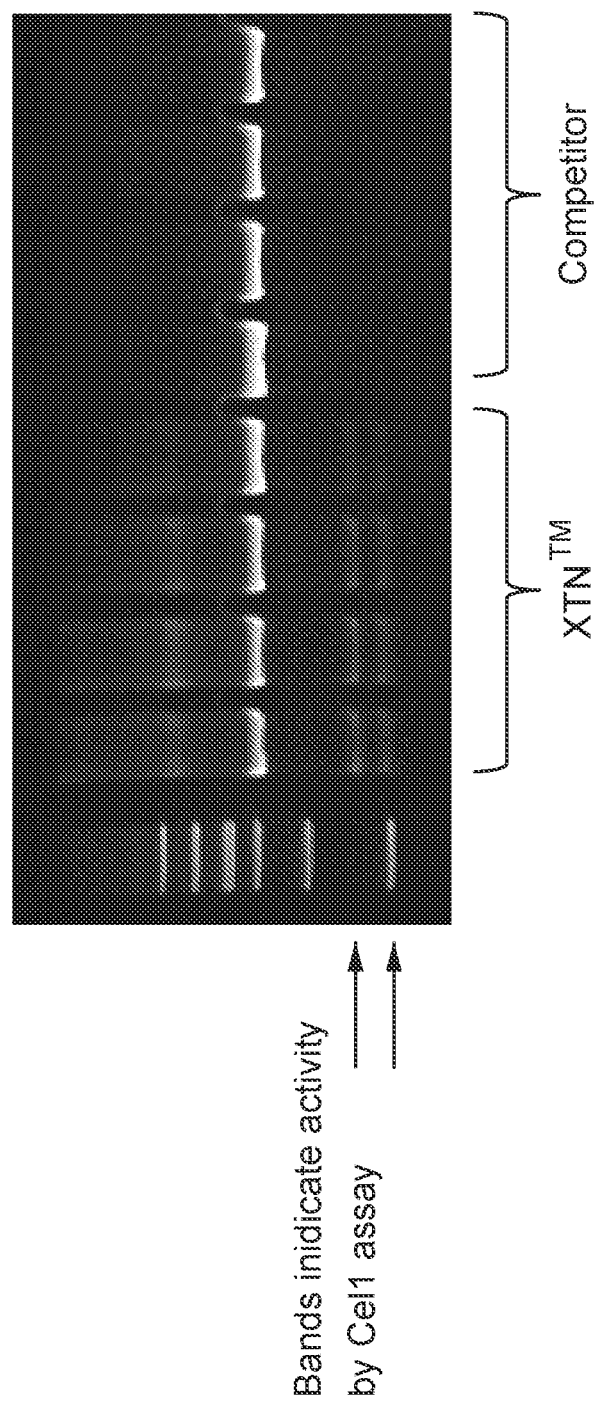
FIG. 8 is a photograph of a gel depicting a Cell assay comparing the relative nuclease activity of the *Xanthomonas*-TALE-Nuclease (XTN) TALEN of the disclosure to TALEN not encompassed by this disclosure. XTN TALENS of the disclosure have significantly higher activity than TALENs not encompassed by this disclosure.

The results of the assay shown in FIG. 8 indicate that XTN TALENS of the disclosure have significantly higher activity than TALENS known in the art.

Figure 11:
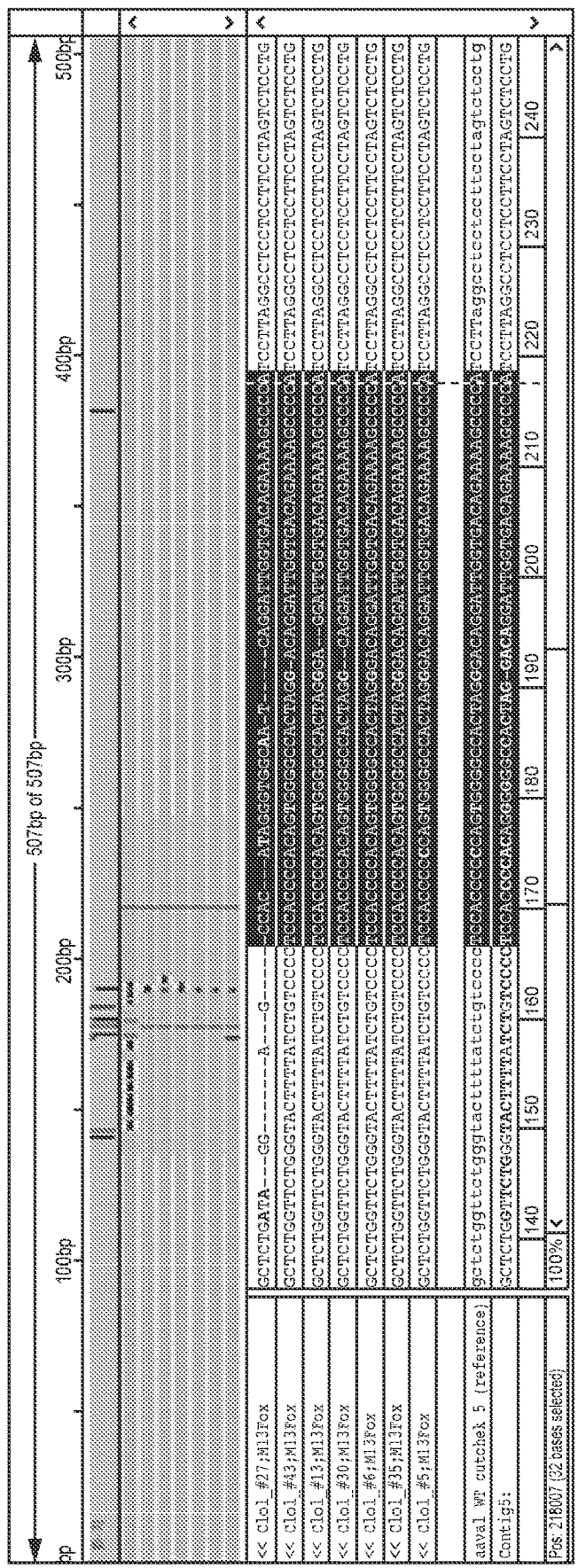
FIG. 11 is a photograph of an alignment of clones of Clo051-XTN. The AAV1 locus was amplified from Clo051-XTN treated samples, TOPO cloned, and 48 clones from each sample were sequenced. Sequencing results indicated that 43 Clo051-XTN clones contained usable sequence. Four of the 43 Clo051-XTN clones had an indel (an insertion or deletion of bases in the sequence) for a 9.3% rate of indel. Among these four Clo051-XTN clones, one clone (#43) has a single base pair (1 bp) deletion, two clones (#13 and 38) have a two base pair (2 bp) deletion, and one clone (#27) has a −52/+24 indel. From top to bottom, SEQ ID Nos 285 to 293 are shown.
Figure 12:
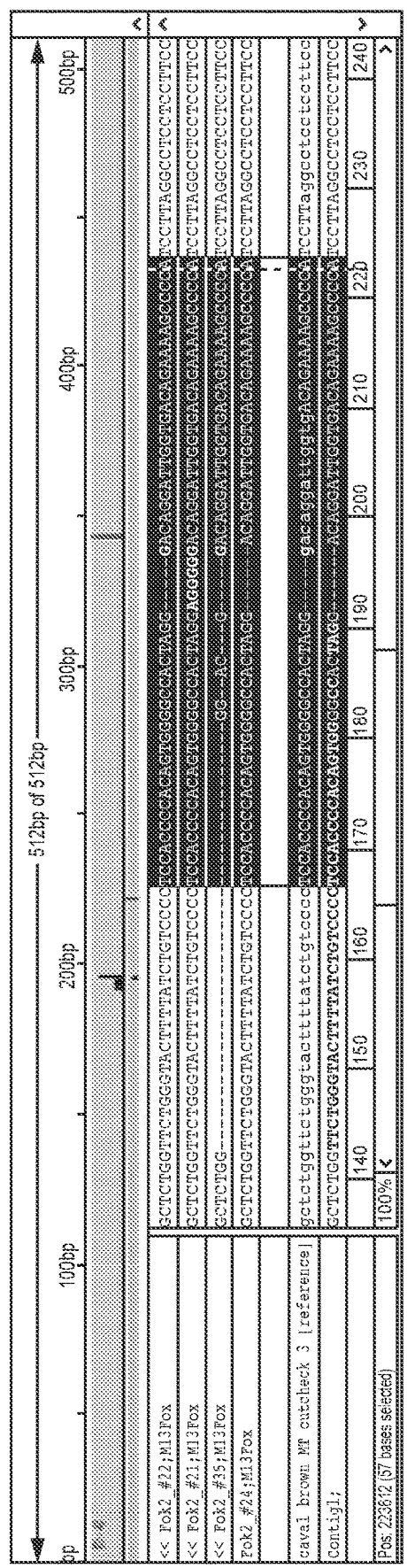
FIG. 12 is a photograph of an alignment of clones of FokI-XTN. The AAV1 locus was amplified from FokI-XTN treated samples, TOPO cloned, and 48 clones from each sample were sequenced. Sequencing results indicated that 46 FokI-XTN clones contained usable sequence. Three of the 46 FokI-XTN clones had an indel (an insertion or deletion of bases in the sequence) for a 6.5% rate of indel. Among these three unique FokI-XTN clones, one clone (#24) has a single base pair (1 bp) deletion, one clone (#21) have a five base pair (5 bp) insertion, and one clone (#35) has a −47/+4 indel. From top to bottom, SEQ ID Nos 294 to 299 are shown.

FIG. 11 depicts an alignment of XTN-Clo051 clones (encoding an XTC polypeptide of the disclosure). Sequence analysis revealed a low rate of insertion or deletion (indel) in the DNA sequences of these clones.

Figure 13:
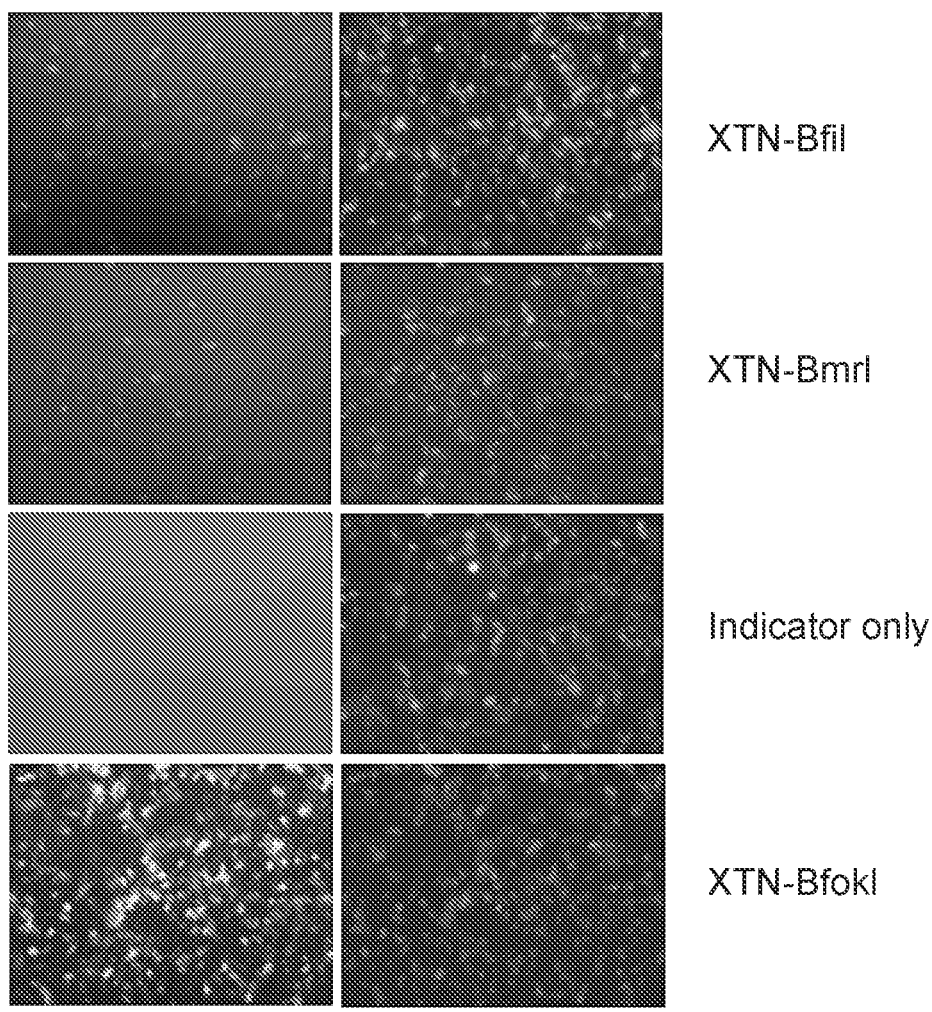
FIG. 13 is a series of photographs depicting the results of transfection and nuclease activity in HEK293 cells treated with either TAL-BfiI (XTN-BfiI) or TAL-BmrI (XTN-BmrI), when compared to treatment with XTN-FokI used herein as a positive control. Indicator only condition used as a negative control. Pictures were captured three days after transfection of the cells with AAVS1 XTN (one or XTN-BfiI, XTN-BmrI or XTN-FokI) with an indicator.

XTN compositions of the disclosure may include any endonuclease, including, but not limited to, *Xanthomonas*-TALE-BfiI and *Xanthomonas*-TALE-BmrI. The activity of these XTN compositions transfected into HEK293 cells is demonstrated in FIG. 13.

An exemplary BfiI nuclease domain may comprise, consist essentially of or consist of, the amino acid sequence below wherein the catalytic residues include H105, K107, N125, and E136:

(SEQ ID NO: 37)
MNFFSLHPNVYATGRPKGLIGMLENVWVSNHTPGEGTLYLISGFSNYNGG
VRFYETFEHINQGGRVIAILGGSTSQRLSSRQVVEELLNRGVEVHIINRK
RILHAKLYGTSNNLGESLVVSSGNFTGPGMSQNIEASLLLDNNTTQSMGF
SWNDMISEMLNQNWHIHNMTNATDASPGWNLLYDERTTNLTL

An exemplary BmrI nuclease domain may comprise, consist essentially of or consist of, the amino acid sequence below wherein the catalytic residues include H105, K107, N125, and E136:

(SEQ ID NO: 38)
MNYFSLHPNVYATGRPKGLINMLESVWISNQKPGDGTMYLISGFANYNGG
IRFYETFTEHINHGGKVIAILGGSTSQRLSSKQVVAELVSRGVDVYIINR
KRLLHAKLYGSSSNSGESLVVSSGNFTGPGMSQNVEASLLLDNNTTSSMG
FSWNGMVNSMLDQKWQIHNLSNSNPTSPSWNLLYDERTTNLTL

*Ralstonia*

The disclosure provides polypeptides derived from *Ralstonia* amino acid sequences or amino acid sequences related thereto, nucleic acids encoding the same, compositions comprising the same, kits comprising the same, non-human transgenic animals comprising the same, and methods of using the same.

Repeat variable diresidues (RVDs) of *Ralstonia* effectors correspond to the nucleotides in their target sites in a direct, linear fashion, one RVD to one nucleotide, with some degeneracy and no apparent context dependence. This finding represents a mechanism for protein-DNA recognition that enables target site prediction for new target-specific *Ralstonia* effectors.

As described herein, effector proteins derived from *Ralstonia*, including TAL proteins, may be used as part of a larger targeted chimeric protein (i.e. a component of a chimeric protein). Chimeric effector proteins of the disclosure, including those comprising or consisting of a TAL protein, or any component thereof, may demonstrate accessory activities related to nucleic acids such as nuclease activity. For instance, in some embodiments, a polypeptide or pronucleases that can facilitate homologous recombination in genome engineering may be used as a component of a chimeric protein. In certain embodiments, a transcription factor may be used as a component of a chimeric protein, making the resultant chimeric protein particularly useful for therapeutic compositions and uses thereof requiring a very high level of specificity (including therapeutic compositions and uses thereof directed against pathogens (e.g., viruses)).

Polypeptides or proteins of the disclosure may be derived from polypeptides or proteins found in *Ralstonia*. Polypeptides or proteins of the disclosure may contain one or more sequences that are neither identical to any polypeptide or protein found in *Ralstonia* nor naturally-occurring in *Ralstonia*.

Polypeptides or proteins of the disclosure may comprise at least a first domain and a second domain, wherein the first domain comprises at least one coding sequence for a nucleic acid recognition element and the second domain comprises at least one coding sequence for a nucleic acid effector element.

As used throughout the disclosure, the term "RTN" refers to a *Ralstonia* TALE Nuclease. RTNs of the disclosure may refer to a polypeptide or protein that comprises at least a first domain wherein the first domain comprises at least one coding sequence for a nucleic acid recognition element derived from an amino acid sequence derived from *Ralstonia*. RTNs of the disclosure may refer to a polypeptide or proteins of the invention that comprise at least a first domain and a second domain, wherein the first domain comprises at least one coding sequence for a nucleic acid recognition element derived from an amino acid sequence derived from *Ralstonia* and the second domain comprises a amino acid that is an effector protein. RTNs of the disclosure may refer to a polypeptide or proteins of the invention that comprise at least a first domain and a second domain, wherein the first domain comprises at least one coding sequence for a nucleic acid recognition element derived from an amino acid sequence derived from *Ralstonia* and the second domain comprises a amino acid that is a nuclease.

RTN DNA binding specificity depends on the number and order of repeat domains in the DNA binding domain. For example, repeats may comprise from about 30 to about 40 amino acids. Alternatively, repeats may comprise from about 32 to about 38 amino acids, from about 33 to about 37 amino acids, from about 34 to about 35 amino acids, from about 33 to about 36 amino acids, or from about 33 to about 35 amino acids. Repeats may consist of 34 to 35 amino acids, consist of 33 to 35 amino acids, or consist of 34 to 36 amino acids.

Nucleotide binding specificity of repeat domains of the disclosure may be determined by the 12 and 13 amino acids of each repeat domain.

Polypeptides or proteins of the disclosure may comprise at least one RVD sequence selected from the following: SI, SN, SI, NP, NH, NT, NK, NN, ND, HN, HY, HD, HH, RN, RS, and GS. Polypeptides or proteins of the disclosure may comprise at least one RVD sequence in any combination selected from the following: SI, SN, SH, NP, NH, NT, NK, NN, ND, HN, HY, HD, HH, RN, RS, NG and GS; wherein SI, SN, SH, NP, and NH bind any nucleic acid base; wherein NT, NK, and NN bind adenine; wherein ND, HN, HY, HD, and HH bind adenine and/or guanine; wherein NG binds thymine; wherein RN, RS, and GS bind guanine. Polypeptides or proteins of the disclosure may comprise at least one RVD sequence in any combination selected from the following: SI, SN, SH, NP, NH, NT, NK, NN, ND, HN, HY, HD, HH, RN, RS, NG and GS; wherein SI, SN, SH, NP, and NH bind any nucleic acid base; wherein NK binds guanine, and NN binds adenine or guanine; wherein ND, HN, HY, HD, and HH bind cytosine; wherein NG binds thymine; wherein RN, RS, and GS bind guanine. Polypeptides or proteins of the disclosure may comprise at least one RVD sequence in any combination selected from the following: SI, SN, SH, NP, NH, NT, NK, NN, ND, HN, HY, HD, HH, RN, RS, NG and GS; wherein SI binds adenine; SN binds guanine and/or adenine, SH, NP, and NH bind any nucleic acid base; wherein NK binds guanine; and NN binds adenine and/or guanine; wherein ND binds cytosine, HN binds guanine, HY, HD, and HH bind cytosine; wherein NG binds thymine; wherein RN binds guanine and/or adenine; wherein RS and GS binds guanine. Polypeptides or proteins of the disclosure may comprise at least one RVD sequence in any combination wherein at least one of the RVD sequences is NP, ND, or HN; and wherein NP binds cytosine, adenine, and guanine; wherein ND binds cytosine; and wherein IN binds adenine and/or guanine.

Polypeptides or proteins of the disclosure may comprise, consist essentially of, or consist of SEQ ID NO: 1.

Polypeptides or proteins of the disclosure may comprise, consist essentially of, or consist of SEQ ID NO: 1, wherein $X_1X_2$ bind to a single nucleic acid. Polypeptides or proteins of the disclosure may comprise, consist essentially of, or consist of SEQ ID NO: 1, wherein $X_1X_2$ bind to at least one nucleic acid.

Polypeptides or proteins of the disclosure may comprise at least 80%, 85%, 90%, 95%, 96%, 97%, 98%, or 99% sequence identity to LSTEQVVAIASX$_1$X$_2$GGKQALEAVKAQLLVLRAAPYE (SEQ ID NO: 1); wherein $X_1$=naturally occurring or non-naturally amino acid and wherein $X_2$=naturally occurring or non-naturally amino acid.

Polypeptides or proteins of the disclosure may comprise at least 80%, 85%, 90%, 95%, 96%, 97%, 98%, or 99% sequence identity to LSTEQVVAIASX$_1$X$_2$GGKQALEAVKAQLLVLRAAPYE (SEQ ID NO: 1); wherein, in any combination, $X_1$ and $X_2$ are independently variable, $X_1$=A, N, H, R or G; and $X_2$=I, N, H, K, Y, T, D, S, or P.

Polypeptides or proteins of the disclosure may comprise at least 80%, 85%, 90%, 95%, 96%, 97%, 98%, or 99% sequence identity to LSTEQVVAIASX$_1$X$_2$GGKQALEAVKAQLLVLRAAPYE (SEQ ID NO: 1); wherein $X_1$=S and $X_2$=I.

Polypeptides or proteins of the disclosure may comprise at least 80%, 85%, 90%, 95%, 96%, 97%, 98%, or 99% sequence identity to LSTEQVVAIASX$_1$X$_2$GGKQALEAVKAQLLVLRAAPYE (SEQ ID NO: 1); wherein $X_1$=S and $X_2$=N.

Polypeptides or proteins of the disclosure may comprise at least 80% sequence identity to SEQ ID NO: 1. Polypeptides or proteins of the disclosure may comprise at least 90% sequence identity to SEQ ID NO: 1. Polypeptides or proteins of the disclosure may comprise at least 91% sequence identity to SEQ ID NO: 1. Polypeptides or proteins of the disclosure may comprise at least 92% sequence identity to SEQ ID NO: 1. Polypeptides or proteins of the disclosure may comprise at least 93% sequence identity to SEQ ID NO: 1. Polypeptides or proteins of the disclosure may comprise at least 94% sequence identity to SEQ ID NO: 1. Polypeptides or proteins of the disclosure may comprise at least 95% sequence identity to SEQ ID NO: 1. Polypeptides or proteins of the disclosure may comprise at least 96% sequence identity to SEQ ID NO: 1. Polypeptides or proteins of the disclosure may comprise at least 97% sequence identity to SEQ ID NO: 1. Polypeptides or proteins of the disclosure may comprise at least 98% sequence identity to SEQ ID NO: 1. Polypeptides or proteins of the disclosure may comprise at least 99% sequence identity to SEQ ID NO: 1.

Polypeptides or proteins of the disclosure may comprise at least 80% sequence identity to SEQ ID NO:1 and comprise more than one of the amino acid substitution in any of the polypeptides chosen from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19.

Polypeptides or proteins of the disclosure may comprise at least 90% sequence identity to SEQ ID NO:1 and comprise more than one of the amino acid substitutions in any of the polypeptides chosen from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19.

Polypeptides or proteins of the disclosure may comprise at least 95% sequence identity to SEQ ID NO:1 and comprise more than one of the amino acid substitutions in any of the polypeptides chosen from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19.

Polypeptides or proteins of the disclosure may comprise at least 99% sequence identity to SEQ ID NO:1 and comprise more than one of the amino acid substitutions in any of the polypeptides chosen from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19.

Polypeptides or proteins of the disclosure may comprise at least 80%, 85%, 90%, 91%, 92%, 93%, 94%, 95%, 96%, 97%, 98%, or 99% sequence identity to SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19.

Polypeptides or proteins of the disclosure may comprise at least one, two, three, or four polypeptide sequences selected from polypeptides comprising at least 80%, 85%, 90%, 91%, 92%, 93%, 94%, 95%, 96%, 97%, 98%, or 99% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19.

Polypeptides or proteins of the disclosure may comprise at least 80%, 85%, 90%, 95%, 96%, 97%, 98%, or 99% sequence identity to

```
                                              (SEQ ID NO: 2)
LSTEQVVAIASSIGGKQALEAVKAQLLVLRAAPYE.
```

Polypeptides or proteins of the disclosure may comprise at least 80%, 85%, 90%, 95%, 96%, 97%, 98%, or 99% sequence identity to

```
                                              (SEQ ID NO: 3)
LSTEQVVAIASSNGGKQALEAVKAQLLVLRAAPYE.
```

Polypeptides or proteins of the disclosure may comprise at least 80%, 85%, 90%, 95%, 96%, 97%, 98%, or 99% sequence identity to

```
                                              (SEQ ID NO: 4)
LSTEQVVAIASSHGGKQALEAVKAQLLVLRAAPYE.
```

Polypeptides or proteins of the disclosure may comprise at least 80%, 85%, 90%, 95%, 96%, 97%, 98%, or 99% sequence identity to

```
                                              (SEQ ID NO: 5)
LSTEQVVAIASNPGGKQALEAVKAQLLVLRAAPYE.
```

Polypeptides or proteins of the disclosure may comprise at least 80%, 85%, 90%, 95%, 96%, 97%, 98%, or 99% sequence identity to

```
                                              (SEQ ID NO: 6)
LSTEQVVAIASNHGGKQALEAVKAQLLVLRAAPYE.
```

Polypeptides or proteins of the disclosure may comprise at least 80%, 85%, 90%, 95%, 96%, 97%, 98%, or 99% sequence identity to

```
                                              (SEQ ID NO: 7)
LSTEQVVAIASNTGGKQALEAVKAQLLVLRAAPYE.
```

Polypeptides or proteins of the disclosure may comprise at least 80%, 85%, 90%, 95%, 96%, 97%, 98%, or 99% sequence identity to

```
                                              (SEQ ID NO: 8)
LSTEQVVAIASNKGGKQALEAVKAQLLVLRAAPYE.
```

Polypeptides or proteins of the disclosure may comprise at least 80%, 85%, 90%, 95%, 96%, 97%, 98%, or 99% sequence identity to

```
                                              (SEQ ID NO: 9)
LSTEQVVAIASNPGGKQALEAVKAQLLVLRAAPYE.
```

Polypeptides or proteins of the disclosure may comprise at least 80%, 85%, 90%, 95%, 96%, 97%, 98%, or 99% sequence identity to (SEQ ID NO: 10)
LSTEQVVAIASNNGGKQALEAVKAQLLVLRAAPYE.

Polypeptides or proteins of the disclosure may comprise at least 80%, 85%, 90%, 95%, 96%, 97%, 98%, or 99% sequence identity to (SEQ ID NO: 11)
LSTEQVVAIASNDGGKQALEAVKAQLLVLRAAPYE.

Polypeptides or proteins of the disclosure may comprise at least 80%, 85%, 90%, 95%, 96%, 97%, 98%, or 99% sequence identity to (SEQ ID NO: 12)
LSTEQVVAIASNGGGKQALEAVKAQLLVLRAAPYE.

Polypeptides or proteins of the disclosure may comprise at least 80%, 85%, 90%, 95%, 96%, 97%, 98%, or 99% sequence identity to (SEQ ID NO: 13)
LSTEQVVAIASHNGGKQALEAVKAQLLVLRAAPYE.

Polypeptides or proteins of the disclosure may comprise at least 80%, 85%, 90%, 95%, 96%, 97%, 98%, or 99% sequence identity to (SEQ ID NO: 14)
LSTEQVVAIASHYGGKQALEAVKAQLLVLRAAPYE.

Polypeptides or proteins of the disclosure may comprise at least 80%, 85%, 90%, 95%, 96%, 97%, 98%, or 99% sequence identity to (SEQ ID NO: 15)
LSTEQVVAIASHDGGKQALEAVKAQLLVLRAAPYE.

Polypeptides or proteins of the disclosure may comprise at least 80%, 85%, 90%, 95%, 96%, 97%, 98%, or 99% sequence identity to (SEQ ID NO: 16)
LSTEQVVAIASHHGGKQALEAVKAQLLVLRAAPYE.

Polypeptides or proteins of the disclosure may comprise at least 80%, 85%, 90%, 95%, 96%, 97%, 98%, or 99% sequence identity to (SEQ ID NO: 17)
LSTEQVVAIASRNGGKQALEAVKAQLLVLRAAPYE.

Polypeptides or proteins of the disclosure may comprise at least 80%, 85%, 90%, 95%, 96%, 97%, 98%, or 99% sequence identity to (SEQ ID NO: 18)
LSTEQVVAIASRSGGKQALEAVKAQLLVLRAAPYE.

Polypeptides or proteins of the disclosure may comprise at least 80%, 85%, 90%, 95%, 96%, 97%, 98%, or 99% sequence identity to (SEQ ID NO: 19)
LSTEQVVAIASGSGGKQALEAVKAQLLVLRAAPYE.

Polypeptides or proteins of the disclosure may comprise, consist essentially of or consist of any combination of polypeptide sequences with at least 80%, 85%, 90%, 91%, 92%, 93%, 94%, 95%, 96%, 97%, 98%, or 99% sequence identity to the polypeptides chosen from: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO: 17, SEQ ID NO: 18, and SEQ ID NO:19.

Polypeptides or proteins of the disclosure may comprise, consist essentially of or consist of any combination of a polypeptide sequences with at least 80%, 85%, 90%, 91%, 92%, 93%, 94%, 95%, 96%, 97%, 98%, or 99% sequence identity to the polypeptides chosen from: SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO: 18, and SEQ ID NO:19, wherein the $12^{th}$ and $13^{th}$ amino acid of at least one of the polypeptide sequences binds at least one nucleic acid.

Polypeptides or proteins of the disclosure may comprise, consist essentially of or consist of any combination of a polypeptide sequences with 80%, 85%, 90%, 91%, 92%, 93%, 94%, 95%, 96%, 97%, 98%, or 99% sequence identity to the polypeptides chosen from: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID NO:12, SEQ ID NO:13, SEQ ID NO:14, SEQ ID NO:15, SEQ ID NO:16, SEQ ID NO:17, SEQ ID NO: 18, and SEQ ID NO: 19.

Polypeptides or proteins of the disclosure may comprise, consist essentially of or consist of a first domain and a second domain, wherein the first domain is a nucleic acid recognition domain that comprises, consists essentially of or consists of at least one combination of polypeptide sequences with 80%, 85%, 90%, 91%, 92%, 93%, 94%, 95%, 96%, 97%, 98%, or 99% sequence identity to the polypeptides chosen from: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, and SEQ ID NO:19.

Polypeptides or proteins of the disclosure may comprise, consist essentially of or consist of a first domain and a second domain, wherein the first domain is a nucleic acid recognition domain that comprises, consists essentially of or consists of at least one combination of a polypeptide sequences with 80%, 85%, 90%, 91%, 92%, 93%, 94%, 95%, 96%, 97%, 98%, or 99% sequence identity to the polypeptides chosen from: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, and SEQ ID NO:19; wherein the $12^{th}$ and $13^{th}$ amino acid of at least one polypeptide sequence bind a nucleic acid.

The disclosure also provides nucleic acids encoding any one or more of the polypeptides or proteins described above. Nucleic acids of the disclosure may comprise, comprise essentially of, or consist of nucleic acid sequences that encode at least 2, 3, 4, 5 or more polypeptides chosen from polypeptides comprising at least 80%, 85%, 90%, 91%, 92%, 93%, 94%, 95%, 96%, 97%, 98%, or 99% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19.

Compositions

The disclosure provides nucleic acid sequences that encode any protein or polypeptide described herein. Compositions of the disclosure may comprise, consist essentially of, or consist of at least one nucleic acid sequence that encodes a protein or polypeptide described herein. Compositions of the disclosure may comprise, consist essentially of, or consist of a plurality of (i.e. one or more) nucleic acid sequences that encode any protein or polypeptide described herein. Compositions of the disclosure may comprise, consist essentially of, or consist of at least one amino acid sequence described herein. Compositions of the disclosure may comprise, consist essentially of, or consist of a plurality of (i.e. one or more) amino acid sequences described herein.

The disclosure provides vectors comprising, consisting essentially of or consisting of any one or more of the nucleic acid sequences of the disclosure encoding any one or more of the proteins of the disclosure. In some embodiments, the vector is a plasmid. In some embodiments, the vector is a retrovirus. Retrovirus vectors of the disclosure may comprise, for example, long terminal repeats, a psi packaging signal, a cloning site, and a sequence encoding a selectable marker.

The disclosure provides cells comprising any one or more of the nucleic acids or vectors of the disclosure. In some embodiments, the cell is a sperm or an egg.

The disclosure provides kits comprising: a vector comprising a nucleic acid encoding any one or more of the proteins of the disclosure.

The disclosure provides non-human, transgenic animals comprising a nucleic acid molecule encoding any one or more of the proteins of the disclosure.

Organisms of the disclosure are unicellular or multicellular. Multicellular organisms may include, but are not limited to, vertebrates. Exemplary vertebrate animals may include, but are not limited to, mammals. Exemplary vertebrate animals may include, but are not limited to, non-human mammals.

Expression Cassettes and Vectors

The DNA sequences of the invention can be provided in expression cassettes for expression in any prokaryotic or eukaryotic cell and/or organism of interest including, but not limited to, bacteria, fungi, algae, plants, and animals. Exemplary cassettes include 5' and 3' regulatory sequences operably linked to a DNA sequence of the invention.

As used throughout the disclosure, the term "operably linked" refers to a functional linkage between two or more elements. For example, an operable linkage between a polynucleotide or gene of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the DNA sequence to be under the transcriptional regulation of the regulatory regions. The expression cassette may additionally contain selectable marker genes.

Exemplary expression cassettes may include in the 5'-3' direction of transcription, a transcriptional and translational initiation region (i.e., a promoter), a DNA sequence of the invention, and a transcriptional and translational termination region (i.e., termination region) functional in plants or other organism or non-human host cell. The regulatory regions (i.e., promoters, transcriptional regulatory regions, and translational termination regions) and/or the DNA sequence of the invention may be native/autologous to the host cell or to each other. Alternatively, the regulatory regions and/or DNA sequence of the invention may be heterologous to the host cell or to each other. As used throughout the disclosure, the term "heterologous" refers to a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

Termination regions of the disclosure may be native with a transcriptional initiation region, may be native with the operably linked DNA sequence of interest, may be native with the host, or may be derived from another source (i.e., foreign or heterologous) to the promoter, the DNA sequence of interest, the plant host, or any combination thereof. Convenient termination regions for use in plants are available from the Ti-plasmid of *A. tumefaciens*, such as the octopine synthase and nopaline synthase termination regions. See also Guerineau et al. (1991) Mol. Gen. Genet. 262:141-144; Proudfoot (1991) Cell 64:671-674; Sanfacon et al. (1991) Genes Dev. 5:141-149; Mogen et al. (1990) Plant Cell 2:1261-1272; Munroe et al. (1990) Gene 91:151-158; Ballas et al. (1989) Nucleic Acids Res. 17:7891-7903; and Joshi et al. (1987) Nucleic Acids Res. 15:9627-9639.

Polynucleotides of the disclosure may be optimized for increased expression in a transformed organism. That is, the polynucleotides can be synthesized using codons preferred by the host for improved expression. See, for example, Campbell and Gown (1990) Plant Physiol. 92:1-11 for a discussion of host-preferred codon usage. Methods are available in the art for synthesizing host-preferred gene, particularly plant-preferred genes. See, for example, U.S. Pat. Nos. 5,380,831, and 5,436,391, and Murray et al. (1989) Nucleic Acids Res. 17:477-498, herein incorporated by reference.

Additional sequence modifications may be used to enhance gene expression in a cellular host. Exemplary sequence modifications include, but are not limited to, elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

Expression cassettes of the disclosure may contain 5' leader sequences. Such leader sequences can act to enhance translation. Translation leaders are known in the art and include, for example: picornavirus leaders, for example, EMCV leader (Encephalomyocarditis 5' noncoding region) (Elroy-Stein et al. (1989) Proc. Natl. Acad. Sci. USA 86:6126-6130); potyvirus leaders, for example, TEV leader (Tobacco Etch Virus) (Gallie et al. (1995) Gene 165(2):233-238), MDMV leader (Maize Dwarf Mosaic Virus) (Virology 154:9-20), and human immunoglobulin heavy-chain binding protein (BiP) (Macejak et al. (1991) Nature 353:90-94); untranslated leader from the coat protein mRNA of alfalfa mosaic virus (AMV RNA 4) (Tabling et al. (1987) Nature 325:622-625); tobacco mosaic virus leader (TMV) (Gallie et al. (1989) in Molecular Biology of RNA, ed. Cech (Liss, New York), pp. 237-256); and maize chlorotic mottle virus leader (MCMV) (Lommel et al. (1991) Virology 81:382-385). See also, Della-Cioppa et al. (1987) Plant Physiol. 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The disclosure provides viral vectors comprising any one or more than one nucleic acid sequence disclosed herein. The viral vector is optionally selected from the group comprising a retroviral vector, an adenoviral vector, an adeno-associated viral vector, spumaviral, a lentiviral vector and a plasmid or other vector, such as transposons, described in the application. The retroviral vector optionally comprises an oncoretroviral vector. The retroviral vector optionally comprises a lentiviral vector.

Numerous plant transformation vectors and methods for transforming plants are available. See, for example, An, G. et al. (1986) Plant Pysiol., 81:301-305; Fry, J., et al. (1987) Plant Cell Rep. 6:321-325; Block, M. (1988) Theor. Appl Genet. 76:767-774; Hinchee, et al. (1990) Stadler. Genet. Symp. 203212.203-212; Cousins, et al. (1991) Aust. J. Plant Physiol. 18:481-494; Chee, P. P. and Slightom, J. L. (1992) Gene. 118:255-260; Christou, et al. (1992) Trends. Biotechnol. 10:239-246; D'Halluin, et al. (1992) Bio/Technol. 10:309-314; Dhir, et al. (1992) Plant Physiol. 99:81-88; Casas et al. (1993) Proc. Nat. Acad Sci. USA 90:11212-11216; Christou, P. (1993) In Vitro Cell. Dev. Biol.-Plant; 29P:119-124; Davies, et al. (1993) Plant Cell Rep. 12:180-183; Dong, J. A. and Mchughen, A. (1993) Plant Sci. 91:139-148; Franklin, C. I. and Trieu, T. N. (1993) Plant. Physiol. 102:167; Golovkin, et al. (1993) Plant Sci. 90:41-52; Guo Chin Sci. Bull. 38:2072-2078; Asano, et al. (1994) Plant Cell Rep. 13; Ayeres N. M. and Park, W. D. (1994) Crit. Rev. Plant. Sci. 13:219-239; Barcelo, et al. (1994) Plant. J. 5:583-592; Becker, et al. (1994) Plant. J. 5:299-307; Borkowska et al. (1994) Acta. Physiol Plant. 16:225-230; Christou, P. (1994) Agro. Food. Ind. Hi Tech. 5: 17-27; Eapen et al. (1994) Plant Cell Rep. 13:582-586; Hartman, et al. (1994) Bio-Technology 12: 919923; Ritala, et al. (1994) Plant. Mol. Biol. 24:317-325; and Wan, Y. C. and Lemaux, P. G. (1994) Plant Physiol. 104:3748.

Pharmaceutical Compositions

Compositions of the disclosure may be pharmaceutical compositions. Pharmaceutical compositions of the disclosure may be used to treat patients having diseases, disorders or abnormal physical states, and comprise an acceptable carrier, auxiliary or excipient.

The pharmaceutical compositions are optionally administered by ex vivo and in vivo methods such as electroporation, DNA microinjection, liposome DNA delivery, and virus vectors that have RNA or DNA genomes including retrovirus vectors, lentivirus vectors, Adenovirus vectors and Adeno-associated virus (AAV) vectors, Semliki Forest Virus. Derivatives or hybrids of these vectors are also useful.

Dosages to be administered depend on patient needs, on the desired effect and on the chosen route of administration. The expression cassettes are optionally introduced into the cells or their precursors using ex vivo or in vivo delivery vehicles such as liposomes or DNA or RNA virus vectors. They are also optionally introduced into these cells using physical techniques such as microinjection or chemical methods such as coprecipitation. The pharmaceutical compositions are typically prepared by known methods for the preparation of pharmaceutically acceptable compositions which are administered to patients, and such that an effective quantity of the nucleic acid molecule is combined in a mixture with a pharmaceutically acceptable vehicle. Suitable vehicles are described, for example in Remington's Pharmaceutical Sciences (Remington's Pharmaceutical Sciences, Mack Publishing Company, Easton, Pa., USA). Any selectable marker gene can be used in the present invention.

On this basis, the pharmaceutical compositions could include an active compound or substance, such as a nucleic acid molecule, in association with one or more pharmaceutically acceptable vehicles or diluents, and contained in buffered solutions with a suitable pH and isoosmotic with the physiological fluids. The methods of combining the expression cassettes with the vehicles or combining them with diluents are well known to those skilled in the art. The composition could include a targeting agent for the transport of the active compound to specified sites within cells. The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as .beta.-galactosidase and fluorescent proteins such as green fluorescent protein (GFP) (Su et al. (2004) Biotechnol Bioeng 85:610-9 and Fetter et al. (2004) Plant Cell 16:215-28), cyan florescent protein (CYP) (Bolte et al. (2004) J. Cell Science 117:943-54 and Kato et al. (2002) Plant Physiol 129:913-42), and yellow florescent protein (PhiYFP™ from Evrogen, see, Bolte et al. (2004) J. Cell Science 117:943-54). For additional selectable markers, see generally, Yarranton (1992) Curr. Opin. Biotech. 3:506-511; Christopherson et al. (1992) Proc. Natl. Acad. Sci. USA 89:6314-6318; Yao et al. (1992) Cell 71:63-72; Reznikoff (1992) Mol. Microbiol. 6:2419-2422; Barkley et al. (1980) in The Operon, pp. 177-220; Hu et al. (1987) Cell 48:555-566; Brown et al. (1987) Cell 49:603-612; Figge et al. (1988) Cell 52:713-722; Deuschle et al. (1989) Proc. Natl. Acad. Aci. USA 86:5400-5404; Fuerst et al. (1989) Proc. Natl. Acad. Sci. USA 86:2549-2553; Deuschle et al. (1990)

Science 248:480-483; Gossen (1993) Ph.D. Thesis, University of Heidelberg; Reines et al. (1993) Proc. Natl. Acad. Sci. USA 90:1917-1921; Labow et al. (1990) Mol. Cell. Biol. 10:3343-3356; Zambretti et al. (1992) Proc. Natl Acad. Sci. USA 89:3952-3956; Baim et al. (1991) Proc. Natl. Acad. Sci. USA 88:5072-5076; Wyborski et al. (1991) Nucleic Acids Res. 19:4647-4653; Hillenand-Wissman (1989) Topics Mol. Struc. Biol. 10:143-162; Degenkolb et al. (1991) Antimicrob. Agents Chemother. 35:1591-1595; Kleinschnidt et al. (1988) Biochemistry 27:1094-1104; Bonin (1993) Ph.D. Thesis, University of Heidelberg; Gossen et al. (1992) Proc. Natl. Acad. Sci. USA 89:5547-5551; Oliva et al. (1992) Antimicrob. Agents Chemother. 36:913-919; Hlavka et al. (1985) Handbook of Experimental Pharmacology, Vol. 78 (Springer-Verlag, Berlin); Gill et al. (1988) Nature 334:721-724. Such disclosures are herein incorporated by reference.

Genetically-Modified Cells and Organisms

The disclosure provides a eukaryotic cell comprising a mutation, a heterologous gene, a variant and/or another genetic modification caused by introduction of one or more nucleic acids or polypeptides described herein.

The disclosure provides a mammalian cell comprising a mutation, a heterologous gene, a variant and/or another genetic modification caused by introduction of one or more nucleic acids or polypeptides described herein.

The disclosure provides a human cell comprising any one or combination of proteins or nucleic acid sequences disclosed herein. For example, the disclosure provides a human cell comprising a mutation, a heterologous gene, a variant, and/or another genetic modification caused by introduction of one or more nucleic acids or polypeptides described herein. Alternatively, the disclosure provides non-human cells comprising a mutation, a heterologous gene, a variant and/or another genetic modification caused by introduction of one or more nucleic acids or polypeptides described herein.

The disclosure provides an insect cell comprising a mutation, a heterologous gene, a variant and/or other genetic modification caused by introduction of one or more nucleic acids or polypeptides described herein.

The disclosure provides a fish cell comprising a mutation, a heterologous gene, a variant and/or other genetic modification caused by introduction of one or more nucleic acids or polypeptides described herein.

The disclosure provides a plant cell comprising a mutation, a heterologous gene, a variant and/or other genetic modification caused by introduction of one or more nucleic acids or polypeptides described herein.

The disclosure provides plants (and portions or parts thereof), seeds, plant cells and other non-human host cells transformed with the isolated nucleic acid molecules of the disclosure and the proteins or polypeptides encoded by the nucleic acid molecules (including coding regions thereof) of the disclosure. Polypeptides and DNA molecules described herein may be introduced into animal and human cells as well as cells of other organisms, including, but not limited to, fungi or plants.

Compositions of the disclosure may be used for site-specific modification of the genome of any cell, including, but not limited to, stem cells and gametes. Exemplary stem cells include pluripotent cells, totipotent cells, somatic stem cells, spermatogonial stem cells (SSCs), embryonic stem (ES) cells, induced pluripotent stem (iPS) cells, embryos, germ cells, primordial germ cells (PGCs), plant tube cells, pollen cells, and spores.

Site-specific engineering of stem cells results in altered function of gene(s) or gene product(s) and genetically modified organisms, and cell or tissue culture models are produced from these engineered stem cells. Modified stem cells and organisms include knockout and knockin cells and organisms.

Genetically modified organisms created by site-specific engineering using the compositions and methods of the disclosure, include, but not limited to mammals (e.g. rats, mice, pigs, rabbits, guinea pigs, dogs, non-human primates, mini-pigs) as well as plants (e.g., maize, soybean, rice, potato, wheat, tobacco, tomato, and *Arabidopsis*, as well as the descendants and ancestors of such organisms).

Gene Therapy

The application includes methods and compositions for providing a coding nucleic acid molecule to the cells of an individual such that expression of the coding nucleic acid molecule in the cells provides the biological activity or phenotype of the polypeptide encoded by the coding nucleic acid molecule. The method also relates to a method for providing an individual having a disease, disorder or abnormal physical state with a biologically active polypeptide by administering a nucleic acid molecule of the present application. The method may be performed ex vivo or in vivo. Gene therapy methods and compositions are demonstrated, for example, in U.S. Pat. Nos. 5,869,040, 5,639,642, 5,928, 214, 5,911,983, 5,830,880, 5,910,488, 5,854,019, 5,672,344, 5,645,829, 5,741,486, 5,656,465, 5,547,932, 5,529,774, 5,436,146, 5,399,346 and 5,670,488, 5,240,846. The amount of polypeptide will vary with the subject's needs. The optimal dosage of vector may be readily determined using empirical techniques, for example by escalating doses (see U.S. Pat. No. 5,910,488 for an example of escalating doses). Vectors containing the nucleic acid molecules of the application are typically administered to mammals, preferably humans, in gene therapy using techniques described below. The polypeptides produced from the nucleic acid molecules are also optionally administered to mammals, preferably humans. The application relates to a method of medical treatment of a mammal in need thereof, preferably a human, by administering to the mammal a vector of the application or a cell containing a vector of the application. A recipient, preferably human, who develops an adverse event, such as graft versus host disease, is typically administered a drug, such as AZT, that is a substrate for the modified tmpk molecules of the application. Diseases, such as blood diseases or neural diseases (neurodegenerative), that are readily treated are described in this application and known in the art (e.g. diseases, such as thalassemia or sickle cell anemia that are treated by administering a globin gene as described in Canadian patent application no. 2,246,005). Blood diseases treatable by stem cell transplant include leukemias, myelodysplastic syndromes, stem cell disorders, myeloproliferative disorders, lymphoproliferative disorders phagocyte disorders, inherited metabolic disorders, histiocytic disorders, inherited erythrocyte abnormalities, inherited immune system disorders, inherited platelet abnormalities, plasma cell disorders, malignancies (See also, Medical Professional's Guide to Unrelated Donor Stem Cell Transplants, 4th Edition). Stem cell nerve diseases to be treated by neural stem cell transplantation include diseases resulting in neural cell damage or loss, (e.g. paralysis, Parkinson's disease, Alzheimer's disease, ALS, multiple sclerosis). The vector of the application is useful as a stem cell marker and to express genes that cause stem cells to differentiate (e.g. growth factor).

Various approaches to gene therapy may be used. The disclosure provides a method for providing a human with a therapeutic polypeptide including: introducing human cells into a human, the human cells having been treated in vitro or ex vivo to insert therein a vector of the application, the human cells expressing in vivo in the human a therapeutically effective amount of the therapeutic polypeptide.

The method also relates to a method for producing a stock of recombinant virus by producing virus suitable for gene therapy comprising modified DNA encoding globin. This method preferably involves transfecting cells permissive for virus replication (the virus containing modified globin) and collecting the virus produced.

Cotransfection (DNA and marker on separate molecules) may be employed (see eg U.S. Pat. Nos. 5,928,914 and 5,817,492). As well, a detection cassette or marker (such as Green Fluorescent Protein marker or a derivative, CD19 or CD25) may be used within the vector itself (preferably a viral vector).

Methods of the disclosure may be used to mutate any eukaryotic stem cell, including, but not limited to, haploid, diploid, triploid, tetraploid, or aneuploid. In one embodiment, the cell is diploid. Stem cells in which the methods of the present invention can be advantageously used include, but are not limited to stem cells such as somatic stem cells, SSCs, ES cells, iPS cells, embryos, or any cell capable of developing into one or more organisms.

The disclosure provides a method to produce a site-specific knockout, knock-in or otherwise genetically modified stem cell. The site-specific mutation is generated using a composition of the disclosure that cleaves the desired site, followed by NHEJ repair, resulting in deletion mutations. The site-specific mutation can be produced in spennatogonial stem cells (SSCs) which are used to generate heterozygous or homozygous genetically modified organisms.

The disclosure provides a method to produce a site-specific knockout, knock-in or otherwise genetically modified stem cell. The site-specific mutation is generated using a composition of the disclosure that the desired site resulting in deletion mutations. The site specific mutation is produced in embryonic stem (ES) cells, which are used to generate heterozygous or homozygous genetically modified organisms.

The disclosure provides methods to produce a site-specific knockout, knock-in or otherwise genetically modified stem cell. The site specific mutation is generated using a composition that cleaves the desired site resulting in deletion mutations. The site-specific mutation is produced in induced pluripotent stem (iPS) cells, which are used to generate heterozygous or homozygous genetically modified organisms.

The disclosure provides methods to produce a site-specific knockout, knockin or otherwise genetically modified stem cell. The site specific mutation is generated using a composition that cleaves the desired site resulting in deletion mutations. The site-specific mutation is produced in embryos which are used to generate heterozygous or homozygous genetically modified organisms.

The disclosure provides methods to mutate cells within the organism or within the native environment as in tissue explants (e.g., in vivo or in situ). Alternatively, tissues or stem cells isolated from the organism using art-known methods and genes can be mutated according to the methods of the disclosure. The tissues or stem cells are either maintained in culture (e.g., in vitro), or re-implanted into a tissue or organism (e.g., ex vivo).

Methods of Making XTNs and RTNs

Similar to the architecture described in the FLASH assembly method of the disclosure, the disclosure provides a preferred assembly method to construct TALE repeat arrays in which three distinct TALE repeat backbones that differ slightly in their amino acid and DNA sequences occur in a repeated pattern. The first, amino-terminal TALE repeat in an array was designated as α unit. This is followed by β, and γ units and then an α unit that is substantially identical to the first α unit, except for the different positioning of a Type IIS restriction site on the 5' and 3' end (required to enable creation of a unique overhangs needed for cloning into an organized array). The α unit is then followed again by repeats of β and γ units.

For each of four repeat variable di-residues (RVDs) that specifies one of the four DNA bases (NI=A, HD=C, NN=G, NG=T), 10 plasmids were synthesized (IDT) and generated, for a library total of forty pRVD plasmids (ampicillin selectable marker). For example, 10 plasmids were generated for the RVD NI such that NI-1 was an α unit, NI-2 was a β unit, NI-3 was a γ unit, NI-4 was an α unit and so on. For all of these pRVD plasmids, the sequence encoding the TALE repeat domain is flanked by BsaI restriction sites such that the overhangs generated by digestion of any pRVD plasmids encoding units designed to be adjacent to one another (eg. 1 and 2, 2 and 3 etc) with BasI are complementary to each other.

Assembly of pRVDs into XTNs was achieved in two broad steps:

Step 1a: Clone pRVDs 1 through 10 (specifying the first 10 targeted nucleotides) into pIN-X.

Step 1b: Clone pRVDs 1 up to 10 (specifying the 11th up to 20th targeted nucleotide) into pIN-Z.

Step 2: Clone the pIN-X array and the pIN-Z array of TALE repeat backbones into the correct XTN-expression backbone to produce an XTN targeting up to 20 specified nucleotide sequence.

With respect to Step 1a: pRVDs (pRVDs 1 through 10) are selected in the correct order to match the first ten targeted DNA sequences. 100 ng of each pRVD is mixed with 100 ng of pIN-X in a single 20 ul reaction containing 1 ul BsaI (10 U, NEB) and 1 ul T4 DNA ligase (2000 U, NEB) in T4 DNA ligase buffer (NEB). The reaction is then incubated in a thermocyler to 10 cycles of 5 min at 37° C. and 10 min at 16° C., then heated to 50° C. for 5 min and then 80° C. for 5 min. The mixture is then used to transform *E. coli* cells and plated on LB agar containing 50 ug/ml Kanamycin. Colonies are then screened by colony PCR and sequenced to identify clones that contain the desired 10RVD array.

With respect to Step 1b: pRVDs are selected in the correct order to match the 11th through (upto) 20th targeted DNA sequence. 100 ng of each pRVD is mixed with 100 ng of pIN-Z and the procedure described in Step 1a above is replicated to identify desired clones.

With respect to Step 2: 150 ng of each pIN-X and pIN-Z plasmids containing the intermediary repeat arrays is mixed with 150 ng of the desired XTN expression plasmid in a single 20 ul reaction containing 1 ul BsmBI (10 U NEB) and 1 ul T4 DNA ligase (2000 U NEB) in T4 DNA ligase buffer (NEB). The reaction is treated and used to transform *E coli* as in Step 1a, except Ampicillin (100 ug/ml) is used in place of Kanamycin for selection of transformants. Clones are screened by colony PCR and sequenced to identify desired clones.

XTN Intermediate Plasmids pIN-X and pIN-Z:

pIN-X and pIN-Z are Kanamycin selectable plasmids that contain two sites each for BsaI and BsmBI such that when digested with BsaI, produce overhangs that complement the BsaI overhangs of pRVD-1 and pRVD-10 to incorporate an array of pRVDs 1 through 10 into the intermediate plasmids. Several versions of pIN-X have been generated for use depending on the number of repeats to be incorporated (6 through 10 repeats). When intermediate plasmids are digested with BsmBI, overhangs (that flank the cloned TALE repeat arrays) are generated that are complementary to the BsmBI overhangs of each other and that of the XTN expression backbones. This enables generation of an XTN of this architecture: N-terminal sequence—TALE repeat array (10 repeats from pIN-X)—TALE repeat array (6 to 10 repeats from pIN-Z)—C-terminal sequence—Nuclease.

XTN Expression Backbones:

Similar to the FLASH system of the disclosure, the last targeted nucleotide specified by the final half Effector Binding Element (EBE), is incorporated in the expression backbone and hence there are four expression backbones that each specify the last targeted nucleotide to be A, C, T or G. The expression backbone contains the XTN N-terminal sequence, the C-terminal sequence linked to a particular obligate dimer nuclease such as FokI (Clo51, BfiI, BmrI).

Methods of Use

The disclosure provides methods of modifying genetic material of a cell or at least one cell of an organism (multicellular or unicellular), the method comprising administering directly to the cell or at least one cell of the organism one or more of the nucleic acids or polypeptides of the disclosure.

Polypeptides of the disclosure may be provided or administered as a nucleic acid encoding the protein. In some embodiments, the nucleic acid encoding the protein is administered with a second nucleic acid sequence that encodes an effector.

The disclosure provide methods for constructing new repeat units and testing the specific binding activities of artificially constructed repeat units specifically recognizing base pairs in a target DNA sequence. The number of repeat units to be used in a repeat domain may be varied for optimal specific binding. Generally, at least 1.5 repeat units are considered as a minimum, although typically at least about 8 repeat units are used. The repeat units are not required to be complete repeat units because repeat units of half the size may be used. Moreover, polypeptides and methods of making and using the polypeptides of the disclosure depend on repeat domains with a particular number of repeat units. Thus, a polypeptide of the disclosure may comprise, for example, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 46, 46.5, 47, 47.5, 48, 48.5, 49, 49.5, 50, 50.5 or more repeat units.

Polypeptides of the disclosure may comprise a repeat domain with repeat units wherein in the repeat units hypervariable regions are included which determine recognition of a base pair in a target DNA sequence. For example, each repeat unit of the repeat domains of the disclosure may include a hypervariable region which determines recognition of one base pair in a target DNA sequence. Alternatively, 1 or 2 repeat units in a repeat domain may be included which do not specifically recognize a base pair in a target DNA sequence.

Considering the recognition code disclosed herein, a modular arrangement of repeat units is contemplated wherein each repeat unit is responsible for the specific recognition of one base pair in a target DNA sequence. Consequently, in this modular arrangement, a sequence of repeat units may correspond to a sequence of base pairs in a target DNA sequence so that 1 repeat unit corresponds to one base pair.

The disclosure provides a method for selectively recognizing a base pair in a target DNA sequence by a polypeptide that comprises at least one repeat domain, the at least one repeat domain comprising a plurality of repeat units, wherein each repeat unit comprises at least one RVD region. RVD regions of the disclosure determine recognition of a base pair or nucleotide in a target DNA sequence. More specifically, the RVD regions of the disclosure include those amino acids in a DNA-binding polypeptide responsible for selective recognition of base pairs in a target DNA sequence. Having defined these recognition codes (i.e. RVD regions), the disclosure provides a general principle for recognizing specific base pairs in a target DNA sequence by selected amino acids in a polypeptide. Distinct types of monomers that are part of a repeat unit array (or polymer) of varying amino acid length have the capacity to recognize one defined/specific base pair. Within each repeat unit forming a repeat domain, a RVD region is responsible for the specific recognition of a base pair in a target DNA sequence.

Thus, the disclosure provides not only a method for selectively recognizing a base pair in a target DNA sequence by a polypeptide comprising at least one repeat domain comprising repeat units, but also methods for generating target DNA sequences that are selectively recognized by repeat domains in a polypeptide. These polypeptides are useful as molecular biology tools for cloning, mutagenizing or otherwise altering an isolated nucleic acid sequence or other in vivo sequence. The polypeptides and methods of use described herein provide an efficient means of selective mutagenesis.

The disclosure also provides a method for constructing and/or making a polypeptide that recognizes a specific DNA sequence. Polypeptides of the disclosure comprise at least one repeat monomer of the disclosure and can be constructed by a modular approach. This modular approach may include preassembling repeat units in target vectors that, subsequently, may be assembled into a final destination vector. DNA constructs of the disclosure may be codon optimized to recombinantly produce and/or secrete recombinant polypeptides of the disclosure. Any recombinant system in the art can be used to produce a recombinant protein of the disclosure. Exemplary recombinant systems include, but not limited to, baculovirus cells, eukaryotic cells (e.g. mammalian cells), or bacterial cells.

When a target DNA sequence is known, compositions and methods of the disclosure may be used to construct of a modular series of repeat units, including specific recognition amino acid sequences, and assemble these repeat units into a polypeptide in the appropriate order to enable recognition of and specific binding to the desired target DNA sequence. Any polypeptide can be modified by combination with a modular repeat unit DNA-binding domain of the disclosure. Such examples include polypeptides that are transcription activator and repressor proteins, resistance-mediating proteins, nucleases, topoisomerases, ligases, integrases, recombinases, resolvases, methylases, acetylases, demethylases, deacetylases, and any other polypeptide capable of modifying DNA, RNA, or proteins.

The modular repeat unit DNA-binding domain of the disclosure may be combined with a cell compartment localization signal (e.g. a nuclear localization signal), to function at any other regulatory regions, including, but not limited to, transcriptional regulatory regions and translational termination regions.

Modularly designed repeat units of the disclosure may be combined with an endonuclease domain capable of cleaving DNA when brought into proximity with DNA (for example, as a result of binding by the repeat domain). Such endonucleolytic breaks stimulate the rate of homologous recombination in eukaryotes, including fungi, plants, and animals. The ability to simulate homologous recombination at a specific site as a result of a site-specific endonucleolytic break allows the recovery of transformed cells that have integrated a DNA sequence of interest at the specific site, at a much higher frequency than is possible without having made the site-specific break. In addition, endonucleolytic breaks such as those caused by polypeptides formed from a repeat domain and an endonuclease domain are sometimes repaired by the cellular DNA metabolic machinery in a way that alters the sequence at the site of the break, for instance by causing a short insertion or deletion at the site of the break compared to the unaltered sequence. These sequence alterations can cause inactivation of the function of a gene or protein, for instance by altering a protein-coding sequence to make a non-functional protein, modifying a splice site so that a gene transcript is not properly cleaved, making a non-functional transcript, and/or changing the promoter sequence of a gene so that it can no longer by appropriately transcribed.

Breaking DNA using site specific endonucleases can increase the rate of homologous recombination in the region of the breakage. In some embodiments, the Clo051 endonuclease may be utilized in an effector to induce DNA breaks. The Clo051 endonuclease domain functions independently of the DNA binding domain and cuts a double stranded DNA typically as a dimer. For example, an effector could be constructed that contains a repeat domain for recognition of a desired target DNA sequence as well as a Clo051 endonuclease domain to induce DNA breakage at or near the target DNA sequence. Utilization of such effectors enables the generation of targeted changes in genomes (including, for example, additions, deletions and other modifications, analogous to those uses reported for zinc finger nucleases as per Bibikova et al. (2003) Science 300, 764; Urnov et al. (2005) Nature 435, 646; Wright et al. (2005) The Plant Journal 44:693-705; and U.S. Pat. Nos. 7,163,824 and 7,001,768, all of which are herein incorporated by reference in their entireties).

Any other endonuclease domain may be operably-linked with heterologous DNA binding domains to be utilized as an effector. The Clo051 endonuclease is one such non-limiting example. Prior to use of a particular endonuclease, if not already present, the recognition site of that endonuclease must be introduced at the desired location to enhance homologous recombination at that site.

Novel endonucleases may be designed and/or synthesize by, for example, modifying known endonucleases or making chimeric versions of one or more such endonucleases that recognize novel target DNA sequences, thus paving the way for generation of such engineered endonuclease domains to cleave endogenous target DNA sequences of interest (Chevalier et al. (2002) Molecular Cell 10:895-905; WO2007/060495; WO2009/095793; Fajardo-Sanchez et al. (2008) Nucleic Acids Res. 36:2163-2173, both of which are incorporated by reference in their entireties). It is contemplated with respect to the compositions and methods of the disclosure that endonuclease domains may be similarly engineered to render the DNA-binding activity non-functional but preserve the DNA cleaving activity of a known endonuclease to induce DNA breaks similar to those induced by the known endonuclease (for example, similar to those breaks induced by the use of Clo051 described above). In such applications, target DNA sequence recognition would preferably be provided by the repeat domain of the effector but DNA cleavage would be accomplished by the engineered endonuclease domain.

Effectors of the disclosure may include a repeat domain with specific recognition for a desired specific target sequence. In preferred embodiments, the effector specifically binds to an endogenous chromosomal DNA sequence. The specific nucleic acid sequence or more preferably specific endogenous chromosomal sequence can be any sequence in a nucleic acid region where it is desired to enhance homologous recombination. For example, the nucleic acid region may be a region which contains a gene in which it is desired to introduce a mutation, such as a point mutation or deletion, or a region into which it is desired to introduce a gene conferring a desired phenotype.

The disclosure provides methods of generating a modified plant in which a desired addition has been introduced. The methods can include obtaining a plant cell that includes an endogenous target DNA sequence into which it is desired to introduce a modification; generating a double-stranded cut within the endogenous target DNA sequence with an effector that includes a repeat domain that binds to an endogenous target DNA sequence and an endonuclease domain; introducing an exogenous nucleic acid that includes a sequence homologous to at least a portion of the endogenous target DNA into the plant cell under conditions which permit homologous recombination to occur between the exogenous nucleic acid and the endogenous target DNA sequence; and generating a plant from the plant cell in which homologous recombination has occurred. These methods may be applied to generate genetically modified plant and animal cells in vivo, in vitro or ex vivo. The target DNA sequence may be artificial or naturally occurring. These methods may be used in any organism (such non-limiting organisms to include animals, humans, fungi, oomycetes bacteria and viruses) using techniques and methods known in the art and utilized for such purposes in such organisms.

Modularly designed repeat domains of the disclosure may be combined with one or more domains responsible for the modulation or control of the expression of a gene, including, but not limited to, plant genes, animal genes, fungal genes, oomycete genes, viral genes, and/or human genes. Methods for modulating gene expression by generating DNA-binding polypeptides containing zinc finger domains have been described (U.S. Pat. Nos. 7,285,416, 7,521,241, 7,361,635, 7,273,923, 7,262,054, 7,220,719, 7,070,934, 7,013,219, 6,979,539, 6,933,113, 6,824,978, each of which is hereby herein incorporated by reference in its entirety). Effectors of the Xanthomonus and/or *Ralstonia* family, for example, may be modified to bind to specific target DNA sequences. Such polypeptides include, for example, transcription activators or repressor proteins of transcription that are modified by the methods of the disclosure to specifically bind to genetic control regions in a promoter of or other regulatory region for a gene of interest in order to activate, repress or otherwise modulate transcription of the gene.

Target DNA sequences of the disclosure may be modified to be specifically recognized by a naturally occurring repeat domain or by a modified repeat domain. As one example, the target DNA sequences for members of the Xanthomonus and/or *Ralstonia* family may be inserted into promoters to generate novel controllable promoters that can be induced by the corresponding effector. Secondary inducible systems may be constructed using a trans-activator and a target gene, wherein the trans-activator is a polypeptide wherein the polypeptide comprises at least a repeat domain comprising repeat units of the present invention that bind to the target gene and induce expression. The trans-activator and the target gene may be introduced into one cell line but may also be present in different cell lines and later be introgressed. Disease-resistant plants may be generated by inserting the target DNA sequence of a repeat domain containing polypeptide of the present invention in front of a gene that, after expression, leads to a defense reaction of the plant by activating a resistance-mediating gene.

Custom DNA-binding polypeptides may be constructed by rearranging repeat unit types resulting in the generation of repeat domains with novel target DNA binding specificity. Individual repeat units of the disclosure are nearly identical at the DNA level which precludes classical cloning strategies. The compositions and methods of the disclosure provide a quick and inexpensive strategy to assemble custom polypeptides with repeat domains. To improve cloning versatility such polypeptides, the disclosure provides a two-step assembly method. This method may be used to assemble polypeptides with novel repeat types to study their target DNA recognition and binding specificity.

Using the compositions and methods of the disclosure, DNA sequences may be generated to enable binding by a repeat domain containing polypeptide of the disclosure by introducing base pairs into any DNA region or specific regions of a gene, or into a genetic control element, to specifically target a polypeptide having a repeat domain comprised of repeat units that will bind a modified DNA sequence to facilitate specific recognition and binding to each other.

Polypeptides of the disclosure may be synthetically manufactured using known amino acid chemistries familiar to one of ordinary skill in organic chemistry synthesis. Such procedures include both solution and solid phase procedures, e.g., using either Boc or Fmoc methodologies.

Compounds of the disclosure may be synthesized using solid phase synthesis techniques.

The disclosure also provides a method for targeted modulation of gene expression by constructing modular repeat units specific for a target DNA sequence of interest, modifying a polypeptide by the addition of the repeat monomers so as to enable the polypeptide to now recognize the target DNA, introducing or expressing the modified polypeptide in a prokaryotic or eurkaryotic cell so as to enable the modified polypeptide to recognize the target DNA sequence, and modulating the expression of the target gene in the cell as a result of such recognition.

The disclosure also provides a method for directed modification of a target DNA sequence by the construction of a polypeptide including at least a repeat domain of the present invention that recognizes the target DNA sequence and that the polypeptide also contains a functional domain capable of modifying the target DNA (such as via site specific recombination, restriction or integration of donor target sequences) thereby enabling targeted DNA modifications in complex genomes.

The disclosure further provides for the production of modified polypeptides including at least a repeat domain comprising repeat units wherein a hypervariable region within each of the repeat units determines selective recognition of a base pair in a target DNA sequence. The disclosure provides DNA that encodes for a polypeptide containing a repeat domain as described above.

The disclosure provides a method for selectively recognizing base pairs in a target DNA sequence by a polypeptide wherein the polypeptide comprises at least a repeat domain comprising repeat units wherein each repeat unit contains a hypervariable region which determines recognition of a base pair in the target DNA sequence wherein consecutive repeat units correspond to consecutive base pairs in the target DNA sequence.

The disclosure provides a method of modulating expression of a target gene in a cell. Exemplary cells include, but are not limited to, a plant cell, a human cell, an animal cell, a fungal cell or any other living cell. Cells of the disclosure may contain a polypeptide of the disclosure that comprises at least a repeat domain comprising repeat units. Repeat units of the disclosure comprise a hypervariable region. Each repeat unit is responsible for the recognition of 1 base pair in a target DNA sequence. Polypeptides of the disclosure are introduced either as DNA encoding for a polypeptide or the polypeptide is introduced per se into the cell by methods described herein. Regardless of how the polypeptide is introduced into a cell, polypeptides of the disclosure comprise at least one repeat domain that specifically recognizes and preferably binds to a target DNA sequence of base pairs and modulates the expression of a target gene. Preferably, all repeat units contain a hypervariable region which determines recognition of base pairs in a target DNA sequence.

Examples of peptide sequences which can be linked to an polypeptide or RTN of the disclosure, for facilitating uptake of effectors into cells, include, but are not limited to: an 11 amino acid peptide of the tat protein of HIV; a 20 residue peptide sequence which corresponds to amino acids 84 103 of the p16 protein (see Fahraeus et al. (1996) Current Biology 6:84); the third helix of the 60-amino acid long homeodomain of Antennapedia (Derossi et al. (1994) J. Biol. Chem. 269:10444); the h region of a signal peptide such as the Kaposi fibroblast growth factor (K-FGF) h region; or the VP22 translocation domain from HSV (Elliot & O'Hare (1997) Cell 88:223 233). Other suitable chemical moieties that provide enhanced cellular uptake may also be chemically linked to effectors. As described herein, effectors can be designed to recognize any suitable target site, for regulation of expression of any endogenous gene of choice. Examples of endogenous genes suitable for regulation include VEGF, CCR5, ER.alpha., Her2/Neu, Tat, Rev, HBV C, S, X, and P, LDL-R, PEPCK, CYP7, Fibrinogen, ApoB, Apo E, Apo(a), renin, NF-.kappa.B, I-.kappa.B, TNF-.alpha., FAS ligand, amyloid precursor protein, atrial naturetic factor, ob-leptin, ucp-1, IL-1, IL-2, IL-3, IL-4, IL-5, IL-6, IL-12, G-CSF, GM-CSF, Epo, PDGF, PAF, p53, Rb, fetal hemoglobin, dystrophin, eutrophin, GDNF, NGF, IGF-1, VEGF receptors flt and flk, topoisomerase, telomerase, bcl-2, cyclins, angiostatin, IGF, ICAM-1, STATS, c-myc, c-myb, TH, PTI-1, polygalacturonase, EPSP synthase, FAD2-1, delta-12 desaturase, delta-9 desaturase, delta-15 desaturase, acetyl-CoA carboxylase, acyl-ACP-thioesterase, ADP-glucose pyrophosphorylase, starch synthase, cellulose synthase, sucrose synthase, senescence-associated genes, heavy metal chelators, fatty acid hydroperoxide lyase, viral genes, protozoal genes, fungal genes, and bacterial genes. In general, suitable genes to be regulated include, but are not limited to, cytokines, lymphokines, growth factors, mitogenic factors, chemotactic factors, onto-active factors, receptors, potassium channels, G-proteins, signal transduction molecules, disease resistance genes, and other disease-related genes.

Toxin molecules may be used to transport polypeptides across cell membranes. Often, such molecules are composed of at least two parts (called "binary toxins"): a translocation or binding domain or polypeptide and a separate toxin domain or polypeptide. Typically, the translocation domain or polypeptide binds to a cellular receptor, and then the toxin is transported into the cell. Several bacterial toxins, including Clostridium perfringens iota toxin, diphtheria toxin (DT), *Pseudomonas* exotoxin A (PE), pertussis toxin (PT), *Bacillus anthracis* toxin, and pertussis adenylate cyclase (CYA), have been used in attempts to deliver peptides to the cell cytosol as internal or amino-terminal fusions (Arora et al. (1993) J. Biol. Chem. 268:3334 3341; Perelle et al. (1993) Infect. Immun. 61:5147 5156 (1993); Stenmark et al. (1991) J. Cell Biol. 113:1025 1032 (1991); Donnelly et al. (1993) Proc. Natl. Acad. Sci. USA 90:3530 3534; Carbonetti et al. (1995) Abstr. Annu. Meet. Am. Soc. Microbiol. 95:295; Sebo et al. (1995) Infect. Immun. 63:3851 3857; Klimpel et al. (1992) Proc. Natl. Acad. Sci. USA 89:10277 10281; and Novak et al. (1992) J. Biol. Chem. 267:17186 17193).

Effectors can also be introduced into an animal cell, preferably a mammalian cell, via liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell, in this case an effector. The liposome fuses with the plasma membrane, thereby releasing the effector into the cytosol. Alternatively, the liposome is phagocytosed or taken up by the cell in a transport vesicle. Once in the endosome or phagosome, the liposome either degrades or fuses with the membrane of the transport vesicle and releases its contents.

The disclosure provides methods of generating a non-human, transgenic animal comprising a germline mutation comprising: introducing a vector comprising a nucleotide sequence encoding one or more of the proteins of the disclosure into a cell of the non-human, transgenic animal. Compositions of the disclosure may be administered to an organism locally or systemically.

The disclosure provides methods of mutagenizing the germ line of a non-human, transgenic animal comprising: introducing a nucleic acid molecule encoding one or more of the proteins of the disclosure into a cell under conditions sufficient to generate a transgenic animal.

Definitions

As used throughout the disclosure, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more standard deviations. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The disclosure provides isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

The disclosure provides fragments and variants of the disclosed DNA sequences and proteins encoded by these DNA sequences. As used throughout the disclosure, the term "fragment" refers to a portion of the DNA sequence or a portion of the amino acid sequence and hence protein encoded thereby. Fragments of a DNA sequence comprising coding sequences may encode protein fragments that retain biological activity of the native protein and hence DNA recognition or binding activity to a target DNA sequence as herein described. Alternatively, fragments of a DNA sequence that are useful as hybridization probes generally do not encode proteins that retain biological activity or do not retain promoter activity. Thus, fragments of a DNA sequence may range from at least about 20 nucleotides, about 50 nucleotides, about 100 nucleotides, and up to the full-length polynucleotide of the invention.

Nucleic acids or proteins of the disclosure can be constructed by a modular approach including preassembling monomer units and/or repeat units in target vectors that can subsequently be assembled into a final destination vector. Polypeptides of the disclosure may comprise repeat monomers of the disclosure and can be constructed by a modular approach by preassembling repeat units in target vectors that can subsequently be assembled into a final destination vector. The disclosure provides polypeptide produced by this method as well nucleic acid sequences encoding these polypeptides. The disclosure provides host organisms and cells comprising nucleic acid sequences encoding polypeptides produced this modular approach.

The term "antibody" is used in the broadest sense and specifically covers single monoclonal antibodies (including agonist and antagonist antibodies) and antibody compositions with polyepitopic specificity. It is also within the scope hereof to use natural or synthetic analogs, mutants, variants, alleles, homologs and orthologs (herein collectively referred to as "analogs") of the antibodies hereof as defined herein.

Thus, according to one embodiment hereof, the term "antibody hereof" in its broadest sense also covers such analogs. Generally, in such analogs, one or more amino acid residues may have been replaced, deleted and/or added, compared to the antibodies hereof as defined herein.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific or multivalent structures formed from antibody fragments. In an antibody fragment comprising one or more heavy chains, the heavy chain(s) can contain any constant domain sequence (e.g. CHI in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s). The term further includes single domain antibodies ("sdAB") which generally refers to an antibody fragment having a single monomeric variable antibody domain, (for example, from camelids). Such antibody fragment types will be readily understood by a person having ordinary skill in the art.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

The term "comprising" is intended to mean that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants or inert carriers. "Consisting of shall mean excluding more than trace elements of other ingredients and substantial method steps. Embodiments defined by each of these transition terms are within the scope of this invention.

The term "effector molecule" means a molecule, such as a protein or protein domain, oftentimes an enzymatic protein, capable of exerting a localized effect in a cell. The effector molecule may take a variety of different forms, including selectively binding to a protein or to DNA, for example, to regulate a biological activity. Effector molecules may have a wide variety of different activities, including, but not limited to nuclease activity, increasing or decreasing enzyme activity, increasing or decreasing gene expression, or affecting cell signaling. Other examples of effector molecules will be readily appreciated by one having ordinary skill in the art.

The term "epitope tag", or otherwise "affinity tag", refers to a short amino acid sequence or peptide enabling a specific interaction with a protein or a ligand.

The term "epitope" refers to an antigenic determinant of a polypeptide. An epitope could comprise three amino acids in a spatial conformation, which is unique to the epitope. Generally, an epitope consists of at least 4, 5, 6, or 7 such amino acids, and more usually, consists of at least 8, 9, or 10 such amino acids. Methods of determining the spatial conformation of amino acids are known in the art, and include, for example, x-ray crystallography and two-dimensional nuclear magnetic resonance.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

"Gene expression" refers to the conversion of the information, contained in a gene, into a gene product. A gene product can be the direct transcriptional product of a gene (e.g., mRNA, tRNA, rRNA, antisense RNA, ribozyme, shRNA, micro RNA, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" or "regulation" of gene expression refers to a change in the activity of a gene. Modulation of expression can include, but is not limited to, gene activation and gene repression.

The term "operatively linked" or its equivalents (e.g., "linked operatively") means two or more molecules are positioned with respect to each other such that they are capable of interacting to affect a function attributable to one or both molecules or a combination thereof.

Non-covalently linked components and methods of making and using non-covalently linked components, are disclosed. The various components may take a variety of different forms as described herein. For example, non-covalently linked (i.e., operatively linked) proteins may be used to allow temporary interactions that avoid one or more problems in the art. The ability of non-covalently linked components, such as proteins, to associate and dissociate enables a functional association only or primarily under circumstances where such association is needed for the desired activity. The linkage may be of duration sufficient to allow the desired effect.

A method for directing proteins to a specific locus in a genome of an organism is disclosed. The method may comprise the steps of providing a DNA localization component and providing an effector molecule, wherein the DNA localization component and the effector molecule are capable of operatively linking via a non-covalent linkage.

The term "scFv" refers to a single-chain variable fragment. scFv is a fusion protein of the variable regions of the heavy (VH) and light chains (VL) of immunoglobulins, connected with a linker peptide. The linker peptide may be from about 5 to 40 amino acids or from about 10 to 30 amino acids or about 5, 10, 15, 20, 25, 30, 35, or 40 amino acids in length. Single-chain variable fragments lack the constant Fc region found in complete antibody molecules, and, thus, the common binding sites (e.g., Protein G) used to purify antibodies. The term further includes a scFv that is an intrabody, an antibody that is stable in the cytoplasm of the cell, and which may bind to an intracellular protein.

The term "single domain antibody" means an antibody fragment having a single monomeric variable antibody domain which is able to bind selectively to a specific antigen. A single-domain antibody generally is a peptide chain of about 110 amino acids long, comprising one variable domain (VH) of a heavy-chain antibody, or of a common IgG, which generally have similar affinity to antigens as whole antibodies, but are more heat-resistant and stable towards detergents and high concentrations of urea. Examples are those derived from camelid or fish antibodies. Alternatively, single-domain antibodies can be made from common murine or human IgG with four chains.

The terms "specifically bind" and "specific binding" as used herein refer to the ability of an antibody, an antibody fragment or a nanobody to preferentially bind to a particular antigen that is present in a homogeneous mixture of different antigens. In certain embodiments, a specific binding interaction will discriminate between desirable and undesirable antigens in a sample, in some embodiments more than about ten- to 100-fold or more (e.g., more than about 1000- or 10,000-fold). "Specificity" refers to the ability of an immunoglobulin or an immunoglobulin fragment, such as a nanobody, to bind preferentially to one antigenic target versus a different antigenic target and does not necessarily imply high affinity.

A "target site" or "target sequence" is a nucleic acid sequence that defines a portion of a nucleic acid to which a binding molecule will bind, provided sufficient conditions for binding exist.

The terms "nucleic acid" or "oligonucleotide" or "polynucleotide" refer to at least two nucleotides covalently linked together. The depiction of a single strand also defines the sequence of the complementary strand. Thus, a nucleic acid may also encompass the complementary strand of a depicted single strand. A nucleic acid of the disclosure also encompasses substantially identical nucleic acids and complements thereof that retain the same structure or encode for the same protein.

Probes of the disclosure may comprise a single stranded nucleic acid that can hybridize to a target sequence under stringent hybridization conditions. Thus, nucleic acids of the disclosure may refer to a probe that hybridizes under stringent hybridization conditions.

Nucleic acids of the disclosure may be single- or double-stranded. Nucleic acids of the disclosure may contain double-stranded sequences even when the majority of the molecule is single-stranded. Nucleic acids of the disclosure may contain single-stranded sequences even when the majority of the molecule is double-stranded. Nucleic acids of the disclosure may include genomic DNA, cDNA, RNA, or a hybrid thereof. Nucleic acids of the disclosure may contain combinations of deoxyribo- and ribo-nucleotides. Nucleic acids of the disclosure may contain combinations of bases including uracil, adenine, thymine, cytosine, guanine, inosine, xanthine hypoxanthine, isocytosine and isoguanine. Nucleic acids of the disclosure may be synthesized to comprise non-natural amino acid modifications. Nucleic acids of the disclosure may be obtained by chemical synthesis methods or by recombinant methods.

Nucleic acids of the disclosure, either their entire sequence, or any portion thereof, may be non-naturally occurring. Nucleic acids of the disclosure may contain one or more mutations, substitutions, deletions, or insertions that do not naturally-occur, rendering the entire nucleic acid sequence non-naturally occurring. Nucleic acids of the disclosure may contain one or more duplicated, inverted or repeated sequences, the resultant sequence of which does not naturally-occur, rendering the entire nucleic acid sequence non-naturally occurring. Nucleic acids of the disclosure may contain modified, artificial, or synthetic nucleotides that do not naturally-occur, rendering the entire nucleic acid sequence non-naturally occurring.

Given the redundancy in the genetic code, a plurality of nucleotide sequences may encode any particular protein. All such nucleotides sequences are contemplated herein.

As used throughout the disclosure, the term "operably linked" refers to the expression of a gene that is under the control of a promoter with which it is spatially connected. A promoter can be positioned 5' (upstream) or 3' (downstream) of a gene under its control. The distance between a promoter and a gene can be approximately the same as the distance between that promoter and the gene it controls in the gene from which the promoter is derived. Variation in the distance between a promoter and a gene can be accommodated without loss of promoter function.

As used throughout the disclosure, the term "promoter" refers to a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

As used throughout the disclosure, the term "substantially complementary" refers to a first sequence that is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

As used throughout the disclosure, the term "substantially identical" refers to a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

As used throughout the disclosure, the term "variant" when used to describe a nucleic acid, refers to (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

As used throughout the disclosure, the term "vector" refers to a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid.

As used throughout the disclosure, the term "variant" when used to describe a peptide or polypeptide, refers to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity.

A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157: 105-132 (1982). The hydropathic index of an amino acid is based on a consideration of its hydrophobicity and charge. Amino acids of similar hydropathic indexes can be substituted and still retain protein function. In one aspect, amino acids having hydropathic indexes of 2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference.

Substitution of amino acids having similar hydrophilicity values can result in peptides retaining biological activity, for example immunogenicity. Substitutions can be performed with amino acids having hydrophilicity values within +2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

As used herein, "conservative" amino acid substitutions may be defined as set out in Tables A, B, or C below. In some embodiments, fusion polypeptides and/or nucleic acids encoding such fusion polypeptides include conservative substitutions have been introduced by modification of polynucleotides encoding polypeptides of the invention. Amino acids can be classified according to physical properties and contribution to secondary and tertiary protein structure. A conservative substitution is a substitution of one amino acid for another amino acid that has similar properties. Exemplary conservative substitutions are set out in Table A.

TABLE A

| Conservative Substitutions I | | |
|---|---|---|
| Side chain characteristics | | Amino Acid |
| Aliphatic | Non-polar | GAPILVF |
|  | Polar-uncharged | CSTMNQ |
|  | Polar-charged | DEKR |
| Aromatic |  | HFWY |
| Other |  | NQDE |

Alternately, conservative amino acids can be grouped as described in Lehninger, (Biochemistry, Second Edition; Worth Publishers, Inc. NY, N.Y. (1975), pp. 71-77) as set forth in Table B.

TABLE B

| Conservative Substitutions II | | |
|---|---|---|
| Side Chain Characteristic | | Amino Acid |
| Non-polar (hydrophobic) | Aliphatic: | ALIVP |
|  | Aromatic: | FWY |
|  | Sulfur-containing: | M |
|  | Borderline: | GY |
| Uncharged-polar | Hydroxyl: | STY |
|  | Amides: | NQ |
|  | Sulfhydryl: | C |
|  | Borderline: | GY |
| Positively Charged (Basic): |  | KRH |
| Negatively Charged (Acidic): |  | DE |

Alternately, exemplary conservative substitutions are set out in Table C.

TABLE C

Conservative Substitutions III

| Original Residue | Exemplary Substitution |
| --- | --- |
| Ala (A) | Val Leu Ile Met |
| Arg (R) | Lys His |
| Asn (N) | Gln |
| Asp (D) | Glu |
| Cys (C) | Ser Thr |
| Gln (Q) | Asn |
| Glu (E) | Asp |
| Gly (G) | Ala Val Leu Pro |
| His (H) | Lys Arg |
| Ile (I) | Leu Val Met Ala Phe |
| Leu (L) | Ile Val Met Ala Phe |
| Lys (K) | Arg His |
| Met (M) | Leu Ile Val Ala |
| Phe (F) | Trp Tyr Ile |
| Pro (P) | Gly Ala Val Leu Ile |
| Ser (S) | Thr |
| Thr (T) | Ser |
| Trp (W) | Tyr Phe Ile |
| Tyr (Y) | Trp Phe Thr Ser |
| Val (V) | Ile Leu Met Ala |

It should be understood that the polypeptides of the disclosure are intended to include polypeptides bearing one or more insertions, deletions, or substitutions, or any combination thereof, of amino acid residues as well as modifications other than insertions, deletions, or substitutions of amino acid residues. Polypeptides or nucleic acids of the disclosure may contain one or more conservative substitution.

As used throughout the disclosure, the term "more than one" of the aforementioned amino acid substitutions refers to 2, 3, 4, 5, 6, 7, 8, 9, 10, 11, 12, 13, 14, 15, 16, 17, 18, 19, or 20 or more of the recited amino acid substitutions. The term "more than one" may refer to 2, 3, 4, or 5 of the recited amino acid substitutions.

Polypeptides and proteins of the disclosure, either their entire sequence, or any portion thereof, may be non-naturally occurring. Polypeptides and proteins of the disclosure may contain one or more mutations, substitutions, deletions, or insertions that do not naturally-occur, rendering the entire amino acid sequence non-naturally occurring. Polypeptides and proteins of the disclosure may contain one or more duplicated, inverted or repeated sequences, the resultant sequence of which does not naturally-occur, rendering the entire amino acid sequence non-naturally occurring. Polypeptides and proteins of the disclosure may contain modified, artificial, or synthetic amino acids that do not naturally-occur, rendering the entire amino acid sequence non-naturally occurring.

As used throughout the disclosure, "sequence identity" may be determined by using the stand-alone executable BLAST engine program for blasting two sequences (bl2seq), which can be retrieved from the National Center for Biotechnology Information (NCBI) ftp site, using the default parameters (Tatusova and Madden, FEMS Microbiol Lett., 1999, 174, 247-250; which is incorporated herein by reference in its entirety). The terms "identical" or "identity" when used in the context of two or more nucleic acids or polypeptide sequences, refer to a specified percentage of residues that are the same over a specified region of each of the sequences. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

As used throughout the disclosure, the term "endogenous" refers to nucleic acid or protein sequence naturally associated with a target gene or a host cell into which it is introduced.

As used throughout the disclosure, the term "exogenous" refers to nucleic acid or protein sequence not naturally associated with a target gene or a host cell into which it is introduced, including non-naturally occurring multiple copies of a naturally occurring nucleic acid, e.g., DNA sequence, or naturally occurring nucleic acid sequence located in a non-naturally occurring genome location.

The disclosure provides methods of introducing a polynucleotide construct comprising a DNA sequence into a host cell. By "introducing" is intended presenting to the plant the polynucleotide construct in such a manner that the construct gains access to the interior of the host cell. The methods of the invention do not depend on a particular method for introducing a polynucleotide construct into a host cell, only that the polynucleotide construct gains access to the interior of one cell of the host. Methods for introducing polynucleotide constructs into bacteria, plants, fungi and animals are known in the art including, but not limited to, stable transformation methods, transient transformation methods, and virus-mediated methods.

By "stable transformation" is intended that the polynucleotide construct introduced into a plant integrates into the genome of the host and is capable of being inherited by progeny thereof. By "transient transformation" is intended that a polynucleotide construct introduced into the host does not integrate into the genome of the host.

As used throughout the disclosure, the term "genetically modified plant (or transgenic plant)" refers to a plant which comprises within its genome an exogenous polynucleotide. Generally, and preferably, the exogenous polynucleotide is stably integrated into the genome such that the polynucleotide is passed on to successive generations. The exogenous polynucleotide may be integrated into the genome alone or as part of a recombinant expression cassette. "Transgenic" is used herein to include any cell, cell line, callus, tissue, plant part or plant, the genotype of which has been altered by the presence of exogenous nucleic acid including those trans genies initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used throughout the disclosure, the term "modifying" is intended to mean that the sequence is considered modified simply by the binding of the polypeptide. It is not intended to suggest that the sequence of nucleotides is changed, although such changes (and others) could ensue following binding of the polypeptide to the nucleic acid of interest. In some embodiments, the nucleic acid sequence is DNA. Modification of the nucleic acid of interest (in the sense of binding thereto by a polypeptide modified to contain modular repeat units) could be detected in any of a number of methods (e.g. gel mobility shift assays, use of labelled polypeptides—labels could include radioactive, fluorescent, enzyme or biotin/streptavidin labels). Modification of the nucleic acid sequence of interest (and detection thereof) may be all that is required (e.g. in diagnosis of disease). Desirably, however, further processing of the sample is performed. Conveniently the polypeptide (and nucleic acid sequences specifically bound thereto) is separated from the rest of the sample. Advantageously the polypeptide-DNA complex is bound to a solid phase support, to facilitate such separation. For example, the polypeptide may be present in an acrylamide or agarose gel matrix or, more preferably, is immobilized on the surface of a membrane or in the wells of a microtitre plate.

All percentages and ratios are calculated by weight unless otherwise indicated.

All percentages and ratios are calculated based on the total composition unless otherwise indicated.

Every maximum numerical limitation given throughout this disclosure includes every lower numerical limitation, as if such lower numerical limitations were expressly written herein. Every minimum numerical limitation given throughout this disclosure will include every higher numerical limitation, as if such higher numerical limitations were expressly written herein. Every numerical range given throughout this disclosure will include every narrower numerical range that falls within such broader numerical range, as if such narrower numerical ranges were all expressly written herein.

The values disclosed herein are not to be understood as being strictly limited to the exact numerical values recited. Instead, unless otherwise specified, each such value is intended to mean both the recited value and a functionally equivalent range surrounding that value. For example, a value disclosed as "20 µm" is intended to mean "about 20 µm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the disclosure have been illustrated and described, various other changes and modifications can be made without departing from the spirit and scope of the disclosure. The scope of the appended claims includes all such changes and modifications that are within the scope of this disclosure.

EXAMPLES

In order that the invention disclosed herein may be more efficiently understood, examples are provided below. It should be understood that these examples are for illustrative purposes only and are not to be construed as limiting the invention in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

Example 1

Generating Nucleic Acid Vectors with *Ralstonia* TALs (RTALs) with Functional Analysis Cluster analysis and review of sequence homologies of *Ralstonia* genome revealed the sequence of SEQ ID NO: 1 which is homologous to known TAL sequences.

Nucleic acid sequences that encode the polypeptides of the claimed invention are made through molecular biology techniques known to those with ordinary skill in the art. DNA sequences, for instance, are synthesized with the XbaI and/or SalI restriction sites flanking each nucleic acid sequence that encodes the polyproteins of the present invention. Polymerase chain reaction is performed to amplify the DNA with certain restriction endonuclease sites. Sequences are gel-purified, isolated, and reconstituted in water or suitable buffer for ligation reactions. A plasmid that encodes a protein with effector function (such as nuclease function) that comprises requisite regulatory elements is ligated to one or more of the nucleic acid sequences that encode the following sequences at the plasmid multiple cloning sites:

```
a.
                                          (SEQ ID NO: 39)
LSTEQVVAIAS NK GGKQALEAVKAHLLDLLGAPYV b.
                                          (SEQ ID NO: 40)
LSTEQVVAIAS NN GGKQALEAVKAQLLELRAAPYE c.
                                          (SEQ ID NO: 41)
LSTAQVVAIAS NG GGKQALEGIGEQLLKLRTAPYG d.
                                          (SEQ ID NO: 42)
LSTAQVVAIAS HD GGKPALEAVWAKLPVLRGVPYA e.
                                          (SEQ ID NO: 43)
LSTEQVVTIAS SI GGKQALEAVKVQLPVLRAAPYE
```

Plasmid sequences are transformed in suitable bacteria for production of high copy numbers of plasmid. Plasmids containing at least one polypeptide above can be selected using antibiotic selection, isolated and purified from bacterial cells using techniques known to those skilled in the art.

Plasmids are built and in-vitro testing of expressed DNA-binding polypeptides is validated using the methods described in *Nature Biotechnology* 2012 May; 30(5):460-5. "FLASH assembly of TALENs for high-throughput genome editing." Reyon D, Tsai S Q, Khayter C, Foden J A, Sander J D, Joung J K, which is incorporated by reference in its entirety.

Construction of a Plasmid Archive Encoding Pre-Assembled TALE Repeats

TALE repeat arrays were constructed using the same architecture first described by Miller, J. C. et al. ("A TALE nuclease architecture for efficient genome editing.", *Nat*

*Biotechnol.* 2011; 29:143-148; the contents of which are herein incorporated by reference) in which distinct TALE repeat backbones that differ slightly in their amino acid and DNA sequences occur in a repeated pattern. The first, amino-terminal TALE repeat in an array was designated as the α unit. This α unit is followed by β, γ, and δ units and then an ε unit that is essentially identical to the α unit, except for the different positioning of a Type IIS restriction site on the 5' end (required to enable creation of a unique overhang on the α unit needed for cloning). The ε unit is then followed again by repeats of β, γ, δ and ε units. Due to constraints related to creation of a 3' end required for cloning, slightly modified DNA sequences were required for TALE repeat arrays that end with a carboxyterminal γ for ε unit.

Preparation of TALE Repeat-Encoding DNA Fragments for FLASH Assembly

To prepare DNA fragments encoding α units for use in FLASH assembly, 20 rounds of PCR are performed with each α unit plasmid as a template using primers oJS2581 (5'-Biotin-TCTAGAGAAGACAAGAACCTGACC-3') (SEQ ID NO: 44) and oJS2582(5'-GGATCCGGTCTCT-TAAGGCCGTGG-3') (SEQ ID NO: 45). The resulting PCR products are biotinylated on the 5' end. Each α PCR product is then digested with 40 units of BsaI-HF restriction enzyme to generate 4 bp overhangs, purified using the QIAquick PCR purification kit (QIAGEN) according to manufacturer's instructions except that the final product will be eluted in 50 μl of 0.1×EB.

To prepare DNA fragments encoding polypeptide repeats, 10 μg of each of these plasmids are digested with 50 units of BbsI restriction enzyme in NEBuffer 2 for 2 hours at 37° C. followed by serial restriction digests performed in NEBuffer 4 at 37° C. using 100 units each of XbaI, BamHI-HF, and SalI-HF enzymes that are added at 5 minute intervals. The latter set of restriction digestions are designed to cleave the plasmid backbone to ensure that this larger DNA fragment will not interfere with subsequent ligations performed during the FLASH assembly process. These restriction digest reactions are then purified using the QIAquick PCR purification kit (QIAGEN) according to manufacturer's instructions, except that the final product will be eluted in 180 μl of 0.1×EB.

Automated FLASH Assembly

All steps of FLASH assembly are performed using a Sciclone G3 liquid-handling workstation (Caliper) or similar device sold by another company in 96-well plates and using a SPRIplate 96-ring magnet (Beckman Coulter Genomics) and a DynaMag-96 Side magnet (Life Technologies). In the first step of FLASH, a biotinylated α unit fragment is ligated to the first βγδε fragment and then the resulting αβγδε fragments are bound to Dynabeads MyOne C1 streptavidin-coated magnetic beads (Life Technologies) in 2×B&W Buffer. Beads are then drawn to the side of the well by placing the plate on the magnet and then washed with 100 μl B&W buffer with 0.005% Tween 20 (Sigma) and again with 100 μl 0.1 mg/ml bovine serum albumin (BSA) (New England Biolabs). Additional βγδε fragments are ligated by removing the plate from the magnet, resuspending the beads in solution in each well, digesting the bead-bound fragment with BsaI-HF restriction enzyme, placing the plate on the magnet, washing with 100 μl B&W/Tween20 followed by 100 μl of 0.1 mg/ml BSA, and then ligating the next fragment. This process is repeated multiple times with additional βγδε units to extend the bead-bound fragment. The last fragment to be ligated is always a β, βγ*, βγδ, or δε* unit to enable cloning of the full-length fragment into expression vectors (note that fragments that end with a δε* unit will always be preceded by ligation of a βγ unit).

The final full-length bead-bound fragment is digested with 40 units of BsaI-HF restriction enzyme followed by 25 units of BbsI restriction enzyme (New England Biolabs). Digestion with BbsI released the fragment from the beads and generates a unique 5' overhang for cloning of the fragment. Digestion with BsaI-HF results in creation of a unique 3' overhang for cloning.

Subcloning of TALE Repeat Array-Encoding DNA Fragments into TALEN Expression Vectors DNA fragments encoding our FLASH assembled TALE repeat arrays are subcloned into TALE expression vectors. In some experiments, there are 4 or more separate plasmids. In some experiments, vectors include a CMV promoter, a translational start codon optimized for mammalian cell expression, a triple FLAG epitope tag, a nuclear localization signal, amino acids 153 to 288 from the TALE 13 protein (as numbered by Miller, J. C. et al. (*Nat Biotechnol.* 2011; 29:143-148; the contents of which are herein incorporated by reference), two unique and closely positioned Type IIS BsmBI restriction sites, a 0.5 TALE repeat domain encoding RVDs, amino acids 715 to 777 from the TALE 13 protein, and the wild-type FokI cleavage domain.

All DNA fragments assembled by FLASH possess overhangs that enable directional cloning into any of the expression vectors that are digested with BsmBI. Standard TALEN expression vectors (each possessing a different 0.5 TALE repeat) are available from suppliers such as Addgene and full sequences of these plasmids are freely available on a web page dedicated to these constructs: www.addgene.org/talengineering/expressionvectors/ for synthetic construction.

To prepare a TALEN expression vector for subcloning, 5 μg of plasmid DNA is digested with 50 units of BsmBI restriction enzyme (New England Biolabs) in NEBuffer 3 for 8 hours at 55 degrees C. Digested DNA will be purified using 90 μl of Ampure XP beads (Agencourt) according to manufacturer's instructions and diluted to a final concentration of 5 ng/μl in 1 mM TrisHCl. FLASH-assembled TALE repeat arrays are ligated into TALEN expression vectors using 400 U of T4 DNA Ligase (New England Biolabs). Ligation products are transformed into chemically competent XL-1 Blue cells. Typically, six colonies are picked for each ligation and plasmid DNA is isolated by an alkaline lysis miniprep procedure. Simultaneously, the same colonies are screened by PCR using primers oSQT34 (5'-GACGGTGGCTGTCAAATACCAAGATATG-3') (SEQ ID NO: 46) and oSQT35 (5'-TCTCCTCCAGTT-CACTTTTGACTAGTTGGG-3') (SEQ ID NO: 47). PCR products are analyzed on a QIAxcel capillary electrophoresis system (Qiagen). Miniprep DNA from clones that contain correctly sized PCR products are sent for DNA sequence confirmation with primers oSQTI (5'-AGTAACAGCGGTAGAGGCAG-3') (SEQ ID NO: 48), oSQT3 (5'-ATTGGGCTAC-GATGGACTCC-3') (SEQ ID NO: 49), and oJS2980 (5'-TTAATTCAATATATTCATGAGGCAC-3') (SEQ ID NO: 50); oSQTI anneals at the 5' end of the TALE repeat array coding sequence and enables sequencing of the amino-terminal half of the assembled array, oSQT3 anneals at the 3' end of the TALE repeat array coding sequence and enables sequencing of the carboxy-terminal half of the assembled array, and oJS2980 primes within the coding sequence of the FokI domain (downstream of oSQT3) and enables sequencing and verification of the carboxy-terminal 0.5 TALE repeat domain.

Six colonies for each assembly are screened as described above, followed by six additional colonies if necessary. With this approach, one or more sequence-verified clones are generated for >90% of assembly reactions. These percentages are derived primarily from experiments designed to construct DNA fragments encoding 16.5 TALE repeats.

EGFP TALEN Activity and Toxicity Assays

EGFP reporter assays are performed in a clonal U2OS human cell line bearing an integrated construct that constitutively expresses an EGFP-PEST fusion protein. This clonal line is derived from a polyclonal U2OS EGFP-PEST reporter line. Clonal U2OS EGFP-PEST cells are cultured in Advanced DMEM (Life Technologies) supplemented with 10% FBS, 2 mM GlutaMax (Life Technologies), penicillin/streptomycin, and 400 µg/ml G418. Cells are transfected in triplicate with 500 ng of each TALEN plasmid DNA and 50 ng ptdTomato-N1 plasmid DNA using a Lonza 4D-Nucleofector System, Solution SE, and program DN-100 according to manufacturer's instructions. 1 µg of ptdTomato-N1 plasmid alone is transfected in triplicate as a negative control. Cells are assayed for EGFP and tdTomato expression at 2 and 5 days post-transfection using a BD FACSAriaII flow cytometer.

PCR Amplification and Sequence Verification of Endogenous Human Genes

PCR reactions to amplify targeted loci are performed.

Standard PCR conditions with Phusion Hot Start II high-fidelity DNA polymerase (Thermo-Fisher) are performed according to manufacturer's instructions for 35 cycles (98° C., 10 s denaturation; 68° C., 15 s annealing; 72° C., 30 s extension). For loci that do not amplify under standard conditions one of the following modifications is used: 1) the addition of betaine to a final concentration of 1.8M, 2) touchdown PCR ([98° C., 10 s; 72-62° C., −1° C./cycle, 15 s; 72° C., 30 s]$_{10\ cycles}$, [98° C., 10 s; 62° C., −1° C./cycle, 15 s; 72° C., 30 s]$_{25\ cycles}$) with 1.8M betaine, and 3) the addition of 3% or 5% DMSO and an annealing temperature of 65° C. PCR products are analyzed for correct size on a QIAxcel capillary electrophoresis system. Correctly sized products are treated with ExoSap-IT (Affymetrix) to remove unincorporated nucleotides or primers and sent for DNA sequencing to confirm the endogenous gene sequence.

T7 Endonuclease I Assay for Quantifying NHEJ-Mediated Mutation of Endogenous Human Genes U2OS-EGFP cells are cultured and transfected in duplicate as described above. Genomic DNA is isolated from cells transfected with TALEN-encoding or control plasmids using a high-throughput magnetic-bead based purification system (Agencourt DNAdvance) according to the manufacturer's instructions. PCR to amplify endogenous loci are performed for 35 cycles as described above and fragments were purified with Ampure XP (Agencourt) according to manufacturer's instructions. 200 ng of purified PCR product are denatured and reannealed in NEBuffer 2 (New England Biolabs) using a thermocycler with the following protocol (95° C., 5 min; 95-85° C. at −2° C./s; 85-25° C. at −0.1° C./s; hold at 4° C.). 33 Hybridized PCR products were treated with 10 U of T7 Endonuclease I at 37° C. for 15 minutes in a reaction volume of 20 µl. Reactions are stopped by the addition of 2 µl 0.5 M EDTA, purified with Ampure XP, and quantified on a QIAxcel capillary electrophoresis system using method OM500. The sum of the area beneath TALEN-specific cleavage peaks (expressed as a percentage of the parent amplicon peak, denoted fraction cleaved) is used to estimate gene modification levels using the following equation as previously described.

$$\% \text{ gene modification}=100\times(1-(1-\text{fraction cleaved})^{1/2})$$

Example 2

RTN Constructs

Five fragments shown below were synthesized and each cloned into a modified pUC57: pUC57-ΔBsaI (vectors as disclosed in Juong et. al. FLASH assembly paper. The modified pUC57: pUC57-ΔBsaI contains single basepair change to disrupt a BsaI site) with XbaI and BamHI.

RTN1 EBEs:

```
NK (SEQ ID NO: 51):
XbaI BbsI
ATGCA T^CTAGA-GAAGACAA^CTGA-

GCACCGAGCAGGTGGTGGCCATCGCCAGCAACAAGGGCGGCAAGCAGGCCCTG

GAGGCCGTGAAGGCCCACCTGCTGGACCTGCTGGGCGCCCCCTACGAG-

CTGA^AGAGACC-G^GATCC(CGGGC)  BsaI
BamHI

NN (SEQ ID NO: 52):
ATGCA
TCTAGAGAAGACAACTGAGCACCGAGCAGGTGGTGGCCATCGCCAGCAACAACG
GCGGCAAGCAGGCCCTGGAGGCCGTGAAGGCCCAGCTGCTGGAGCTGAGGGCCG
CCCCCTACGAGCTGAAGAGACCGGATCC CGGGC

NG (SEQ ID NO: 53):
ATGCA
TCTAGAGAAGACAACTGAGCACCGagCAGGTGGTGGCCATCGCCAGCAACGGCG
GCGGCAAGCAGGCCCTGGAGGGCATCGGCGAGCAGCTGCTGAAGCTGAGGACC
GCCCCCTACGAGCTGAAGAGACCGGATCC CGGGC
```

-continued

HD (SEQ ID NO: 54):
ATGCA

TCTAGAGAAGACAACTGAGCACCGagCAGGTGGTGGCCATCGCCAGCCACGACG

GCGGCAAGCCCGCCCTGGAGGCCGTGTGGGCCAAGCTGCCCGTGCTGAGGGGCG

TGCCCTACGAGCTGAAGAGACCGGATCC CGGGC

SI (SEQ ID NO: 55):
ATGCA

TCTAGAGAAGACAACTGAGCACCGAGCAGGTGGTGACCATCGCCAGCAGCATC

GCGGCAAGCAGGCCCTGGAGGCCGTGAAGGTGCAGCTGCCCGTGCTGAGGGCC

CCCCCTACGAGCTGAAGAGACCGGATCC CGGGC

For proof of principle, these cloned fragments are used to generate chimeric proteins of six repeat units fused to FokI nuclease, i.e. a chimeric protein that targets a string of A (C, T and G) nucleotides. These chimeric proteins are then tested for binding/targeting efficiency to desired DNA bases using a reporter construct.

Once the binding efficiency of these units are confirmed, a library of *Ralstonia* EBEs are generated that are a copy of FLASH TALEN's *Xanthomonas* EBE library. This library can then be used to generate *Ralstonia* TALENs following the exact protocol of the FLASH TALEN system.

Example 3

Generating Nucleic Acid Vectors with Methylesterase

Additional sequences cloned from other species or cloned from the same species may be used functionally as an enzyme either by itself or in series as a monomer or polymer (protein fusion) for performing any of the experiments disclosed herein with DNA recognition. A RVD identification consensus sequence was created using sequence optimization techniques known in the art. A BLAST search was performed across methlyesterase sequences in bacterial species (see FIG. 1). The following polypeptides were identified as having DNA base pair recognition capability similar to the nucleic acid sequences and polypeptides disclosed herein SEQ ID NO: 1-19:

TABLE D

| TAL EBE against methylesterases | | | | |
|---|---|---|---|---|
| #1<br>Xanthomonas Consensus EBEs | | | | |
| LTPDQVVAIASNGGGKQALETVQRLLPVLCQDHG (SEQ ID NO: 56) | | | | |
| LTPEQVVAIANNNGGKQALETVQRLLPVLCQAHG (SEQ ID NO: 57) | | | | |
| LTPDQVVAIASHDGGKQALETVQRLLPVLCQAHG (SEQ ID NO: 58) | | | | |
| LTPAQVVAIASNIGGKQALETVQRLLPVLCQDHG (SEQ ID NO: 59) | | | | |
| EJ092907 | 166 | TTDRVVALGTSTGGTQALEVVLRQLPVDC | 194 | (SEQ ID NO: 60) |
| YP_001187060 | 166 | TTDRVVALGTSTGGTQALEVVLRQLPVDC | 194 | (SEQ ID NO: 61) |
| YP_003847734 | 169 | MTSEQIVAIGTSTGGTQALEAVLTALPRVC | 198 | (SEQ ID NO: 62) |
| ZP_08780698 | 167 | TTDRVVAIGTSTGGTALEVVLTALPRVC | 195 | (SEQ ID NO: 63) |
| YP_004846745 | 185 | TTERIVAIGTSTGGTALETVLHRLPATC | 213 | (SEQ ID NO: 64) |
| YP_005027668 | 186 | TTDKIIAIGTSTGGTALEAVLTKLPAVC | 214 | (SEQ ID NO: 65) |
| ZP_ 10991552 | 174 | TTERIVAIGTSTGGTQALETVLTALPRVC | 202 | cSEQ ID NO: 66) |
| YP_001792820 | 162 | TTERVVALGTSTGGTALEVVLRTLPRVC | 190 | (SEQ ID NO: 67) |
| EKE17764 | 172 | TTDOLIAIGTSTGGTQALEAILTKLPATC | 200 | (SEQ ID NO: 68) |
| ZP_03698248 | 178 | TTERIVAIGTSTGGTALETVLPRLPATC | 206 | (SEQ ID NO: 69) |
| EGH48032 | 11 | TTERIVAIGTSTGGTALEAVLTALPRVC | 39 | (SEQ ID NO: 70) |
| ZP_06495900 | 1 | TTERIVAIGTSTGGTALEAVLTALPRVC | 29 | (SEQ ID NO: 71) |
| ZP_10381001 | 76 | TTERIVAIGTSTGGTALEAVLTALPRVC | 104 | (SEQ ID NO: 72) |
| ZP_10442431 | 158 | TSDKVVAIGASTGGTQALELLLTGLPAVC | 186 | (SEQ ID NO: 73) |
| #2 | | | | |
| ZP_10991552 | 174 | TTERIVAIGTSTGGTALETVLTALPRVC | 202 | (SEQ ID NO: 74) |
| EGH48032 | 11 | TTERIVAIGTSTGGTQALEAVLTALPRVC | 39 | (SEQ ID NO: 751 |
| ZP_06495900 | 1 | TTERIVAIGTSTGGTQALEAVLTALPRVC | 29 | (SEQ ID NO: 76) |
| EGH61007 | 172 | TTERIVAIGTSTGGTALEAVLTALPRVC | 200 | (SEQ ID NO: 77) |
| EGH06695 | 172 | TTERIVAIGTSTGGTQALEAVLTALPRVC | 200 | (SEQ ID NO: 78) |
| EGH31878 | 172 | TTERIVAIGTSTGGTQALEAVLTALPRVC | 200 | (SEQ ID NO: 79) |
| EGH66597 | 172 | TTERIVAIGTSTGGTQALEAVLTALPRVC | 200 | (SEQ ID NO: 80) |
| ZP_07003572 | 172 | TTERIVAIGTSTGGTQALEAVLTALPRVC | 200 | (SEQ ID NO: 81) |
| ZP_06457223 | 172 | TTERIVAIGTSTGGTQALEAVLTALPRVC | 200 | (SEQ ID NO: 82) |
| ZP_04590480 | 172 | TTERIVAIGTSTGGTQALEAVLTALPRVC | 200 | (SEQ ID NO: 83 |
| ZP_07251539 | 172 | TTERIVAIGTSTGGTQALEAVLTALPRVC | 200 | (SEQ ID NO: 84) |
| NP_790747 | 172 | TTERIVAIGTSTGGTQALEAVLTALPRVC | 200 | (SEQ ID NO: 85) |

TABLE D-continued

TAL EBE against methylesterases

#1
Xanthomonas Consensus EBEs

| | | | | |
|---|---|---|---|---|
| EGH77388 | 172 | TTERIVAIGTSTGGTQALEAVLTALPRVC | 200 | (SEQ ID NO: 86) |
| EFW86187 | 172 | TTERIVAIGTSTGGTQALEAVLTALPRVC | 200 | (SEQ ID NO: 871) |
| EG1154563 | 172 | TTERIVAIGTSTGGTQALEAVLTALPRVC | 200 | (SEQ ID NO: 88) |
| YP_233877 | 172 | TTERIVAIGTSTGGTALEAVLTALPRVC | 200 | (SEQ ID NO: 89) |
| EGH23390 | 172 | TTERIVAIGTSTGGTQALEAVLTALPRVC | 200 | (SEQ ID NO: 90) |
| ZP_05638023 | 172 | TTERIVAIGTSTGGTQALEAVLTALPRVC | 200 | (SEQ ID NO: 91) |
| EGH71924 | 106 | TTERIVAIGTSTGGTQALEAVLTALPRVC | 134 | (SEQ ID NO: 92) |
| EFW82095 | 172 | TTERIVAIGTSTGGTQALEAVLTALPRVC | 200 | (SEQ ID NO: 93) |
| ZP_07265841 | 172 | TTERIVAIGTSTGGTQALEAVLTALPRVC | 200 | (SEQ ID NO: 94) |
| YP_273082 | 172 | TTERIVAIGTSTGGTALEAVLTALPRVC | 200 | (SEQ ID NO: 951) |
| YP_004030667 | 117 | FSQADIVRIADNIGGAQALKAVLEHGPTL | 145 | (SEQ ID NO: 96) |
| YP_004030667 | 186 | ADIVKIASNGGGAQALEAVAMHGSTLCE | 213 | (SEQ ID NO: 97) |
| YP_004030667 | 153 | ADIVKIAGNGGGARALKAVVMHGPTLCE | 180 | (SEQ ID NO: 98) |
| ZP_10995147 | 155 | TTDRVVALGCSTGGTQALEFILRQLPRDC | 183 | (SEQ ID NO: 99) |
| EGH56182 | 30 | ALAAAVGGKGALEVPANLIPANCE | 53 | (SEQ ID NO: 100) |
| YP_003907367 | 173 | RIVAIGTSTGGTQALEVVLTALP | 195 | (SEQ ID NO: 101) |
| EBE1 | | LTPDQVVAIASNGGGKQALETVQRLLPVLCQDHG | 34 | (SEQ ID NO: 102) |
| EBE4 | | LTPAQVVAIASNIGGKQALETVQRLLPVLCQDHG | 34 | (SEQ ID NO: 103) |
| EBE3 | | LTPDQVVAIASHDGGKQALETVQRLLPVLCQAHG | 34 | (SEQ ID NO: 104) |
| EBE2 | | LTPEQVVAIANNNGGKQALETVQRLLPVLCQAHG | 34 | (SEQ ID NO: 105) |
| ZP_07265841_2 | | -TTERIVAIGTSTGGTQALEAVLTALPRVC---- | 29 | (SEQ ID NO: 106) |
| YP_273082_2 | | -TTERIVAIGTSTGGTQALEAVLTALPRVC---- | 29 | (SEQ ID NO: 107) |
| EFW82095_2 | | -TTERIVAIGTSTGGTQALEAVLTALPRVC---- | 29 | (SEQ ID NO: 108) |
| EG1171924_2 | | -TTERIVAIGTSTGGTQALEAVLTALPRVC---- | 29 | (SEQ ID NO: 109) |
| ZP_05638023_2 | | -TTERIVAIGTSTGGTQALEAVLTALPRVC---- | 29 | (SEQ ID NO: 110) |
| EGH23390_2 | | -TTERIVAIGTSTGGTQALEAVLTALPRVC---- | 29 | (SEQ ID NO: 111) |
| YP_233877_2 | | -TTERIVAIGTSTGGTQALEAVLTALPRVC---- | 29 | (SEQ ID NO: 112) |
| EGH54563_2 | | -TTERIVAIGTSTGGTQALEAVLTALPRVC---- | 29 | (SEQ ID NO: 113) |
| EFW86187_2 | | -TTERIVAIGTSTGGTQALEAVLTALPRVC---- | 29 | (SEQ ID NO: 114) |
| EGH77388_2 | | -TTERIVAIGTSTGGTQALEAVLTALPRVC---- | 29 | (SEQ ID NO: 115) |
| NP_790747_2 | | -TTERIVAIGTSTGGTQALEAVLTALPRVC---- | 29 | (SEQ ID NO: 116) |
| ZP_07251539_2 | | -TTERIVAIGTSTGGTQALEAVLTALPRVC---- | 29 | (SEQ ID NO: 117) |
| ZP_04590480_2 | | -TTERIVAIGTSTGGTQALEAVLTALPRVC---- | 29 | (SEQ ID NO: 118) |
| ZP_06457223_2 | | -TTERIVAIGTSTGGTQALEAVLTALPRVC---- | 29 | (SEQ ID NO: 119) |
| ZP_07003572_2 | | -TTERIVAIGTSTGGTQALEAVLTALPRVC---- | 29 | (SEQ ID NO: 120) |
| EGH66597_2 | | -TTERIVAIGTSTGGTQALEAVLTALPRVC---- | 29 | (SEQ ID NO: 121) |
| EGH3I878_2 | | -TTERIVAIGTSTGGTQALEAVLTALPRVC---- | 29 | (SEQ ID NO: 122) |
| EGH06695_2 | | -TTERIVAIGTSTGGTQALEAVLTALPRVC---- | 29 | (SEQ ID NO: 123) |
| EGH6I007_2 | | -TTERIVAIGTSTGGTQALEAVLTALPRVC---- | 29 | (SEQ ID NO: 124) |
| ZP_06495900_2 | | -TTERIVAIGTSTGGTQALEAVLTALPRVC---- | 29 | (SEQ ID NO: 125) |
| EGH48032_2 | | -TTERIVAIGTSTGGTQALEAVLTALPRVC---- | 29 | (SEQ ID NO: 126) |
| ZP_10381001 | | -TTERIVAIGTSTGGTQALEAVLTALPRVC---- | 29 | (SEQ ID NO: 127) |
| ZP_06495900 | | -TTERIVAIGTSTGGTQALEAVLTALPRVC---- | 29 | (SEQ ID NO: 128) |
| EGH48032 | | -TTERIVAIGTSTGGTQALEAVLTALPRVC---- | 29 | (SEQ ID NO: 129) |
| YP_003847734 | | MTSEQIVAIGTSTGGTQALEAVLTALPRVC---- | 30 | (SEQ ID NO: 130) |
| ZP_10991552 | | -TTERIVAIGTSTGGTQALETVLTALPRVC---- | 29 | (SEQ ID NO: 131) |
| ZP_10991552_2 | | -TTERIVAIGTSTGGTQALETVLTALPRVC---- | 29 | (SEQ ID NO: 132) |
| YP_003907367_2 | | ----RIVAIGTSTGGTQALEVVLTALP------- | 23 | (SEQ ID NO: 133) |
| EJ092907 | | -TTDRVVALGTSTGGTQALEVVLRQLPVDC---- | 29 | (SEQ ID NO: 134) |
| YP_001187060 | | -TTDRVVALGTSTGGTQALEVVLRQLPVDC---- | 29 | (SEQ ID NO: 135) |
| ZP_10995147_2 | | -TTDRVVALGCSTGGTQALEFILRQLPRDC---- | 29 | (SEQ ID NO: 136) |
| YP_001792820 | | -TTERVVALGTSTGGTQALEVVLRTLPRVC---- | 29 | (SEQ ID NO: 137) |
| ZP_08780698 | | -TTDRVVAIGTSTGGTQALEVVLTALPRVC---- | 29 | (SEQ ID NO: 138) |
| YP_004846745 | | -TTERIVAIGTSTGGTQALETVLHRLPATC---- | 29 | (SEQ ID NO: 139) |
| ZP_03698248 | | -TTERIVAIGTSTGGTQALETVLPRLPATC---- | 29 | (SEQ ID NO: 140) |
| YP_005027668 | | -TTDKIIAIGTSTGGTQALEAVLTKLPAVC---- | 29 | (SEQ ID NO: 141) |
| EKE17764 | | -TTDQUAIGTSTGGTQALEAILTKLPATC---- | 29 | (SEQ ID NO: 142) |
| ZP_10442431 | | -TSDKVVAIGASTGGTQALELLLTGLPAVC---- | 29 | (SEQ ID NO: 143) |
| YP_004030667_2b | | ---ADIVKIASNGGGAQALEAVAMHGSTLCE--- | 28 | (SEQ ID NO: 144) |
| YP_004030667_2c | | ---ADIVKIAGNGGGARALKAVVMHGPTLCE--- | 28 | (SEQ ID NO: 145) |
| YP_004030667_2a | | FSQADIVRIADNIGGAQALKAVLEHGPTL----- | 29 | (SEQ ID NO: 146) |
| EGH56182_2 | | -------ALAAAVGGKGALEVPANLIPANCE--- | 24 | (SEQ ID NO: 147) |

Example 4

A pair of Bmpr2 specific EBEs (*Ralstonia* DNA binding domain, 16EBEs each) are gene synthesized and cloned into XTN-BB (*Xanthomonas* TAL backbone fused to FokI). These constructs are co-transfected into Rat C6 cells and gDNA extracted after 48 hrs for Cell surveyor nuclease assay. A successful assay should produce 240 bp and 150 bp subpopulations from the original 400 bp amplicon of the locus. The results are shown in the FIG. 2.

The assay reveals the expected 250 bp and 150 bp bands in the *Ralstonia* and *Xanthomonas* TALEN transfected cells, which are absent in the WT negative control. This indicates that the *Ralstonia* EBEs target this locus and the fusion of FokI nuclease to *Ralstonia* EBEs lead to targeted digestion of genomic DNA. Using the 250 bp band, 5.75% for XTN, 1.82% for RTN. Using the 150 bp band, 3.66% for XTN, 5.43% for RTN.

| | |
|---|---|
| Bmpr2 Target site (SEQ ID NO: 148) | T-T-GATA-GTCG-CCTT-ATG-Ttttggatacagaatgt**T-GAC-AGGT-AAAC-GAAA-T-A** |
| Fwd RTN | TGATAGTCGCCTTATG (SEQ ID NO: 149) |
| Rev RTN | ATTTGGTTTACCTGTC (SEQ ID NO: 150) |

Note:

the first and the last nucleotide of the targeted site (underlined) are not specified by the RTNs. These are specified by the Xanthomonas TALEN backbone.

Bmpr2 FWD RTN EBEs' amino acid sequence:

(SEQ ID NO: 151)
LSTAQVVAIAS NG GGKQALEGIGEQLLKLRTAPYG (SEQ ID NO: 152)
LSTEQVVAIAS NK GGKQALEAVKAHLLDLLGAPYV (SEQ ID NO: 153)
LSTEQVVAIAS NN GGKQALEAVKAQLLELRAAPYE (SEQ ID NO: 154)
LSTAQVVAIAS NG GGKQALEGIGEQLLKLRTAPYG (SEQ ID NO: 155)
LSTEQVVAIAS NN GGKQALEAVKAQLLELRAAPYE (SEQ ID NO: 156)
LSTEQVVAIAS NK GGKQALEAVKAHLLDLLGAPYV (SEQ ID NO: 157)
LSTAQVVAIAS NG GGKQALEGIGEQLLKLRTAPYG (SEQ ID NO: 158)
LSTAQVVAIAS HD GGKPALEAVWAKLPVLRGVPYA (SEQ ID NO: 159)
LSTEQVVAIAS NK GGKQALEAVKAHLLDLLGAPYV (SEQ ID NO: 160)
LSTAQVVAIAS HD GGKPALEAVWAKLPVLRGVPYA (SEQ ID NO: 161)
LSTAQVVAIAS HD GGKPALEAVWAKLPVLRGVPYA (SEQ ID NO: 162)
LSTAQVVAIAS NG GGKQALEGIGEQLLKLRTAPYG (SEQ ID NO: 163)
LSTAQVVAIAS NG GGKQALEGIGEQLLKLRTAPYG (SEQ ID NO: 164)
LSTEQVVAIAS NN GGKQALEAVKAQLLELRAAPYE (SEQ ID NO: 165)
LSTAQVVAIAS NG GGKQALEGIGEQLLKLRTAPYG (SEQ ID NO: 166)
LSTEQVVAIAS NK GGKQALEAVKAHLLDLLGAPYV

Bmpr2 FWD RTN DNA sequence:
(Bolded font: synthesized Ralstonia EBEs) This sequence is contiguous (SEQ ID NO: 167):
GACGGATCGGGAGATCTCCCGATCCCCTATGGTCGACTCTCAGTACAATCTGCTCTGATGCCGCATAGTTAAGCCAGTATCTGCTCCCT GCTTGTGTGTTGGAGGTCGCTGAGTAGTGCGCGAGCAAAATTTAAGCTACAACAAGGCAAGGCTTGACCGACAATTGCATGAAGAAT CTGCTTAGGGTTAGGCGTTTTGCGCTGCTTCGCGATGTACGGGCCAGATATACGCGTTGACATTGATTATTGACTAGTTATTAATAGTA ATCAATTACGGGGTCATTAGTTCATAGCCCATATATGGAGTTCCGCGTTACATAACTTACGGTAAATGGCCCGCCTGGCTGACCGCCC AACGACCCCCGCCCATTGACGTCAATAATGACGTATGTTCCCATAGTAACGCCAATAGGGACTTTCCATTGACGTCAATGGGTGGAgT ATTTACGGTAAACTGCCCACTTGGCAGTACATCAAGTGTATCATATGCCAAGTACGCCCCCTATTGACGTCAATGACGGTAAATGGCC CGCCTGGCATTATGCCCAGTACATGACCTTATGGGACTTTCCTACTTGGCAGTACATCTACGTATTAGTCATCGCTATTACCATGGTGA TGCGGTTTTGGCAGTACATCAATGGGCGTGGATAGCGGTTTGACTCACGGGGATTTCCAAGTCTCCACCCCATTGACGTCAATGGGAG TTTGTTTTGGCACCAAAATCAACGGGACTTTCCAAAATGTCGTAACAACTCCGCCCCATTGACGCAAATGGGCGGTAGGCGTGTACGG TGGGAGGTCTATATAAGCAGAGCTCTCTGGCTAACTAGAGAACCCACTGCTTACTGGCTTATCGAAATTAATACGACTCACTATAGGG AGACCCAAGCTGGCTAGCACCATGGACTACAAAGACCATGACGGTGATTATAAAGATCATGACATCGATTACAAGGATGACGATGAC AAGATGGCCCCCAAGAAGAAGAGGAAGGTGGGCATTCACCGCGGGGTACCTATGGTGGACTTGAGGACACTCGGTTATTCGCAACAG CAACAGGAGAAAATCAAGCCTAAGGTCAGGAGCACCGTCGCGCAACACCACGAGGCGCTTGTGGGGCATGGCTTCACTCATGCGCAT ATTGTCGCGCTTTCACAGCACCCTGCGGCGCTTGGGACGGTGGCTGTCAAATACCAAGATATGATTGCGGCCCTGCCCGAAGCCACGC ACGAGGCAATTGTAGGGGTCGGTAAACAGTGGTCGGGAGCGCGAGCACTTGAGGCGCTGCTGACTGTGGCGGGTGAGCTTAGGGGGC CTCCGCTCCAGCTCGACACCGGGCAGCTGCTGAAGATCGCGAAGAGAGGGGGAGTAACAGCGGTAGAGGCAGTGCACGCCTGGCGC

AATGCGCTCACCGGGGCCCCCTTGAAC

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGAGCAGGTGGTGGCCATCGCCAGCAACAAG

GGCGGCAAGCAGGCCCTGGAGGCCGTGAAGGCCCACCTGCTGGACCTGCTGGGCGCCCCCTACGTG

CTGAGCACCGAGCAGGTGGTGGCCATCGCCAGCAACAAC

GGCGGCAAGCAGGCCCTGGAGGCCGTGAAGGCCCAGCTGCTGGAGCTGAGGGCCGCCCCCTACGAG

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGAGCAGGTGGTGGCCATCGCCAGCAACAAC

GGCGGCAAGCAGGCCCTGGAGGCCGTGAAGGCCCAGCTGCTGGAGCTGAGGGCCGCCCCCTACGAG

CTGAGCACCGAGCAGGTGGTGGCCATCGCCAGCAACAAG

GGCGGCAAGCAGGCCCTGGAGGCCGTGAAGGCCCACCTGCTGGACCTGCTGGGCGCCCCCTACGTG

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGCCCAGGTGGTGGCCATCGCCAGCCACGAC

GGCGGCAAGCCCGCCCTGGAGGCCGTGTGGGCCAAGCTGCCCGTGCTGAGGGGCGTGCCCTACGCC

CTGAGCACCGAGCAGGTGGTGGCCATCGCCAGCAACAAG

GGCGGCAAGCAGGCCCTGGAGGCCGTGAAGGCCCACCTGCTGGACCTGCTGGGCGCCCCCTACGTG

CTGAGCACCGCCCAGGTGGTGGCCATCGCCAGCCACGAC

GGCGGCAAGCCCGCCCTGGAGGCCGTGTGGGCCAAGCTGCCCGTGCTGAGGGGCGTGCCCTACGCC

CTGAGCACCGCCCAGGTGGTGGCCATCGCCAGCCACGAC

GGCGGCAAGCCCGCCCTGGAGGCCGTGTGGGCCAAGCTGCCCGTGCTGAGGGGCGTGCCCTACGCC

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGAGCAGGTGGTGGCCATCGCCAGCAACAAC

GGCGGCAAGCAGGCCCTGGAGGCCGTGAAGGCCCAGCTGCTGGAGCTGAGGGCCGCCCCCTACGAG

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGAGCAGGTGGTGGCCATCGCCAGCAACAAG

GGCGGCAAGCAGGCCCTGGAGGCCGTGAAGGCCCACCTGCTGGACCTGCTGGGCGCCCCCTACGTG

CTGAGCACCGCCCAGGTGGTGGCCATCGCCAGCAACGGCGGAGGACGGCCAGCCTTGGAGTCCATCGTAGCCCAATTGTCCAGGCCC

GATCCCGCGTTGGCTGCGTTAACGAATGACCATCTGGTGGCGTTGGCATGTCTTGGTGGACGACCCGCGCTTGATGCAGTCAAAAAGG

GTCTGCCTCATGCTCCCGCATTGATCAAAAGAACCAACCGGCGGATTCCCGAGAGAACTTCCCATCGAGTCGCGGGATCCCAACTAGT

CAAAAGTGAACTGGAGGAGAAGAAATCTGAACTTCGTCATAAATTGAAATATGTGCCTCATGAATATATTGAATTAATTGAAATTGCC

AGAAATTCCACTCAGGATAGAATTCTTGAAATGAAGGTAATGGAATTTTTTATGAAAGTTTATGGATATAGAGGTAAACATTTGGGTG

GATCAAGGAAACCGGACGGAGCAATTTATACTGTCGGATCTCCTATTGATTACGGTGTGATCGTGGATACTAAAGCTTATAGCGGAGG

TTATAATCTGCCAATTGGCCAAGCAGATGAAATGCAACGATATGTCGAAGAAAATCAAACACGAAACAAACATATCAACCCTAATGA

ATGGTGGAAAGTCTATCCATCTTCTGTAACGGAATTTAAGTTTTTATTTGTGAGTGGTCCTTTAAAGGAAACTACAAAGCTCAGCTTA

CACGATTAAATCATATCACTAATTGTAATGGAGCTGTTCTTAGTGTAGAAGAGCTTTTAATTGGTGGAGAAATGATTAAAGCCGGCTTT

ATTAACCTTAGAGGAAGTCAGACGGAAATTTAATAACGGCGAGATAAACTTTTAAGGGCCCTTCGAAGGTAAGCCTATCCCTAACCCT

CTCCTCGGTCTCGATTCTACGCGTACCGGTCATCATCACCATCACCATTGAGTTTAAACCCGCTGATCAGCCTCGACTGTGCCTTCTAG

TTGCCAGCCATCTGTTGTTTGCCCCTCCCCCGTGCCTTCCTTGACCCTGGAAGGTGCCACTCCCACTGTCCTTTCCTAATAAAATGAGG

AAATTGCATCGCATTGTCTGAGTAGGTGTCATTCTATTCTGGGGGGTGGGTGGGGCAGGACAGCAAGGGGGAGGATTGGGAAGACA

ATGCAGGCATGCTGGGGATGCGGTGGGCTCTATGGCTTCTGAGGCGGAAAGAACCAGCTGGGGCTCTAGGGGGTATCCCCATGCGC

CCTGTAGCGGCGCATTAAGCGCGGCGGGTGTGGTGGTTACGCGCAGCGTGACCGCTACACTTGCCAGCGCCCTAGCGCCCGCTCCTTT

CGCTTTCTTCCCTTCCTTTCTCGCCACGTTCGCCGGCTTTCCCCGTCAAGCTCTAAATCGGGGCATCCTTTTAGGGTTCCGATTTAGTGC

TTTACGGCACCTCGACCCCAAAAAACTTGATTAGGGTGATGGTTCACGTAGTGGGCCATCGCCCTGATAGACGGTTTTTCGCCCTTTGA

CGTTGGAGTCCACGTTCTTTAATAGTGGACTCTTGTTCCATTACTGGAACAACACTCAACCCTATCTCGGTCTATTTTCTGATTTATAA

GGGATTTTGGGGATTTCGGCCTATTGGTTAAAAAATGAGCTGATTTAACAAAAATTTAACGCGAATTAATTCTGTGGAATGTGTGTCA

GTTAGGGTGTGGAAAGTCCCCAGGCTCCCCAGGCAGGCAGAAGTATGCAAAGCATGCATCTCAATTAGTCAGCAACCAGGTGTGGAA

AGTCCCCAGGCTCCCCAGCAGGCAGAAGTATGCAAAGCATGCATCTCAATTAGTCAGCAACCATAGTCCCGCCCCTAACTCCGCCCAT

CCCGCCCCTAACTCCGCCCAGTTCCGCCCATTCTCCGCCCCATGGCTGACTAATTTTTTTATTTATGCAGAGGCCGAGGCCGCCTCTG

CCTCTGAGCTATTCCAGAAGTAGTGAGGAGGCTTTTTTGGAGGCCTAGGCTTTTTCAAAAAGCTCCCGGGAGCTTGTATATCCATTTTC

GGATCTGATCAGCACGTGTTGACAATTAATCATCGGCATAGTATATCGGCATAGTATAATACGACAAGGTGAGGAACTAAACCATGG

CCAAGCCTTTGTCTCAAGAAGAATCCACCCTCATTGAAAGAGCAACGGCTACAATCAACAGCATCCCCATCTCTGAAGACTACAGCGT

CGCCAGCGCAGCTCTCTCTAGCGACGGCCGCATCTTCACTGGTGTCAATGTATATCATTTTACTGGGGGACCTTGTGCAGAACTCGTGG

TGCTGGGCACTGCTGCTGCTGCGGCAGCTGGCAACCTGACTTGTATCGTCGCGATCGGAAATGAGAACAGGGGCATCTTGAGCCCCTG

CGGACGGTGTCGACAGGTGCTTCTCGATCTGCATCTGGGATCAAAGCGATAGTGAAGGACAGTGATGGACAGCCGACGGCAGTTGG

GATTCGTGAATTGCTGCCCTCTGGTTATGTGTGGGAGGGCTAAGCACTTCGTGGCCGAGGAGCAGGACTGACACGTGCTACGAGATTT

CGATTCCACCGCCGCCTTCTATGAAAGGTTGGGCTTCGGAATCGTTTTCCGGGACGCCGGCTGGATGATCCTCCAGCGCGGGGATCTC

ATGCTGGAGTTCTTCGCCCACCCCAACTTGTTTATTGCAGCTTATAATGGTTACAAATAAAGCAATAGCATCACAAATTTCACAAATA

```
AAGCATTTTTTTcACTGCATTCTAGTTGTGGTTTGTCCAAACTCATCAATGTATCTTATCATGTCTGTATACCGTCGACCTCTAGCTAGA

GCTTGGCGTAATCATGGTCATAGCTGTTTCCTGTGTGAAATTGTTATCCGCTCACAATTCCACACAACATACGAGCCGGAAGCATAAA

GTGTAAAGCCTGGGGTGCCTAATGAGTGAGCTAACTCACATTAATTGCGTTGCGCTCACTGCCCGCTTCCAGTCGGGAAACCTGTCG

TGCCAGCTGCATTAATGAATCGGCCAACGCGCGGGGAGAGGCGGTTTGCGTATTGGGCGCTCTTCCGCTTCCTCGCTCACTGACTCGC

TGCGCTCGGTCGTTCGGCTGCGGCGAGCGGTATCAGCTCACTCAAAGGCGGTAATACGGTTATCCACAGAATTCAGGGGATAACGCAG

GAAAGAACATGTGAGCAAAAGGCCAGCAAAAGGCCAGGAACCGTAAAAAGGCCGCGTTGCTGGCGTTTTTCCATAGGCTCCGCCCCC

CTGACGAGCATCACAAAAATCGACGCTCAAGTCAGAGGTGGCGAAACCCGACAGGACTATAAAGATACCAGGCGTTTCCCCCTGGAA

GCTCCCTCGTGCGCTCTCCTGTTCCGACCCTGCCGCTTACCGGATACCTGTCCGCCTTTCTCCCTTCGGGAAGCGTGGCGCTTTCTCAAT

GCTCACGCTGTAGGTATCTCAGTTCGGTGTAGGTCGTTCGCTCCAAGCTGGGCTTTTGTGCACGAACCCCCCGTTCAGCCCGACCGCTG

CGCCTTTTTCCGGTAACTATCGTCTTGAGTCCAACCCGGTAAGACACGACTTATCGC-
CACTTTGCAGCAGCCACTGGTAACAGGTTTTAGC

AGAGCGAGGTATGTAGGCGGTGCTACAGAGTTTTTTGAAGTGGTGGCCTAACTACGGCTACACTAGAAGGACAGTATTTGGTATCTGC

GCTCTGCTGAAGCCAGTTACCTTCGGAAAAAGAGTTGGTAGCTCTTGATCCGGCATTACAAACCACCGCTGGTAGCGGTGGTTTTTTTG

TTTGCAAGCAGCAGATTACGCGCAGAAAAAAAGGATCTCAAGAAGATCCTTTGATCTTTTCTACGGGGTCTGACGCTCAGTGGAACGA

AAACTCACGTTAAGGGATTTTGGTCTTTGAGATTATCAAAAAGGATCTTCACCTAGATCCTTTTAAATTAAAAATGAAGTTTTAAATCA

ATCTAAAGTATATATGAGTAAACTTGGTCTGACAGTTACCAATGCTTAATCAGTGAGGCACCTATCTCAGTGATCTGTCTATTTTGTTC

ATCCATAGTTGCCTGACTCCCCGTCGTGTAGATAACTACGATACGGGAGGGCTTACCATCTGGCCCCAGTGCTGCAATGATACCGCGA

GACCCACGCTCACCGGCTCCAGATTTATCAGCAATAAACCAGCCAGCCGGAAGGGCCGAGCGCAGAAGTGGTCCTGCAACTTTATCC

GCCTCCATCCAGTCTATTAATTGTTGCCGGGAAGCTAGAGTAAGTAGTTCGCCAGTTAATAGTTTGCGCAACGTTGTTGCCATTGCTAC

AGGCATCGTGGTGTCACGCTCGTCGTTTGGTATGGCTTCATTCAGCTCCGGTTCCCAACGATCAAGGCGAGTTACATGATCCCCCATGT

TGTGCAAAAAAGCGGTTAGCTCCTTCGGTCCTCCGATCGTTGTCAGAAGTAAGTTGGCCGCAGTGTTATCACTCATGGTTATGGCAGC

ACTGCATAATTCTCTTACTGTCATGCCATCCGTAAGATGCTTTTCTGTGACTGGTGAGTACTCAACCAAGTCATTCTGAGAATAGTGTA

TTCGGCGACCGAGTTGCTCTTGCCCGGCGTCAATACGGGATAATACCGCGCCACATAGCAGAACTTTAAAAGTGCTCATCATTGGAAA

ACGTTCTTCGGGGCGAAAACTCTCAAGGATCTTACCGCTGTTGAGATCCAGTTCGATGTAACCCACTCGTGCACCCAACTGATCTTCA

GCATCTTTTACTTTCACCAGCGTTTCTGGGTGAGCAAAAACAGGAAGGCAAAATGCCGCAAAAAAGGGAATAAGGGCGACACGGAAA

TGTTGAATACTCATACTCTTCCTTTTCAATATTATTGAAGCATTTATCAGGGTTATTGTCTCATGAGCGGATACATATTTGAATGTATT

TAGAAAAATAAACAAATAGGGGTTCCGCGCACATTTCCCCGAAAAGTGCCACCTGACGTC
```

Bmpr2 REV RTN EBEs' amino acid sequence:

LSTEQVVAIAS NN GGKQALEAVKAQLLELRAAPYE (SEQ ID NO: 168)

LSTAQVVAIAS NG GGKQALEGIGEQLLKLRTAPYG (SEQ ID NO: 169)

LSTAQVVAIAS NG GGKQALEGIGEQLLKLRTAPYG (SEQ ID NO: 170)

LSTAQVVAIAS NG GGKQALEGIGEQLLKLRTAPYG (SEQ ID NO: 171)

LSTAQVVAIAS HD GGKPALEAVWAKLPVLRGVPYA (SEQ ID NO: 172)

LSTEQVVAIAS NK GGKQALEAVKAHLLDLLGAPYV (SEQ ID NO: 173)

LSTAQVVAIAS NG GGKQALEGIGEQLLKLRTAPYG (SEQ ID NO: 174)

LSTAQVVAIAS NG GGKQALEGIGEQLLKLRTAPYG (SEQ ID NO: 175)

LSTAQVVAIAS NG GGKQALEGIGEQLLKLRTAPYG (SEQ ID NO: 176)

-continued (SEQ ID NO: 177)
LSTEQVVAIAS NN GGKQALEAVKAQLLELRAAPYE (SEQ ID NO: 178)
LSTAQVVAIAS HD GGKPALEAVWAKLPVLRGVPYA (SEQ ID NO: 179)
LSTAQVVAIAS HD GGKPALEAVWAKLPVLRGVPYA (SEQ ID NO: 180)
LSTAQVVAIAS NG GGKQALEGIGEQLLKLRTAPYG (SEQ ID NO: 181)
LSTEQVVAIAS NK GGKQALEAVKAHLLDLLGAPYV (SEQ ID NO: 182)
LSTAQVVAIAS NG GGKQALEGIGEQLLKLRTAPYG (SEQ ID NO: 183)
LSTAQVVAIAS HD GGKPALEAVWAKLPVLRGVPYA Bmpr2 REV RTN DNA Sequence:
(Bolded Font: synthesized Ralstonia EBEs) this sequence is contiguous (SEQ ID NO: 184):
GACGGATCGGGAGATCTCCCGATCCCCTATGGTCGACTCTCAGTACAATCTGCTCTGATGCCGCATAGTTAAGCCAGTATCTGCTCCCT GCTTGTGTGTTGGAGGTCGCTGAGTAGTGCGCGAGCAAAATTTAAGCTACAACAAGGCAAGGCTTGACCGACAATTGCATGAAGAAT CTGCTTAGGGTTAGGCGTTTTGCGCTGCTTCGCGATGTACGGGCCAGATATACGCGTTGACATTGATTATTGACTAGTTATTAATAGTA ATCAATTACGGGGTCATTAGTTCATAGCCCATATATGGAGTTCCGCGTTACATAACTTACGGTAAATGGCCCGCCTGGCTGACCGCCC AACGACCCCCGCCCATTGACGTCAATAATGACGTATGTTCCCATAGTAACGCCAATAGGGACTTTCCATTGACGTCAATGGGTGGAgT ATTTACGGTAAACTGCCCACTTGGCAGTACATCAAGTGTATCATATGCCAAGTACGCCCCCTATTGACGTCAATGACGGTAAATGGCC CGCCTGGCATTATGCCCAGTACATGACCTTATGGGACTTTCCTACTTGGCAGTACATCTACGTATTAGTCATCGCTATTACCATGGTGA TGCGGTTTTGGCAGTACATCAATGGGCGTGGATAGCGGTTTGACTCACGGGGATTTCCAAGTCTCCACCCCATTGACGTCAATGGGAG TTTGTTTTGGCACCAAAATCAACGGGACTTTCCAAAATGTCGTAACAACTCCGCCCCATTGACGCAAATGGGCGGTAGGCGTGTACGG TGGGAGGTCTATATAAGCAGAGCTCTCTGGCTAACTAGAGAACCCACTGCTTACTGGCTTATCGAAATTAATACGACTCACTATAGGG AGACCCAAGCTGGCTAGCACCATGGACTACAAAGACCATGACGGTGATTATAAAGATCATGACATCGATTACAAGGATGACGATGAC AAGATGGCCCCCAAGAAGAAGAGGAAGGTGGGCATTCACCGCGGGGTACCTATGGTGGACTTGAGGACACTCGGTTATTCGCAACAG CAACAGGAGAAAATCAAGCCTAAGGTCAGGAGCACCGTCGCGCAACACCACGAGGCGCTTGTGGGGCATGGCTTCACTCATGCGCAT ATTGTCGCGCTTTCACAGCACCCTGCGGCGCTTGGGACGGTGGCTGTCAAATACCAAGATATGATTGCGGCCCTGCCCGAAGCCACGC ACGAGGCAATTGTAGGGGTCGGTAAACAGTGGTCGGGAGCGCGAGCACTTGAGGCGCTGCTGACTGTGGCGGGTGAGCTTAGGGGGC CTCCGCTCCAGCTCGACACCGGGCAGCTGCTGAAGATCGCGAAGAGAGGGGGAGTAACAGCGGTAGAGGCAGTGCACGCCTGGCGC

AATGCGCTCACCGGGGCCCCCTT

CTGAGCACCGAGCAGGTGGTGGCCATCGCCAGCAACAAC

GGCGGCAAGCAGGCCCTGGAGGCCGTGAAGGCCCAGCTGCTGGAGCTGAGGGCCGCCCCCTACGAG

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGCCCAGGTGGTGGCCATCGCCAGCCACGAC

GGCGGCAAGCCCGCCCTGGAGGCCGTGTGGGCCAAGCTGCCCGTGCTGAGGGGCGTGCCCTACGCC

CTGAGCACCGAGCAGGTGGTGGCCATCGCCAGCAACAAG

```
GGCGGCAAGCAGGCCCTGGAGGCCGTGAAGGCCCACCTGCTGGACCTGCTGGGCGCCCCCTACGTG

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGAGCAGGTGGTGGCCATCGCCAGCAACAAC

GGCGGCAAGCAGGCCCTGGAGGCCGTGAAGGCCCAGCTGCTGGAGCTGAGGGCCGCCCCCTACGAG

CTGAGCACCGCCCAGGTGGTGGCCATCGCCAGCCACGAC

GGCGGCAAGCCCGCCCTGGAGGCCGTGTGGGCCAAGCTGCCCGTGCTGAGGGGCGTGCCCTACGCC

CTGAGCACCGCCCAGGTGGTGGCCATCGCCAGCCACGAC

GGCGGCAAGCCCGCCCTGGAGGCCGTGTGGGCCAAGCTGCCCGTGCTGAGGGGCGTGCCCTACGCC

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGAGCAGGTGGTGGCCATCGCCAGCAACAAG

GGCGGCAAGCAGGCCCTGGAGGCCGTGAAGGCCCACCTGCTGGACCTGCTGGGCGCCCCCTACGTG

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGCCCAGGTGGTGGCCATCGCCAGCCACGAC

GGCGGCAAGCCCGCCCTGGAGGCCGTGTGGGCCAAGCTGCCCGTGCTGAGGGGCGTGCCCTACGCC

CTGAGCACCGAGCAGGTGGTGACCATCGCCAGC

AGCATCGGAGGACGGCCAGCCTTGGAGTCCATCGTAGCCCAATTGTCCAGGCCCGATCCCGCGTTGGCTGCGTTAACGAATGACCATC

TGGTTTGCGTTGGCATGTCTTGGTGGACGACCCGCGCTCGATGCAGTCAAAAAGGGTCTGCCTCATGCTCCCGCATTGATCAAAAGAAC

CAACCGGCGGATTCCCGAGAGAACTTCCCATCGAGTCGCGGGATCCCAACTAGTCAAAAGTGAACTGGAGGAGAAGAAATCTGAACT

TCGTCATAAATTGAAATATGTGCCTCATGAATATATTGAATTAATTGAAATTGCCAGAAATTCCACTCAGGATAGAATTCTTGAAATG

AAGGTAATGGAATTTTTTATGAAAGTTTATGGATATAGAGGTTAACATTTGGGTGGATCAAGGAAACCGGACGGAGCAATTTATACT

GTCGGATCTCCTATTGATTACGGTGTGATCGTGGATACTAAAGCTTATAGCGGAGGTTATAATCTGCCAATTGGCCAAGCAGATGAAA

TGCAACGATATGTCGAAGAAAATCAAACACGAAACAAACATATCAACCCTAATGAATGGTGGAAAGTCTATCCATCTTCTGTAACGG

AATTTAAGTTTTTATTTGTGAGTGGTTACTTTAAAGGAAACTACAAAGCTCAGCTTACACGATTAAATCATATCACTAATTGTAATGGA

GCTGTTCTTAGTGTAGAAGAGCTTTTAATTGGTGGAGAAATGATTAAAGCCGGCACATTAACCTTAGAGGAAGTCAGACGGAAATTTA

ATAACGGCGAGATAAACTTTTAAGGGCCCTTCGAAGGTAAGCCTATCCCTAACCCTCTCCTCCGTCTCGATTCTACGCCTACCGGTCAT

CATCACCATCACCATTGAGTTTAAACCCGCTGATCAGCCTCGACTGTGCCTTCTAGTTGCCAGCCATCTGTTGTTTGCCCCTCCCCCGT

GCCTTCCTTGACCCTGGAAGGTGCCACTCCCACTGTCCTTTCCTAATAAAATGAGGAAATTGCATCGCATTGTCTGAGTAGGTGTCATT

CTATTCTGGGGGGTGGGGTGGGGCAGGACAGCAAGGGGGAGGATTGGGAAGACAATAGCAGGCATGCTGGGGATGCGGTGGGCTCT

ATGGCTTCTGAGGCGGAAAGAACCAGCTGGGGCTCTAGGGGTATCCCCACGCGCCCTGTAGCGGCGCATTAAGCGCGGCGGGTGTG

GTGGTTACGCGCAGCGTGACCGCTACACTTGCCAGCGCCCTAGCGCCCGCTCCTTTCGCTTTCTTCCCTTCCTTTCTCGCCACGTTCGCC

GGCTTTCCCCGTCAAGCTCTAAATCGGGGCATCCCTTTAGGGTTCCGATTTAGTTTCTTTACGGCACCTCGACCCCAAAAAACTTGATTA

GGGTGATGGTTCACGTAGTGGGCCATCGCCCTGATAGACGGTTTTTCGCCCTTTGACGTTGGAGTCCACGTTCTTTAATAGTGGACTCT

TGTTCCAAACTGGAACAACACTCAACCCTATCTCGGTCTATTCTTTTGATTTATAAGGGATTTTGGGGATTTCGGCCTATTGGTTAAAA

AATGAGCTGATTTAACAAAAATTTAACGCGAATTAATTCTGTGGAATGTGTGTCAGTTAGGGTGTGGAAAGTCCCCAGGCTCCCCAGG
```

```
CAGGCAGAAGTATGCAAAGCATGCATCTCAATTAGTCAGCAACCAGGTGTGGAGTCCCCAGGCTCCCCAGCAGGCAGAAGTATGC

AAAGCATGCATCTCAATTAGTCAGCAACCATAGTCCCGCCCCTAACTCCGCCCATCCCGCCCCTAACTCCGCCCAGTTCCGCCCATTCT

CCGCCCCATGGCTGACTAATTTTTTTTATTTATGCAGAGGCCGAGGCCGCCTCTGCCTCTGAGCTATTCCAGAAGTAGTGAGGAGGCTT

TTTTGGAGGCCTAGGCTTTTGCAAAAAGCTCCCGGGAGCTTGTATATCCATTTTCGGATCTGATCAGCACGTGTTGACAATTAATCATC

GGCATAGTATATCGGCATAGTATAATACGACAAGGTGAGGAACTAAACCATGGCCAAGCCTTTGTCTCAAGAAGAATCCACCCTCATT

GAAAGAGCAACGGCTACAATCAACAGCATCCCCATCTCTGAAGACTACAGCGTCGCCAGCGCAGCTCTCTCTAGCGACGGCCGCATC

TTCACTGGTGTCAATGTATATCATTTTACTGGGGGACCTTTTTGCAGAACTCGTGGTGCTGGGCACTGCTGCTGCGGCAGCTGGCA

ACCTGACTTGTATCGTCGCGATCGGAAATGAGAACAGGGGCATCTTGAGCCCCTGCGGACGGTGTCGACAGGTGCTTCTCGATCTGCA

TCCTGGGATCAAAGCGATAGTGAAGGACAGTGATGGACAGCCGACGGCAGTTGGGATTCGTGAATTGCTGCCCTCTGGTTATGTGTGG

GAGGGCTAAGCACTTCGTGGCCGAGGAGCAGGACTGACACGTGCTACGAGATTTCGATTCCACCGCCGCCTTCTATGAAAGGTTGGG

CTTCGGAATCGTTTTCCGGGACGCCGGCTGGATGATCCTCCAGCGCGGGGATCTCATGCTGGAGTTCTTCGCCCACCCCAACTTGTTTA

TTGCAGCTTATAATGGTTACAAATAAAGCAATAGCATCACAAATTTCACAAATAAAGCATTTTTTTCACTGCATTCTAGTTGTGGTTTG

TCCAAACTCATCAATGTATCTTATCATGTCTGTATACCGTCGACCTCTAGCTAGAGCTTGGCGTAATCATGGTCATAGCTGTTTCCTGT

GTGAAATTGTTATCCGCTCACAATTCCACACAACATACGAGCCGGAAGCATAAAGTGTAAAGCCTGGGGTGCCTAATGAGTGAGCTA

ACTCACATTAATTGCGTTGCGCTCACTGCCCGCTTTCCAGTCGGGAAACCTGTCGTGCCAGCTGCATTAATGAATCGGCCAACGCGCG

GGGAGAGGCGGTTTGCGTATTGGGCGCTTTTCCGCTTCCTCGCTCACTGACTCGCTGCGCTCGGTCGTTCGGCTGCGGCGAGCGGTATC

AGCTCACTCAAAGGCGGTAATACGGTTATCCACAGAATCAGGGGATAACGCAGGAAAGAACATGTGAGCAAAAGGCCAGCAAAAGG

CCAGGAACCGTAAAAAGGCCGCGTTGCTGGCGTTTTTCCATAGGCTCCGCCCCCCTTTACGAGCATCACAAAAATCGACGCTCAAGTCA

GAGGTGGCGAAACCCGACAGGACTATAAAGATACCAGGCGTTTCCCCCTGGAAGCTCCCTCGTGCGCTCTCCTGTTCCGACCCTGCCG

TTTACCGGATACCTGTCCGCCTTTCTCCCTTCGGGAAGCGTGGCGCTTTCTCAATGCTCACGCTGTAGGTATCTCAGTTCGGTGTAGGT

CGTTCGCTCCAAGCTGGGCTGTGTGCACGAACCCCCCGTTCAGCCCGACCGCTGCGCCTTATCCGGTAACTATCGTCTTGAGTCCAACC

CGGTAAGACACGACTTATCGCCACTGGCAGCAGCCACTGGTAACAGGATTAGCAGAGCGAGGTATGTAGGCGGTGCTACAGAGTTCT

TGAAGTGGTGGCCTAACTACGGCTACACTAGAAGGACAGTATTTGGTATCTGCGCTCTGCTGAAGCCAGTTCCCTTCGGAAAAAGAGT

TGGTAGCTCTTGATCCGGCAAACAAACCACCGCTGGTAGCGGTGGTTTTTTTGTTTGCAAGCAGCAGATTACGCGCAGAAAAAAAGGA

TCTCAAGAAGATCCTTTGATCTTTTCTACGGGGTCTGACGCTCAGTGGAACGAAAACTCACGTTAAGGGATTTTGGTCATGAGATTATC

AAAAAGGATCTTCACCTAGATCCTTTTAAATTAAAAATGAAGTTTTAAATCAATCTAAAGTATATATGAGTAAACTTGGTCTGACAGT

TACCAATGCTTAATCAGTGAGGCACCTATCTCAGCGATCTGTCTATTTCGTTCATCCATAGTTGCCTGACTCCCCGTCGTGTAGATAAC

TACGATACGGGAGGGCTTACCATCTGGCCCCAGTGCTGCAATGATACCGCGAGACCCATGCTCACCGGCTCCAGATTTATCAGCAATA

AACCAGCCAGCCGGAAGGGCCGAGCGCAGAAGTGGTCCTGCAACTTTATCCGCCTCCATCCAGTCTATTAATTGTTGCCGGGAAGCTA

GAGTAAGTAGTTCGCCAGTTAATAGTTTGCGCAACGTTGTTGCCATTGCTACAGGCATCGTGGTGTCACGCTCGTCGTTTGGTATGGCT

TCATTCAGCTCCGGTTCCCAACGATCAAGGCGAGTTACATGATCCCCCATGTTGTGCAAAAAAGCGGTTAGCTCCTTCGGTCCTCCGAT

CGTTGTCAGAAGTAAGTTGGCCGCAGTGTTATCATTCATGGTTATGGCAGCACTGCATAATTCTCTTACTGTCATGCCATCCGTAAGAT

GCTTCCTGTGACTGGTGAGTACTCAACCAAGTCATTCTGAGAATAGTGTATGCGGCGACCGAGTTGCTCTTGCCCGGCGTCAATACG

GGATAATACCGCGCCACATAGCAGAACTTTAAAAGTGCTCATCATTGGAAAACGTTCTTCGGGGCGAAAACTCTCAAGGATCTTACCG

CTGTTGAGATCCAGTTCGATGTAACCCACTCGTGCACCCAACTGATCTTCAGCATCTTTTACTTTCACCAGCGTTTCTGGGTGAGCAAA

AACAGGAAGGCAAAATGCCGCAAAAAAGGGAATAAGGGCGACACGGAAATGTTGAATACTCATACTCTTCCTTTTTCAATATTATTG

AAGCATTTATCAGGGTTATTGTCTCATGAGCGGATACATATTTGAATGTATTTAGAAAAATAAACAAATAGGGGTTCCGCGCACATTT

CCCCGAAAAGTGCCACCTGACGTC
```

Example 5

A library of *Ralstonia* EBEs and backbone vectors were made which could be used to assemble full length *Ralstonia* DNA binding domains into *Ralstonia* or *Xanthomonas* TALEN backbones, utilizing the golden gate assembly method. The RTNs were co-transfected into the Rat C6 cell line and gDNA extracted for analysis 48 hrs post transfection. A 420 bp gDNA fragment containing the RTN binding site was amplified by PCR. This amplicon was then subjected to the Cell assay using Surveyor Mutation Detection Kit (Transgenomic) as per manufacturer protocol. In brief, the amplicon is denatured into single stranded DNA and slowly re-annealed back to double stranded DNA. During this process, considering the original pool was a mixture of WT and mutated sequences, there will be cross hybridization between WT and mutant strands leading to formation of heteroduplexes. Upon treatment of this re-annealed pool with the Surveyor Nuclease, it recognizes the heteroduplexes and cleaves them, which generated two shorter fragments from (255 bp and 165 bp) the original amplicon (420 bp).

Terminology pRVD: plasmid containing a single *Ralstonia* EBE. Individual EBEs were gene synthesized and cloned in FLASH-XTN sub-array backbone (XbaI, BamHI).

pFus X: a sub-array plasmid that holds the first 10 EBEs of any given RTN. The required piece was gene synthesized and cloned into pHSG-298 (SacI, SbfI).

pFUS Z: a sub-array plasmid that holds EBE 11 up to the second-last EBE of any given RTN. Eg: Z4 holds EBEs 11-14, Z5 holds EBEs 11-15 and Z6 holds EBEs 11-16. Gene synthesized and cloned into pHSG-298 (SacI, SbfI).

XTN-bb: *Xanthomonas* TAL backbone that contains the N-terminal and C-terminal *Xanthomonas* TAL domains fused to FokI nuclease. This backbone specifies a T nucleotide 5' of the target sequence specified by the EBEs. It also contains the last half EBE that specifies the last nucleotide of the targeted sequence. Therefore there are four XTN-bb plasmids, each specifying a different final nucleotide of the targeted sequence (same as FLASH XTN backbones).

All plasmids are stored at 150 ng/ul in 0.1×TE buffer.

Methods: (building a 16EBE DNA binding domain and cloning it into a *Xanthomonas* TALEN backbone).

Assembly of a custom TALEN or TAL effector construct involves two steps: (i) assembly of repeat modules (pRVDs) into sub-arrays of 1-10 repeats and (ii) joining of the sub-arrays into a backbone to make the final construct.

Construction of a TALEN monomer with a 17 RVD array (5'-TGATAGTCGC-CTTATG-T-3'): Select from the pRVD plasmids those that encode RVDs 1-10 in the array using plasmids numbered in that order. For example, the plasmid for the first RVD would be gRTN-1T, the second gRTN-2G, the third gRTN-3A etc. Modules from these plasmids are cloned into sub-array plasmid pFUS-X. Next, select modules for RVDs 11-16 in the 16 RVD array again starting with plasmids numbered from 1. Thus for RVD 11 gRTN-1C would be used, for RVD 12 gRTN-2T, etc. The pFUS-Z plasmids are numbered 1-10 and should be selected according to the number of EBEs going in. Thus, in our example, pFUS-Z6 should be used.

The pRVDs and sub-array plasmids (150 ng each) are subjected to digestion and ligation in a single 20 μl reaction containing 1 μl BsaI (10 U, New England BioLabs) and 1 μl T4 DNA Ligase (2000 U, New England BioLabs) in T4 DNA ligase buffer (New England BioLabs). The reaction is incubated in a thermocycler for 10 cycles of 5 min at 37° C. and 10 min at 16° C., then heated to 50° C. for 5 min and then 80° C. for 5 min. Then, 1 μl 25 mM ATP and 1 μl Plasmid Safe DNase (10 U, Epicentre) are added. The mixture is incubated at 37° C. for 1 h, then used to transform *Escherichia coli* cells. Cells are plated on LB agar containing 50 mg/ml Kanamycin, overnight at 37° C.

Up to six colonies from each transformation were screened with M13 forward (fwd) and reverse (rev) primers, via colony PCR, to identify clones that contain a full-length sub-array. Full length pFUS-X sub-array clones should produce a 1.1 kb band and full-length pFUS-Z6 clones should produce a 700 bp band (add or subtract 105 bp for each EBE more or less). Cultures were started overnight cultures of a full-length pFUS-X and a full-length pFUS-Z6 clone.

Plasmid DNA was isolated from the pFUS-X and pFUS-Z cultures. Sub-arrays were joined into one of the four backbone plasmids. A 20 μl digestion and ligation reaction mixture is prepared with 150 ng each of the pFUS-X and pFUS-Z plasmids, 150 ng of the backbone plasmid, in this case XTN-bbT, 1 μl d Esp3I (10 U, Thermo Scientific) and 1 μl T4 DNA Ligase (2000 U, New England Biolabs) in T4 DNA ligase buffer. The reaction is then incubated in a thermocycler for 3 cycles of 10 min at 37° C. and 15 min at 16° C. The reaction is then incubated at 37° C. for an additional 30 min and heated to 50° C. for 5 min, then 80° C. for 5 min. After cooling to room temperature, 1 μl 25 mM ATP and 1 μl Plasmid Safe DNase (10 U, Epicenter) were added and incubated at 37° C. for 1 hr. The reaction is then used to transform *E. coli* as above, except that Plasmid Safe. Also, in this step, ampicillin (100 mg/ml) is used in place of Kanamycin for selection of transformants.

Up to three colonies were screened from each transformation via colony PCR with XTN-VF and XTN-VR2 primers and started overnight cultures of 1 full length clone for each RTN (2.1 kb band indicates 17EBE array). We then isolated plasmid DNA and identify clones containing the final, full-length repeat array by DNA sequencing with XTN-VF, XTN-VR1 and XTN-VR2.

```
XbaI and BamHI digested XTN sub-array backbone
(sites underlined) (SEQ ID NO: 185):
(BamHI)GGATCCCGGGCCCGTCGACTGCAGAGGCCTGCATGCAAGCTTG

GCGTAATCATGGTCATAGCTGTTTCCTGTGTGAAATTGTTATCCGCTCAC

AATTCCACACAACATACGAGCCGGAAGCATAAAGTGTAAAGCCTGGGGTG

CCTAATGAGTGAGCTAACTCACATTAATTGCGTTGCGCTCACTGCCCGCT

TTCCAGTCGGGAAACCTGTCGTGCCAGCTGCATTAATGAATCGGCCAACG

CGCGGGGAGAGGCGGTTTGCGTATTGGGCGCTCTTCCGCTTCCTCGCTCA

CTGACTCGCTGCGCTCGGTCGTTCGGCTGCGGCGAGCGGTATCAGCTCAC

TCAAAGGCGGTAATACGGTTATCCACAGAATCAGGGGATAACGCAGGAAA

GAACATGTGAGCAAAAGGCCAGCAAAAGGCCAGGAACCGTAAAAAGGCCG

CGTTGCTGGCGTTTTTCCATAGGCTCCGCCCCCCTGACGAGCATCACAAA

AATCGACGCTCAAGTCAGAGGTGGCGAAACCCGACAGGACTATAAAGATA

CCAGGCGTTTCCCCCTGGAAGCTCCCTCGTGCGCTCTCCTGTTCCGACCC

TGCCGCTTACCGGATACCTGTCCGCCTTTCTCCCTTCGGGAAGCGTGGCG
```

-continued

CTTTCTCATAGCTCACGCTGTAGGTATCTCAGTTCGGTGTAGGTCGTTCG

CTCCAAGCTGGGCTGTGTGCACGAACCCCCCGTTCAGCCCGACCGCTGCG

CCTTATCCGGTAACTATCGTCTTGAGTCCAACCCGGTAAGACACGACTTA

TCGCCACTGGCAGCAGCCACTGGTAACAGGATTAGCAGAGCGAGGTATGT

AGGCGGTGCTACAGAGTTCTTGAAGTGGTGGCCTAACTACGGCTACACTA

GAAGAACAGTATTTGGTATCTGCGCTCTGCTGAAGCCAGTTACCTTCGGA

AAAAGAGTTGGTAGCTCTTGATCCGGCAAACAAACCACCGCTGGTAGCGG

TGGTTTTTTTGTTTGCAAGCAGCAGATTACGCGCAGAAAAAAAGGATCTC

AAGAAGATCCTTTGATCTTTTCTACGGGGTCTGACGCTCAGTGGAACGAA

AACTCACGTTAAGGGATTTTGGTCATGAGATTATCAAAAAGGATCTTCAC

CTAGATCCTTTTAAATTAAAAATGAAGTTTTAAATCAATCTAAAGTATAT

ATGAGTAAACTTGGTCTGACAGTTACCAATGCTTAATCAGTGAGGCACCT

ATCTCAGCGATCTGTCTATTTCGTTCATCCATAGTTGCCTGACTCCCCGT

CGTGTAGATAACTACGATACGGGAGGGCTTACCATCTGGCCCCAGTGCTG

CAATGATACCGCGAGAgCCACGCTCACCGGCTCCAGATTTATCAGCAATA

AACCAGCCAGCCGGAAGGGCCGAGCGCAGAAGTGGTCCTGCAACTTTATC

CGCCTCCATCCAGTCTATTAATTGTTGCCGGGAAGCTAGAGTAAGTAGTT

CGCCAGTTAATAGTTTGCGCAACGTTGTTGCCATTGCTACAGGCATCGTG

GTGTCACGCTCGTCGTTTGGTATGGCTTCATTCAGCTCCGGTTCCCAACG

ATCAAGGCGAGTTACATGATCCCCCATGTTGTGCAAAAAAGCGGTTAGCT

CCTTCGGTCCTCCGATCGTTGTCAGAAGTAAGTTGGCCGCAGTGTTATCA

CTCATGGTTATGGCAGCACTGCATAATTCTCTTACTGTCATGCCATCCGT

AAGATGCTTTTCTGTGACTGGTGAGTACTCAACCAAGTCATTCTGAGAAT

AGTGTATGCGGCGACCGAGTTGCTCTTGCCCGGCGTCAATACGGGATAAT

ACCGCGCCACATAGCAGAACTTTAAAAGTGCTCATCATTGGAAAACGTTC

TTCGGGGCGAAAACTCTCAAGGATCTTACCGCTGTTGAGATCCAGTTCGA

TGTAACCCACTCGTGCACCCAACTGATCTTCAGCATCTTTTACTTTCACC

AGCGTTTCTGGGTGAGCAAAAACAGGAAGGCAAAATGCCGCAAAAAAGGG

AATAAGGGCGACACGGAAATGTTGAATACTCATACTCTTCCTTTTTCAAT

ATTATTGAAGCATTTATCAGGGTTATTGTCTCATGAGCGGATACATATTT

GAATGTATTTAGAAAAATAAACAAATAGGGGTTCCGCGCACATTTCCCCG

AAAAGTGCCACCTGACGTCTAAGAAACCATTATTATCATGACATTAACCT

ATAAAAATAGGCGTATCACGAGGCCCTTTCGTCTCGCGCGTTTCGGTGAT

GACGGTGAAAACCTCTGACACATGCAGCTCCCGGAGACGGTCACAGCTTG

TCTGTAAGCGGATGCCGGGAGCAGACAAGCCCGTCAGGGCGCGTCAGCGG

GTGTTGGCGGGTGTCGGGGCTGGCTTAACTATGCGGCATCAGAGCAGATT

GTACTGAGAGTGCACCATATGCGGTGTGAAATACCGCACAGATGCGTAAG

GAGAAAATACCGCATCAGGCGCCATTCGCCATTCAGGCTGCGCAACTGTT

GGGAAGGGCGATCGGTGCGGGCCTCTTCGCTATTACGCCAGCTGGCGAAA

-continued

GGGGGATGTGCTGCAAGGCGATTAAGTTGGGTAACGCCAGGGTTTTCCCA

GTCACGACGTTGTAAAACGACGGCCAGTGAATTCGAGCTCGGTACCTCGC

GAATGCATCTAGA(XbaI)

XTN-bb (BsmBI digested, sites are self-excised from the backbone during digestion):

Underlined sequences overlap with sub-arrays pFUS-X and pFUS-Z.
(SEQ ID NO: 186)
XTN-bbA: NNNNNNNNN is replaced with TCTAACATC (SEQ ID NO: 187)
XTN-bbC: NNNN is replaced with TCCCACGAC (SEQ ID NO: 188)
XTN-bbG: NNNN is replaced with AATAATAA (SEQ ID NO: 189)
XTN-bbT: NNNN is replaced with TCTAATGGG (SEQ ID NO: 190)
pFUS-Z overlap CTGACACCCGAACAGGTGGTCGCCATTGC

TNNNNNNNNN

GGAGGACGGCCAGCCTTGGAGTCCATCGTAGCCCAATTGTCCAGGCCCGA

TCCCGCGTTGGCTGCGTTAACGAATGACCATCTGGTGGCGTTGGCATGTC

TTGGTGGACGACCCGCGCTCGATGCAGTCAAAAAGGGTCTGCCTCATGCT

CCCGCATTGATCAAAAGAACCAACCGGCGGATTCCCGAGAGAACTTCCCA

TCGAGTCGCGGGATCCCAACTAGTCAAAAGTGAACTGGAGGAGAAGAAAT

CTGAACTTCGTCATAAATTGAAATATGTGCCTCATGAATATATTGAATTA

ATTGAAATTGCCAGAAATTCCACTCAGATAGAATTCTTGAAATGAAGGTA

ATGGAATTTTTATGAAAGTTTATGGATATAGAGGTAAACATTTGGGTGG

ATCAAGGAAACCGGACGGAGCAATTTATACTGTCGGATCTCCTATTGATT

ACGGTGTGATCGTGGATACTAAAGCTTATAGCGGAGGTTATAATCTGCCA

ATTGGCCAAGCAGATGAAATGCAACGATATGTCGAAGAAAATCAAACACG

AAACAAACATATCAACCCTAATGAATGGTGGAAAGTCTATCCATCTTCTG

TAACGGAATTTAAGTTTTTATTTGTGAGTGGTCACTTTAAAGGAAACTAC

AAACTCAGCTTACACGATTAAATCATATCACTAATTGTAATGGAGCTGTT

CTTAGTGTAGAAGAGCTTTTAATTGGTGGAGAAATGATTAAAGCCGGCAC

ATTAACCTAGAGGAAGTCAGACGGAAATTTAATAACGGCGAGATAAACT

TTTAAGGGCCCTTCGAAGGTAAGCCTATCCCTAACCCTCTCCTCGGTCTC

GATTCTACGCGTACCGGTCATCATCACCATCACCATTGAGTTTAAACCCG

CTGATCAGCCTCGACTGTGCCTTCTAGTTGCCAGCCATCTGTTGTTTGCC

CCTCCCCCGTGCCTTCCTTGACCCTGGAAGGTGCCACTCCCACTGTCCTT

TCCTAATAAAATGAGGAAATTGCATCGCATTGTCTGAGTAGGTGTCATTC

TATTCTGGGGGGTGGGTGGGGCAGGACAGCAAGGGGGAGGATTGGGAAG

ACAATAGCAGGCATGCTGGGGATGCGGTGGGCTCTATGGCTTCTGAGGCG

GAAAGAACCAGCTGGGGCTCTAGGGGGTATCCCCACGCGCCCTGTAGCGG

CGCATTAAGCGCGGCGGGTGTGGTGGTTACGCGCAGCGTGACCGCTACAC

TTGCCAGCGCCCTAGCGCCCGCTCCTTTCGCTTTCTTCCCTTCCTTTCTC

```
GCCACGTTCGCCGGCTTTCCCCGTCAAGCTCTAAATCGGGGCATCCCTTT
AGGGTTCCGATTTAGTGCTTTACGGCACCTCGACCCCAAAAAACTTGATT
AGGGTGATGGTTCACGTAGTGGGCCATCGCCCTGATAGACGGTTTTTCGC
CCTTTGACGTTGGAGTCCACGTTCTTTAATAGTGGACTCTTGTTCCAAAC
TGGAACAACACTCAACCCTATCTCGGTCTATTCTTTTGATTTATAAGGGA
TTTTGGGGATTTCGGCCTATTGGTTAAAAAATGAGCTGATTTAACAAAAA
TTTAACGCGAATTAATTCTGTGGAATGTGTGTCAGTTAGGGTGTGGAAAG
TCCCCAGGCTCCCCAGGCAGGCAGAAGTATGCAAAGCATGCATCTCAATT
AGTCAGCAACCAGGTGTGGAAAGTCCCCAGGCTCCCCAGCAGGCAGAAGT
ATGCAAAGCATGCATCTCAATTAGTCAGCAACCATAGTCCCGCCCCTAAC
TCCGCCCATCCCGCCCCTAACTCCGCCCAGTTCCGCCCATTCTCCGCCCC
ATGGCTGACTAATTTTTTTATTTATGCAGAGGCCGAGGCCGCCTCTGCC
TCTGAGCTATTCCAGAAGTAGTGAGGAGGCTTTTTGGAGGCCTAGGCTT
TTGCAAAAAGCTCCCGGGAGCTTGTATATCCATTTTCGGATCTGATCAGC
ACGTGTTGACAATTAATCATCGGCATAGTATATCGGCATAGTATAATACG
ACAAGGTGAGGAACTAAACCATGGCCAAGCCTTTGTCTCAAGAAGAATCC
ACCCTCATTGAAAGAGCAACGGCTACAATCAACAGCATCCCCATCTCTGA
AGACTACAGCGTCGCCAGCGCAGCTCTCTCTAGCGACGGCCGCATCTTCA
CTGGTGTCAATGTATATCATTTTACTGGGGGACCTTGTGCAGAACTCGTG
GTGCTGGGCACTGCTGCTGCTGCGGCAGCTGGCAACCTGACTTGTATCGT
CGCGATCGGAAATGAGAACAGGGGCATCTTGAGCCCCTGCGGACGGTGTC
GACAGGTGCTTCTCGATCTGCATCCTGGGATCAAAGCGATAGTGAAGGAC
AGTATGGACAGCCGACGGCAGTTGGGATTCGTGAATTGCTGCCCTCTGGT
TATGTGTGGGAGGGCTAAGCACTTCGTGGCCGAGGAGCAGGACTGACACG
TGCTACGAGATTTCGATTCCACCGCCGCCTTCTATGAAAGGTTGGGCTTC
GGAATCGTTTTCCGGGACGCCGGCTGGATGATCCTCCAGCGCGGGGATCT
CATGCTGGAGTTCTTCGCCCACCCCAACTTGTTTATTGCAGCTTATAATG
GTTACAAATAAAGCAATAGCATCACAAATTTCACAAATAAAGCATTTTTT
TCACTGCATTCTAGTTGTGGTTTGTCCAAACTCATCAATGTATCTTATCA
TGTCTGTATACCGTCGACCTCTAGCTAGAGCTTGGCGTAATCATGGTCAT
AGCTGTTTCCTGTGTGAAATTGTTATCCGCTCACAATTCCACACAACATA
CGAGCCGGAAGCATAAAGTGTAAAGCCTGGGGTGCCTAATGAGTGAGCTA
ACTCACATTAATTGCGTTGCGCTCACTGCCCGCTTTCCAGTCGGGAAACC
TGTCGTGCCAGCTGCATTAATGAATCGGCCAACGCGCGGGGAGAGGCGGT
TTGCGTATTGGGCGCTCTTCCGCTTCCTCGCTCACTGACTCGCTGCGCTC
GGTCGTTCGGCTGCGGCGAGCGGTATCAGCTCACTCAAAGGCGGTAATAC
GGTTATCCACAGAATCAGGGGATAACGCAGGAAAGAACATGTGAGCAAAA
GGCCAGCAAAAGGCCAGGAACCGTAAAAAGGCCGCGTTGCTGGCGTTTTT
CCATAGGCTCCGCCCCCCTGACGACATCACAAAAATCGACGCTCAAGTCA
GAGGTGGCGAAACCCGACAGGACTATAAAGATACCAGGCGTTTCCCCCTG
GAAGCTCCCTCGTGCGCTCTCCTGTTCCGACCCTGCCGCTTACCGGATAC
CTGTCCGCCTTTCTCCCTTCGGGAAGCGTGGCGCTTTCTCAATGCTCACG
CTGTAGGTATCTCAGTTCGGTGTAGGTCGTTCGCTCCAAGCTGGGCTGTG
TGCACGAACCCCCCGTTCAGCCCGACCGCTGCGCCTTATCCGGTAACTAT
CGTCTTGAGTCCAACCCGGTAAGACACGACTTATCGCCACTGGCAGCAGC
CACTGGTAACAGGATTAGCAGAGCGAGGTATGTAGGCGGTGCTACAGAGT
TCTTGAAGTGGTGGCCTAACTACGGCTACACTAGAAGGACAGTATTTGGT
ATCTGCGCTCTGCTGAAGCCAGTTACCTTCGGAAAAAGAGTTGGTAGCTC
TTGATCCGGCAAACAAACCACCGCTGGTAGCGGTGGTTTTTTTGTTTGCA
AGCAGCAGATTACGCGCAGAAAAAAAGGATCTCAAGAAGATCCTTTGATC
TTTTCTACGGGGTCTGACGCTCAGTGGAACGAAAACTCACGTTAAGGGAT
TTTGGTCATGAGATTATCAAAAAGGATCTTCACCTAGATCCTTTTAAATT
AAAAATGAAGTTTTAAATCAATCTAAAGTATATATGAGTAAACTTGGTCT
GACAGTTACCAATGCTTAATCAGTGAGGCACCTATCTCAGCGATCTGTCT
ATTTCGTTCATCCATAGTTGCCTGACTCCCCGTCGTGTAGATAACTACGA
TACGGGAGGGCTTACCATCTGGCCCCAGTGCTGCAATGATACCGCGAGAC
CCACGCTCACCGGCTCCAGATTTATCAGCAATAAACCAGCCAGCCGGAAG
GGCCAGCGCAGAAGTGGTCCTGCAACTTTATCCGCCTCCATCCAGTCTAT
TAATTGTTGCCGGGAAGCTAGAGTAAGTAGTTCGCCAGTTAATAGTTTGC
GCAACGTTGTTGCCATTGCTACAGGCATCGTGGTGTCACGCTCGTCGTTT
GGTATGGCTTCATTCAGCTCCGGTTCCCAACGATCAAGGCGAGTTACATG
ATCCCCCATGTTGTGCAAAAAAGCGGTTAGCTCCTTCGGTCCTCCGATCG
TTGTCAGAAGTAAGTTGGCCGCAGTGTTATCACTCATGGTTATGGCAGCA
CTGCATAATTCTCTTACTGTCATGCCATCCGTAAGATGCTTTTCTGTGAC
TGGTGAGTACTCAACCAAGTCATTCTGAGAATAGTGTATGCGGCGACCGA
GTTGCTCTTGCCCGGCGTCAATACGGGATAATACCGCGCCACATAGCAGA
ACTTTAAAAGTGCTCATCATTGGAAAACGTTCTTCGGGGCGAAAACTCTC
AAGGATCTTACCGCTGTTGAGATCCAGTTCGATGTAACCCACTCGTGCAC
CCAACTGATCTTCAGCATCTTTTACTTTCACCAGCGTTTCTGGGTGAGCA
AAAACAGGAAGGCAAAATGCCGCAAAAAAGGGAATAAGGGCGACACGGAA
ATGTTGAATACTCATACTCTTCCTTTTTCAATATTATTGAAGCATTTATC
AGGGTTATTGTCTCATGAGCGGATACATATTTGAATGTATTTAGAAAAAT
AAACAAATAGGGGTTCCGCGCACATTTCCCCGAAAAGTGCCACCTGACGT
CGACGGATCGGGAGATCTCCCGATCCCCTATGGTCGACTCTCAGTACAAT
CTGCTCTGATGCCGCATAGTTAAGCCAGTATCTGCTCCCTGCTTGTGTGT
TGGAGGTCGCTGAGTAGTGCGCGAGCAAAATTTAAGCTACAACAAGGCAA
GGCTTGACCGACAATGCATGAAGAATCTGCTTAGGGTTAGGCGTTTTGCG
CTGCTTCGCGATGTACGGGCCAGATATACGCGTTGACATTGATTATTGAC
TAGTTATTAATAGTAATCAATTACGGGGTCATTAGTTCATAGCCCATATA
TGGAGTTCCGCGTTACATAACTTACGGTAAATGGCCCGCCTGGCTGACCG
CCCAACGACCCCCGCCCATTGACGTCAATAATGACGTATGTTCCCATAGT
```

-continued

AACGCCAATAGGGACTTTCCATTGACGTCAATGGGTGGAgTATTTACGGT

AAACTGCCCACTTGGCAGTACATCAAGTGTATCATATGCCAAGTACGCCC

CCTATTGACGTCAATGACGGTAAATGGCCCGCCTGGCATTATGCCCAGTA

CATGACCTTATGGGACTTTCCTACTTGGCAGTACATCTACGTATTAGTCA

TCGCTATTACCATGGTGATGCGGTTTTGGCAGTACATCAATGGGCGTGGA

TAGCGGTTTGACTCACGGGGATTTCCAAGTCTCCACCCCATTGACGTCAA

TGGGAGTTTGTTTTGGCACCAAAATCAACGGGACTTTCCAAAATGTCGTA

ACAACTCCGCCCCATTGACGCAAATGGGCGGTAGGCGTGTACGGTGGGAG

GTCTATATAAGCAGAGCTCTCTGGCTAACTAGAGAACCCACTGCTTACTG

GCTTATCGAAATTAATACGACTCACTATAGGGAGACCCAAGCTGGCTAGC

ACCATGGACTACAAAGACCATGACGGTGATATAAAGATCATGACATCGAT

TACAAGGATGACGATGACAAGATGGCCCCCAAGAAGAAGAGGAAGGTGGG

CATTCACCGCGGGGTACCTATGGTGGACTTGAGGACACTCGGTTATTCGC

AACAGCAACAGGAGAAAATCAAGCCTAAGGTCAGGAGCACCGTCGCGCAA

CACCACGAGGCGCTTGTGGGGCATGGCTTCACTCATGCGCATATTGTCGC

GCTTTCACAGCACCCTGCGGCGCTTGGGACGGTGGCTGTCAAATACCAAG

ATATGATTGCGGCCCTGCCCGAAGCCACGCACGAGGCAATTGTAGGGGTC

GGTAAACAGTGGTCGGGAGCGCGAGCACTTGAGGCGCTGCTGACTGTGGC

GGGTGAGCTTAGGGGGCCTCCGCTCCAGCTCGACACCGGGCAGCTGCTGA

AGATCGCGAAGAGAGGGGGAGTAACAGCGGTAGAGGCAGTGCACGCCTGG

CGCAATGCGCTCACCGGGGCCCCCTT<u>GAAC pFUS-X overlap</u>

BamHI and XbaI flanked pRVD fragments (gene synthesized, BamHI-EBE-XbaI)):

gXTN-1C:
(SEQ ID NO: 191)
<u>TCTAGA</u>GGTCTCATTGACCCCAGACCAGGTAGTCGCAATCGCGTCAcatg
acGGGGGAAAGCAAGCCCTGGAAACCGTGCAAAGGTTGTTGCCGGTCCTT
TGTCAAGACCACGGCAGAGACC<u>GGATCC</u> gXTN-2C:
(SEQ ID NO: 192)
TCTAGAGGTCTCACGGCctgactcccgatcaagttgtagcgattgcgtcg
CATGACggagggaaacaagcattggagactgtccaacggctccttcccgt
gttgtgtcaagcccacggAGAGACCGGATCC gXTN-3C:
(SEQ ID NO: 193)
TCTAGAGGTCTCAacggtTTGACGCCTGCACAAGTGGTCGCCATCGCCAG
CcatgatGGCGGTAAGCAGGCGCTGGAAACAGTACAGCGCCTGCTGCCTG
TACTGTGCCAGGATCATGAGAGACCGGATCC gXTN-4C:
(SEQ ID NO: 194)
TCTAGAGGTCTCACATGGActgaccccagaccaggtagtcgcaatcgcgt
caCATGACgggggaaagcaagccctggaaaccgtgcaaaggttgttgccg
gtcattgtcaagaccacAGAGACCGGATCC gXTN-5C:
(SEQ ID NO: 195)
TCTAGAGGTCTCAccacggcCTGACCCCAGACCAGGTAGTCGCAATCGCG
TCAcatgacGGGGGAAAGCAAGCCCTGGAAACCGTGCAAAGGTTGTTGCC
GGTCCTTTGTCAAGACCAAGAGACCGGATCC gXTN-6C:
(SEQ ID NO: 196)
TCTAGAGGTCTCAACCACGGCctgactcccgatcaagttgtagcgattgc
gtcgCATGACggagggaaacaagcattggagactgtccaacggctccttc
ccgtgttgtgtcaagcccAGAGACCGGATCC gXTN-7C:
(SEQ ID NO: 197)
TCTAGAGGTCTCAgcccacggtTTGACGCCTGCACAAGTGGTCGCCATCG
CCAGCCATGATGGCGGTAAGCAGGCGCTGGAAACAGTACAGCGCCTGCTG
CCTGTACTGTGCCAGGATAGAGACCGGATCC gXTN-8C:
(SEQ ID NO: 198)
TCTAGAGGTCTCAGGATCATGGActgaccccagaccaggtagtcgcaatc
gcgtcacatgacgggggaaagcaagccctggaaaccgtgcaaaggttgtt
gccggtcattgtcaagaAGAGACCGGATCC gXTN-9C:
(SEQ ID NO: 199)
TCTAGAGGTCTCAaagaccacggcCTGACCCCAGACCAGGTAGTCGCAAT
CGCGTCAcatgacGGGGGAAAGCAAGCCCTGGAAACCGTGCAAAGGTTGT
TGCCGGTCCTTTGTCAAGAGAGACCGGATCC gXTN-10C:
(SEQ ID NO: 200)
<u>TCTAGA</u>GGTCTCACAAGACCACGGCctgactcccgatcaagttgtagcga
ttgcgtcgcatgacggagggaaacaagcattggagactgtccaacggctc
cttcccgtgttgtgtcaagcccaTggAAGAGACC<u>GGATCC</u> gXTN-1T:
(SEQ ID NO: 201)
TCTAGAGGTCTCATTGACCCCAGACCAGGTAGTCGCAATCGCGTCAAACG
GAGGGGGAAAGCAAGCCCTGGAAACCGTGCAAAGGTTGTTGCCGGTCCTT
TGTCAAGACCACGGCAGAGACCGGATCC gXTN-2T:
(SEQ ID NO: 202)
TCTAGAGGTCTCACGGCctgactcccgatcaagttgtagcgattgcgtcg
AACGGTggagggaaacaagcattggagactgtccaacggctccttcccgt
gttgtgtcaagcccacggAGAGACCGGATCC gXTN-3T:
(SEQ ID NO: 203)
TCTAGAGGTCTCAacggtTTGACGCCTGCACAAGTGGTCGCCATCGCCTC
GAATGGCGGCGGTAAGCAGGCGCTGGAAACAGTACAGCGCCTGCTGCCTG
TACTGTGCCAGGATCATGAGAGACCGGATCC gXTN-4T:
(SEQ ID NO: 204)
TCTAGAGGTCTCACATGGActgaccccagaccaggtagtcgcaatcgcgt
caaacggaggggaaagcaagccctggaaaccgtgcaaaggttgttgccg
gtcctagtcaagaccacAGAGACCGGATCC gXTN-5T:
(SEQ ID NO: 205)
TCTAGAGGTCTCAccacggcCTGACCCCAGACCAGGTAGTCGCAATCGCG
TCAaacggaGGGGGAAAGCAAGCCCTGGAAACCGTGCAAAGGTTGTTGCC
GGTCCTTTGTCAAGACCAAGAGACCGGATCC gXTN-6T:
(SEQ ID NO: 206)
TCTAGAGGTCTCAACCACGGCctgactcccgatcaagttgtagcgattgc
gtcgAACGGTggagggaaacaagcattggagactgtccaacggctccttc
ccgtgttgtgtcaagcccAGAGACCGGATCC gXTN-7T:
(SEQ ID NO: 207)
TCTAGAGGTCTCAgcccacggtTTGACGCCTGCACAAGTGGTCGCCATCG
CCAGCaatggcGGCGGTAAGCAGGCGCTGGAAACAGTACAGCGCCTGCTG
CCTGTACTGTGCCAGGATAGAGACCGGATCC gXTN-8T:
(SEQ ID NO: 208)
TCTAGAGGTCTCAGGATCATGGActgaccccagaccaggtagtcgcaatc
gcgtcaAACGGAggggaaagcaagccctggaaaccgtgcaaaggttgtt
gccggtcattgtcaagaAGAGACCGGATCC -continued gXTN-9T:

(SEQ ID NO: 209)
TCTAGAGGTCTCAaagaccacggcCTGACCCCAGACCAGGTAGTCGCAAT
CGCGTCAAACGGAGGGGAAAGCAAGCCCTGGAAACCGTGCAAAGGTTGT
TGCCGGTCCTTTGTCAAGAGAGACCGGATCC gXTN-10T:

(SEQ ID NO: 210)
TCTAGAGGTCTCACAAGACCACGGCctgactcccgatcaagttgtagcga
ttgcgtccaacggtggagggaaacaagcattggagactgtccaacggctc
cttcccgtgttgtgtcaagcccaTggAAGAGACCGGATCC gXTN-1A:

(SEQ ID NO: 211)
TCTAGAGGTCTCATTGACCCCAGACCAGGTAGTCGCAATCGCGTCAaaca
ttGGGGGAAAGCAAGCCCTGGAAACCGTGCAAAGGTTGTTGCCGGTCCTT
TGTCAAGACCACGGCAGAGACCGGATCC gXTN-2A:

(SEQ ID NO: 212)
TCTAGAGGTCTCACGGCctgactcccgatcaagttgtagcgattgcgtcg
aacattggagggaaacaagcattggagactgtccaacggctccttcccgt
gttgtgtcaagcccacggAGAGACCGGATCC gXTN-3A:

(SEQ ID NO: 213)
TCTAGAGGTCTCAacggtTTGACGCCTGCACAAGTGGTCGCCATCGCCAG
CaatattGGCGGTAAGCAGGCGCTGGAAACAGTACAGCGCCTGCTGCCTG
TACTGTGCCAGGATCATGAGAGACCGGATCC gXTN-4A:

(SEQ ID NO: 214)
TCTAGAGGTCTCACATGGActgaccccagaccaggtagtcgcaatcgcgt
caAACATTggggggaaagcaagcccctggaaaccgtgcaaaggttgttgccg
gtcattgtcaagaccacAGAGACCGGATCC gXTN-5A:

(SEQ ID NO: 215)
TCTAGAGGTCTCAccacggcCTGACCCCAGACCAGGTAGTCGCAATCGCG
TCGAACATTGGGGGAAAGCAAGCCCTGGAAACCGTGCAAAGGTTGTTGCC
GGTCCTTTGTCAAGACCAAGAGACCGGATCC gXTN-6A:

(SEQ ID NO: 216)
TCTAGAGGTCTCAACCAtGGCctgactcccgatcaagttgtagcgattgc
gtcgaacattggagggaaacaagcattggagactgtccaacggctccttc
ccgtgttgtgtcaagcccAGAGACCGGATCC gXTN-7A:

(SEQ ID NO: 217)
TCTAGAGGTCTCAgcccacggtTTGACGCCTGCACAAGTGGTCGCCATCG
CCTCCAATATTGGCGGTAAGCAGGCGCTGGAAACAGTACAGCGCCTGCTG
CCTGTACTGTGCCAGGATAGAGACCGGATCC gXTN-8A:

(SEQ ID NO: 218)
TCTAGAGGTCTCAGGATCATGGActgaccccagaccaggtagtcgcaatc
gcgtcgaacattggggggaaagcaagcccctggaaaccgtgcaaaggttgtt
gccggtcattgtcaagaAGAGACCGGATCC gXTN-9A:

(SEQ ID NO: 219)
TCTAGAGGTCTCAaagaccacggcCTGACCCCAGACCAGGTAGTCGCAAT
CGCGTCGAACATTGGGGAAAGCAAGCCCTGGAAACCGTGCAAAGGTTGT
TGCCGGTCCTTTGTCAAGAGAGACCGGATCC gXTN-10A:

(SEQ ID NO: 220)
TCTAGAGGTCTCACAAGACCACGGCctgactcccgatcaagttgtagcga
ttgcgtcgAACATTggagggaaacaagcattggagactgtccaacggctc
cttcccgtgttgtgtcaagcccaTggAAGAGACCGGATCC gXTN-1G:

(SEQ ID NO: 221)
TCTAGAGGTCTCATTGACCCCAGACCAGGTAGTCGCAATCGCGaacaata
atGGGGGAAAGCAAGCCCTGGAAACCGTGCAAAGGTTGTTGCCGGTCCTT
TGTCAAGACCACGGCAGAGACCGGATCC gXTN-2G:

(SEQ ID NO: 222)
TCTAGAGGTCTCACGGCctgactcccgatcaagttgtagcgattgcgaat
aacaatggagggaaacaagcattggagactgtccaacggctccttcccgt
gttgtgtcaagcccacggAGAGACCGGATCC gXTN-3G:

(SEQ ID NO: 223)
TCTAGAGGTCTCAacggtTTGACGCCTGCACAAGTGGTCGCCATCGCCAA
CAACAACGGCGGTAAGCAGGCGCTGGAAACAGTACAGCGCCTGCTGCCTG
TACTGTGCCAGGATCATGAGAGACCGGATCC gXTN-4G:

(SEQ ID NO: 224)
TCTAGAGGTCTCACATGGActgaccccagaccaggtagtcgcaatcgcga
acaataatgggggaaagcaagcccctggaaaccgtgcaaaggttgttgccg
gtcattgtcaagaccacAGAGACCGGATCC gXTN-5G:

(SEQ ID NO: 225)
TCTAGAGGTCTCAccacggcCTGACCCCAGACCAGGTAGTCGCAATCGCG
AACAATAATGGGGGAAAGCAAGCCCTGGAAACCGTGCAAAGGTTGTTGCC
GGTCCTTTGTCAAGACCAAGAGACCGGATCC gXTN-6G:

(SEQ ID NO: 226)
TCTAGAGGTCTCAACCAtGGCctgactcccgatcaagttgtagcgattgc
gaataacaatggagggaaacaagcattggagactgtccaacggctccttc
ccgtgttgtgtcaagcccAGAGACCGGATCC gXTN-7G:

(SEQ ID NO: 227)
TCTAGAGGTCTCAgcccacggtTTGACGCCTGCACAAGTGGTCGCCATCG
CCAACAACAACGGCGGTAAGCAGGCGCTGGAAACAGTACAGCGCCTGCTG
CCTGTACTGTGCCAGGATAGAGACCGGATCC gXTN-8G:

(SEQ ID NO: 228)
TCTAGAGGTCTCAGGATCATGGActgaccccagaccaggtagtcgcaatc
gcgaacaataatgggggaaagcaagcccctggaaaccgtgcaaaggttgtt
gccggtcctttgtcaagaAGAGACCGGATCC gXTN-9G:

(SEQ ID NO: 229)
TCTAGAGGTCTCAaagaccacggcCTGACCCCAGACCAGGTAGTCGCAAT
CGCGAACAATAATGGGGGAAAGCAAGCCCTGGAAACCGTGCAAAGGTTGT
TGCCGGTCCTTTGTCAAGAGAGACCGGATCC gXTN-10G:

(SEQ ID NO: 230)
TCTAGAGGTCTCACAAGACCACGGCctgactcccgatcaagttgtagcga
ttgcgaataacaatggagggaaacaagcattggagactgtccaacggctc
cttcccgtgttgtgtcaagcccaTggAAGAGACCGGATCC SbfI and SacI flanked pFUS fragments (gene synthesized, SbfI-pFUS-SacI)

pFUS-X:

(SEQ ID NO: 231)
(SbfI) CCTGCAGGTCGACCGTCTCAGAACTTGAAGAGACCGTACGTGAT
CGTGGTCTCATggaTTGAAGAGACG GGTACCGAGCTC(SacI)

pFUS-Z1:

(SEQ ID NO: 232)
CCTGCAGGTCGACCGTCTCATTGAAGAGACCGTACTGgatcgtGGTCTCA
CGGCctgaAGAGACGGGTACCGAGCTC pFUS-Z2:

(SEQ ID NO: 233)
CCTGCAGGTCGACCGTCTCATTGAAGAGACCGTACTGgatcgtGGTCTCA
acggtctgaAGAGACGGGTACCGAGCTC pFUS-Z3:

(SEQ ID NO: 234)
CCTGCAGGTCGACCGTCTCATTGAAGAGACCGTACTGgatcgtGGTCTCA
CATGGActgaAGAGACGGGTACCGAGCTC pFUS-Z4:
(SEQ ID NO: 235)
CCTGCAGGTCGACCGTCTCATTGAAGAGACCGTACTGgatcgtGGTCTCA
ccacggcctgaAGAGACGGGTACCGAGCTC pFUS-Z5:
(SEQ ID NO: 236)
CCTGCAGGTCGACCGTCTCATTGAAGAGACCGTACTGgatcgtGGTCTCA
ACCACGGCctgaAGAGACGGGTACCGAGCTC pFUS-Z6:
(SEQ ID NO: 237)
CCTGCAGGTCGACCGTCTCATTGAAGAGACCGTACTGgatcgtGGTCTCA
gcccacggtctgaAGAGACGGGTACCGAGCTC pFUS-Z7:
(SEQ ID NO: 238)
CCTGCAGGTCGACCGTCTCATTGAAGAGACCGTACTGgatcgtGGTCTCA
GGATCATGGActgaAGAGACGGGTACCGAGCTC pFUS-Z8:
(SEQ ID NO: 239)
CCTGCAGGTCGACCGTCTCATTGAAGAGACCGTACTGgatcgtGGTCTCA
aagaccacggcctgaAGAGACGGGTACCGAGCTC pFUS-Z9:
(SEQ ID NO: 240)
CCTGCAGGTCGACCGTCTCATTGAAGAGACCGTACTGgatcgtGGTCTCA
CAAGACCACGGCctgaAGAGACGGGTACCGAGCTC pFUS-Z10:
(SEQ ID NO: 241)
CCTGCAGGTCGACCGTCTCATTGAAGAGACCGTACTGgatcgtGGTCTCA
TggActgaAGAGACGGGTACCGAGCTC

Example 7

Methylesterases and Methyltransferases 34aa Consensus EBE:
(SEQ ID NO: 300)
QTTERIVAIGT nn (nn is replaced with relevant RVD)

(SEQ ID NO: 242)
GGTQALEAVLTALPRVCPGMV

Backtranseq of 34aa
(SEQ ID NO: 301)
QTTERIVAIGT

SH (SH is anon-specific RVD
(SEQ ID NO: 243)
GGTQALEAVLTALPRVCPGMV
and (SEQ ID NO: 244)
CAGACCACCGAGAGGATCGTGGCCATCGGCACCAGCCACGGCGGCACCCA
GGCCCTGGAGGCCGTGCTGACCGCCCTGCCCAGGGTGTGCCCCGGCATGG
TG Methylesterase EBE (14EBEs in XTN backbone) (SEQ ID NO: 245):

Bold Font: Methylesterse EBEs. All with non-specific RVD SH in this example.

Black Font: FLASH XTN Backbone.

GACGGATCGGGAGATCTCCCGATCCCCTATGGTCGACTCTCAGTACAATCTGCTCTGATGCCGCATAGTTAAGCCAGTATCTGCTCCCT

GCTTGTGTGTTGGAGGTCGCTGAGTAGTGCGCGAGCAAAATTTAAGCTACAACAAGGCAAGGCTTGACCGACAATTGCATGAAGAAT

CTGCTTAGGGTTAGGCGTTTTGCGCTGCTTCGCGATGTACGGGCCAGATATACGCGTTGACATTGATTATTGACTAGTTATTAATAGTA

ATCAATTACGGGGTCATTAGTTCATAGCCCATATATGGAGTTCCGCGTTACATAACTTACGGTAAATGGCCCGCCTGGCTGACCGCCC

AACGACCCCCGCCCATTGACGTCAATAATGACGTATGTTCCCATAGTAACGCCAATAGGGACTTTCCATTGACGTCAATGGGTGGAgT

ATTTACGGTAAACTGCCCACTTGGCAGTACATCAAGTGTATCATATGCCAAGTACGCCCCCTATTGACGTCAATGACGGTAAATGGCC

CGCCTGGCATTATGCCCAGTACATGACCTTATGGGACTTTCCTACTTGGCAGTACATCTACGTATTAGTCATCGCTATTACCATGGTGA

TGCGGTTTTGGCAGTACATCAATGGGCGTGGATAGCGGTTTGACTCACGGGGATTTCCAAGTCTCCACCCCATTGACGTCAATGGGAG

TTTGTTTTGGCACCAAAATCAACGGGACTTTCCAAAATGTCGTAACAACTCCGCCCCATTGACGCAAATGGGCGGTAGGCGTGTACGG

TGGGAGGTCTATATAAGCAGAGCTCTCTGGCTAACTAGAGAACCCACTGCTTACTGGCTTATCGAAATTAATACGACTCACTATAGGG

AGACCCAAGCTGGCTAGCACCATGGACTACAAAGACCATGACGGTGATTATAAAGATCATGACATCGATTACAAGGATGACGATGAC

AAGATGGCCCCAAGAAGAAGAGGAAGGTGGGCATTCACCGCGGGGTACCTATGGTGGACTTGAGGACACTCGGTTATTCGCAACAG

CAACAGGAGAAAATCAAGCCTAAGGTCAGGAGCACCGTCGCGCAACACCACGAGGCGCTTGTGGGGCATGGCTTCACTCATGCGCAT

ATTGTCGCGCTTTCACAGCACCCTGCGGCGCTTGGGACGGTGGCTGTCAAATACCAAGATATGATTGCGGCCCTGCCCGAAGCCACGC

ACGAGGCAATTGTAGGGGTCGGTAAACAGTGGTCGGGAGCGCGAGCACTTGAGGCGCTGCTGACTGTGGCGGGTGAGCTTAGGGGGC

CTCCGCTCCAGCTCGACACCGGGCAGCTGCTGAAGATCGCGAAGAGAGGGGGAGTAACAGCGGTAGAGGCAGTGCACGCCTGGCGC

AATGCGCTCACCGGGGCCCCCTTGAAC

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

-continued

```
CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

CTGACACCCGAACAGGTGGTCGCCATTGCTAATAATAACGGAGGACGGCCAGCCTTGGAGTCCATCGTAGCCCAATTGTCCAGGCCC

GATCCCGCGTTGGCTGCGTTAACGAATGACCATCTGGTGGCGTTGGCATGTCTTGGTGGACGACCCGCGCTCGATGCAGTCAAAAAGG

GTCTGCCTCATGCTCCCGCATTGATCAAAAGAACCAACCGGCGGATTCCCGAGAGAACTTCCCATCGAGTCGCGGGATCCCAACTAGT

C
```

Example 8: Generation of an Exemplary Non-Covalent Linkage

Phage display is used to identify a scFv antibody against a FLAG affinity tag that provides an optimal linkage. A large diversity in scFv affinity is obtained by limiting the stringency of the affinity selection process. This diversity may represent a key advantage of a PhD approach for identifying a successful linkage between a FLAG affinity tag and a scFv with affinity for the FLAG tag. In some instances, a single-chain variable fragment (scFv) antibody with a faster off-rate may provide permissive "breathing" of a scFv-FLAG complex. A near-exhaustive search among scFv antibodies allows one to select from among a large diversity of possible conformations of scFv-FLAG affinity tag complexes. A PhD strategy may create such diversity through the generation of unique monovalent scFvs against the FLAG epitope.

A non-covalent linkage method, such as that achieved through the use of a scFv antibody employs a protein fused to a scFv that provides a reversible association between a FLAG affinity tag and the scFv, which may circumvent any permanent interference with the target protein that may occur when it is subjected to covalent linkage.

Immunization for Producing Anti-FLAG Antibodies.

An antibody library is produced from immunized rabbits as is well known in the art. Six New Zealand White rabbits are immunized each with 200 µg of a FLAG affinity tag peptide sequence plus adjuvant, and serum is collected six weeks after immunization for determining antibody titers. Titers are determined by ELISAs on immobilized FLAG affinity tag and the animals with the highest titers (at least 1:1000) are sacrificed for isolating the spleen and bone marrow. If rabbits do not produce sufficient titers, a naïve library from embryonic rabbit tissue is used. This provides an unbiased collection of un-rearranged heavy and light chain genes. Total RNA is extracted from tissues using Trizol (Invitrogen), and cDNA synthesis is performed with the iScript cDNA synthesis kit (BioRad).

Generating scFv Gene Fusions.

To isolate expressed variable regions of heavy and light chain genes from rabbit, several primers are used. Eight primers are used for kappa and lambda light chain amplification and five primers are used for heavy chain gene amplification. Primers also contain the coding sequence for an 18 amino acid linker sequence (SSGGGGSGGGGGGSSRSS) (SEQ ID NO: 246), which links the variable regions of the heavy and light chains (VH and VL). This longer linker sequence provides better stability of monomeric forms of scFv fragments. The PCR products of the VII and VL genes overlap in this linker region and can then be assembled by overlap-extension (OLE) PCR (FIG. 1). PCR products are then digested with Sfil, ligated with Sfil-digested pComb3H, and DNA will then be size-selected by gel electrophoresis. This plasmid enables phagemid display of an scFv fused to the pill coat protein. About 5 molecules of pill phage coat protein is present on each phage particle. The pComb3H plasmid expresses the scFv-plll fusion at a level such that about one or two molecules are integrated with wild-type pill (which is provided by helper phage). Since up to 1012 phage particles can be generated in a single preparation, a very large number of scFvs can thus be screened. In PhD the scFv coding sequence is always linked to the phage particle displaying the protein, so subsequent DNA sub-cloning is conveniently achieved.

Producing and Screening the Phage Library.

Ligated plasmid DNA (50 to 100 ng) is electroporated into ER2538 E. coli (New England Biolabs). E. coli will then be recovered by shaking for 1 hour at 37° C. in 5 mLs of SOC. Phage is produced with the VCSM13 helper phage, which has a defective origin of replication. Phage particles will be precipitated with PEG-8000 and then isolated by further centrifugation. This phage prep is the primary library, and will be affinity selected by "panning." Double recognition panning is performed in which the phage elution is re-incubated with the immobilized antigen, washed, and eluted again. This helps eliminate non-specific phage. To test each round of selection, phage pools are assayed by ELISAs for affinity to the PB antigen. PB or BSA are coated to 96-well plates, incubated with phage, and then incubated with a horseradish peroxidase (HRP) conjugated anti-M13 antibody, which recognizes the M13 phage coat protein. An increasing ELISA titer indicates successful affinity selection of each phage pool.

Transferring the scFv Library into a Lentiviral Vector, and Expansion in E. coli.

Phagemid DNA is isolated from bacteria after the 2nd (R2) and 3rd (R3) rounds of panning by infecting E. coli with each phage pool, selecting with carbenicillin, followed by standard plasmid preparation. Plasmid DNA is digested with Sfi1 to liberate the scFv coding sequence, and ligated upstream of the E2c coding sequence within the pLVX-IRES-ZsGreen1 (Clontech) vector. The E2c coding sequence also has a short linker sequence (GGSSRSS) (SEQ ID NO: 247) and creates a fusion of the scFv library to the N-terminal portion of E2c. The two ensuing plasmid libraries (R

```
Leu Ser Thr Glu Gln Val Val Ala Ile Ala Ser Ser Ile Gly Gly Lys
1               5                   10                  15

Gln Ala Leu Glu Ala Val Lys Ala Gln Leu Leu Val Leu Arg Ala Ala
            20                  25                  30

Pro Tyr Glu
        35

<210> SEQ ID NO 3
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 3

Leu Ser Thr Glu Gln Val Val Ala Ile Ala Ser Ser Asn Gly Gly Lys
1               5                   10                  15

Gln Ala Leu Glu Ala Val Lys Ala Gln Leu Leu Val Leu Arg Ala Ala
            20                  25                  30

Pro Tyr Glu
        35

<210> SEQ ID NO 4
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 4

Leu Ser Thr Glu Gln Val Val Ala Ile Ala Ser Ser His Gly Gly Lys
1               5                   10                  15

Gln Ala Leu Glu Ala Val Lys Ala Gln Leu Leu Val Leu Arg Ala Ala
            20                  25                  30

Pro Tyr Glu
        35

<210> SEQ ID NO 5
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 5

Leu Ser Thr Glu Gln Val Val Ala Ile Ala Ser Asn Pro Gly Gly Lys
1               5                   10                  15

Gln Ala Leu Glu Ala Val Lys Ala Gln Leu Leu Val Leu Arg Ala Ala
            20                  25                  30

Pro Tyr Glu
        35

<210> SEQ ID NO 6
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 6

Leu Ser Thr Glu Gln Val Val Ala Ile Ala Ser Asn His Gly Gly Lys
1               5                   10                  15
```

-continued

Gln Ala Leu Glu Ala Val Lys Ala Gln Leu Leu Val Leu Arg Ala Ala
            20                  25                  30

Pro Tyr Glu
        35

<210> SEQ ID NO 7
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 7

Leu Ser Thr Glu Gln Val Val Ala Ile Ala Ser Asn Thr Gly Gly Lys
1               5                   10                  15

Gln Ala Leu Glu Ala Val Lys Ala Gln Leu Leu Val Leu Arg Ala Ala
            20                  25                  30

Pro Tyr Glu
        35

<210> SEQ ID NO 8
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 8

Leu Ser Thr Glu Gln Val Val Ala Ile Ala Ser Asn Lys Gly Gly Lys
1               5                   10                  15

Gln Ala Leu Glu Ala Val Lys Ala Gln Leu Leu Val Leu Arg Ala Ala
            20                  25                  30

Pro Tyr Glu
        35

<210> SEQ ID NO 9
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 9

Leu Ser Thr Glu Gln Val Val Ala Ile Ala Ser Asn Pro Gly Gly Lys
1               5                   10                  15

Gln Ala Leu Glu Ala Val Lys Ala Gln Leu Leu Val Leu Arg Ala Ala
            20                  25                  30

Pro Tyr Glu
        35

<210> SEQ ID NO 10
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 10

Leu Ser Thr Glu Gln Val Val Ala Ile Ala Ser Asn Asn Gly Gly Lys
1               5                   10                  15

Gln Ala Leu Glu Ala Val Lys Ala Gln Leu Leu Val Leu Arg Ala Ala
            20                  25                  30

Pro Tyr Glu
        35

<210> SEQ ID NO 11
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 11

Leu Ser Thr Glu Gln Val Val Ala Ile Ala Ser Asn Asp Gly Gly Lys
1               5                   10                  15

Gln Ala Leu Glu Ala Val Lys Ala Gln Leu Leu Val Leu Arg Ala Ala
            20                  25                  30

Pro Tyr Glu
        35

<210> SEQ ID NO 12
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 12

Leu Ser Thr Glu Gln Val Val Ala Ile Ala Ser Asn Gly Gly Gly Lys
1               5                   10                  15

Gln Ala Leu Glu Ala Val Lys Ala Gln Leu Leu Val Leu Arg Ala Ala
            20                  25                  30

Pro Tyr Glu
        35

<210> SEQ ID NO 13
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 13

Leu Ser Thr Glu Gln Val Val Ala Ile Ala Ser His Asn Gly Gly Lys
1               5                   10                  15

Gln Ala Leu Glu Ala Val Lys Ala Gln Leu Leu Val Leu Arg Ala Ala
            20                  25                  30

Pro Tyr Glu
        35

<210> SEQ ID NO 14
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 14

Leu Ser Thr Glu Gln Val Val Ala Ile Ala Ser His Tyr Gly Gly Lys
1               5                   10                  15

Gln Ala Leu Glu Ala Val Lys Ala Gln Leu Leu Val Leu Arg Ala Ala
            20                  25                  30

Pro Tyr Glu
        35

```
<210> SEQ ID NO 15
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 15

Leu Ser Thr Glu Gln Val Val Ala Ile Ala Ser His Asp Gly Gly Lys
1               5                   10                  15

Gln Ala Leu Glu Ala Val Lys Ala Gln Leu Leu Val Leu Arg Ala Ala
            20                  25                  30

Pro Tyr Glu
        35

<210> SEQ ID NO 16
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 16

Leu Ser Thr Glu Gln Val Val Ala Ile Ala Ser His His Gly Gly Lys
1               5                   10                  15

Gln Ala Leu Glu Ala Val Lys Ala Gln Leu Leu Val Leu Arg Ala Ala
            20                  25                  30

Pro Tyr Glu
        35

<210> SEQ ID NO 17
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 17

Leu Ser Thr Glu Gln Val Val Ala Ile Ala Ser Arg Asn Gly Gly Lys
1               5                   10                  15

Gln Ala Leu Glu Ala Val Lys Ala Gln Leu Leu Val Leu Arg Ala Ala
            20                  25                  30

Pro Tyr Glu
        35

<210> SEQ ID NO 18
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 18

Leu Ser Thr Glu Gln Val Val Ala Ile Ala Ser Arg Ser Gly Gly Lys
1               5                   10                  15

Gln Ala Leu Glu Ala Val Lys Ala Gln Leu Leu Val Leu Arg Ala Ala
            20                  25                  30

Pro Tyr Glu
        35

<210> SEQ ID NO 19
```

```
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 19

Leu Ser Thr Glu Gln Val Ala Ile Ala Ser Gly Ser Gly Gly Lys
1               5                   10                  15

Gln Ala Leu Glu Ala Val Lys Ala Gln Leu Leu Val Leu Arg Ala Ala
            20                  25                  30

Pro Tyr Glu
        35

<210> SEQ ID NO 20
<211> LENGTH: 1053
<212> TYPE: PRT
<213> ORGANISM: Staphylococcus aureus

<400> SEQUENCE: 20

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Glu Asn Val Phe
        275                 280                 285
```

```
Lys Gln Lys Lys Lys Pro Thr Leu Lys Gln Ile Ala Lys Glu Ile Leu
290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
                340                 345                 350

Lys Ile Leu Thr Ile Tyr Gln Ser Glu Asp Ile Gln Glu Glu Leu
                355                 360                 365

Thr Asn Leu Asn Ser Glu Leu Thr Gln Glu Glu Ile Glu Gln Ile Ser
370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
                420                 425                 430

Gln Lys Glu Ile Pro Thr Thr Leu Val Asp Asp Phe Ile Leu Ser Pro
                435                 440                 445

Val Val Lys Arg Ser Phe Ile Gln Ser Ile Lys Val Ile Asn Ala Ile
450                 455                 460

Ile Lys Lys Tyr Gly Leu Pro Asn Asp Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
                500                 505                 510

Gly Lys Glu Asn Ala Lys Tyr Leu Ile Glu Lys Ile Lys Leu His Asp
                515                 520                 525

Met Gln Glu Gly Lys Cys Leu Tyr Ser Leu Glu Ala Ile Pro Leu Glu
530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
                580                 585                 590

Ser Ser Ser Asp Ser Lys Ile Ser Tyr Glu Thr Phe Lys Lys His Ile
                595                 600                 605

Leu Asn Leu Ala Lys Gly Lys Gly Arg Ile Ser Lys Thr Lys Lys Glu
610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
                660                 665                 670

Val Lys Ser Ile Asn Gly Gly Phe Thr Ser Phe Leu Arg Arg Lys Trp
                675                 680                 685

Lys Phe Lys Lys Glu Arg Asn Lys Gly Tyr Lys His His Ala Glu Asp
690                 695                 700

Ala Leu Ile Ile Ala Asn Ala Asp Phe Ile Phe Lys Glu Trp Lys Lys
```

```
                705                 710                 715                 720
Leu Asp Lys Ala Lys Lys Val Met Glu Asn Gln Met Phe Glu Glu Lys
                    725                 730                 735

Gln Ala Glu Ser Met Pro Glu Ile Glu Thr Glu Gln Glu Tyr Lys Glu
                740                 745                 750

Ile Phe Ile Thr Pro His Gln Ile Lys His Ile Lys Asp Phe Lys Asp
                755                 760                 765

Tyr Lys Tyr Ser His Arg Val Asp Lys Lys Pro Asn Arg Glu Leu Ile
        770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
                820                 825                 830

Asp Pro Gln Thr Tyr Gln Lys Leu Lys Leu Ile Met Glu Gln Tyr Gly
            835                 840                 845

Asp Glu Lys Asn Pro Leu Tyr Lys Tyr Tyr Glu Glu Thr Gly Asn Tyr
        850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                    885                 890                 895

Tyr Pro Asn Ser Arg Asn Lys Val Val Lys Leu Ser Leu Lys Pro Tyr
                900                 905                 910

Arg Phe Asp Val Tyr Leu Asp Asn Gly Val Tyr Lys Phe Val Thr Val
        915                 920                 925

Lys Asn Leu Asp Val Ile Lys Lys Glu Asn Tyr Tyr Glu Val Asn Ser
    930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr Tyr Arg Glu Tyr Leu Glu Asn Met
                995                 1000                1005

Asn Asp Lys Arg Pro Pro Arg Ile Ile Lys Thr Ile Ala Ser Lys
    1010                1015                1020

Thr Gln Ser Ile Lys Lys Tyr Ser Thr Asp Ile Leu Gly Asn Leu
    1025                1030                1035

Tyr Glu Val Lys Ser Lys Lys His Pro Gln Ile Ile Lys Lys Gly
    1040                1045                1050

<210> SEQ ID NO 21
<211> LENGTH: 1368
<212> TYPE: PRT
<213> ORGANISM: Staphylococcus pyogenes

<400> SEQUENCE: 21

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30
```

-continued

```
Lys Val Leu Gly Asn Thr Asp Arg His Ser Ile Lys Lys Asn Leu Ile
             35                  40                  45
Gly Ala Leu Leu Phe Asp Ser Gly Thr Ala Glu Ala Thr Arg Leu
         50                  55                  60
Lys Arg Thr Ala Arg Arg Tyr Thr Arg Arg Lys Asn Arg Ile Cys
 65                  70                  75                  80
Tyr Leu Gln Glu Ile Phe Ser Asn Glu Met Ala Lys Val Asp Asp Ser
                 85                  90                  95
Phe Phe His Arg Leu Glu Glu Ser Phe Leu Val Glu Glu Asp Lys Lys
                100                 105                 110
His Glu Arg His Pro Ile Phe Gly Asn Ile Val Asp Glu Val Ala Tyr
            115                 120                 125
His Glu Lys Tyr Pro Thr Ile Tyr His Leu Arg Lys Lys Leu Val Asp
        130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
            180                 185                 190
Asn Gln Leu Phe Glu Glu Asn Pro Ile Asn Ala Ser Gly Val Asp Ala
        195                 200                 205
Lys Ala Ile Leu Ser Ala Arg Leu Ser Lys Ser Arg Arg Leu Glu Asn
    210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
            260                 265                 270
Asp Asp Leu Asp Asn Leu Leu Ala Gln Ile Gly Asp Gln Tyr Ala Asp
        275                 280                 285
Leu Phe Leu Ala Ala Lys Asn Leu Ser Asp Ala Ile Leu Leu Ser Asp
    290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
```

```
              450                 455                 460
Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
                530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
                610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
                690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
                770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880
```

```
Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275
```

```
Arg Val Ile Leu Ala Asp Ala Asn Leu Asp Lys Val Leu Ser Ala
    1280            1285                1290

Tyr Asn Lys His Arg Asp Lys Pro Ile Arg Glu Gln Ala Glu Asn
    1295            1300                1305

Ile Ile His Leu Phe Thr Leu Thr Asn Leu Gly Ala Pro Ala Ala
    1310            1315                1320

Phe Lys Tyr Phe Asp Thr Thr Ile Asp Arg Lys Arg Tyr Thr Ser
    1325            1330                1335

Thr Lys Glu Val Leu Asp Ala Thr Leu Ile His Gln Ser Ile Thr
    1340            1345                1350

Gly Leu Tyr Glu Thr Arg Ile Asp Leu Ser Gln Leu Gly Gly Asp
    1355            1360                1365

<210> SEQ ID NO 22
<211> LENGTH: 1053
<212> TYPE: PRT
<213> ORGANISM: Staphylococcus aureus

<400> SEQUENCE: 22

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
            35                  40                  45

Ser Lys Arg Gly Ala Arg Arg Leu Lys Arg Arg Arg His Arg Ile
        50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285
```

```
Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
        435                 440                 445

Val Val Lys Arg Ser Phe Ile Gln Ser Ile Lys Val Ile Asn Ala Ile
    450                 455                 460

Ile Lys Lys Tyr Gly Leu Pro Asn Asp Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
            500                 505                 510

Gly Lys Glu Asn Ala Lys Tyr Leu Ile Glu Lys Ile Lys Leu His Asp
        515                 520                 525

Met Gln Glu Gly Lys Cys Leu Tyr Ser Leu Glu Ala Ile Pro Leu Glu
    530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
        595                 600                 605

Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
        675                 680                 685

Lys Phe Lys Lys Glu Arg Asn Lys Gly Tyr Lys His His Ala Glu Asp
    690                 695                 700
```

-continued

```
Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Lys
            725                 730                 735

Gln Ala Glu Ser Met Pro Glu Ile Glu Thr Glu Gln Glu Tyr Lys Glu
        740                 745                 750

Ile Phe Ile Thr Pro His Gln Ile Lys His Ile Lys Asp Phe Lys Asp
            755                 760                 765

Tyr Lys Tyr Ser His Arg Val Asp Lys Lys Pro Asn Arg Glu Leu Ile
770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
                820                 825                 830

Asp Pro Gln Thr Tyr Gln Lys Leu Lys Leu Ile Met Glu Gln Tyr Gly
        835                 840                 845

Asp Glu Lys Asn Pro Leu Tyr Lys Tyr Glu Glu Thr Gly Asn Tyr
850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
        900                 905                 910

Arg Phe Asp Val Tyr Leu Asp Asn Gly Val Tyr Lys Phe Val Thr Val
        915                 920                 925

Lys Asn Leu Asp Val Ile Lys Lys Glu Asn Tyr Tyr Glu Val Asn Ser
930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
            965                 970                 975

Glu Leu Tyr Arg Val Ile Gly Val Asn Asn Asp Leu Leu Asn Arg Ile
            980                 985                 990

Glu Val Asn Met Ile Asp Ile Thr  Tyr Arg Glu Tyr Leu  Glu Asn Met
                995                 1000                1005

Asn Asp Lys Arg Pro Pro Arg  Ile Ile Lys Thr Ile  Ala Ser Lys
        1010                1015                 1020

Thr Gln Ser Ile Lys Lys Tyr  Ser Thr Asp Ile Leu  Gly Asn Leu
        1025                1030                 1035

Tyr Glu Val Lys Ser Lys Lys  His Pro Gln Ile Ile  Lys Lys Gly
        1040                1045                 1050
```

<210> SEQ ID NO 23
<211> LENGTH: 1053
<212> TYPE: PRT
<213> ORGANISM: Staphylococcus aureus

<400> SEQUENCE: 23

```
Met Lys Arg Asn Tyr Ile Leu Gly Leu Ala Ile Gly Ile Thr Ser Val
1               5                   10                  15

Gly Tyr Gly Ile Ile Asp Tyr Glu Thr Arg Asp Val Ile Asp Ala Gly
            20                  25                  30
```

```
Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg His Arg Ile
 50                  55                  60

Gln Arg Val Lys Lys Leu Leu Phe Asp Tyr Asn Leu Leu Thr Asp His
 65                  70                  75                  80

Ser Glu Leu Ser Gly Ile Asn Pro Tyr Glu Ala Arg Val Lys Gly Leu
                 85                  90                  95

Ser Gln Lys Leu Ser Glu Glu Phe Ser Ala Ala Leu Leu His Leu
            100                 105                 110

Ala Lys Arg Arg Gly Val His Asn Val Asn Glu Val Glu Glu Asp Thr
            115                 120                 125

Gly Asn Glu Leu Ser Thr Lys Glu Gln Ile Ser Arg Asn Ser Lys Ala
130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
            195                 200                 205

Arg Thr Tyr Tyr Glu Gly Pro Gly Glu Gly Ser Pro Phe Gly Trp Lys
        210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
        435                 440                 445
```

```
Val Val Lys Arg Ser Phe Ile Gln Ser Ile Lys Val Ile Asn Ala Ile
450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
                500                 505                 510

Gly Lys Glu Asn Ala Lys Tyr Leu Ile Glu Lys Ile Lys Leu His Asp
                515                 520                 525

Met Gln Glu Gly Lys Cys Leu Tyr Ser Leu Glu Ala Ile Pro Leu Glu
530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Ala Ser Lys Lys Gly Asn Arg Thr Pro Phe Gln Tyr Leu
                580                 585                 590

Ser Ser Ser Asp Ser Lys Ile Ser Tyr Glu Thr Phe Lys Lys His Ile
                595                 600                 605

Leu Asn Leu Ala Lys Gly Lys Gly Arg Ile Ser Lys Thr Lys Lys Glu
610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
                660                 665                 670

Val Lys Ser Ile Asn Gly Gly Phe Thr Ser Phe Leu Arg Arg Lys Trp
                675                 680                 685

Lys Phe Lys Lys Glu Arg Asn Lys Gly Tyr Lys His His Ala Glu Asp
                690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
                740                 745                 750

Ile Phe Ile Thr Pro His Gln Ile Lys His Ile Lys Asp Phe Lys Asp
                755                 760                 765

Tyr Lys Tyr Ser His Arg Val Asp Lys Lys Pro Asn Arg Glu Leu Ile
                770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
                820                 825                 830

Asp Pro Gln Thr Tyr Gln Lys Leu Lys Leu Ile Met Glu Gln Tyr Gly
                835                 840                 845

Asp Glu Lys Asn Pro Leu Tyr Lys Tyr Glu Glu Thr Gly Asn Tyr
850                 855                 860

Leu Thr Lys Tyr Ser Lys Lys Asp Asn Gly Pro Val Ile Lys Lys Ile
```

```
              865                 870                 875                 880
Lys Tyr Tyr Gly Asn Lys Leu Asn Ala His Leu Asp Ile Thr Asp Asp
                    885                 890                 895

Tyr Pro Asn Ser Arg Asn Lys Val Val Lys Leu Ser Leu Lys Pro Tyr
                900                 905                 910

Arg Phe Asp Val Tyr Leu Asp Asn Gly Val Tyr Lys Phe Val Thr Val
                915                 920                 925

Lys Asn Leu Asp Val Ile Lys Lys Glu Asn Tyr Tyr Glu Val Asn Ser
930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
                980                 985                 990

Glu Val Asn Met Ile Asp Ile Thr Tyr Arg Glu Tyr Leu Glu Asn Met
                995                 1000                1005

Asn Asp Lys Arg Pro Pro Arg Ile Ile Lys Thr Ile Ala Ser Lys
     1010                1015                1020

Thr Gln Ser Ile Lys Lys Tyr Ser Thr Asp Ile Leu Gly Asn Leu
     1025                1030                1035

Tyr Glu Val Lys Ser Lys Lys His Pro Gln Ile Ile Lys Lys Gly
     1040                1045                1050

<210> SEQ ID NO 24
<211> LENGTH: 1787
<212> TYPE: PRT
<213> ORGANISM: Staphylococcus aureus

<400> SEQUENCE: 24

Met Gly Asp His Tyr Leu Asp Ile Arg Leu Arg Pro Asp Pro Glu Phe
1               5                   10                  15

Pro Pro Ala Gln Leu Met Ser Val Leu Phe Gly Lys Leu His Gln Ala
                20                  25                  30

Leu Val Ala Gln Gly Gly Asp Arg Ile Gly Val Ser Phe Pro Asp Leu
            35                  40                  45

Asp Glu Ser Arg Ser Arg Leu Gly Glu Arg Leu Arg Ile His Ala Ser
        50                  55                  60

Ala Asp Asp Leu Arg Ala Leu Leu Ala Arg Pro Trp Leu Glu Gly Leu
65                  70                  75                  80

Arg Asp His Leu Gln Phe Gly Glu Pro Ala Val Val Pro His Pro Thr
                85                  90                  95

Pro Tyr Arg Gln Val Ser Arg Val Gln Ala Lys Ser Asn Pro Glu Arg
                100                 105                 110

Leu Arg Arg Arg Leu Met Arg Arg His Asp Leu Ser Glu Glu Glu Ala
            115                 120                 125

Arg Lys Arg Ile Pro Asp Thr Val Ala Arg Ala Leu Asp Leu Pro Phe
        130                 135                 140

Val Thr Leu Arg Ser Gln Ser Thr Gly Gln His Phe Arg Leu Phe Ile
145                 150                 155                 160

Arg His Gly Pro Leu Gln Val Thr Ala Glu Glu Gly Phe Thr Cys
                165                 170                 175

Tyr Gly Leu Ser Lys Gly Gly Phe Val Pro Trp Phe Thr Glu Gly
                180                 185                 190
```

```
Arg Gly Ser Leu Leu Thr Cys Gly Asp Val Glu Glu Asn Pro Gly Pro
        195                 200                 205
Met Pro Lys Lys Arg Lys Val Glu Gly Ile Lys Ser Asn Ile Ser
    210                 215                 220
Leu Leu Lys Asp Glu Leu Arg Gly Gln Ile Ser His Ile Ser His Glu
225                 230                 235                 240
Tyr Leu Ser Leu Ile Asp Leu Ala Phe Asp Ser Lys Gln Asn Arg Leu
                245                 250                 255
Phe Glu Met Lys Val Leu Glu Leu Leu Val Asn Glu Tyr Gly Phe Lys
            260                 265                 270
Gly Arg His Leu Gly Gly Ser Arg Lys Pro Asp Gly Ile Val Tyr Ser
        275                 280                 285
Thr Thr Leu Glu Asp Asn Phe Gly Ile Ile Val Asp Thr Lys Ala Tyr
    290                 295                 300
Ser Glu Gly Tyr Ser Leu Pro Ile Ser Gln Ala Asp Glu Met Glu Arg
305                 310                 315                 320
Tyr Val Arg Glu Asn Ser Asn Arg Asp Glu Glu Val Asn Pro Asn Lys
                325                 330                 335
Trp Trp Glu Asn Phe Ser Glu Glu Val Lys Lys Tyr Tyr Phe Val Phe
            340                 345                 350
Ile Ser Gly Ser Phe Lys Gly Lys Phe Glu Glu Gln Leu Arg Arg Leu
        355                 360                 365
Ser Met Thr Thr Gly Val Asn Gly Ser Ala Val Asn Val Val Asn Leu
    370                 375                 380
Leu Leu Gly Ala Glu Lys Ile Arg Ser Gly Glu Met Thr Ile Glu Glu
385                 390                 395                 400
Leu Glu Arg Ala Met Phe Asn Asn Ser Glu Phe Ile Leu Lys Tyr Gly
                405                 410                 415
Gly Gly Gly Ser Asp Lys Lys Tyr Ser Ile Gly Leu Ala Ile Gly Thr
            420                 425                 430
Asn Ser Val Gly Trp Ala Val Ile Thr Asp Glu Tyr Lys Val Pro Ser
        435                 440                 445
Lys Lys Phe Lys Val Leu Gly Asn Thr Asp Arg His Ser Ile Lys Lys
    450                 455                 460
Asn Leu Ile Gly Ala Leu Leu Phe Asp Ser Gly Glu Thr Ala Glu Ala
465                 470                 475                 480
Thr Arg Leu Lys Arg Thr Ala Arg Arg Arg Tyr Thr Arg Arg Lys Asn
                485                 490                 495
Arg Ile Cys Tyr Leu Gln Glu Ile Phe Ser Asn Glu Met Ala Lys Val
            500                 505                 510
Asp Asp Ser Phe Phe His Arg Leu Glu Glu Ser Phe Leu Val Glu Glu
        515                 520                 525
Asp Lys Lys His Glu Arg His Pro Ile Phe Gly Asn Ile Val Asp Glu
    530                 535                 540
Val Ala Tyr His Glu Lys Tyr Pro Thr Ile Tyr His Leu Arg Lys Lys
545                 550                 555                 560
Leu Val Asp Ser Thr Asp Lys Ala Asp Leu Arg Leu Ile Tyr Leu Ala
                565                 570                 575
Leu Ala His Met Ile Lys Phe Arg Gly His Phe Leu Ile Glu Gly Asp
            580                 585                 590
Leu Asn Pro Asp Asn Ser Asp Val Asp Lys Leu Phe Ile Gln Leu Val
        595                 600                 605
Gln Thr Tyr Asn Gln Leu Phe Glu Glu Asn Pro Ile Asn Ala Ser Gly
```

```
                    610                 615                 620
Val Asp Ala Lys Ala Ile Leu Ser Ala Arg Leu Ser Lys Ser Arg Arg
625                 630                 635                 640

Leu Glu Asn Leu Ile Ala Gln Leu Pro Gly Glu Lys Lys Asn Gly Leu
                    645                 650                 655

Phe Gly Asn Leu Ile Ala Leu Ser Leu Gly Leu Thr Pro Asn Phe Lys
                    660                 665                 670

Ser Asn Phe Asp Leu Ala Glu Asp Ala Lys Leu Gln Leu Ser Lys Asp
                    675                 680                 685

Thr Tyr Asp Asp Asp Leu Asp Asn Leu Leu Ala Gln Ile Gly Asp Gln
                    690                 695                 700

Tyr Ala Asp Leu Phe Leu Ala Ala Lys Asn Leu Ser Asp Ala Ile Leu
705                 710                 715                 720

Leu Ser Asp Ile Leu Arg Val Asn Thr Glu Ile Thr Lys Ala Pro Leu
                    725                 730                 735

Ser Ala Ser Met Ile Lys Arg Tyr Asp Glu His His Gln Asp Leu Thr
                    740                 745                 750

Leu Leu Lys Ala Leu Val Arg Gln Gln Leu Pro Glu Lys Tyr Lys Glu
                    755                 760                 765

Ile Phe Phe Asp Gln Ser Lys Asn Gly Tyr Ala Gly Tyr Ile Asp Gly
                    770                 775                 780

Gly Ala Ser Gln Glu Glu Phe Tyr Lys Phe Ile Lys Pro Ile Leu Glu
785                 790                 795                 800

Lys Met Asp Gly Thr Glu Glu Leu Leu Val Lys Leu Asn Arg Glu Asp
                    805                 810                 815

Leu Leu Arg Lys Gln Arg Thr Phe Asp Asn Gly Ser Ile Pro His Gln
                    820                 825                 830

Ile His Leu Gly Glu Leu His Ala Ile Leu Arg Arg Gln Glu Asp Phe
                    835                 840                 845

Tyr Pro Phe Leu Lys Asp Asn Arg Glu Lys Ile Glu Lys Ile Leu Thr
                    850                 855                 860

Phe Arg Ile Pro Tyr Tyr Val Gly Pro Leu Ala Arg Gly Asn Ser Arg
865                 870                 875                 880

Phe Ala Trp Met Thr Arg Lys Ser Glu Glu Thr Ile Thr Pro Trp Asn
                    885                 890                 895

Phe Glu Glu Val Val Asp Lys Gly Ala Ser Ala Gln Ser Phe Ile Glu
                    900                 905                 910

Arg Met Thr Asn Phe Asp Lys Asn Leu Pro Asn Glu Lys Val Leu Pro
                    915                 920                 925

Lys His Ser Leu Leu Tyr Glu Tyr Phe Thr Val Tyr Asn Glu Leu Thr
                    930                 935                 940

Lys Val Lys Tyr Val Thr Glu Gly Met Arg Lys Pro Ala Phe Leu Ser
945                 950                 955                 960

Gly Glu Gln Lys Lys Ala Ile Val Asp Leu Leu Phe Lys Thr Asn Arg
                    965                 970                 975

Lys Val Thr Val Lys Gln Leu Lys Glu Asp Tyr Phe Lys Lys Ile Glu
                    980                 985                 990

Cys Phe Asp Ser Val Glu Ile Ser  Gly Val Glu Asp Arg  Phe Asn Ala
                    995                 1000                1005

Ser Leu  Gly Thr Tyr His Asp  Leu Leu Lys Ile Ile  Lys Asp Lys
       1010                1015                1020

Asp Phe  Leu Asp Asn Glu Glu  Asn Glu Asp Ile Leu  Glu Asp Ile
       1025                1030                1035
```

```
Val Leu Thr Leu Thr Leu Phe Glu Asp Arg Glu Met Ile Glu Glu
    1040            1045                1050

Arg Leu Lys Thr Tyr Ala His Leu Phe Asp Asp Lys Val Met Lys
    1055            1060                1065

Gln Leu Lys Arg Arg Arg Tyr Thr Gly Trp Gly Arg Leu Ser Arg
    1070            1075                1080

Lys Leu Ile Asn Gly Ile Arg Asp Lys Gln Ser Gly Lys Thr Ile
    1085            1090                1095

Leu Asp Phe Leu Lys Ser Asp Gly Phe Ala Asn Arg Asn Phe Met
    1100            1105                1110

Gln Leu Ile His Asp Asp Ser Leu Thr Phe Lys Glu Asp Ile Gln
    1115            1120                1125

Lys Ala Gln Val Ser Gly Gln Gly Asp Ser Leu His Glu His Ile
    1130            1135                1140

Ala Asn Leu Ala Gly Ser Pro Ala Ile Lys Lys Gly Ile Leu Gln
    1145            1150                1155

Thr Val Lys Val Val Asp Glu Leu Val Lys Val Met Gly Arg His
    1160            1165                1170

Lys Pro Glu Asn Ile Val Ile Glu Met Ala Arg Glu Asn Gln Thr
    1175            1180                1185

Thr Gln Lys Gly Gln Lys Asn Ser Arg Glu Arg Met Lys Arg Ile
    1190            1195                1200

Glu Glu Gly Ile Lys Glu Leu Gly Ser Gln Ile Leu Lys Glu His
    1205            1210                1215

Pro Val Glu Asn Thr Gln Leu Gln Asn Glu Lys Leu Tyr Leu Tyr
    1220            1225                1230

Tyr Leu Gln Asn Gly Arg Asp Met Tyr Val Asp Gln Glu Leu Asp
    1235            1240                1245

Ile Asn Arg Leu Ser Asp Tyr Asp Val Asp Ala Ile Val Pro Gln
    1250            1255                1260

Ser Phe Leu Lys Asp Asp Ser Ile Asp Asn Lys Val Leu Thr Arg
    1265            1270                1275

Ser Asp Lys Asn Arg Gly Lys Ser Asp Asn Val Pro Ser Glu Glu
    1280            1285                1290

Val Val Lys Lys Met Lys Asn Tyr Trp Arg Gln Leu Leu Asn Ala
    1295            1300                1305

Lys Leu Ile Thr Gln Arg Lys Phe Asp Asn Leu Thr Lys Ala Glu
    1310            1315                1320

Arg Gly Gly Leu Ser Glu Leu Asp Lys Ala Gly Phe Ile Lys Arg
    1325            1330                1335

Gln Leu Val Glu Thr Arg Gln Ile Thr Lys His Val Ala Gln Ile
    1340            1345                1350

Leu Asp Ser Arg Met Asn Thr Lys Tyr Asp Glu Asn Asp Lys Leu
    1355            1360                1365

Ile Arg Glu Val Lys Val Ile Thr Leu Lys Ser Lys Leu Val Ser
    1370            1375                1380

Asp Phe Arg Lys Asp Phe Gln Phe Tyr Lys Val Arg Glu Ile Asn
    1385            1390                1395

Asn Tyr His His Ala His Asp Ala Tyr Leu Asn Ala Val Val Gly
    1400            1405                1410

Thr Ala Leu Ile Lys Lys Tyr Pro Lys Leu Glu Ser Glu Phe Val
    1415            1420                1425
```

Tyr Gly Asp Tyr Lys Val Tyr Asp Val Arg Lys Met Ile Ala Lys
1430                1435                1440

Ser Glu Gln Glu Ile Gly Lys Ala Thr Ala Lys Tyr Phe Phe Tyr
1445                1450                1455

Ser Asn Ile Met Asn Phe Phe Lys Thr Glu Ile Thr Leu Ala Asn
1460                1465                1470

Gly Glu Ile Arg Lys Arg Pro Leu Ile Glu Thr Asn Gly Glu Thr
1475                1480                1485

Gly Glu Ile Val Trp Asp Lys Gly Arg Asp Phe Ala Thr Val Arg
1490                1495                1500

Lys Val Leu Ser Met Pro Gln Val Asn Ile Val Lys Lys Thr Glu
1505                1510                1515

Val Gln Thr Gly Gly Phe Ser Lys Glu Ser Ile Leu Pro Lys Arg
1520                1525                1530

Asn Ser Asp Lys Leu Ile Ala Arg Lys Lys Asp Trp Asp Pro Lys
1535                1540                1545

Lys Tyr Gly Gly Phe Asp Ser Pro Thr Val Ala Tyr Ser Val Leu
1550                1555                1560

Val Val Ala Lys Val Glu Lys Gly Lys Ser Lys Lys Leu Lys Ser
1565                1570                1575

Val Lys Glu Leu Leu Gly Ile Thr Ile Met Glu Arg Ser Ser Phe
1580                1585                1590

Glu Lys Asn Pro Ile Asp Phe Leu Glu Ala Lys Gly Tyr Lys Glu
1595                1600                1605

Val Lys Lys Asp Leu Ile Ile Lys Leu Pro Lys Tyr Ser Leu Phe
1610                1615                1620

Glu Leu Glu Asn Gly Arg Lys Arg Met Leu Ala Ser Ala Gly Glu
1625                1630                1635

Leu Gln Lys Gly Asn Glu Leu Ala Leu Pro Ser Lys Tyr Val Asn
1640                1645                1650

Phe Leu Tyr Leu Ala Ser His Tyr Glu Lys Leu Lys Gly Ser Pro
1655                1660                1665

Glu Asp Asn Glu Gln Lys Gln Leu Phe Val Glu Gln His Lys His
1670                1675                1680

Tyr Leu Asp Glu Ile Ile Glu Gln Ile Ser Glu Phe Ser Lys Arg
1685                1690                1695

Val Ile Leu Ala Asp Ala Asn Leu Asp Lys Val Leu Ser Ala Tyr
1700                1705                1710

Asn Lys His Arg Asp Lys Pro Ile Arg Glu Gln Ala Glu Asn Ile
1715                1720                1725

Ile His Leu Phe Thr Leu Thr Asn Leu Gly Ala Pro Ala Ala Phe
1730                1735                1740

Lys Tyr Phe Asp Thr Thr Ile Asp Arg Lys Arg Tyr Thr Ser Thr
1745                1750                1755

Lys Glu Val Leu Asp Ala Thr Leu Ile His Gln Ser Ile Thr Gly
1760                1765                1770

Leu Tyr Glu Thr Arg Ile Asp Leu Ser Gln Leu Gly Gly Asp
1775                1780                1785

<210> SEQ ID NO 25
<211> LENGTH: 199
<212> TYPE: PRT
<213> ORGANISM: Staphylococcus aureus

<400> SEQUENCE: 25

Glu Gly Ile Lys Ser Asn Ile Ser Leu Leu Lys Asp Glu Leu Arg Gly
1               5                   10                  15

Gln Ile Ser His Ile Ser His Glu Tyr Leu Ser Leu Ile Asp Leu Ala
                20                  25                  30

Phe Asp Ser Lys Gln Asn Arg Leu Phe Glu Met Lys Val Leu Glu Leu
            35                  40                  45

Leu Val Asn Glu Tyr Gly Phe Lys Gly Arg His Leu Gly Gly Ser Arg
        50                  55                  60

Lys Pro Asp Gly Ile Val Tyr Ser Thr Thr Leu Glu Asp Asn Phe Gly
65                  70                  75                  80

Ile Ile Val Asp Thr Lys Ala Tyr Ser Glu Gly Tyr Ser Leu Pro Ile
                85                  90                  95

Ser Gln Ala Asp Glu Met Glu Arg Tyr Val Arg Glu Asn Ser Asn Arg
            100                 105                 110

Asp Glu Glu Val Asn Pro Asn Lys Trp Trp Glu Asn Phe Ser Glu Glu
            115                 120                 125

Val Lys Lys Tyr Tyr Phe Val Phe Ile Ser Gly Ser Phe Lys Gly Lys
        130                 135                 140

Phe Glu Glu Gln Leu Arg Arg Leu Ser Met Thr Thr Gly Val Asn Gly
145                 150                 155                 160

Ser Ala Val Asn Val Val Asn Leu Leu Gly Ala Glu Lys Ile Arg
                165                 170                 175

Ser Gly Glu Met Thr Ile Glu Glu Leu Glu Arg Ala Met Phe Asn Asn
            180                 185                 190

Ser Glu Phe Ile Leu Lys Tyr
            195

<210> SEQ ID NO 26
<211> LENGTH: 193
<212> TYPE: PRT
<213> ORGANISM: Staphylococcus aureus

<400> SEQUENCE: 26

Met Asn Phe Phe Ser Leu His Pro Asn Val Tyr Ala Thr Gly Arg Pro
1               5                   10                  15

Lys Gly Leu Ile Gly Met Leu Glu Asn Val Trp Val Ser Asn His Thr
                20                  25                  30

Pro Gly Glu Gly Thr Leu Tyr Leu Ile Ser Gly Phe Ser Asn Tyr Asn
            35                  40                  45

Gly Gly Val Arg Phe Tyr Glu Thr Phe Thr Glu His Ile Asn Gln Gly
        50                  55                  60

Gly Arg Val Ile Ala Ile Leu Gly Gly Ser Thr Ser Gln Arg Leu Ser
65                  70                  75                  80

Ser Arg Gln Val Val Glu Leu Leu Asn Arg Gly Val Glu Val His
                85                  90                  95

Ile Ile Asn Arg Lys Arg Ile Leu His Ala Lys Leu Tyr Gly Thr Ser
            100                 105                 110

Asn Asn Leu Gly Glu Ser Leu Val Val Ser Ser Gly Asn Phe Thr Gly
            115                 120                 125

Pro Gly Met Ser Gln Asn Ile Glu Ala Ser Leu Leu Leu Asp Asn Asn
            130                 135                 140

Thr Thr Gln Ser Met Gly Phe Ser Trp Asn Asp Met Ile Ser Glu Met
145                 150                 155                 160

Leu Asn Gln Asn Trp His Ile His Asn Met Thr Asn Ala Thr Asp Ala

```
                    165                 170                 175

Ser Pro Gly Trp Asn Leu Leu Tyr Asp Glu Arg Thr Thr Asn Leu Thr
                180                 185                 190

Leu

<210> SEQ ID NO 27
<211> LENGTH: 193
<212> TYPE: PRT
<213> ORGANISM: Staphylococcus aureus

<400> SEQUENCE: 27

Met Asn Tyr Phe Ser Leu His Pro Asn Val Tyr Ala Thr Gly Arg Pro
1               5                   10                  15

Lys Gly Leu Ile Asn Met Leu Glu Ser Val Trp Ile Ser Asn Gln Lys
                20                  25                  30

Pro Gly Asp Gly Thr Met Tyr Leu Ile Ser Gly Phe Ala Asn Tyr Asn
            35                  40                  45

Gly Gly Ile Arg Phe Tyr Glu Thr Phe Thr Glu His Ile Asn His Gly
    50                  55                  60

Gly Lys Val Ile Ala Ile Leu Gly Gly Ser Thr Ser Gln Arg Leu Ser
65                  70                  75                  80

Ser Lys Gln Val Val Ala Glu Leu Val Ser Arg Gly Val Asp Val Tyr
                85                  90                  95

Ile Ile Asn Arg Lys Arg Leu Leu His Ala Lys Leu Tyr Gly Ser Ser
                100                 105                 110

Ser Asn Ser Gly Glu Ser Leu Val Val Ser Ser Gly Asn Phe Thr Gly
            115                 120                 125

Pro Gly Met Ser Gln Asn Val Glu Ala Ser Leu Leu Leu Asp Asn Asn
        130                 135                 140

Thr Thr Ser Ser Met Gly Phe Ser Trp Asn Gly Met Val Asn Ser Met
145                 150                 155                 160

Leu Asp Gln Lys Trp Gln Ile His Asn Leu Ser Asn Ser Asn Pro Thr
                165                 170                 175

Ser Pro Ser Trp Asn Leu Leu Tyr Asp Glu Arg Thr Thr Asn Leu Thr
                180                 185                 190

Leu

<210> SEQ ID NO 28
<211> LENGTH: 176
<212> TYPE: PRT
<213> ORGANISM: Artificial Sequence
<220> FEATURE:
<223> OTHER INFORMATION: synthetic polypeptide

<400> SEQUENCE: 28

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
                20                  25                  30

Gly Ile His Arg Gly Val Pro Met Val Asp Leu Arg Thr Leu Gly Tyr
            35                  40                  45

Ser Gln Gln Gln Gln Glu Lys Ile Lys Pro Lys Val Arg Ser Thr Val
        50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
```

```
                85                  90                  95
Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
        115                 120                 125

Leu Leu Thr Val Ala Gly Glu Leu Arg Gly Pro Pro Leu Gln Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

<210> SEQ ID NO 29
<211> LENGTH: 23
<212> TYPE: PRT
<213> ORGANISM: Artificial Sequence
<220> FEATURE:
<223> OTHER INFORMATION: synthetic polypeptide

<400> SEQUENCE: 29

Met Asp Tyr Lys Asp His Asp Gly Asp Tyr Lys Asp His Asp Ile Asp
1               5                   10                  15

Tyr Lys Asp Asp Asp Asp Lys
            20

<210> SEQ ID NO 30
<211> LENGTH: 153
<212> TYPE: PRT
<213> ORGANISM: Artificial Sequence
<220> FEATURE:
<223> OTHER INFORMATION: synthetic polypeptide

<400> SEQUENCE: 30

Met Ala Pro Lys Lys Arg Lys Val Gly Ile His Arg Gly Val Pro
1               5                   10                  15

Met Val Asp Leu Arg Thr Leu Gly Tyr Ser Gln Gln Gln Gln Glu Lys
            20                  25                  30

Ile Lys Pro Lys Val Arg Ser Thr Val Ala Gln His His Glu Ala Leu
        35                  40                  45

Val Gly His Gly Phe Thr His Ala His Ile Val Ala Leu Ser Gln His
    50                  55                  60

Pro Ala Ala Leu Gly Thr Val Ala Val Lys Tyr Gln Asp Met Ile Ala
65                  70                  75                  80

Ala Leu Pro Glu Ala Thr His Glu Ala Ile Val Gly Val Gly Lys Gln
                85                  90                  95

Trp Ser Gly Ala Arg Ala Leu Glu Ala Leu Leu Thr Val Ala Gly Glu
            100                 105                 110

Leu Arg Gly Pro Pro Leu Gln Leu Asp Thr Gly Gln Leu Leu Lys Ile
        115                 120                 125

Ala Lys Arg Gly Gly Val Thr Ala Val Glu Ala Val His Ala Trp Arg
    130                 135                 140

Asn Ala Leu Thr Gly Ala Pro Leu Asn
145                 150

<210> SEQ ID NO 31
<211> LENGTH: 85
<212> TYPE: PRT
<213> ORGANISM: Artificial Sequence
<220> FEATURE:
```

<223> OTHER INFORMATION: synthetic polypeptide
<220> FEATURE:
<221> NAME/KEY: misc_feature
<222> LOCATION: (11)..(13)
<223> OTHER INFORMATION: Xaa can be any naturally occurring amino acid

<400> SEQUENCE: 31

```
Leu Thr Pro Glu Gln Val Val Ala Ile Ala Xaa Xaa Xaa Gly Gly Arg
1               5                   10                  15

Pro Ala Leu Glu Ser Ile Val Ala Gln Leu Ser Arg Pro Asp Pro Ala
            20                  25                  30

Leu Ala Ala Leu Thr Asn Asp His Leu Val Ala Leu Ala Cys Leu Gly
        35                  40                  45

Gly Arg Pro Ala Leu Asp Ala Val Lys Lys Gly Leu Pro His Ala Pro
    50                  55                  60

Ala Leu Ile Lys Arg Thr Asn Arg Arg Ile Pro Glu Arg Thr Ser His
65                  70                  75                  80

Arg Val Ala Gly Ser
                85
```

<210> SEQ ID NO 32
<211> LENGTH: 85
<212> TYPE: PRT
<213> ORGANISM: Artificial Sequence
<220> FEATURE:
<223> OTHER INFORMATION: synthetic polypeptide

<400> SEQUENCE: 32

```
Leu Thr Pro Glu Gln Val Val Ala Ile Ala Asn Asn Asn Gly Gly Arg
1               5                   10                  15

Pro Ala Leu Glu Ser Ile Val Ala Gln Leu Ser Arg Pro Asp Pro Ala
            20                  25                  30

Leu Ala Ala Leu Thr Asn Asp His Leu Val Ala Leu Ala Cys Leu Gly
        35                  40                  45

Gly Arg Pro Ala Leu Asp Ala Val Lys Lys Gly Leu Pro His Ala Pro
    50                  55                  60

Ala Leu Ile Lys Arg Thr Asn Arg Arg Ile Pro Glu Arg Thr Ser His
65                  70                  75                  80

Arg Val Ala Gly Ser
                85
```

<210> SEQ ID NO 33
<211> LENGTH: 85
<212> TYPE: PRT
<213> ORGANISM: Artificial Sequence
<220> FEATURE:
<223> OTHER INFORMATION: synthetic polypeptide

<400> SEQUENCE: 33

```
Leu Thr Pro Glu Gln Val Val Ala Ile Ala Ser Asn Gly Gly Gly Arg
1               5                   10                  15

Pro Ala Leu Glu Ser Ile Val Ala Gln Leu Ser Arg Pro Asp Pro Ala
            20                  25                  30

Leu Ala Ala Leu Thr Asn Asp His Leu Val Ala Leu Ala Cys Leu Gly
        35                  40                  45

Gly Arg Pro Ala Leu Asp Ala Val Lys Lys Gly Leu Pro His Ala Pro
    50                  55                  60

Ala Leu Ile Lys Arg Thr Asn Arg Arg Ile Pro Glu Arg Thr Ser His
65                  70                  75                  80
```

Arg Val Ala Gly Ser
            85

<210> SEQ ID NO 34
<211> LENGTH: 85
<212> TYPE: PRT
<213> ORGANISM: Artificial Sequence
<220> FEATURE:
<223> OTHER INFORMATION: synthetic polypeptide

<400> SEQUENCE: 34

Leu Thr Pro Glu Gln Val Val Ala Ile Ala Ser His Asp Gly Gly Arg
1               5                   10                  15

Pro Ala Leu Glu Ser Ile Val Ala Gln Leu Ser Arg Pro Asp Pro Ala
            20                  25                  30

Leu Ala Ala Leu Thr Asn Asp His Leu Val Ala Leu Ala Cys Leu Gly
        35                  40                  45

Gly Arg Pro Ala Leu Asp Ala Val Lys Lys Gly Leu Pro His Ala Pro
    50                  55                  60

Ala Leu Ile Lys Arg Thr Asn Arg Arg Ile Pro Glu Arg Thr Ser His
65                  70                  75                  80

Arg Val Ala Gly Ser
            85

<210> SEQ ID NO 35
<211> LENGTH: 85
<212> TYPE: PRT
<213> ORGANISM: Artificial Sequence
<220> FEATURE:
<223> OTHER INFORMATION: synthetic polypeptide

<400> SEQUENCE: 35

Leu Thr Pro Glu Gln Val Val Ala Ile Ala Ser Asn Ile Gly Gly Arg
1               5                   10                  15

Pro Ala Leu Glu Ser Ile Val Ala Gln Leu Ser Arg Pro Asp Pro Ala
            20                  25                  30

Leu Ala Ala Leu Thr Asn Asp His Leu Val Ala Leu Ala Cys Leu Gly
        35                  40                  45

Gly Arg Pro Ala Leu Asp Ala Val Lys Lys Gly Leu Pro His Ala Pro
    50                  55                  60

Ala Leu Ile Lys Arg Thr Asn Arg Arg Ile Pro Glu Arg Thr Ser His
65                  70                  75                  80

Arg Val Ala Gly Ser
            85

<210> SEQ ID NO 36
<211> LENGTH: 199
<212> TYPE: PRT
<213> ORGANISM: Artificial Sequence
<220> FEATURE:
<223> OTHER INFORMATION: synthetic polypeptide

<400> SEQUENCE: 36

Glu Gly Ile Lys Ser Asn Ile Ser Leu Leu Lys Asp Glu Leu Arg Gly
1               5                   10                  15

Gln Ile Ser His Ile Ser His Glu Tyr Leu Ser Leu Ile Asp Leu Ala
            20                  25                  30

Phe Asp Ser Lys Gln Asn Arg Leu Phe Glu Met Lys Val Leu Glu Leu
        35                  40                  45

Leu Val Asn Glu Tyr Gly Phe Lys Gly Arg His Leu Gly Gly Ser Arg

```
            50                  55                  60
Lys Pro Asp Gly Ile Val Tyr Ser Thr Thr Leu Glu Asp Asn Phe Gly
 65                  70                  75                  80

Ile Ile Val Asp Thr Lys Ala Tyr Ser Glu Gly Tyr Ser Leu Pro Ile
                 85                  90                  95

Ser Gln Ala Asp Glu Met Glu Arg Tyr Val Arg Glu Asn Ser Asn Arg
                100                 105                 110

Asp Glu Glu Val Asn Pro Asn Lys Trp Trp Glu Asn Phe Ser Glu Glu
                115                 120                 125

Val Lys Lys Tyr Tyr Phe Val Phe Ile Ser Gly Ser Phe Lys Gly Lys
                130                 135                 140

Phe Glu Glu Gln Leu Arg Arg Leu Ser Met Thr Thr Gly Val Asn Gly
145                 150                 155                 160

Ser Ala Val Asn Val Val Asn Leu Leu Leu Gly Ala Glu Lys Ile Arg
                165                 170                 175

Ser Gly Glu Met Thr Ile Glu Glu Leu Glu Arg Ala Met Phe Asn Asn
                180                 185                 190

Ser Glu Phe Ile Leu Lys Tyr
                195

<210> SEQ ID NO 37
<211> LENGTH: 193
<212> TYPE: PRT
<213> ORGANISM: Artificial Sequence
<220> FEATURE:
<223> OTHER INFORMATION: synthetic polypeptide

<400> SEQUENCE: 37

Met Asn Phe Phe Ser Leu His Pro Asn Val Tyr Ala Thr Gly Arg Pro
  1                   5                  10                  15

Lys Gly Leu Ile Gly Met Leu Glu Asn Val Trp Val Ser Asn His Thr
                 20                  25                  30

Pro Gly Glu Gly Thr Leu Tyr Leu Ile Ser Gly Phe Ser Asn Tyr Asn
                 35                  40                  45

Gly Gly Val Arg Phe Tyr Glu Thr Phe Thr Glu His Ile Asn Gln Gly
 50                  55                  60

Gly Arg Val Ile Ala Ile Leu Gly Gly Ser Thr Ser Gln Arg Leu Ser
 65                  70                  75                  80

Ser Arg Gln Val Val Glu Glu Leu Leu Asn Arg Gly Val Glu Val His
                 85                  90                  95

Ile Ile Asn Arg Lys Arg Ile Leu His Ala Lys Leu Tyr Gly Thr Ser
                100                 105                 110

Asn Asn Leu Gly Glu Ser Leu Val Val Ser Ser Gly Asn Phe Thr Gly
                115                 120                 125

Pro Gly Met Ser Gln Asn Ile Glu Ala Ser Leu Leu Leu Asp Asn Asn
                130                 135                 140

Thr Thr Gln Ser Met Gly Phe Ser Trp Asn Asp Met Ile Ser Glu Met
145                 150                 155                 160

Leu Asn Gln Asn Trp His Ile His Asn Met Thr Asn Ala Thr Asp Ala
                165                 170                 175

Ser Pro Gly Trp Asn Leu Leu Tyr Asp Glu Arg Thr Thr Asn Leu Thr
                180                 185                 190

Leu

<210> SEQ ID NO 38
```

<211> LENGTH: 193
<212> TYPE: PRT
<213> ORGANISM: Artificial Sequence
<220> FEATURE:
<223> OTHER INFORMATION: synthetic polypeptide

<400> SEQUENCE: 38

Met Asn Tyr Phe Ser Leu His Pro Asn Val Tyr Ala Thr Gly Arg Pro
1               5                   10                  15

Lys Gly Leu Ile Asn Met Leu Glu Ser Val Trp Ile Ser Asn Gln Lys
            20                  25                  30

Pro Gly Asp Gly Thr Met Tyr Leu Ile Ser Gly Phe Ala Asn Tyr Asn
        35                  40                  45

Gly Gly Ile Arg Phe Tyr Glu Thr Phe Thr Glu His Ile Asn His Gly
    50                  55                  60

Gly Lys Val Ile Ala Ile Leu Gly Gly Ser Thr Ser Gln Arg Leu Ser
65                  70                  75                  80

Ser Lys Gln Val Val Ala Glu Leu Val Ser Arg Gly Val Asp Val Tyr
                85                  90                  95

Ile Ile Asn Arg Lys Arg Leu Leu His Ala Lys Leu Tyr Gly Ser Ser
            100                 105                 110

Ser Asn Ser Gly Glu Ser Leu Val Val Ser Ser Gly Asn Phe Thr Gly
        115                 120                 125

Pro Gly Met Ser Gln Asn Val Glu Ala Ser Leu Leu Asp Asn Asn
    130                 135                 140

Thr Thr Ser Ser Met Gly Phe Ser Trp Asn Gly Met Val Asn Ser Met
145                 150                 155                 160

Leu Asp Gln Lys Trp Gln Ile His Asn Leu Ser Asn Ser Asn Pro Thr
                165                 170                 175

Ser Pro Ser Trp Asn Leu Leu Tyr Asp Glu Arg Thr Thr Asn Leu Thr
            180                 185                 190

Leu

<210> SEQ ID NO 39
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 39

Leu Ser Thr Glu Gln Val Val Ala Ile Ala Ser Asn Lys Gly Gly Lys
1               5                   10                  15

Gln Ala Leu Glu Ala Val Lys Ala His Leu Leu Asp Leu Leu Gly Ala
            20                  25                  30

Pro Tyr Val
        35

<210> SEQ ID NO 40
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 40

Leu Ser Thr Glu Gln Val Val Ala Ile Ala Ser Asn Asn Gly Gly Lys
1               5                   10                  15

Gln Ala Leu Glu Ala Val Lys Ala Gln Leu Leu Glu Leu Arg Ala Ala

```
                  20                  25                  30

Pro Tyr Glu
        35

<210> SEQ ID NO 41
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 41

Leu Ser Thr Ala Gln Val Val Ala Ile Ala Ser Asn Gly Gly Gly Lys
1               5                   10                  15

Gln Ala Leu Glu Gly Ile Gly Glu Gln Leu Leu Lys Leu Arg Thr Ala
            20                  25                  30

Pro Tyr Gly
        35

<210> SEQ ID NO 42
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 42

Leu Ser Thr Ala Gln Val Val Ala Ile Ala Ser His Asp Gly Gly Lys
1               5                   10                  15

Pro Ala Leu Glu Ala Val Trp Ala Lys Leu Pro Val Leu Arg Gly Val
            20                  25                  30

Pro Tyr Ala
        35

<210> SEQ ID NO 43
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 43

Leu Ser Thr Glu Gln Val Val Thr Ile Ala Ser Ser Ile Gly Gly Lys
1               5                   10                  15

Gln Ala Leu Glu Ala Val Lys Val Gln Leu Pro Val Leu Arg Ala Ala
            20                  25                  30

Pro Tyr Glu
        35

<210> SEQ ID NO 44
<211> LENGTH: 24
<212> TYPE: DNA
<213> ORGANISM: Artificial Sequence
<220> FEATURE:
<223> OTHER INFORMATION: synthetic polynucleotide

<400> SEQUENCE: 44
tctagagaag acaagaacct gacc                                          24

<210> SEQ ID NO 45
<211> LENGTH: 24
<212> TYPE: DNA
<213> ORGANISM: Artificial Sequence
```

```
<220> FEATURE:
<223> OTHER INFORMATION: synthetic polynucleotide

<400> SEQUENCE: 45
ggatccggtc tcttaaggcc gtgg                                              24

<210> SEQ ID NO 46
<211> LENGTH: 28
<212> TYPE: DNA
<213> ORGANISM: Artificial Sequence
<220> FEATURE:
<223> OTHER INFORMATION: synthetic polynucleotide

<400> SEQUENCE: 46
gacggtggct gtcaaatacc aagatatg                                          28

<210> SEQ ID NO 47
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 47
tctcctccag ttcacttttg actagttggg                                        30

<210> SEQ ID NO 48
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 48
agtaacagcg gtagaggcag                                                   20

<210> SEQ ID NO 49
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 49
attgggctac gatggactcc                                                   20

<210> SEQ ID NO 50
<211> LENGTH: 25
<212> TYPE: DNA
<213> ORGANISM: Artificial Sequence
<220> FEATURE:
<223> OTHER INFORMATION: synthetic polynucleotide

<400> SEQUENCE: 50
ttaattcaat atattcatga ggcac                                             25

<210> SEQ ID NO 51
<211> LENGTH: 146
<212> TYPE: DNA
<213> ORGANISM: Artificial Sequence
<220> FEATURE:
<223> OTHER INFORMATION: synthetic polynucleotide

<400> SEQUENCE: 51
atgcatctag agaagacaac tgagcaccga gcaggtggtg gccatcgcca gcaacaaggg       60
```
cggcaagcag gccctggagg ccgtgaaggc ccacctgctg gacctgctgg gcgcccccta    120
cgagctgaag agaccggatc ccgggc                                        146

<210> SEQ ID NO 52
<211> LENGTH: 146
<212> TYPE: DNA
<213> ORGANISM: Artificial Sequence
<220> FEATURE:
<223> OTHER INFORMATION: synthetic polynucleotide

<400> SEQUENCE: 52
atgcatctag agaagacaac tgagcaccga gcaggtggtg gccatcgcca gcaacaacgg    60
cggcaagcag gccctggagg ccgtgaaggc ccagctgctg gagctgaggg ccgcccccta   120
cgagctgaag agaccggatc ccgggc                                        146

<210> SEQ ID NO 53
<211> LENGTH: 146
<212> TYPE: DNA
<213> ORGANISM: Artificial Sequence
<220> FEATURE:
<223> OTHER INFORMATION: synthetic polynucleotide

<400> SEQUENCE: 53
atgcatctag agaagacaac tgagcaccga gcaggtggtg gccatcgcca gcaacggcgg    60
cggcaagcag gccctggagg gcatcggcga gcagctgctg aagctgagga ccgcccccta   120
cgagctgaag agaccggatc ccgggc                                        146

<210> SEQ ID NO 54
<211> LENGTH: 146
<212> TYPE: DNA
<213> ORGANISM: Artificial Sequence
<220> FEATURE:
<223> OTHER INFORMATION: synthetic polynucleotide

<400> SEQUENCE: 54
atgcatctag agaagacaac tgagcaccga gcaggtggtg gccatcgcca gccacgacgg    60
cggcaagccc gccctggagg ccgtgtgggc caagctgccc gtgctgaggg gcgtgcccta   120
cgagctgaag agaccggatc ccgggc                                        146

<210> SEQ ID NO 55
<211> LENGTH: 146
<212> TYPE: DNA
<213> ORGANISM: Artificial Sequence
<220> FEATURE:
<223> OTHER INFORMATION: synthetic polyncletoide

<400> SEQUENCE: 55
atgcatctag agaagacaac tgagcaccga gcaggtggtg accatcgcca gcagcatcgg    60
cggcaagcag gccctggagg ccgtgaaggt gcagctgccc gtgctgaggg ccgcccccta   120
cgagctgaag agaccggatc ccgggc                                        146

<210> SEQ ID NO 56
<211> LENGTH: 34
<212> TYPE: PRT
<213> ORGANISM: Artificial Sequence
<220> FEATURE:
<223> OTHER INFORMATION: synthetic polypeptide

<400> SEQUENCE: 56

Leu Thr Pro Asp Gln Val Val Ala Ile Ala Ser Asn Gly Gly Gly Lys

```
                1               5                  10                  15
Gln Ala Leu Glu Thr Val Gln Arg Leu Leu Pro Val Leu Cys Gln Asp
            20                  25                  30

His Gly

<210> SEQ ID NO 57
<211> LENGTH: 34
<212> TYPE: PRT
<213> ORGANISM: Artificial Sequence
<220> FEATURE:
<223> OTHER INFORMATION: synthetic polypeptide

<400> SEQUENCE: 57

Leu Thr Pro Glu Gln Val Val Ala Ile Ala Asn Asn Asn Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 58
<211> LENGTH: 34
<212> TYPE: PRT
<213> ORGANISM: Artificial Sequence
<220> FEATURE:
<223> OTHER INFORMATION: synthetic polypeptide

<400> SEQUENCE: 58

Leu Thr Pro Asp Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 59
<211> LENGTH: 34
<212> TYPE: PRT
<213> ORGANISM: Artificial Sequence
<220> FEATURE:
<223> OTHER INFORMATION: synthetic polypeptide

<400> SEQUENCE: 59

Leu Thr Pro Ala Gln Val Val Ala Ile Ala Ser Asn Ile Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 60
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 60

Thr Thr Asp Arg Val Val Ala Leu Gly Thr Ser Thr Gly Gly Thr Gln
1               5                   10                  15

Ala Leu Glu Val Val Leu Arg Gln Leu Pro Val Asp Cys
            20                  25

<210> SEQ ID NO 61
```

```
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 61

Thr Thr Asp Arg Val Val Ala Leu Gly Thr Ser Thr Gly Gly Thr Gln
1               5                   10                  15

Ala Leu Glu Val Val Leu Arg Gln Leu Pro Val Asp Cys
            20                  25

<210> SEQ ID NO 62
<211> LENGTH: 30
<212> TYPE: PRT
<213> ORGANISM: Artificial Sequence
<220> FEATURE:
<223> OTHER INFORMATION: synthetic polypeptide

<400> SEQUENCE: 62

Met Thr Ser Glu Gln Ile Val Ala Ile Gly Thr Ser Thr Gly Gly Thr
1               5                   10                  15

Gln Ala Leu Glu Ala Val Leu Thr Ala Leu Pro Arg Val Cys
            20                  25                  30

<210> SEQ ID NO 63
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 63

Thr Thr Asp Arg Val Val Ala Ile Gly Thr Ser Thr Gly Gly Thr Gln
1               5                   10                  15

Ala Leu Glu Val Val Leu Thr Ala Leu Pro Arg Val Cys
            20                  25

<210> SEQ ID NO 64
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 64

Thr Thr Glu Arg Ile Val Ala Ile Gly Thr Ser Thr Gly Gly Thr Gln
1               5                   10                  15

Ala Leu Glu Thr Val Leu His Arg Leu Pro Ala Thr Cys
            20                  25

<210> SEQ ID NO 65
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 65

Thr Thr Asp Lys Ile Ile Ala Ile Gly Thr Ser Thr Gly Gly Thr Gln
1               5                   10                  15

Ala Leu Glu Ala Val Leu Thr Lys Leu Pro Ala Val Cys
            20                  25
```

```
<210> SEQ ID NO 66
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 66

Thr Thr Glu Arg Ile Val Ala Ile Gly Thr Ser Thr Gly Gly Thr Gln
1               5                   10                  15

Ala Leu Glu Thr Val Leu Thr Ala Leu Pro Arg Val Cys
            20                  25

<210> SEQ ID NO 67
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 67

Thr Thr Glu Arg Val Val Ala Leu Gly Thr Ser Thr Gly Gly Thr Gln
1               5                   10                  15

Ala Leu Glu Val Val Leu Arg Thr Leu Pro Arg Val Cys
            20                  25

<210> SEQ ID NO 68
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 68

Thr Thr Asp Gln Leu Ile Ala Ile Gly Thr Ser Thr Gly Gly Thr Gln
1               5                   10                  15

Ala Leu Glu Ala Ile Leu Thr Lys Leu Pro Ala Thr Cys
            20                  25

<210> SEQ ID NO 69
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 69

Thr Thr Glu Arg Ile Val Ala Ile Gly Thr Ser Thr Gly Gly Thr Gln
1               5                   10                  15

Ala Leu Glu Thr Val Leu Pro Arg Leu Pro Ala Thr Cys
            20                  25

<210> SEQ ID NO 70
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 70

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25
```

-continued

<210> SEQ ID NO 71
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 71

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 72
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 72

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 73
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 73

Thr Ser Asp Lys Val Val Ala Ile Gly Ala Ser Thr Gly Gly Thr Gln
1               5                   10                  15

Ala Leu Glu Leu Leu Leu Thr Gly Leu Pro Ala Val Cys
            20                  25

<210> SEQ ID NO 74
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 74

Thr Thr Glu Arg Ile Val Ala Ile Gly Thr Ser Thr Gly Gly Thr Gln
1               5                   10                  15

Ala Leu Glu Thr Val Leu Thr Ala Leu Pro Arg Val Cys
            20                  25

<210> SEQ ID NO 75
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 75

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

```
<210> SEQ ID NO 76
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 76

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 77
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 77

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 78
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 78

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 79
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 79

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 80
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 80

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
```

20                  25

<210> SEQ ID NO 81
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 81

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 82
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 82

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 83
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 83

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 84
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 84

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 85
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 85

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 86
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 86

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 87
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 87

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 88
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 88

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 89
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 89

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 90
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 90

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 91
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 91

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 92
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 92

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 93
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 93

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 94
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 94

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 95
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 95

Thr Thr Glu Arg Ile Val Ala Ile Gly Thr Ser Thr Gly Gly Thr Gln

```
                1               5                  10                  15
Ala Leu Glu Ala Val Leu Thr Ala Leu Pro Arg Val Cys
                20                  25
```

<210> SEQ ID NO 96
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 96

```
Phe Ser Gln Ala Asp Ile Val Arg Ile Ala Asp Asn Ile Gly Gly Ala
1               5                   10                  15
Gln Ala Leu Lys Ala Val Leu Glu His Gly Pro Thr Leu
                20                  25
```

<210> SEQ ID NO 97
<211> LENGTH: 28
<212> TYPE: PRT
<213> ORGANISM: Artificial Sequence
<220> FEATURE:
<223> OTHER INFORMATION: synthetic polypeptide

<400> SEQUENCE: 97

```
Ala Asp Ile Val Lys Ile Ala Ser Asn Gly Gly Gly Ala Gln Ala Leu
1               5                   10                  15
Glu Ala Val Ala Met His Gly Ser Thr Leu Cys Glu
                20                  25
```

<210> SEQ ID NO 98
<211> LENGTH: 28
<212> TYPE: PRT
<213> ORGANISM: Artificial Sequence
<220> FEATURE:
<223> OTHER INFORMATION: synthetic polypeptide

<400> SEQUENCE: 98

```
Ala Asp Ile Val Lys Ile Ala Gly Asn Gly Gly Gly Ala Arg Ala Leu
1               5                   10                  15
Lys Ala Val Val Met His Gly Pro Thr Leu Cys Glu
                20                  25
```

<210> SEQ ID NO 99
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 99

```
Thr Thr Asp Arg Val Val Ala Leu Gly Cys Ser Thr Gly Gly Thr Gln
1               5                   10                  15
Ala Leu Glu Phe Ile Leu Arg Gln Leu Pro Arg Asp Cys
                20                  25
```

<210> SEQ ID NO 100
<211> LENGTH: 24
<212> TYPE: PRT
<213> ORGANISM: Artificial Sequence
<220> FEATURE:
<223> OTHER INFORMATION: synthetic polypeptide

<400> SEQUENCE: 100

Ala Leu Ala Ala Ala Val Gly Gly Lys Gly Ala Leu Glu Val Pro Ala
1               5                   10                  15

Asn Leu Ile Pro Ala Asn Cys Glu
            20

<210> SEQ ID NO 101
<211> LENGTH: 23
<212> TYPE: PRT
<213> ORGANISM: Artificial Sequence
<220> FEATURE:
<223> OTHER INFORMATION: synthetic polypeptide

<400> SEQUENCE: 101

Arg Ile Val Ala Ile Gly Thr Ser Thr Gly Thr Gln Ala Leu Glu
1               5                   10                  15

Val Val Leu Thr Ala Leu Pro
            20

<210> SEQ ID NO 102
<211> LENGTH: 34
<212> TYPE: PRT
<213> ORGANISM: Artificial Sequence
<220> FEATURE:
<223> OTHER INFORMATION: synthetic polypeptide

<400> SEQUENCE: 102

Leu Thr Pro Asp Gln Val Val Ala Ile Ala Ser Asn Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 103
<211> LENGTH: 34
<212> TYPE: PRT
<213> ORGANISM: Artificial Sequence
<220> FEATURE:
<223> OTHER INFORMATION: synthetic polypeptide

<400> SEQUENCE: 103

Leu Thr Pro Ala Gln Val Val Ala Ile Ala Ser Asn Ile Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 104
<211> LENGTH: 34
<212> TYPE: PRT
<213> ORGANISM: Artificial Sequence
<220> FEATURE:
<223> OTHER INFORMATION: synthetic polypeptide

<400> SEQUENCE: 104

Leu Thr Pro Asp Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 105
<211> LENGTH: 34

```
<212> TYPE: PRT
<213> ORGANISM: Artificial Sequence
<220> FEATURE:
<223> OTHER INFORMATION: synthetic polypeptide

<400> SEQUENCE: 105

Leu Thr Pro Glu Gln Val Val Ala Ile Ala Asn Asn Asn Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 106
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 106

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 107
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 107

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 108
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 108

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 109
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 109

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25
```

-continued

```
<210> SEQ ID NO 110
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 110

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 111
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 111

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 112
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 112

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 113
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 113

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 114
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 114

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25
```

<210> SEQ ID NO 115
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 115

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 116
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 116

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 117
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 117

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 118
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 118

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 119
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 119

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys

<210> SEQ ID NO 120
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 120

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 121
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 121

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 122
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 122

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 123
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 123

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 124
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 124

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 125
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 125

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 126
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 126

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 127
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 127

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 128
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 128

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 129
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 129

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 130
<211> LENGTH: 30
<212> TYPE: PRT
<213> ORGANISM: Artificial Sequence
<220> FEATURE:
<223> OTHER INFORMATION: synthetic polypeptide

<400> SEQUENCE: 130

Met Thr Ser Glu Gln Ile Val Ala Ile Gly Thr Ser Thr Gly Gly Thr
1               5                   10                  15

Gln Ala Leu Glu Ala Val Leu Thr Ala Leu Pro Arg Val Cys
            20                  25                  30

<210> SEQ ID NO 131
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 131

Thr Thr Glu Arg Ile Val Ala Ile Gly Thr Ser Thr Gly Gly Thr Gln
1               5                   10                  15

Ala Leu Glu Thr Val Leu Thr Ala Leu Pro Arg Val Cys
            20                  25

<210> SEQ ID NO 132
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 132

Thr Thr Glu Arg Ile Val Ala Ile Gly Thr Ser Thr Gly Gly Thr Gln
1               5                   10                  15

Ala Leu Glu Thr Val Leu Thr Ala Leu Pro Arg Val Cys
            20                  25

<210> SEQ ID NO 133
<211> LENGTH: 23
<212> TYPE: PRT
<213> ORGANISM: Artificial Sequence
<220> FEATURE:
<223> OTHER INFORMATION: synthetic polypeptide

<400> SEQUENCE: 133

Arg Ile Val Ala Ile Gly Thr Ser Thr Gly Gly Thr Gln Ala Leu Glu
1               5                   10                  15

Val Val Leu Thr Ala Leu Pro
            20

<210> SEQ ID NO 134
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 134

Thr Thr Asp Arg Val Val Ala Leu Gly Thr Ser Thr Gly Gly Thr Gln

```
                1               5                  10                  15
Ala Leu Glu Val Val Leu Arg Gln Leu Pro Val Asp Cys
            20                  25

<210> SEQ ID NO 135
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 135

Thr Thr Asp Arg Val Val Ala Leu Gly Thr Ser Thr Gly Gly Thr Gln
1               5                   10                  15

Ala Leu Glu Val Val Leu Arg Gln Leu Pro Val Asp Cys
            20                  25

<210> SEQ ID NO 136
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 136

Thr Thr Asp Arg Val Val Ala Leu Gly Cys Ser Thr Gly Gly Thr Gln
1               5                   10                  15

Ala Leu Glu Phe Ile Leu Arg Gln Leu Pro Arg Asp Cys
            20                  25

<210> SEQ ID NO 137
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 137

Thr Thr Glu Arg Val Val Ala Leu Gly Thr Ser Thr Gly Gly Thr Gln
1               5                   10                  15

Ala Leu Glu Val Val Leu Arg Thr Leu Pro Arg Val Cys
            20                  25

<210> SEQ ID NO 138
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 138

Thr Thr Asp Arg Val Val Ala Ile Gly Thr Ser Thr Gly Gly Thr Gln
1               5                   10                  15

Ala Leu Glu Val Val Leu Thr Ala Leu Pro Arg Val Cys
            20                  25

<210> SEQ ID NO 139
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 139
```

-continued

Thr Thr Glu Arg Ile Val Ala Ile Gly Thr Ser Thr Gly Gly Thr Gln
1               5                   10                  15

Ala Leu Glu Thr Val Leu His Arg Leu Pro Ala Thr Cys
            20                  25

<210> SEQ ID NO 140
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 140

Thr Thr Glu Arg Ile Val Ala Ile Gly Thr Ser Thr Gly Gly Thr Gln
1               5                   10                  15

Ala Leu Glu Thr Val Leu Pro Arg Leu Pro Ala Thr Cys
            20                  25

<210> SEQ ID NO 141
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 141

Thr Thr Asp Lys Ile Ile Ala Ile Gly Thr Ser Thr Gly Gly Thr Gln
1               5                   10                  15

Ala Leu Glu Ala Val Leu Thr Lys Leu Pro Ala Val Cys
            20                  25

<210> SEQ ID NO 142
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 142

Thr Thr Asp Gln Leu Ile Ala Ile Gly Thr Ser Thr Gly Gly Thr Gln
1               5                   10                  15

Ala Leu Glu Ala Ile Leu Thr Lys Leu Pro Ala Thr Cys
            20                  25

<210> SEQ ID NO 143
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 143

Thr Ser Asp Lys Val Val Ala Ile Gly Ala Ser Thr Gly Gly Thr Gln
1               5                   10                  15

Ala Leu Glu Leu Leu Leu Thr Gly Leu Pro Ala Val Cys
            20                  25

<210> SEQ ID NO 144
<211> LENGTH: 28
<212> TYPE: PRT
<213> ORGANISM: Artificial Sequence
<220> FEATURE:
<223> OTHER INFORMATION: synthetic polypeptide

<400> SEQUENCE: 144

Ala Asp Ile Val Lys Ile Ala Ser Asn Gly Gly Gly Ala Gln Ala Leu
1               5                   10                  15

Glu Ala Val Ala Met His Gly Ser Thr Leu Cys Glu
            20                  25

<210> SEQ ID NO 145
<211> LENGTH: 28
<212> TYPE: PRT
<213> ORGANISM: Artificial Sequence
<220> FEATURE:
<223> OTHER INFORMATION: synthetic polypeptide

<400> SEQUENCE: 145

Ala Asp Ile Val Lys Ile Ala Gly Asn Gly Gly Gly Ala Arg Ala Leu
1               5                   10                  15

Lys Ala Val Val Met His Gly Pro Thr Leu Cys Glu
            20                  25

<210> SEQ ID NO 146
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 146

Phe Ser Gln Ala Asp Ile Val Arg Ile Ala Asp Asn Ile Gly Gly Ala
1               5                   10                  15

Gln Ala Leu Lys Ala Val Leu Glu His Gly Pro Thr Leu
            20                  25

<210> SEQ ID NO 147
<211> LENGTH: 24
<212> TYPE: PRT
<213> ORGANISM: Artificial Sequence
<220> FEATURE:
<223> OTHER INFORMATION: synthetic polypeptide

<400> SEQUENCE: 147

Ala Leu Ala Ala Ala Val Gly Gly Lys Gly Ala Leu Glu Val Pro Ala
1               5                   10                  15

Asn Leu Ile Pro Ala Asn Cys Glu
            20

<210> SEQ ID NO 148
<211> LENGTH: 52
<212> TYPE: DNA
<213> ORGANISM: Artificial Sequence
<220> FEATURE:
<223> OTHER INFORMATION: synthetic polynucleotide

<400> SEQUENCE: 148
ttgatagtcg ccttatgttt tggatacaga atgttgacag gtaaacgaaa ta         52

<210> SEQ ID NO 149
<211> LENGTH: 16
<212> TYPE: DNA
<213> ORGANISM: Artificial Sequence
<220> FEATURE:
<223> OTHER INFORMATION: synthetic polynucleotide

<400> SEQUENCE: 149
tgatagtcgc cttatg                                                 16

<210> SEQ ID NO 150
<211> LENGTH: 16
<212> TYPE: DNA
<213> ORGANISM: Artificial Sequence
<220> FEATURE:
<223> OTHER INFORMATION: synthetic polynucleotide

<400> SEQUENCE: 150
atttggttta cctgtc                                                      16

<210> SEQ ID NO 151
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 151

Leu Ser Thr Ala Gln Val Val Ala Ile Ala Ser Asn Gly Gly Gly Lys
1               5                   10                  15

Gln Ala Leu Glu Gly Ile Gly Glu Gln Leu Leu Lys Leu Arg Thr Ala
            20                  25                  30

Pro Tyr Gly
        35

<210> SEQ ID NO 152
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 152

Leu Ser Thr Glu Gln Val Val Ala Ile Ala Ser Asn Lys Gly Gly Lys
1               5                   10                  15

Gln Ala Leu Glu Ala Val Lys Ala His Leu Leu Asp Leu Leu Gly Ala
            20                  25                  30

Pro Tyr Val
        35

<210> SEQ ID NO 153
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 153

Leu Ser Thr Glu Gln Val Val Ala Ile Ala Ser Asn Asn Gly Gly Lys
1               5                   10                  15

Gln Ala Leu Glu Ala Val Lys Ala Gln Leu Leu Glu Leu Arg Ala Ala
            20                  25                  30

Pro Tyr Glu
        35

<210> SEQ ID NO 154
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 154

Leu Ser Thr Ala Gln Val Val Ala Ile Ala Ser Asn Gly Gly Lys
1               5                   10                  15

Gln Ala Leu Glu Gly Ile Gly Glu Gln Leu Leu Lys Leu Arg Thr Ala
            20                  25                  30

Pro Tyr Gly
        35

<210> SEQ ID NO 155
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 155

Leu Ser Thr Glu Gln Val Val Ala Ile Ala Ser Asn Asn Gly Gly Lys
1               5                   10                  15

Gln Ala Leu Glu Ala Val Lys Ala Gln Leu Leu Glu Leu Arg Ala Ala
            20                  25                  30

Pro Tyr Glu
        35

<210> SEQ ID NO 156
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 156

Leu Ser Thr Glu Gln Val Val Ala Ile Ala Ser Asn Lys Gly Gly Lys
1               5                   10                  15

Gln Ala Leu Glu Ala Val Lys Ala His Leu Leu Asp Leu Leu Gly Ala
            20                  25                  30

Pro Tyr Val
        35

<210> SEQ ID NO 157
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 157

Leu Ser Thr Ala Gln Val Val Ala Ile Ala Ser Asn Gly Gly Gly Lys
1               5                   10                  15

Gln Ala Leu Glu Gly Ile Gly Glu Gln Leu Leu Lys Leu Arg Thr Ala
            20                  25                  30

Pro Tyr Gly
        35

<210> SEQ ID NO 158
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 158

Leu Ser Thr Ala Gln Val Val Ala Ile Ala Ser His Asp Gly Gly Lys
1               5                   10                  15

```
Pro Ala Leu Glu Ala Val Trp Ala Lys Leu Pro Val Leu Arg Gly Val
            20                  25                  30

Pro Tyr Ala
        35

<210> SEQ ID NO 159
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 159

Leu Ser Thr Glu Gln Val Val Ala Ile Ala Ser Asn Lys Gly Gly Lys
1               5                   10                  15

Gln Ala Leu Glu Ala Val Lys Ala His Leu Leu Asp Leu Leu Gly Ala
            20                  25                  30

Pro Tyr Val
        35

<210> SEQ ID NO 160
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 160

Leu Ser Thr Ala Gln Val Val Ala Ile Ala Ser His Asp Gly Gly Lys
1               5                   10                  15

Pro Ala Leu Glu Ala Val Trp Ala Lys Leu Pro Val Leu Arg Gly Val
            20                  25                  30

Pro Tyr Ala
        35

<210> SEQ ID NO 161
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 161

Leu Ser Thr Ala Gln Val Val Ala Ile Ala Ser His Asp Gly Gly Lys
1               5                   10                  15

Pro Ala Leu Glu Ala Val Trp Ala Lys Leu Pro Val Leu Arg Gly Val
            20                  25                  30

Pro Tyr Ala
        35

<210> SEQ ID NO 162
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 162

Leu Ser Thr Ala Gln Val Val Ala Ile Ala Ser Asn Gly Gly Gly Lys
1               5                   10                  15

Gln Ala Leu Glu Gly Ile Gly Glu Gln Leu Leu Lys Leu Arg Thr Ala
            20                  25                  30
```

```
Pro Tyr Gly
        35

<210> SEQ ID NO 163
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 163

Leu Ser Thr Ala Gln Val Val Ala Ile Ala Ser Asn Gly Gly Gly Lys
1               5                   10                  15

Gln Ala Leu Glu Gly Ile Gly Glu Gln Leu Leu Lys Leu Arg Thr Ala
            20                  25                  30

Pro Tyr Gly
        35

<210> SEQ ID NO 164
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 164

Leu Ser Thr Glu Gln Val Val Ala Ile Ala Ser Asn Asn Gly Gly Lys
1               5                   10                  15

Gln Ala Leu Glu Ala Val Lys Ala Gln Leu Leu Glu Leu Arg Ala Ala
            20                  25                  30

Pro Tyr Glu
        35

<210> SEQ ID NO 165
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 165

Leu Ser Thr Ala Gln Val Val Ala Ile Ala Ser Asn Gly Gly Gly Lys
1               5                   10                  15

Gln Ala Leu Glu Gly Ile Gly Glu Gln Leu Leu Lys Leu Arg Thr Ala
            20                  25                  30

Pro Tyr Gly
        35

<210> SEQ ID NO 166
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 166

Leu Ser Thr Glu Gln Val Val Ala Ile Ala Ser Asn Lys Gly Gly Lys
1               5                   10                  15

Gln Ala Leu Glu Ala Val Lys Ala His Leu Leu Asp Leu Leu Gly Ala
            20                  25                  30

Pro Tyr Val
        35
```

<210> SEQ ID NO 167
<211> LENGTH: 8106
<212> TYPE: DNA
<213> ORGANISM: Artificial Sequence
<220> FEATURE:
<223> OTHER INFORMATION: synthetic polynucleotide

<400> SEQUENCE: 167

```
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
accatggact acaaagacca tgacggtgat tataaagatc atgacatcga ttacaaggat     960
gacgatgaca agatggcccc caagaagaag aggaaggtgg gcattcaccg cggggtacct    1020
atggtggact tgaggacact cggttattcg caacagcaac aggagaaaat caagcctaag    1080
gtcaggagca ccgtcgcgca acaccacgag gcgcttgtgg ggcatggctt cactcatgcg    1140
catattgtcg cgctttcaca gcaccctgcg gcgcttggga cggtggctgt caaataccaa    1200
gatatgattg cggccctgcc cgaagccacg cacgaggcaa ttgtaggggt cggtaaacag    1260
tggtcgggag cgcgagcact tgaggcgctg ctgactgtgg cgggtgagct tagggggcct    1320
ccgctccagc tcgacaccgg cagctgctg aagatcgcga agagaggggg agtaacagcg    1380
gtagaggcag tgcacgcctg gcgcaatgcg ctcaccgggg ccccttgaa cctgagcacc    1440
gcccaggtgg tggccatcgc cagcaacggc ggcggcaagc aggccctgga gggcatcggc    1500
gagcagctgc tgaagctgag gaccgccccc tacggcctga gcaccgagca ggtggtggcc    1560
atcgccagca caagggcgg caagcaggcc ctggaggccg tgaaggccca cctgctggac    1620
ctgctgggcg cccctacgt gctgagcacc gagcaggtgg tggccatcgc cagcaacaac    1680
ggcggcaagc aggccctgga ggccgtgaag gcccagctgc tggagctgag gccgccccc    1740
tacgagctga gcaccgccca ggtggtggcc atcgccagca acggcggcgg caagcaggcc    1800
ctggagggca tcgcgagca gctgctgaag ctgaggaccg cccctacgg cctgagcacc    1860
gagcaggtgg tggccatcgc cagcaacaac ggcggcaagc aggccctgga ggccgtgaag    1920
gcccagctgc tggagctgag gccgccccc tacgagctga gcaccgagca ggtggtggcc    1980
atcgccagca caagggcgg caagcaggcc ctggaggccg tgaaggccca cctgctggac    2040
ctgctgggcg cccctacgt gctgagcacc gcccaggtgg tggccatcgc cagcaacggc    2100
```

| | |
|---|---|
| ggcggcaagc aggccctgga gggcatcggc gagcagctgc tgaagctgag gaccgccccc | 2160 |
| tacggcctga gcaccgccca ggtggtggcc atcgccagcc acgacggcgg caagcccgcc | 2220 |
| ctggaggccg tgtgggccaa gctgcccgtg ctgaggggcg tgccctacgc cctgagcacc | 2280 |
| gagcaggtgg tggccatcgc cagcaacaag ggcggcaagc aggccctgga ggccgtgaag | 2340 |
| gcccacctgc tggacctgct gggcgccccc tacgtgctga gcaccgccca ggtggtggcc | 2400 |
| atcgccagcc acgacggcgg caagcccgcc ctggaggccg tgtgggccaa gctgcccgtg | 2460 |
| ctgaggggcg tgccctacgc cctgagcacc gcccaggtgg tggccatcgc cagccacgac | 2520 |
| ggcggcaagc ccgccctgga ggccgtgtgg gccaagctgc ccgtgctgag gggcgtgccc | 2580 |
| tacgccctga gcaccgccca ggtggtggcc atcgccagca cggcggcgg caagcaggcc | 2640 |
| ctggagggca tcgcgagca gctgctgaag ctgaggaccg cccctacgg cctgagcacc | 2700 |
| gcccaggtgg tggccatcgc cagcaacggc ggcggcaagc aggccctgga gggcatcggc | 2760 |
| gagcagctgc tgaagctgag gaccgccccc tacggcctga gcaccgagca ggtggtggcc | 2820 |
| atcgccagca acggcggcaa gcaggcc ctggaggccg tgaaggccca gctgctggag | 2880 |
| ctgagggccg cccctacga gctgagcacc gcccaggtgg tggccatcgc cagcaacggc | 2940 |
| ggcggcaagc aggccctgga gggcatcggc gagcagctgc tgaagctgag gaccgccccc | 3000 |
| tacggcctga gcaccgagca ggtggtggcc atcgccagca acaagggcgg caagcaggcc | 3060 |
| ctggaggccg tgaaggccca cctgctggac ctgctgggcg cccctacgt gctgagcacc | 3120 |
| gcccaggtgg tggccatcgc cagcaacggc ggaggacggc cagccttgga gtccatcgta | 3180 |
| gcccaattgt ccaggcccga tccgcgttg gctgcgttaa cgaatgacca tctggtggcg | 3240 |
| ttggcatgtc ttggtggacg acccgcgctc gatgcagtca aaaagggtct gcctcatgct | 3300 |
| cccgcattga tcaaaagaac caaccggcgg attcccgaga gaacttccca tcgagtcgcg | 3360 |
| ggatcccaac tagtcaaaag tgaactggag gagaagaaat ctgaacttcg tcataaattg | 3420 |
| aaatatgtgc ctcatgaata tattgaatta attgaaattg ccagaaattc cactcaggat | 3480 |
| agaattcttg aaatgaaggt aatgaatttt tttatgaaag tttatggata tagaggtaaa | 3540 |
| catttgggtg gatcaaggaa accggacgga gcaatttata ctgtcggatc tcctattgat | 3600 |
| tacggtgtga tcgtggatac taaagcttat agcggaggtt ataatctgcc aattggccaa | 3660 |
| gcagatgaaa tgcaacgata tgtcgaagaa atcaaacac gaaacaaaca tatcaaccct | 3720 |
| aatgaatggt ggaaagtcta tccatcttct gtaacggaat ttaagttttt atttgtgagt | 3780 |
| ggtcactta aggaaacta caaagctcag cttacacgat taaatcatat cactaattgt | 3840 |
| aatggagctg ttcttagtgt agaagagctt ttaattggtg agaaatgat taaagccggc | 3900 |
| acattaacct tagaggaagt cagacggaaa tttaataacg gcgagataaa cttttaaggg | 3960 |
| cccttcgaag gtaagcctat ccctaaccct ctcctcggtc tcgattctac gcgtaccggt | 4020 |
| catcatcacc atcaccattg agtttaaacc cgctgatcag cctcgactgt gccttctagt | 4080 |
| tgccagccat ctgttgtttg cccctccccc gtgccttcct tgaccctgga aggtgccact | 4140 |
| cccactgtcc tttcctaata aaatgaggaa attgcatcgc attgtctgag taggtgtcat | 4200 |
| tctattctgg ggggtgggt ggggcaggac agcaaggggg aggattggga agacaatagc | 4260 |
| aggcatgctg gggatgcggt gggctctatg gcttctgagg cggaaagaac cagctggggc | 4320 |
| tctaggggt atccccacgc gccctgtagc ggcgcattaa gcgcggcggg tgtggtggtt | 4380 |
| acgcgcagcg tgaccgctac acttgccagc gccctagcgc ccgctccttt cgctttcttc | 4440 |

```
ccttcctttc tcgccacgtt cgccggcttt ccccgtcaag ctctaaatcg gggcatccct      4500
ttagggttcc gatttagtgc tttacggcac ctcgaccccca aaaaacttga ttagggtgat     4560
ggttcacgta gtgggccatc gccctgatag acggtttttc gccctttgac gttggagtcc     4620
acgttcttta atagtggact cttgttccaa actggaacaa cactcaaccc tatctcggtc     4680
tattcttttg atttataagg gattttgggg atttcggcct attggttaaa aaatgagctg     4740
atttaacaaa aatttaacgc gaattaattc tgtggaatgt gtgtcagtta gggtgtggaa     4800
agtccccagg ctccccaggc aggcagaagt atgcaaagca tgcatctcaa ttagtcagca     4860
accaggtgtg aaagtcccc aggctcccca gcaggcagaa gtatgcaaag catgcatctc      4920
aattagtcag caaccatagt cccgcccta actccgccca tcccgcccct aactccgccc      4980
agttccgccc attctccgcc ccatggctga ctaatttttt ttatttatgc agaggccgag     5040
gccgcctctg cctctgagct attccagaag tagtgaggag gctttttttgg aggcctaggc    5100 ttttgcaaaa agctcccggg agcttgtata tccattttcg gatctgatca gcacgtgttg     5160
acaattaatc atcggcatag tatatcggca tagtataata cgacaaggtg aggaactaaa    5220
ccatggccaa gccttttgtct caagaagaat ccaccctcat tgaaagagca acggctacaa    5280
tcaacagcat ccccatctct gaagactaca gcgtcgccag cgcagctctc tctagcgacg    5340
gccgcatctt cactggtgtc aatgtatatc attttactgg gggaccttgt gcagaactcg    5400
tggtgctggg cactgctgct gctgcggcag ctggcaaccct gacttgtatc gtcgcgatcg    5460
gaaatgagaa caggggcatc ttgagccccct gcggacggtg tcgacaggtg cttctcgatc    5520
tgcatcctgg gatcaaagcg atagtgaagg acagtgatgg acagccgacg gcagttggga    5580
ttcgtgaatt gctgccctct ggttatgtgt gggagggcta agcacttcgt ggccgaggag    5640
caggactgac acgtgctacg agatttcgat tccaccgccg ccttctatga aaggttgggc    5700
ttcggaatcg ttttccggga cgccggctgg atgatcctcc agcgcgggga tctcatgctg    5760
gagttcttcg cccaccccaa cttgtttatt gcagcttata atggttacaa ataaagcaat    5820
agcatcacaa atttcacaaa taaagcattt ttttcactgc attctagttg tggtttgtcc    5880
aaactcatca atgtatctta tcatgtctgt ataccgtcga cctctagcta gagcttggcg    5940
taatcatggt catagctgtt tcctgtgtga aattgttatc cgctcacaat tccacacaac    6000
atacgagccg gaagcataaa gtgtaaagcc tggggtgcct aatgagtgag ctaactcaca    6060
ttaattgcgt tgcgctcact gcccgctttc cagtcgggaa acctgtcgtg ccagctgcat    6120
taatgaatcg gccaacgcgc ggggagaggc ggtttgcgta ttgggcgctc ttccgcttcc    6180
tcgctcactg actcgctgcg ctcggtcgtt cggctgcggc gagcggtatc agctcactca    6240
aaggcggtaa tacggttatc cacagaatca ggggataacg caggaaagaa catgtgagca    6300
aaaggccagc aaaaggccag gaaccgtaaa aaggccgcgt tgctggcgtt tttccatagg    6360
ctccgccccc ctgacgagca tcacaaaaat cgacgctcaa gtcagaggtg gcgaaacccg    6420
acaggactat aaagatacca ggcgtttccc cctggaagct ccctcgtgcg ctctcctgtt    6480
ccgaccctgc cgcttaccgg atacctgtcc gcctttctcc cttcgggaag cgtggcgctt    6540
tctcaatgct cacgctgtag gtatctcagt tcggtgtagg tcgttcgctc caagctgggc    6600
tgtgtgcacg aaccccccgt tcagcccgac cgctgcgcct tatccggtaa ctatcgtctt    6660
gagtccaacc cggtaagaca cgacttatcg ccactggcag cagccactgg taacaggatt    6720
agcagagcga ggtatgtagg cggtgctaca gagttcttga agtggtggcc taactacggc    6780
tacactagaa ggacagtatt tggtatctgc gctctgctga agccagttac cttcggaaaa    6840
```

-continued

```
agagttggta gctcttgatc cggcaaacaa accaccgctg gtagcggtgg ttttttttgtt    6900 tgcaagcagc agattacgcg cagaaaaaaa ggatctcaag aagatccttt gatcttttct    6960
acggggtctg acgctcagtg gaacgaaaac tcacgttaag ggattttggt catgagatta    7020
tcaaaaagga tcttcaccta gatcctttta aattaaaaat gaagttttaa atcaatctaa    7080
agtatatatg agtaaacttg gtctgacagt taccaatgct taatcagtga ggcacctatc    7140
tcagcgatct gtctatttcg ttcatccata gttgcctgac tccccgtcgt gtagataact    7200
acgatacggg agggcttacc atctggcccc agtgctgcaa tgataccgcg agacccacgc    7260
tcaccggctc cagatttatc agcaataaac cagccagccg gaagggccga gcgcagaagt    7320
ggtcctgcaa ctttatccgc ctccatccag tctattaatt gttgccggga agctagagta    7380
agtagttcgc cagttaatag tttgcgcaac gttgttgcca ttgctacagg catcgtggtg    7440
tcacgctcgt cgtttggtat ggcttcattc agctccggtt cccaacgatc aaggcgagtt    7500
acatgatccc ccatgttgtg caaaaaagcg gttagctcct tcggtcctcc gatcgttgtc    7560
agaagtaagt tggccgcagt gttatcactc atggttatgg cagcactgca taattctctt    7620
actgtcatgc catccgtaag atgcttttct gtgactggtg agtactcaac caagtcattc    7680
tgagaatagt gtatgcggcg accgagttgc tcttgcccgg cgtcaatacg ggataatacc    7740
gcgccacata gcagaacttt aaaagtgctc atcattggaa aacgttcttc ggggcgaaaa    7800
ctctcaagga tcttaccgct gttgagatcc agttcgatgt aacccactcg tgcacccaac    7860
tgatcttcag catcttttac tttcaccagc gtttctgggt gagcaaaaac aggaaggcaa    7920
aatgccgcaa aaaagggaat aagggcgaca cggaaatgtt gaatactcat actcttcctt    7980
tttcaatatt attgaagcat ttatcagggt tattgtctca tgagcggata catatttgaa    8040
tgtatttaga aaataaaca aataggggtt ccgcgcacat ttccccgaaa agtgccacct    8100
gacgtc                                                              8106
```

<210> SEQ ID NO 168
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 168

```
Leu Ser Thr Glu Gln Val Val Ala Ile Ala Ser Asn Asn Gly Gly Lys
1               5                   10                  15

Gln Ala Leu Glu Ala Val Lys Ala Gln Leu Leu Glu Leu Arg Ala Ala
            20                  25                  30

Pro Tyr Glu
        35
```

<210> SEQ ID NO 169
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 169

```
Leu Ser Thr Ala Gln Val Val Ala Ile Ala Ser Asn Gly Gly Gly Lys
1               5                   10                  15

Gln Ala Leu Glu Gly Ile Gly Glu Gln Leu Leu Lys Leu Arg Thr Ala
            20                  25                  30
```

Pro Tyr Gly
        35

<210> SEQ ID NO 170
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 170

Leu Ser Thr Ala Gln Val Val Ala Ile Ala Ser Asn Gly Gly Gly Lys
1               5                   10                  15

Gln Ala Leu Glu Gly Ile Gly Glu Gln Leu Leu Lys Leu Arg Thr Ala
            20                  25                  30

Pro Tyr Gly
        35

<210> SEQ ID NO 171
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 171

Leu Ser Thr Ala Gln Val Val Ala Ile Ala Ser Asn Gly Gly Gly Lys
1               5                   10                  15

Gln Ala Leu Glu Gly Ile Gly Glu Gln Leu Leu Lys Leu Arg Thr Ala
            20                  25                  30

Pro Tyr Gly
        35

<210> SEQ ID NO 172
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 172

Leu Ser Thr Ala Gln Val Val Ala Ile Ala Ser His Asp Gly Gly Lys
1               5                   10                  15

Pro Ala Leu Glu Ala Val Trp Ala Lys Leu Pro Val Leu Arg Gly Val
            20                  25                  30

Pro Tyr Ala
        35

<210> SEQ ID NO 173
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 173

Leu Ser Thr Glu Gln Val Val Ala Ile Ala Ser Asn Lys Gly Gly Lys
1               5                   10                  15

Gln Ala Leu Glu Ala Val Lys Ala His Leu Leu Asp Leu Leu Gly Ala
            20                  25                  30

Pro Tyr Val
        35

<210> SEQ ID NO 174
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 174

Leu Ser Thr Ala Gln Val Val Ala Ile Ala Ser Asn Gly Gly Gly Lys
1               5                   10                  15

Gln Ala Leu Glu Gly Ile Gly Glu Gln Leu Leu Lys Leu Arg Thr Ala
            20                  25                  30

Pro Tyr Gly
        35

<210> SEQ ID NO 175
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 175

Leu Ser Thr Ala Gln Val Val Ala Ile Ala Ser Asn Gly Gly Gly Lys
1               5                   10                  15

Gln Ala Leu Glu Gly Ile Gly Glu Gln Leu Leu Lys Leu Arg Thr Ala
            20                  25                  30

Pro Tyr Gly
        35

<210> SEQ ID NO 176
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 176

Leu Ser Thr Ala Gln Val Val Ala Ile Ala Ser Asn Gly Gly Gly Lys
1               5                   10                  15

Gln Ala Leu Glu Gly Ile Gly Glu Gln Leu Leu Lys Leu Arg Thr Ala
            20                  25                  30

Pro Tyr Gly
        35

<210> SEQ ID NO 177
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 177

Leu Ser Thr Glu Gln Val Val Ala Ile Ala Ser Asn Asn Gly Gly Lys
1               5                   10                  15

Gln Ala Leu Glu Ala Val Lys Ala Gln Leu Leu Glu Leu Arg Ala Ala
            20                  25                  30

Pro Tyr Glu
        35

<210> SEQ ID NO 178

<211> LENGTH: 35
<212> TYPE: PRT
<213> ORGANISM: Artificial Sequence
<220> FEATURE:
<223> OTHER INFORMATION: synthetic polypeptide

<400> SEQUENCE: 178

Leu Ser Thr Ala Gln Val Val Ala Ile Ala Ser His Asp Gly Gly Lys
1               5                   10                  15

Pro Ala Leu Glu Ala Val Trp Ala Lys Leu Pro Val Leu Arg Gly Val
            20                  25                  30

Pro Tyr Ala
        35

<210> SEQ ID NO 179
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 179

Leu Ser Thr Ala Gln Val Val Ala Ile Ala Ser His Asp Gly Gly Lys
1               5                   10                  15

Pro Ala Leu Glu Ala Val Trp Ala Lys Leu Pro Val Leu Arg Gly Val
            20                  25                  30

Pro Tyr Ala
        35

<210> SEQ ID NO 180
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 180

Leu Ser Thr Ala Gln Val Val Ala Ile Ala Ser Asn Gly Gly Gly Lys
1               5                   10                  15

Gln Ala Leu Glu Gly Ile Gly Glu Gln Leu Leu Lys Leu Arg Thr Ala
            20                  25                  30

Pro Tyr Gly
        35

<210> SEQ ID NO 181
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 181

Leu Ser Thr Glu Gln Val Val Ala Ile Ala Ser Asn Lys Gly Gly Lys
1               5                   10                  15

Gln Ala Leu Glu Ala Val Lys Ala His Leu Leu Asp Leu Leu Gly Ala
            20                  25                  30

Pro Tyr Val
        35

<210> SEQ ID NO 182
<211> LENGTH: 35
<212> TYPE: PRT
<213> ORGANISM: Artificial Sequence

```
<220> FEATURE:
<223> OTHER INFORMATION: synthetic polypeptide

<400> SEQUENCE: 182

Leu Ser Thr Ala Gln Val Val Ala Ile Ala Ser Asn Gly Gly Lys
1               5                   10                  15

Gln Ala Leu Glu Gly Ile Gly Glu Gln Leu Leu Lys Leu Arg Thr Ala
                20                  25                  30

Pro Tyr Gly
        35

<210> SEQ ID NO 183
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 183

Leu Ser Thr Ala Gln Val Val Ala Ile Ala Ser His Asp Gly Gly Lys
1               5                   10                  15

Pro Ala Leu Glu Ala Val Trp Ala Lys Leu Pro Val Leu Arg Gly Val
                20                  25                  30

Pro Tyr Ala
        35

<210> SEQ ID NO 184
<211> LENGTH: 8102
<212> TYPE: DNA
<213> ORGANISM: Artificial Sequence
<220> FEATURE:
<223> OTHER INFORMATION: synthetic polynucleotide

<400> SEQUENCE: 184
gacggatcgg gagatctccc gatccctat  ggtcgactct  cagtacaatc  tgctctgatg     60
ccgcatagtt aagccagtat ctgctccctg  cttgtgtgtt  ggaggtcgct  gagtagtgcg    120
cgagcaaaat ttaagctaca acaaggcaag  gcttgaccga  caattgcatg  aagaatctgc    180
ttagggttag gcgttttgcg ctgcttcgcg  atgtacgggc  cagatatacg  cgttgacatt    240
gattattgac tagttattaa tagtaatcaa  ttacggggtc  attagttcat  agcccatata    300
tggagttccg cgttacataa cttacggtaa  atggcccgcc  tggctgaccg  cccaacgacc    360
cccgcccatt gacgtcaata atgacgtatg  ttcccatagt  aacgccaata  gggactttcc    420
attgacgtca atgggtggag tatttacggt  aaactgccca  cttggcagta  catcaagtgt    480
atcatatgcc aagtacgccc cctattgacg  tcaatgacgg  taaatggccc  gcctggcatt    540
atgcccagta catgacctta tgggactttc  ctacttggca  gtacatctac  gtattagtca    600
tcgctattac catggtgatg cggttttggc  agtacatcaa  tgggcgtgga  tagcggtttg    660
actcacgggg atttccaagt ctccacccca  ttgacgtcaa  tgggagtttg  ttttggcacc    720
aaaatcaacg ggactttcca aaatgtcgta  acaactccgc  ccattgacg   caaatgggcg    780 gtaggcgtgt acggtgggag gtctatataa  gcagagctct  ctggctaact  agagaaccca    840
ctgcttactg gcttatcgaa attaatacga  ctcactatag  ggagacccaa  gctggctagc    900
accatggact acaaagacca tgacggtgat  tataaagatc  atgacatcga  ttacaaggat    960
gacgatgaca gatggcccc  caagaagaag  aggaaggtgg  gcattcaccg  cggggtacct   1020
atggtggact tgaggacact cggttattcg  caacagcaac  aggagaaaat  caagcctaag   1080
```

| | |
|---|---|
| gtcaggagca ccgtcgcgca acaccacgag gcgcttgtgg ggcatggctt cactcatgcg | 1140 |
| catattgtcg cgcttttcaca gcaccctgcg gcgcttggga cggtggctgt caaataccaa | 1200 |
| gatatgattg cggccctgcc cgaagccacg cacgaggcaa ttgtaggggt cggtaaacag | 1260 |
| tggtcgggag cgcgagcact tgaggcgctg ctgactgtgg cgggtgagct taggggggcct | 1320 |
| ccgctccagc tcgacaccgg gcagctgctg aagatcgcga agagaggggg agtaacagcg | 1380 |
| gtagaggcag tgcacgcctg cgcaatgcg ctcaccgggg ccccccttctg agcaccgagc | 1440 |
| aggtggtggc catcgccagc aacaacggcg gcaagcaggc cctggaggcc gtgaaggccc | 1500 |
| agctgctgga gctgagggcc gccccctacg agctgagcac cgcccaggtg gtggccatcg | 1560 |
| ccagcaacgg cggcggcaag caggccctgg agggcatcgg cgagcagctg ctgaagctga | 1620 |
| ggaccgcccc ctacgccctg agcaccgccc aggtggtggc catcgccagc aacggcggcg | 1680 |
| gcaagcaggc cctggagggc atcggcgagc agctgctgaa gctgaggacc gccccctacg | 1740 |
| gcctgagcac cgcccaggtg gtggccatcg ccagcaacgg cggcggcaag caggccctgg | 1800 |
| agggcatcgg cgagcagctg ctgaagctga ggaccgcccc ctacgccctg agcaccgccc | 1860 |
| aggtggtggc catcgccagc cacgacggcg gcaagcccgc cctggaggcc gtgtgggcca | 1920 |
| agctgcccgt gctgaggggc gtgccctacg ccctgagcac cgagcaggtg gtggccatcg | 1980 |
| ccagcaacaa gggcggcaag caggccctgg aggccgtgaa ggcccacctg ctggacctgc | 2040 |
| tgggcgcccc ctacgtgctg agcaccgccc aggtggtggc catcgccagc aacggcggcg | 2100 |
| gcaagcaggc cctggagggc atcggcgagc agctgctgaa gctgaggacc gccccctacg | 2160 |
| gcctgagcac cgcccaggtg gtggccatcg ccagcaacgg cggcggcaag caggccctgg | 2220 |
| agggcatcgg cgagcagctg ctgaagctga ggaccgcccc ctacggcctg agcaccgccc | 2280 |
| aggtggtggc catcgccagc aacggcggcg gcaagcaggc cctggagggc atcggcgagc | 2340 |
| agctgctgaa gctgaggacc gccccctacg gcctgagcac cgagcaggtg gtggccatcg | 2400 |
| ccagcaacaa cggcggcaag caggccctgg aggccgtgaa ggcccagctg ctggagctga | 2460 |
| gggccgcccc ctacgagctg agcaccgccc aggtggtggc catcgccagc cacgacggcg | 2520 |
| gcaagcccgc cctggaggcc gtgtgggcca agctgcccgt gctgaggggc gtgccctacg | 2580 |
| ccctgagcac cgcccaggtg gtggccatcg ccagccacga cggcggcaag cccgccctgg | 2640 |
| aggccgtgtg ggccaagctg cccgtgctga ggggcgtgcc ctacgccctg agcaccgccc | 2700 |
| aggtggtggc catcgccagc aacggcggcg gcaagcaggc cctggagggc atcggcgagc | 2760 |
| agctgctgaa gctgaggacc gccccctacg gcctgagcac cgagcaggtg gtggccatcg | 2820 |
| ccagcaacaa gggcggcaag caggccctgg aggccgtgaa ggcccacctg ctggacctgc | 2880 |
| tgggcgcccc ctacgtgctg agcaccgccc aggtggtggc catcgccagc aacggcggcg | 2940 |
| gcaagcaggc cctggagggc atcggcgagc agctgctgaa gctgaggacc gccccctacg | 3000 |
| gcctgagcac cgcccaggtg gtggccatcg ccagccacga cggcggcaag cccgccctgg | 3060 |
| aggccgtgtg ggccaagctg cccgtgctga ggggcgtgcc ctacgccctg agcaccgagc | 3120 |
| aggtggtgac catcgccagc agcatcggag gacggccagc cttggagtcc atcgtagccc | 3180 |
| aattgtccag gcccgatccc gcgttggctg cgttaacgaa tgaccatctg gtggcgttgg | 3240 |
| catgtcttgg tggacgaccc gcgctcgatg cagtcaaaaa gggtctgcct catgctcccg | 3300 |
| cattgatcaa aagaaccaac cggcggattc ccgagagaac ttcccatcga gtcgcgggat | 3360 |
| cccaactagt caaaagtgaa ctggaggaga agaaatctga acttcgtcat aaattgaaat | 3420 |
| atgtgcctca tgaatatatt gaattaattg aaattgccag aaattccact caggatagaa | 3480 |

```
ttcttgaaat gaaggtaatg gaatttttta tgaaagttta tggatataga ggtaaacatt    3540
tgggtggatc aaggaaaccg gacggagcaa tttatactgt cggatctcct attgattacg    3600
gtgtgatcgt ggatactaaa gcttatagcg gaggttataa tctgccaatt ggccaagcag    3660
atgaaatgca acgatatgtc gaagaaaatc aaacacgaaa caaacatatc aaccctaatg    3720
aatggtggaa agtctatcca tcttctgtaa cggaatttaa gttttattt gtgagtggtc      3780
acttaaaagg aaactacaaa gctcagctta cacgattaaa tcatatcact aattgtaatg    3840
gagctgttct tagtgtagaa gagcttttaa ttggtggaga aatgattaaa gccggcacat    3900
taaccttaga ggaagtcaga cggaaattta ataacggcga gataaacttt taagggccct    3960
tcgaaggtaa gcctatccct aaccctctcc tcggtctcga ttctacgcgt accggtcatc    4020
atcaccatca ccattgagtt taaacccgct gatcagcctc gactgtgcct tctagttgcc    4080
agccatctgt tgtttgcccc tcccccgtgc cttccttgac cctggaaggt gccactccca    4140
ctgtcctttc ctaataaaat gaggaaattg catcgcattg tctgagtagg tgtcattcta    4200
ttctgggggg tggggtgggg caggacagca agggggagga ttgggaagac aatagcaggc    4260
atgctgggga tgcggtgggc tctatggctt ctgaggcgga agaaccagc tggggctcta     4320
gggggtatcc ccacgcgccc tgtagcggcg cattaagcgc ggcgggtgtg gtggttacgc    4380
gcagcgtgac cgctacactt gccagcgccc tagcgcccgc tcctttcgct ttcttccctt    4440
cctttctcgc cacgttcgcc ggctttcccc gtcaagctct aaatcggggc atccctttag    4500
ggttccgatt tagtgcttta cggcacctcg accccaaaaa acttgattag ggtgatggtt    4560
cacgtagtgg gccatcgccc tgatagacgg ttttcgccc tttgacgttg gagtccacgt     4620
tctttaatag tggactcttg ttccaaactg gaacaacact caaccctatc tcggtctatt    4680
cttttgattt ataagggatt tgggggatttt cggcctattg gttaaaaaat gagctgattt   4740
aacaaaaatt taacgcgaat taattctgtg gaatgtgtgt cagttagggt gtggaaagtc    4800
cccaggctcc ccaggcaggc agaagtatgc aaagcatgca tctcaattag tcagcaacca    4860
ggtgtggaaa gtccccaggc tccccagcag gcagaagtat gcaaagcatg catctcaatt    4920
agtcagcaac catagtcccg cccctaactc cgcccatccc gcccctaact ccgcccagtt    4980
ccgcccattc tccgccccat ggctgactaa ttttttttat ttatgcagag gccgaggccg    5040
cctctgcctc tgagctattc cagaagtagt gaggaggctt ttttggaggc ctaggctttt    5100
gcaaaaagct cccgggagct tgtatatcca ttttcggatc tgatcagcac gtgttgacaa    5160
ttaatcatcg gcatagtata tcggcatagt ataatacgac aaggtgagga actaaaccat    5220
ggccaagcct ttgtctcaag aagaatccac cctcattgaa agagcaacgg ctacaatcaa    5280
cagcatcccc atctctgaag actacagcgt cgccagcgca gctctctcta cgacggccg    5340
catcttcact ggtgtcaatg tatatcattt tactggggga ccttgtgcag aactcgtggt    5400
gctgggcact gctgctgctg cggcagctgg caacctgact tgtatcgtcg cgatcggaaa    5460
tgagaacagg ggcatcttga gccctgcgg acggtgtcga caggtgcttc tcgatctgca    5520
tcctgggatc aaagcgatag tgaaggacag tgatggacag ccgacggcag ttgggattcg    5580
tgaattgctg ccctctggtt atgtgtggga gggctaagca cttcgtggcc gaggagcagg    5640
actgacacgt gctacgagat ttcgattcca ccgccgcctt ctatgaaagg ttgggcttcg    5700
gaatcgtttt ccgggacgcc ggctggatga tcctccagcg cggggatctc atgctggagt    5760
tcttcgccca ccccaacttg tttattgcag cttataatgg ttacaaataa agcaatagca    5820
```

```
tcacaaattt cacaaataaa gcatttttt cactgcattc tagttgtggt ttgtccaaac    5880
tcatcaatgt atcttatcat gtctgtatac cgtcgacctc tagctagagc ttggcgtaat    5940
catggtcata gctgtttcct gtgtgaaatt gttatccgct cacaattcca cacaacatac    6000
gagccggaag cataaagtgt aaagcctggg gtgcctaatg agtgagctaa ctcacattaa    6060
ttgcgttgcg ctcactgccc gctttccagt cgggaaacct gtcgtgccag ctgcattaat    6120
gaatcggcca acgcgcgggg agaggcggtt tgcgtattgg gcgctcttcc gcttcctcgc    6180
tcactgactc gctgcgctcg gtcgttcggc tgcggcgagc ggtatcagct cactcaaagg    6240
cggtaatacg gttatccaca gaatcagggg ataacgcagg aaagaacatg tgagcaaaag    6300
gccagcaaaa ggccaggaac cgtaaaaagg ccgcgttgct ggcgtttttc cataggctcc    6360
gcccccctga cgagcatcac aaaaatcgac gctcaagtca gaggtggcga aacccgacag    6420
gactataaag ataccaggcg tttccccctg gaagctccct cgtgcgctct cctgttccga    6480
ccctgccgct taccggatac ctgtccgcct ttctcccttc gggaagcgtg gcgctttctc    6540
aatgctcacg ctgtaggtat ctcagttcgg tgtaggtcgt tcgctccaag ctgggctgtg    6600
tgcacgaacc ccccgttcag cccgaccgct gcgccttatc cggtaactat cgtcttgagt    6660
ccaacccggt aagacacgac ttatcgccac tggcagcagc cactggtaac aggattagca    6720
gagcgaggta tgtaggcggt gctacagagt tcttgaagtg gtggcctaac tacggctaca    6780
ctagaaggac agtatttggt atctgcgctc tgctgaagcc agttaccttc ggaaaaagag    6840
ttggtagctc ttgatccggc aaacaaacca ccgctggtag cggtggtttt tttgtttgca    6900
agcagcagat tacgcgcaga aaaaaggat ctcaagaaga tcctttgatc ttttctacgg    6960
ggtctgacgc tcagtggaac gaaaactcac gttaagggat tttggtcatg agattatcaa    7020
aaaggatctt cacctagatc cttttaaatt aaaaatgaag ttttaaatca atctaaagta    7080
tatatgagta aacttggtct gacagttacc aatgcttaat cagtgaggca cctatctcag    7140
cgatctgtct atttcgttca tccatagttg cctgactccc cgtcgtgtag ataactacga    7200
tacgggaggg cttaccatct ggccccagtg ctgcaatgat accgcgagac ccacgctcac    7260
cggctccaga tttatcagca ataaaccagc cagccggaag ggccgagcgc agaagtggtc    7320
ctgcaacttt atccgcctcc atccagtcta ttaattgttg ccgggaagct agagtaagta    7380
gttcgccagt taatagtttg cgcaacgttg ttgccattgc tacaggcatc gtggtgtcac    7440
gctcgtcgtt tggtatggct tcattcagct ccggttccca acgatcaagg cgagttacat    7500
gatccccat gttgtgcaaa aaagcggtta gctccttcgg tcctccgatc gttgtcagaa    7560
gtaagttggc cgcagtgtta tcactcatgg ttatggcagc actgcataat tctcttactg    7620
tcatgccatc cgtaagatgc ttttctgtga ctggtgagta ctcaaccaag tcattctgag    7680
aatagtgtat gcggcgaccg agttgctctt gcccggcgtc aatacgggat aataccgcgc    7740
cacatagcag aactttaaaa gtgctcatca ttggaaaacg ttcttcgggg cgaaaactct    7800
caaggatctt accgctgttg agatccagtt cgatgtaacc cactcgtgca cccaactgat    7860
cttcagcatc ttttactttc accagcgttt ctgggtgagc aaaaacagga aggcaaaatg    7920
ccgcaaaaaa gggaataagg gcgacacgga aatgttgaat actcatactc ttcctttttc    7980
aatattattg aagcatttat cagggttatt gtctcatgag cggatacata tttgaatgta    8040
tttagaaaaa taaacaaata ggggttccgc gcacatttcc ccgaaaagtg ccacctgacg    8100
tc                                                                   8102
```

<210> SEQ ID NO 185
<211> LENGTH: 2706
<212> TYPE: DNA
<213> ORGANISM: Artificial Sequence
<220> FEATURE:
<223> OTHER INFORMATION: synthetic polynucleotide

<400> SEQUENCE: 185

| | | | | | |
|---|---|---|---|---|---|
| ggatcccggg | cccgtcgact | gcagaggcct | gcatgcaagc | ttggcgtaat | catggtcata | 60 |
| gctgtttcct | gtgtgaaatt | gttatccgct | cacaattcca | cacaacatac | gagccggaag | 120 |
| cataaagtgt | aaagcctggg | gtgcctaatg | agtgagctaa | ctcacattaa | ttgcgttgcg | 180 |
| ctcactgccc | gctttccagt | cgggaaacct | gtcgtgccag | ctgcattaat | gaatcggcca | 240 |
| acgcgcgggg | agaggcggtt | tgcgtattgg | gcgctcttcc | gcttcctcgc | tcactgactc | 300 |
| gctgcgctcg | gtcgttcggc | tgcggcgagc | ggtatcagct | cactcaaagg | cggtaatacg | 360 |
| gttatccaca | gaatcagggg | ataacgcagg | aaagaacatg | tgagcaaaag | gccagcaaaa | 420 |
| ggccaggaac | cgtaaaaagg | ccgcgttgct | ggcgtttttc | cataggctcc | gcccccctga | 480 |
| cgagcatcac | aaaaatcgac | gctcaagtca | gaggtggcga | aacccgacag | gactataaag | 540 |
| ataccaggcg | tttccccctg | gaagctccct | cgtgcgctct | cctgttccga | ccctgccgct | 600 |
| taccggatac | ctgtccgcct | ttctcccttc | gggaagcgtg | gcgctttctc | atagctcacg | 660 |
| ctgtaggtat | ctcagttcgg | tgtaggtcgt | tcgctccaag | ctgggctgtg | tgcacgaacc | 720 |
| ccccgttcag | cccgaccgct | gcgccttatc | cggtaactat | cgtcttgagt | ccaacccggt | 780 |
| aagacacgac | ttatcgccac | tggcagcagc | cactggtaac | aggattagca | gagcgaggta | 840 |
| tgtaggcggt | gctacagagt | tcttgaagtg | gtggcctaac | tacggctaca | ctagaagaac | 900 |
| agtatttggt | atctgcgctc | tgctgaagcc | agttaccttc | ggaaaaagag | ttggtagctc | 960 |
| ttgatccggc | aaacaaacca | ccgctggtag | cggtggtttt | tttgtttgca | agcagcagat | 1020 |
| tacgcgcaga | aaaaaggat | ctcaagaaga | tcctttgatc | ttttctacgg | ggtctgacgc | 1080 |
| tcagtggaac | gaaaactcac | gttaagggat | tttggtcatg | agattatcaa | aaaggatctt | 1140 |
| cacctagatc | cttttaaatt | aaaaatgaag | ttttaaatca | atctaaagta | tatatgagta | 1200 |
| aacttggtct | gacagttacc | aatgcttaat | cagtgaggca | cctatctcag | cgatctgtct | 1260 |
| atttcgttca | tccatagttg | cctgactccc | cgtcgtgtag | ataactacga | tacgggaggg | 1320 |
| cttaccatct | ggccccagtg | ctgcaatgat | accgcgagag | ccacgctcac | cggctccaga | 1380 |
| tttatcagca | ataaaccagc | cagccggaag | ggccgagcgc | agaagtggtc | ctgcaacttt | 1440 |
| atccgcctcc | atccagtcta | ttaattgttg | ccgggaagct | agagtaagta | gttcgccagt | 1500 |
| taatagtttg | cgcaacgttg | ttgccattgc | tacaggcatc | gtggtgtcac | gctcgtcgtt | 1560 |
| tggtatggct | tcattcagct | ccggttccca | acgatcaagg | cgagttacat | gatcccccat | 1620 |
| gttgtgcaaa | aaagcggtta | gctccttcgg | tcctccgatc | gttgtcagaa | gtaagttggc | 1680 |
| cgcagtgtta | tcactcatgg | ttatggcagc | actgcataat | tctcttactg | tcatgccatc | 1740 |
| cgtaagatgc | ttttctgtga | ctggtgagta | ctcaaccaag | tcattctgag | aatagtgtat | 1800 |
| gcggcgaccg | agttgctctt | gcccggcgtc | aatacgggat | aataccgcgc | cacatagcag | 1860 |
| aactttaaaa | gtgctcatca | ttggaaaacg | ttcttcgggg | cgaaaactct | caaggatctt | 1920 |
| accgctgttg | agatccagtt | cgatgtaacc | cactcgtgca | cccaactgat | cttcagcatc | 1980 |
| ttttactttc | accagcgttt | ctgggtgagc | aaaaacagga | aggcaaaatg | ccgcaaaaaa | 2040 |
| gggaataagg | gcgacacgga | aatgttgaat | actcatactc | ttcctttttc | aatattattg | 2100 |

```
aagcatttat cagggttatt gtctcatgag cggatacata tttgaatgta tttagaaaaa    2160
taaacaaata ggggttccgc gcacatttcc ccgaaaagtg ccacctgacg tctaagaaac    2220
cattattatc atgacattaa cctataaaaa taggcgtatc acgaggccct ttcgtctcgc    2280
gcgtttcggt gatgacggtg aaaacctctg acacatgcag ctcccggaga cggtcacagc    2340
ttgtctgtaa gcggatgccg ggagcagaca agcccgtcag ggcgcgtcag cgggtgttgg    2400
cgggtgtcgg ggctggctta actatgcggc atcagagcag attgtactga gagtgcacca    2460
tatgcggtgt gaaataccgc acagatgcgt aaggagaaaa taccgcatca ggcgccattc    2520
gccattcagg ctgcgcaact gttgggaagg gcgatcggtg cgggcctctt cgctattacg    2580
ccagctggcg aaagggggat gtgctgcaag gcgattaagt tgggtaacgc cagggttttc    2640
ccagtcacga cgttgtaaaa cgacggccag tgaattcgag ctcggtacct cgcgaatgca    2700
tctaga                                                              2706
```

<210> SEQ ID NO 186
<211> LENGTH: 9
<212> TYPE: DNA
<213> ORGANISM: Artificial Sequence
<220> FEATURE:
<223> OTHER INFORMATION: synthetic polynucleotide

<400> SEQUENCE: 186 tctaacatc                                                                9

<210> SEQ ID NO 187
<211> LENGTH: 9
<212> TYPE: DNA
<213> ORGANISM: Artificial Sequence
<220> FEATURE:
<223> OTHER INFORMATION: synthetic polynucleotide

<400> SEQUENCE: 187 tcccacgac                                                                9

<210> SEQ ID NO 188
<211> LENGTH: 9
<212> TYPE: DNA
<213> ORGANISM: Artificial Sequence
<220> FEATURE:
<223> OTHER INFORMATION: synthetic polynucleotide

<400> SEQUENCE: 188 aataataac                                                                9

<210> SEQ ID NO 189
<211> LENGTH: 9
<212> TYPE: DNA
<213> ORGANISM: Artificial Sequence
<220> FEATURE:
<223> OTHER INFORMATION: synthetic polynucleotide

<400> SEQUENCE: 189 tctaatggg                                                                9

<210> SEQ ID NO 190
<211> LENGTH: 6426
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (31)..(39)
<223> OTHER INFORMATION: n is a, c, g, or t

<400> SEQUENCE: 190

| | | | | | |
|---|---|---|---|---|---|
| ctgacacccg | aacaggtggt | cgccattgct | nnnnnnnnng | gaggacggcc | agccttggag | 60 |
| tccatcgtag | cccaattgtc | caggcccgat | cccgcgttgg | ctgcgttaac | gaatgaccat | 120 |
| ctggtggcgt | tggcatgtct | tggtggacga | cccgcgctcg | atgcagtcaa | aaagggtctg | 180 |
| cctcatgctc | ccgcattgat | caaaagaacc | aaccggcgga | ttcccgagag | aacttcccat | 240 |
| cgagtcgcgg | gatcccaact | agtcaaaagt | gaactggagg | agaagaaatc | tgaacttcgt | 300 |
| cataaattga | aatatgtgcc | tcatgaatat | attgaattaa | ttgaaattgc | cagaaattcc | 360 |
| actcaggata | gaattcttga | aatgaaggta | atggaatttt | ttatgaaagt | ttatggatat | 420 |
| agaggtaaac | atttgggtgg | atcaaggaaa | ccggacggag | caatttatac | tgtcggatct | 480 |
| cctattgatt | acggtgtgat | cgtggatact | aaagcttata | gcggaggtta | taatctgcca | 540 |
| attggccaag | cagatgaaat | gcaacgatat | gtcgaagaaa | atcaaacacg | aaacaaacat | 600 |
| atcaaccta | atgaatggtg | gaaagtctat | ccatcttctg | taacggaatt | taagtttta | 660 |
| tttgtgagtg | gtcactttaa | aggaaactac | aaagctcagc | ttacacgatt | aaatcatatc | 720 |
| actaattgta | atggagctgt | tcttagtgta | gaagagcttt | taattggtgg | agaaatgatt | 780 |
| aaagccggca | cattaacctt | agaggaagtc | agacggaaat | ttaataacgg | cgagataaac | 840 |
| ttttaagggc | ccttcgaagg | taagcctatc | cctaaccctc | tcctcggtct | cgattctacg | 900 |
| cgtaccggtc | atcatcacca | tcaccattga | gtttaaaccc | gctgatcagc | ctcgactgtg | 960 |
| ccttctagtt | gccagccatc | tgttgtttgc | cctcccccg | tgccttcctt | gaccctggaa | 1020 |
| ggtgccactc | ccactgtcct | ttcctaataa | aatgaggaaa | ttgcatcgca | ttgtctgagt | 1080 |
| aggtgtcatt | ctattctggg | gggtggggtg | gggcaggaca | gcaggggga | ggattgggaa | 1140 |
| gacaatagca | ggcatgctgg | ggatgcggtg | ggctctatgg | cttctgaggc | ggaaagaacc | 1200 |
| agctggggct | ctagggggta | tccccacgcg | ccctgtagcg | gcgcattaag | cgcggcgggt | 1260 |
| gtggtggtta | cgcgcagcgt | gaccgctaca | cttgccagcg | ccctagcgcc | cgctccttc | 1320 |
| gctttcttcc | cttcctttct | cgccacgttc | gccggctttc | cccgtcaagc | tctaaatcgg | 1380 |
| ggcatccctt | tagggttccg | atttagtgct | ttacggcacc | tcgacccaa | aaaacttgat | 1440 |
| tagggtgatg | gttcacgtag | tgggccatcg | ccctgataga | cggttttcg | cccttgacg | 1500 |
| ttggagtcca | cgttctttaa | tagtggactc | ttgttccaaa | ctggaacaac | actcaaccct | 1560 |
| atctcggtct | attcttttga | tttataaggg | attttgggga | tttcggccta | ttggttaaaa | 1620 |
| aatgagctga | tttaacaaaa | atttaacgcg | aattaattct | gtggaatgtg | tgtcagttag | 1680 |
| ggtgtggaaa | gtccccaggc | tccccaggca | ggcagaagta | tgcaaagcat | gcatctcaat | 1740 |
| tagtcagcaa | ccaggtgtgg | aaagtcccca | ggctccccag | caggcagaag | tatgcaaagc | 1800 |
| atgcatctca | attagtcagc | aaccatagtc | ccgcccctaa | ctccgcccat | cccgccccta | 1860 |
| actccgccca | gttccgccca | ttctccgccc | catggctgac | taatttttt | tatttatgca | 1920 |
| gaggccgagg | ccgcctctgc | ctctgagcta | ttccagaagt | agtgaggagg | cttttttgga | 1980 |
| ggcctaggct | tttgcaaaaa | gctcccggga | gcttgtatat | ccattttcgg | atctgatcag | 2040 |
| cacgtgttga | caattaatca | tcggcatagt | atatcggcat | agtataatac | gacaaggtga | 2100 |
| ggaactaaac | catggccaag | cctttgtctc | aagaagaatc | caccctcatt | gaaagagcaa | 2160 |
| cggctacaat | caacagcatc | cccatctctg | aagactacag | cgtcgccagc | gcagctctct | 2220 |

```
ctagcgacgg ccgcatcttc actggtgtca atgtatatca ttttactggg ggaccttgtg   2280
cagaactcgt ggtgctgggc actgctgctg ctgcggcagc tggcaacctg acttgtatcg   2340
tcgcgatcgg aaatgagaac aggggcatct tgagcccctg cggacggtgt cgacaggtgc   2400
ttctcgatct gcatcctggg atcaaagcga tagtgaagga cagtgatgga cagccgacgg   2460
cagttgggat tcgtgaattg ctgccctctg gttatgtgtg ggagggctaa gcacttcgtg   2520
gccgaggagc aggactgaca cgtgctacga gatttcgatt ccaccgccgc cttctatgaa   2580
aggttgggct tcggaatcgt tttccgggac gccggctgga tgatcctcca gcgcggggat   2640
ctcatgctgg agttcttcgc ccaccccaac ttgtttattg cagcttataa tggttacaaa   2700
taaagcaata gcatcacaaa tttcacaaat aaagcatttt tttcactgca ttctagttgt   2760
ggtttgtcca aactcatcaa tgtatcttat catgtctgta taccgtcgac ctctagctag   2820
agcttggcgt aatcatggtc atagctgttt cctgtgtgaa attgttatcc gctcacaatt   2880
ccacacaaca tacgagccgg aagcataaag tgtaaagcct ggggtgccta atgagtgagc   2940
taactcacat taattgcgtt gcgctcactg cccgctttcc agtcgggaaa cctgtcgtgc   3000
cagctgcatt aatgaatcgg ccaacgcgcg gggagaggcg gtttgcgtat tgggcgctct   3060
tccgcttcct cgctcactga ctcgctgcgc tcggtcgttc ggctgcggcg agcggtatca   3120
gctcactcaa aggcggtaat acggttatcc acagaatcag gggataacgc aggaaagaac   3180
atgtgagcaa aaggccagca aaaggccagg aaccgtaaaa aggccgcgtt gctggcgttt   3240
ttccataggc tccgcccccc tgacgagcat cacaaaaatc gacgctcaag tcagaggtgg   3300
cgaaacccga caggactata agataccagg cgtttccccc tggaagctc cctcgtgcgc   3360 tctcctgttc cgaccctgcc gcttaccgga tacctgtccg cctttctccc ttcgggaagc   3420
gtggcgcttt ctcaatgctc acgctgtagg tatctcagtt cggtgtaggt cgttcgctcc   3480
aagctgggct gtgtgcacga accccccgtt cagcccgacc gctgcgcctt atccggtaac   3540
tatcgtcttg agtccaaccc ggtaagacac gacttatcgc cactggcagc agccactggt   3600
aacaggatta gcagagcgag gtatgtaggc ggtgctacag agttcttgaa gtggtggcct   3660
aactacggct acactagaag gacagtattt ggtatctgcg ctctgctgaa gccagttacc   3720
ttcggaaaaa gagttggtag ctcttgatcc ggcaaacaaa ccaccgctgg tagcggtggt   3780 tttttgttt gcaagcagca gattacgcgc agaaaaaaag gatctcaaga agatcctttg   3840
atcttttcta cggggtctga cgctcagtgg aacgaaaact cacgttaagg gattttggtc   3900
atgagattat caaaaaggat cttcacctag atccttttaa attaaaaatg aagttttaaa   3960
tcaatctaaa gtatatatga gtaaacttgg tctgacagtt accaatgctt aatcagtgag   4020
gcacctatct cagcgatctg tctatttcgt tcatccatag ttgcctgact ccccgtcgtg   4080
tagataacta cgatacggga gggcttacca tctggcccca gtgctgcaat gataccgcga   4140
gacccacgct caccggctcc agatttatca gcaataaacc agccagccgg aagggccgag   4200
cgcagaagtg gtcctgcaac tttatccgcc tccatccagt ctattaattg ttgccgggaa   4260
gctagagtaa gtagttcgcc agttaatagt ttgcgcaacg ttgttgccat tgctacaggc   4320
atcgtggtgt cacgctcgtc gtttggtatg gcttcattca gctccggttc ccaacgatca   4380
aggcgagtta catgatcccc catgttgtgc aaaaaagcgg ttagctcctt cggtcctccg   4440
atcgttgtca gaagtaagtt ggccgcagtg ttatcactca tggttatggc agcactgcat   4500
aattctctta ctgtcatgcc atccgtaaga tgcttttctg tgactggtga gtactcaacc   4560
aagtcattct gagaatagtg tatgcggcga ccgagttgct cttgcccggc gtcaatacgg   4620
```

```
gataataccg cgccacatag cagaacttta aaagtgctca tcattggaaa acgttcttcg    4680
gggcgaaaac tctcaaggat cttaccgctg ttgagatcca gttcgatgta acccactcgt    4740
gcacccaact gatcttcagc atcttttact ttcaccagcg tttctgggtg agcaaaaaca    4800
ggaaggcaaa atgccgcaaa aagggaata agggcgacac ggaaatgttg aatactcata    4860
ctcttccttt ttcaatatta ttgaagcatt tatcagggtt attgtctcat gagcggatac    4920
atatttgaat gtatttagaa aaataaacaa ataggggttc cgcgcacatt tccccgaaaa    4980
gtgccacctg acgtcgacgg atcgggagat ctcccgatcc cctatggtcg actctcagta    5040
caatctgctc tgatgccgca tagttaagcc agtatctgct ccctgcttgt gtgttggagg    5100
tcgctgagta gtgcgcgagc aaaatttaag ctacaacaag gcaaggcttg accgacaatt    5160
gcatgaagaa tctgcttagg gttaggcgtt ttgcgctgct tcgcgatgta cgggccagat    5220
atacgcgttg acattgatta ttgactagtt attaatagta atcaattacg ggtcattag    5280 ttcatagccc atatatggag ttccgcgtta cataacttac ggtaaatggc ccgcctggct    5340
gaccgcccaa cgacccccgc ccattgacgt caataatgac gtatgttccc atagtaacgc    5400
caatagggac tttccattga cgtcaatggg tggagtattt acggtaaact gcccacttgg    5460
cagtacatca agtgtatcat atgccaagta cgccccctat tgacgtcaat gacggtaaat    5520
ggcccgcctg gcattatgcc cagtacatga ccttatggga ctttcctact ggcagtaca    5580 tctacgtatt agtcatcgct attaccatgg tgatgcggtt ttggcagtac atcaatgggc    5640
gtggatagcg gtttgactca cggggatttc caagtctcca ccccattgac gtcaatggga    5700
gtttgttttg gcaccaaaat caacgggact ttccaaaatg tcgtaacaac tccgccccat    5760
tgacgcaaat gggcggtagg cgtgtacggt gggaggtcta taagcaga gctctctggc    5820 taactagaga acccactgct tactggctta tcgaaattaa tacgactcac tatagggaga    5880
cccaagctgg ctagcaccat ggactacaaa gaccatgacg gtgattataa agatcatgac    5940
atcgattaca aggatgacga tgacaagatg gcccccaaga agaagaggaa ggtgggcatt    6000
caccgcgggg tacctatggt ggacttgagg acactcggtt attcgcaaca gcaacaggag    6060
aaaatcaagc ctaaggtcag gagcaccgtc gcgcaacacc acgagcgct tgtgggcat    6120 ggcttcactc atgcgcatat tgtcgcgctt tcacagcacc ctgcggcgct tgggacggtg    6180
gctgtcaaat accaagatat gattgcggcc ctgcccgaag ccacgcacga ggcaattgta    6240
ggggtcggta acagtggtc gggagcgcga gcacttgagg cgctgctgac tgtggcgggt    6300
gagcttaggg ggcctccgct ccagctcgac accgggcagc tgctgaagat cgcgaagaga    6360
gggggagtaa cagcggtaga ggcagtgcac gcctggcgca atgcgctcac cggggccccc    6420
ttgaac                                                               6426
```

<210> SEQ ID NO 191
<211> LENGTH: 128
<212> TYPE: DNA
<213> ORGANISM: Artificial Sequence
<220> FEATURE:
<223> OTHER INFORMATION: synthetic polynucleotide

<400> SEQUENCE: 191

```
tctagaggtc tcattgaccc cagaccaggt agtcgcaatc gcgtcacatg acggggaaa     60 gcaagccctg gaaaccgtgc aaaggttgtt gccggtcctt tgtcaagacc acggcagaga    120
ccggatcc                                                             128
```

<210> SEQ ID NO 192
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 192
tctagaggtc tcacggcctg actcccgatc aagttgtagc gattgcgtcg catgacggag    60
ggaaacaagc attggagact gtccaacggc tccttcccgt gttgtgtcaa gcccacggag   120
agaccggatc c                                                        131

<210> SEQ ID NO 193
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 193
tctagaggtc tcaacggttt gacgcctgca caagtggtcg ccatcgccag ccatgatggc    60
ggtaagcagg cgctggaaac agtacagcgc ctgctgcctg tactgtgcca ggatcatgag   120
agaccggatc c                                                        131

<210> SEQ ID NO 194
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 194
tctagaggtc tcacatggac tgaccccaga ccaggtagtc gcaatcgcgt cacatgacgg    60
gggaaagcaa gccctggaaa ccgtgcaaag gttgttgccg gtcctttgtc aagaccacag   120
agaccggatc c                                                        131

<210> SEQ ID NO 195
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 195
tctagaggtc tcaccacggc ctgaccccag accaggtagt cgcaatcgcg tcacatgacg    60
ggggaaagca agccctggaa accgtgcaaa ggttgttgcc ggtcctttgt caagaccaag   120
agaccggatc c                                                        131

<210> SEQ ID NO 196
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 196
tctagaggtc tcaaccacgg cctgactccc gatcaagttg tagcgattgc gtcgcatgac    60
ggagggaaac aagcattgga gactgtccaa cggctccttc ccgtgttgtg tcaagcccag   120
agaccggatc c                                                        131

<210> SEQ ID NO 197
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 197
tctagaggtc tcagcccacg gtttgacgcc tgcacaagtg gtcgccatcg ccagccatga      60
tggcggtaag caggcgctgg aaacagtaca gcgcctgctg cctgtactgt gccaggatag     120
agaccggatc c                                                          131

<210> SEQ ID NO 198
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 198
tctagaggtc tcaggatcat ggactgaccc cagaccaggt agtcgcaatc gcgtcacatg      60 acggggaaa gcaagccctg gaaaccgtgc aaaggttgtt gccggtcctt tgtcaagaag      120
agaccggatc c                                                          131

<210> SEQ ID NO 199
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 199
tctagaggtc tcaaagacca cggcctgacc ccagaccagg tagtcgcaat cgcgtcacat      60
gacgggggaa agcaagccct ggaaaccgtg caaaggttgt tgccggtcct ttgtcaagag     120
agaccggatc c                                                          131

<210> SEQ ID NO 200
<211> LENGTH: 140
<212> TYPE: DNA
<213> ORGANISM: Artificial Sequence
<220> FEATURE:
<223> OTHER INFORMATION: synthetic polynucleotide

<400> SEQUENCE: 200
tctagaggtc tcacaagacc acggcctgac tcccgatcaa gttgtagcga ttgcgtcgca      60
tgacggaggg aaacaagcat tggagactgt ccaacggctc cttcccgtgt tgtgtcaagc     120
ccatggaaga gaccggatcc                                                 140

<210> SEQ ID NO 201
<211> LENGTH: 128
<212> TYPE: DNA
<213> ORGANISM: Artificial Sequence
<220> FEATURE:
<223> OTHER INFORMATION: synthetic polynucleotide

<400> SEQUENCE: 201
tctagaggtc tcattgaccc cagaccaggt agtcgcaatc gcgtcaaacg gagggggaaa      60
gcaagccctg gaaaccgtgc aaaggttgtt gccggtcctt tgtcaagacc acggcagaga     120

```
ccggatcc                                                                  128

<210> SEQ ID NO 202
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 202
tctagaggtc tcacggcctg actcccgatc aagttgtagc gattgcgtcg aacggtggag         60
ggaaacaagc attggagact gtccaacggc tccttcccgt gttgtgtcaa gcccacggag        120
agaccggatc c                                                             131

<210> SEQ ID NO 203
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 203
tctagaggtc tcaacggttt gacgcctgca caagtggtcg ccatcgcctc gaatggcggc         60
ggtaagcagg cgctggaaac agtacagcgc ctgctgcctg tactgtgcca ggatcatgag        120
agaccggatc c                                                             131

<210> SEQ ID NO 204
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 204
tctagaggtc tcacatggac tgaccccaga ccaggtagtc gcaatcgcgt caaacggagg         60
gggaaagcaa gccctggaaa ccgtgcaaag gttgttgccg gtcctttgtc aagaccacag        120
agaccggatc c                                                             131

<210> SEQ ID NO 205
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 205
tctagaggtc tcaccacggc ctgacccag accaggtagt cgcaatcgcg tcaaacggag          60
ggggaaagca agccctggaa accgtgcaaa ggttgttgcc ggtcctttgt caagaccaag        120
agaccggatc c                                                             131

<210> SEQ ID NO 206
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 206
tctagaggtc tcaaccacgg cctgactccc gatcaagttg tagcgattgc gtcgaacggt         60
ggagggaaac aagcattgga gactgtccaa cggctccttc ccgtgttgtg tcaagcccag        120
```

```
agaccggatc c                                                          131

<210> SEQ ID NO 207
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 207
tctagaggtc tcagcccacg gtttgacgcc tgcacaagtg gtcgccatcg ccagcaatgg        60
cggcggtaag caggcgctgg aaacagtaca gcgcctgctg cctgtactgt gccaggatag       120
agaccggatc c                                                          131

<210> SEQ ID NO 208
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 208
tctagaggtc tcaggatcat ggactgaccc cagaccaggt agtcgcaatc gcgtcaaacg        60 gaggggaaa gcaagccctg gaaaccgtgc aaaggttgtt gccggtcctt tgtcaagaag       120
agaccggatc c                                                          131

<210> SEQ ID NO 209
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 209
tctagaggtc tcaaagacca cggcctgacc ccagaccagg tagtcgcaat cgcgtcaaac        60 ggaggggaa agcaagccct ggaaaccgtg caaaggttgt tgccggtcct ttgtcaagag       120
agaccggatc c                                                          131

<210> SEQ ID NO 210
<211> LENGTH: 140
<212> TYPE: DNA
<213> ORGANISM: Artificial Sequence
<220> FEATURE:
<223> OTHER INFORMATION: synthetic polynucleotide

<400> SEQUENCE: 210
tctagaggtc tcacaagacc acggcctgac tcccgatcaa gttgtagcga ttgcgtccaa        60
cggtggaggg aaacaagcat ggagactgt ccaacggctc cttcccgtgt tgtgtcaagc       120
ccatggaaga gaccggatcc                                                 140

<210> SEQ ID NO 211
<211> LENGTH: 128
<212> TYPE: DNA
<213> ORGANISM: Artificial Sequence
<220> FEATURE:
<223> OTHER INFORMATION: synthetic polynucleotide

<400> SEQUENCE: 211
tctagaggtc tcattgaccc cagaccaggt agtcgcaatc gcgtcaaaca ttgggggaaa        60
```

```
gcaagccctg gaaaccgtgc aaaggttgtt gccggtcctt tgtcaagacc acggcagaga    120
ccggatcc                                                             128

<210> SEQ ID NO 212
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 212
tctagaggtc tcacggcctg actcccgatc aagttgtagc gattgcgtcg aacattggag    60
ggaaacaagc attggagact gtccaacggc tccttcccgt gttgtgtcaa gcccacggag    120
agaccggatc c                                                         131

<210> SEQ ID NO 213
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 213
tctagaggtc tcaacggttt gacgcctgca caagtggtcg ccatcgccag caatattggc    60
ggtaagcagg cgctggaaac agtacagcgc ctgctgcctg tactgtgcca ggatcatgag    120
agaccggatc c                                                         131

<210> SEQ ID NO 214
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 214
tctagaggtc tcacatggac tgaccccaga ccaggtagtc gcaatcgcgt caaacattgg    60
gggaaagcaa gccctggaaa ccgtgcaaag gttgttgccg gtcctttgtc aagaccacag    120
agaccggatc c                                                         131

<210> SEQ ID NO 215
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 215
tctagaggtc tcaccacggc ctgaccccag accaggtagt cgcaatcgcg tcgaacattg    60
ggggaaagca agccctggaa accgtgcaaa ggttgttgcc ggtcctttgt caagaccaag    120
agaccggatc c                                                         131

<210> SEQ ID NO 216
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 216
tctagaggtc tcaaccatgg cctgactccc gatcaagttg tagcgattgc gtcgaacatt    60
```

```
<210> SEQ ID NO 217
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 217
tctagaggtc tcagcccacg gtttgacgcc tgcacaagtg gtcgccatcg cctccaatat    60
tggcggtaag caggcgctgg aaacagtaca gcgcctgctg cctgtactgt gccaggatag   120
agaccggatc c                                                        131

<210> SEQ ID NO 218
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 218
tctagaggtc tcaggatcat ggactgaccc cagaccaggt agtcgcaatc gcgtcgaaca    60
ttgggggaaa gcaagccctg gaaaccgtgc aaaggttgtt gccggtcctt tgtcaagaag   120
agaccggatc c                                                        131

<210> SEQ ID NO 219
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 219
tctagaggtc tcaaagacca cggcctgacc ccagaccagg tagtcgcaat cgcgtcgaac    60
attgggggaa agcaagccct ggaaaccgtg caaaggttgt tgccggtcct ttgtcaagag   120
agaccggatc c                                                        131

<210> SEQ ID NO 220
<211> LENGTH: 140
<212> TYPE: DNA
<213> ORGANISM: Artificial Sequence
<220> FEATURE:
<223> OTHER INFORMATION: synthetic polynucleotide

<400> SEQUENCE: 220
tctagaggtc tcacaagacc acggcctgac tcccgatcaa gttgtagcga ttgcgtcgaa    60
cattggaggg aaacaagcat tggagactgt ccaacggctc cttcccgtgt tgtgtcaagc   120
ccatggaaga gaccggatcc                                               140

<210> SEQ ID NO 221
<211> LENGTH: 128
<212> TYPE: DNA
<213> ORGANISM: Artificial Sequence
<220> FEATURE:
<223> OTHER INFORMATION: synthetic polynucleotide

<400> SEQUENCE: 221
```

(preceding continuation at top of page:)

```
ggagggaaac aagcattgga gactgtccaa cggctccttc ccgtgttgtg tcaagcccag   120
agaccggatc c                                                        131
```

```
tctagaggtc tcattgaccc cagaccaggt agtcgcaatc gcgaacaata atgggggaaa      60
gcaagccctg gaaaccgtgc aaaggttgtt gccggtcctt tgtcaagacc acggcagaga    120
ccggatcc                                                             128
```

```
<210> SEQ ID NO 222
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 222
tctagaggtc tcacggcctg actcccgatc aagttgtagc gattgcgaat aacaatggag     60
ggaaacaagc attggagact gtccaacggc tccttcccgt gttgtgtcaa gcccacggag    120
agaccggatc c                                                         131
```

```
<210> SEQ ID NO 223
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 223
tctagaggtc tcaacggttt gacgcctgca caagtggtcg ccatcgccaa caacaacggc     60
ggtaagcagg cgctggaaac agtacagcgc ctgctgcctg tactgtgcca ggatcatgag    120
agaccggatc c                                                         131
```

```
<210> SEQ ID NO 224
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 224
tctagaggtc tcacatggac tgaccccaga ccaggtagtc gcaatcgcga acaataatgg     60
gggaaagcaa gccctggaaa ccgtgcaaag gttgttgccg gtcctttgtc aagaccacag    120
agaccggatc c                                                         131
```

```
<210> SEQ ID NO 225
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 225
tctagaggtc tcaccacggc ctgaccccag accaggtagt cgcaatcgcg aacaataatg     60
ggggaaagca agccctggaa accgtgcaaa ggttgttgcc ggtcctttgt caagaccaag    120
agaccggatc c                                                         131
```

```
<210> SEQ ID NO 226
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 226
```

```
tctagaggtc tcaaccatgg cctgactccc gatcaagttg tagcgattgc gaataacaat    60
ggagggaaac aagcattgga gactgtccaa cggctccttc ccgtgttgtg tcaagcccag   120
agaccggatc c                                                        131
```

<210> SEQ ID NO 227
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 227

```
tctagaggtc tcagcccacg gtttgacgcc tgcacaagtg gtcgccatcg ccaacaacaa    60
cggcggtaag caggcgctgg aaacagtaca gcgcctgctg cctgtactgt gccaggatag   120
agaccggatc c                                                        131
```

<210> SEQ ID NO 228
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 228

```
tctagaggtc tcaggatcat ggactgaccc cagaccaggt agtcgcaatc gcgaacaata    60 atggggaaa gcaagccctg gaaaccgtgc aaaggttgtt gccggtcctt tgtcaagaag   120
agaccggatc c                                                        131
```

<210> SEQ ID NO 229
<211> LENGTH: 131
<212> TYPE: DNA
<213> ORGANISM: Artificial Sequence
<220> FEATURE:
<223> OTHER INFORMATION: synthetic polynucleotide

<400> SEQUENCE: 229

```
tctagaggtc tcaaagacca cggcctgacc ccagaccagg tagtcgcaat cgcgaacaat    60
aatgggggaa agcaagccct ggaaaccgtg caaaggttgt tgccggtcct tgtcaagag   120 agaccggatc c                                                        131
```

<210> SEQ ID NO 230
<211> LENGTH: 140
<212> TYPE: DNA
<213> ORGANISM: Artificial Sequence
<220> FEATURE:
<223> OTHER INFORMATION: synthetic polynucleotide

<400> SEQUENCE: 230

```
tctagaggtc tcacaagacc acggcctgac tcccgatcaa gttgtagcga ttgcgaataa    60
caatggaggg aaacaagcat tggagactgt ccaacggctc cttcccgtgt tgtgtcaagc   120
ccatggaaga gaccggatcc                                               140
```

<210> SEQ ID NO 231
<211> LENGTH: 81
<212> TYPE: DNA
<213> ORGANISM: Artificial Sequence
<220> FEATURE:
<223> OTHER INFORMATION: synthetic polynucleotide

```
<400> SEQUENCE: 231
cctgcaggtc gaccgtctca gaacttgaag agaccgtacg tgatcgtggt ctcatggatt    60
gaagagacgg gtaccgagct c                                              81

<210> SEQ ID NO 232
<211> LENGTH: 77
<212> TYPE: DNA
<213> ORGANISM: Artificial Sequence
<220> FEATURE:
<223> OTHER INFORMATION: synthetic polynucleotide

<400> SEQUENCE: 232
cctgcaggtc gaccgtctca ttgaagagac cgtactggat cgtggtctca cggcctgaag    60
agacgggtac cgagctc                                                   77

<210> SEQ ID NO 233
<211> LENGTH: 78
<212> TYPE: DNA
<213> ORGANISM: Artificial Sequence
<220> FEATURE:
<223> OTHER INFORMATION: synthetic polynucleotide

<400> SEQUENCE: 233
cctgcaggtc gaccgtctca ttgaagagac cgtactggat cgtggtctca acggtctgaa    60
gagacgggta ccgagctc                                                  78

<210> SEQ ID NO 234
<211> LENGTH: 79
<212> TYPE: DNA
<213> ORGANISM: Artificial Sequence
<220> FEATURE:
<223> OTHER INFORMATION: synthetic polynucleotide

<400> SEQUENCE: 234
cctgcaggtc gaccgtctca ttgaagagac cgtactggat cgtggtctca catggactga    60
agagacgggt accgagctc                                                 79

<210> SEQ ID NO 235
<211> LENGTH: 80
<212> TYPE: DNA
<213> ORGANISM: Artificial Sequence
<220> FEATURE:
<223> OTHER INFORMATION: synthetic polynucleotide

<400> SEQUENCE: 235
cctgcaggtc gaccgtctca ttgaagagac cgtactggat cgtggtctca ccacggcctg    60
aagagacggg taccgagctc                                                80

<210> SEQ ID NO 236
<211> LENGTH: 81
<212> TYPE: DNA
<213> ORGANISM: Artificial Sequence
<220> FEATURE:
<223> OTHER INFORMATION: synthetic polynucleotide

<400> SEQUENCE: 236
cctgcaggtc gaccgtctca ttgaagagac cgtactggat cgtggtctca accacggcct    60
gaagagacgg gtaccgagct c                                              81

<210> SEQ ID NO 237
<211> LENGTH: 82
```

```
<212> TYPE: DNA
<213> ORGANISM: Artificial Sequence
<220> FEATURE:
<223> OTHER INFORMATION: synthetic polynucleotide

<400> SEQUENCE: 237
cctgcaggtc gaccgtctca ttgaagagac cgtactggat cgtggtctca gcccacggtc      60
tgaagagacg ggtaccgagc tc                                               82

<210> SEQ ID NO 238
<211> LENGTH: 83
<212> TYPE: DNA
<213> ORGANISM: Artificial Sequence
<220> FEATURE:
<223> OTHER INFORMATION: synthetic polynucleotide

<400> SEQUENCE: 238
cctgcaggtc gaccgtctca ttgaagagac cgtactggat cgtggtctca ggatcatgga      60
ctgaagagac gggtaccgag ctc                                              83

<210> SEQ ID NO 239
<211> LENGTH: 84
<212> TYPE: DNA
<213> ORGANISM: Artificial Sequence
<220> FEATURE:
<223> OTHER INFORMATION: synthetic polynucleotide

<400> SEQUENCE: 239
cctgcaggtc gaccgtctca ttgaagagac cgtactggat cgtggtctca aagaccacgg      60
cctgaagaga cgggtaccga gctc                                             84

<210> SEQ ID NO 240
<211> LENGTH: 85
<212> TYPE: DNA
<213> ORGANISM: Artificial Sequence
<220> FEATURE:
<223> OTHER INFORMATION: synthetic polynucleotide

<400> SEQUENCE: 240
cctgcaggtc gaccgtctca ttgaagagac cgtactggat cgtggtctca caagaccacg      60
gcctgaagag acgggtaccg agctc                                            85

<210> SEQ ID NO 241
<211> LENGTH: 77
<212> TYPE: DNA
<213> ORGANISM: Artificial Sequence
<220> FEATURE:
<223> OTHER INFORMATION: synthetic polynucleotide

<400> SEQUENCE: 241
cctgcaggtc gaccgtctca ttgaagagac cgtactggat cgtggtctca tggactgaag      60
agacgggtac cgagctc                                                     77

<210> SEQ ID NO 242
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 242

Gly Gly Thr Gln Ala Leu Glu Ala Val Leu Thr Ala Leu Pro Arg Val
1               5                   10                  15
```

Cys Pro Gly Met Val
        20

<210> SEQ ID NO 243
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 243

Gly Gly Thr Gln Ala Leu Glu Ala Val Leu Thr Ala Leu Pro Arg Val
1               5                   10                  15

Cys Pro Gly Met Val
        20

<210> SEQ ID NO 244
<211> LENGTH: 102
<212> TYPE: DNA
<213> ORGANISM: Artificial Sequence
<220> FEATURE:
<223> OTHER INFORMATION: synthetic polynucleotide

<400> SEQUENCE: 244
cagaccaccg agaggatcgt ggccatcggc accagccacg gcggcaccca ggccctggag     60
gccgtgctga ccgccctgcc cagggtgtgc cccggcatgg tg                       102

<210> SEQ ID NO 245
<211> LENGTH: 3123
<212> TYPE: DNA
<213> ORGANISM: Artificial Sequence
<220> FEATURE:
<223> OTHER INFORMATION: synthetic polynucleotide

<400> SEQUENCE: 245
gacggatcgg gagatctccc gatccctat ggtcgactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aatgtcgta acaactccgc cccattgacg caaatgggcg     780
gtaggcgtgt acggtgggag gtctatataa gcagagctct ctggctaact agagaaccca    840
ctgcttactg gcttatcgaa attaatacga ctcactatag ggagacccaa gctggctagc    900
accatggact acaaagacca tgacggtgat tataaagatc atgacatcga ttacaaggat    960
gacgatgaca gatggccccc caagaagaag aggaaggtgg gcattcaccg cggggtacct   1020
atggtggact tgaggacact cggttattcg caacagcaac aggagaaaat caagcctaag   1080

```
gtcaggagca ccgtcgcgca acaccacgag gcgcttgtgg ggcatggctt cactcatgcg      1140
catattgtcg cgctttcaca gcaccctgcg gcgcttggga cggtggctgt caaataccaa      1200
gatatgattg cggccctgcc cgaagccacg cacgaggcaa ttgtaggggt cggtaaacag      1260
tggtcgggag cgcgagcact tgaggcgctg ctgactgtgg cgggtgagct tagggggcct      1320
ccgctccagc tcgacaccgg gcagctgctg aagatcgcga agagaggggg agtaacagcg      1380
gtagaggcag tgcacgcctg cgcaatgcgc tcaccgggg ccccttgaa ccagaccacc       1440 gagaggatcg tggccatcgg caccagccac ggcggcaccc aggccctgga ggccgtgctg      1500
accgccctgc cagggtgtg ccccggcatg gtgcagacca ccgagaggat cgtggccatc       1560
ggcaccagcc acggcggcac ccaggccctg gaggccgtgc tgaccgccct gcccagggtg      1620
tgccccggca tggtgcagac caccgagagg atcgtggcca tcggcaccag ccacggcggc      1680
acccaggccc tggaggccgt gctgaccgcc ctgcccaggg tgtgccccgg catggtgcag      1740
accaccgaga ggatcgtggc catcggcacc agccacggcg gcacccaggc cctggaggcc      1800
gtgctgaccg ccctgcccag ggtgtgcccc ggcatggtgc agaccaccga ggatcgtg       1860 gccatcggca ccagccacgg cggcacccag gccctggagg ccgtgctgac cgccctgccc      1920
agggtgtgcc ccggcatggt gcagaccacc gagaggatcg tggccatcgg caccagccac      1980
ggcggcaccc aggccctgga ggccgtgctg accgccctgc cagggtgtg ccccggcatg       2040 gtgcagacca ccgagaggat cgtggccatc ggcaccagcc acggcggcac ccaggccctg      2100
gaggccgtgc tgaccgccct gcccagggtg tgccccggca tggtgcagac caccgagagg      2160
atcgtggcca tcggcaccag ccacggcggc acccaggccc tggaggccgt gctgaccgcc      2220
ctgcccaggg tgtgccccgg catggtgcag accaccgaga ggatcgtggc catcggcacc      2280
agccacggcg gcacccaggc cctggaggcc gtgctgaccg ccctgcccag gtgtgcccc       2340 ggcatggtgc agaccaccga ggatcgtg gccatcggca ccagccacgg cggcacccag        2400
gccctggagg ccgtgctgac cgccctgccc agggtgtgcc ccggcatggt gcagaccacc      2460
gagaggatcg tggccatcgg caccagccac ggcggcaccc aggccctgga ggccgtgctg      2520
accgccctgc cagggtgtg ccccggcatg gtgcagacca ccgagaggat cgtggccatc       2580
ggcaccagcc acggcggcac ccaggccctg gaggccgtgc tgaccgccct gcccagggtg      2640
tgccccggca tggtgcagac caccgagagg atcgtggcca tcggcaccag ccacggcggc      2700
acccaggccc tggaggccgt gctgaccgcc ctgcccaggg tgtgccccgg catggtgcag      2760
accaccgaga ggatcgtggc catcggcacc agccacggcg gcacccaggc cctggaggcc      2820
gtgctgaccg ccctgcccag ggtgtgcccc ggcatggtgc tgacacccga acaggtggtc      2880
gccattgcta ataatacgg aggacggcca gccttggagt ccatcgtagc caattgtcc        2940 aggcccgatc ccgcgttggc tgcgttaacg aatgaccatc tggtggcgtt ggcatgtctt      3000
ggtggacgac ccgcgctcga tgcagtcaaa aagggtctgc ctcatgctcc cgcattgatc      3060
aaaagaacca accggcggat tcccgagaga acttcccatc gagtcgcggg atcccaacta      3120
gtc                                                                   3123
```

<210> SEQ ID NO 246
<211> LENGTH: 18
<212> TYPE: PRT
<213> ORGANISM: Artificial Sequence
<220> FEATURE:
<223> OTHER INFORMATION: synthetic polypeptide

```
<400> SEQUENCE: 246

Ser Ser Gly Gly Gly Gly Ser Gly Gly Gly Gly Gly Ser Ser Arg
1               5                   10                  15

Ser Ser

<210> SEQ ID NO 247
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 247

Gly Gly Ser Ser Arg Ser Ser
1               5

<210> SEQ ID NO 248
<211> LENGTH: 34
<212> TYPE: PRT
<213> ORGANISM: Artificial Sequence
<220> FEATURE:
<223> OTHER INFORMATION: synthetic polypeptide

<400> SEQUENCE: 248

Leu Thr Pro Asp Gln Val Val Ala Ile Ala Ser Asn Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 249
<211> LENGTH: 34
<212> TYPE: PRT
<213> ORGANISM: Artificial Sequence
<220> FEATURE:
<223> OTHER INFORMATION: synthetic polypeptide

<400> SEQUENCE: 249

Leu Thr Pro Ala Gln Val Val Ala Ile Ala Ser Asn Ile Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 250
<211> LENGTH: 34
<212> TYPE: PRT
<213> ORGANISM: Artificial Sequence
<220> FEATURE:
<223> OTHER INFORMATION: synthetic polypeptide

<400> SEQUENCE: 250

Leu Thr Pro Asp Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 251
<211> LENGTH: 34
<212> TYPE: PRT
<213> ORGANISM: Artificial Sequence
```

<220> FEATURE:
<223> OTHER INFORMATION: synthetic polypeptide

<400> SEQUENCE: 251

Leu Thr Pro Glu Gln Val Val Ala Ile Ala Asn Asn Asn Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 252
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 252

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 253
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 253

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 254
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 254

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 255
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 255

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 256

```
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 256

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 257
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 257

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 258
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 258

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 259
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 259

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 260
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 260

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25
```

```
<210> SEQ ID NO 261
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 261

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 262
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 262

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 263
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 263

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 264
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 264

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 265
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 265

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25
```

<210> SEQ ID NO 266
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 266

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 267
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 267

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 268
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 268

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 269
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 269

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 270
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 270

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 271
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 271

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 272
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 272

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 273
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 273

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 274
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 274

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 275
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 275

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys

```
                    20                  25

<210> SEQ ID NO 276
<211> LENGTH: 30
<212> TYPE: PRT
<213> ORGANISM: Artificial Sequence
<220> FEATURE:
<223> OTHER INFORMATION: synthetic polypeptide

<400> SEQUENCE: 276

Met Thr Ser Glu Gln Ile Val Ala Ile Gly Thr Ser Thr Gly Gly Thr
1               5                   10                  15

Gln Ala Leu Glu Ala Val Leu Thr Ala Leu Pro Arg Val Cys
            20                  25                  30

<210> SEQ ID NO 277
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 277

Thr Thr Glu Arg Ile Val Ala Ile Gly Thr Ser Thr Gly Gly Thr Gln
1               5                   10                  15

Ala Leu Glu Thr Val Leu Thr Ala Leu Pro Arg Val Cys
            20                  25

<210> SEQ ID NO 278
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 278

Thr Thr Glu Arg Ile Val Ala Ile Gly Thr Ser Thr Gly Gly Thr Gln
1               5                   10                  15

Ala Leu Glu Thr Val Leu Thr Ala Leu Pro Arg Val Cys
            20                  25

<210> SEQ ID NO 279
<211> LENGTH: 23
<212> TYPE: PRT
<213> ORGANISM: Artificial Sequence
<220> FEATURE:
<223> OTHER INFORMATION: synthetic polypeptide

<400> SEQUENCE: 279

Arg Ile Val Ala Ile Gly Thr Ser Thr Gly Gly Thr Gln Ala Leu Glu
1               5                   10                  15

Val Val Leu Thr Ala Leu Pro
            20

<210> SEQ ID NO 280
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 280

Thr Thr Asp Arg Val Val Ala Leu Gly Thr Ser Thr Gly Gly Thr Gln
1               5                   10                  15
```

Ala Leu Glu Val Val Leu Arg Gln Leu Pro Val Asp Cys
            20                  25

<210> SEQ ID NO 281
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 281

Thr Thr Asp Arg Val Val Ala Leu Gly Thr Ser Thr Gly Gly Thr Gln
1               5                   10                  15

Ala Leu Glu Val Val Leu Arg Gln Leu Pro Val Asp Cys
            20                  25

<210> SEQ ID NO 282
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 282

Thr Thr Asp Arg Val Val Ala Leu Gly Cys Ser Thr Gly Gly Thr Gln
1               5                   10                  15

Ala Leu Glu Phe Ile Leu Arg Gln Leu Pro Arg Asp Cys
            20                  25

<210> SEQ ID NO 283
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 283

Thr Thr Glu Arg Val Val Ala Leu Gly Thr Ser Thr Gly Gly Thr Gln
1               5                   10                  15

Ala Leu Glu Val Val Leu Arg Thr Leu Pro Arg Val Cys
            20                  25

<210> SEQ ID NO 284
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 284

Thr Thr Glu Arg Ile Val Ala Ile Gly Thr Ser Thr Gly Gly Thr Gln
1               5                   10                  15

Ala Leu Glu Ala Val Leu Thr Ala Leu Pro Arg Val Cys
            20                  25

<210> SEQ ID NO 285
<211> LENGTH: 85
<212> TYPE: DNA
<213> ORGANISM: Artificial Sequence
<220> FEATURE:
<223> OTHER INFORMATION: synthetic polynucleotide

<400> SEQUENCE: 285
gctctgatag gagccacata gggtggcaat caggattggt gacagaaaag ccccatcctt    60
aggcctcctc cttcctagtc tcctg                                              85

<210> SEQ ID NO 286
<211> LENGTH: 112
<212> TYPE: DNA
<213> ORGANISM: Artificial Sequence
<220> FEATURE:
<223> OTHER INFORMATION: synthetic polynucleotide

<400> SEQUENCE: 286
gctctggtac tgggtacttt tatctgtccc ctccacccca cagtggggcc actaggacag        60
gattggtgac agaaaagccc catccttagg cctcctcctt cctagtctcc tg              112

<210> SEQ ID NO 287
<211> LENGTH: 111
<212> TYPE: DNA
<213> ORGANISM: Artificial Sequence
<220> FEATURE:
<223> OTHER INFORMATION: synthetic polynucleotide

<400> SEQUENCE: 287
gctctggtac tgggtacttt tatctgtccc ctccacccca cagtggggcc actagggagg        60
attggtgaca gaaaagcccc atccttaggc ctcctccttc ctagtctcct g               111

<210> SEQ ID NO 288
<211> LENGTH: 111
<212> TYPE: DNA
<213> ORGANISM: Artificial Sequence
<220> FEATURE:
<223> OTHER INFORMATION: synthetic polynucleotide

<400> SEQUENCE: 288
gctctggtac tgggtacttt tatctgtccc ctccacccca cagtggggcc actaggcagg        60
attggtgaca gaaaagcccc atccttaggc ctcctccttc ctagtctcct g               111

<210> SEQ ID NO 289
<211> LENGTH: 113
<212> TYPE: DNA
<213> ORGANISM: Artificial Sequence
<220> FEATURE:
<223> OTHER INFORMATION: synthetic polynucleotide

<400> SEQUENCE: 289
gctctggtac tgggtacttt tatctgtccc ctccacccca cagtggggcc actagggaca        60
ggattggtga cagaaaagcc ccatccttag gcctcctcct tcctagtctc ctg             113

<210> SEQ ID NO 290
<211> LENGTH: 113
<212> TYPE: DNA
<213> ORGANISM: Artificial Sequence
<220> FEATURE:
<223> OTHER INFORMATION: synthetic polynuleotide

<400> SEQUENCE: 290
gctctggtac tgggtacttt tatctgtccc ctccacccca cagtggggcc actagggaca        60
ggattggtga cagaaaagcc ccatccttag gcctcctcct tcctagtctc ctg             113

<210> SEQ ID NO 291
<211> LENGTH: 113
<212> TYPE: DNA
<213> ORGANISM: Artificial Sequence
<220> FEATURE:
<223> OTHER INFORMATION: synthetic polynucleotide

<400> SEQUENCE: 291
gctctggtac tgggtacttt tatctgtccc ctccaccccc cagtggggcc actagggaca    60
ggattggtga cagaaaagcc ccatccttag gcctcctcct tcctagtctc ctg           113

<210> SEQ ID NO 292
<211> LENGTH: 113
<212> TYPE: DNA
<213> ORGANISM: Artificial Sequence
<220> FEATURE:
<223> OTHER INFORMATION: synthetic polynucleotide

<400> SEQUENCE: 292
gctctggtac tgggtacttt tatctgtccc ctccacccca cagtggggcc actagggaca    60
ggattggtga cagaaaagcc ccatccttag gcctcctcct tcctagtctc ctg           113

<210> SEQ ID NO 293
<211> LENGTH: 112
<212> TYPE: DNA
<213> ORGANISM: Artificial Sequence
<220> FEATURE:
<223> OTHER INFORMATION: synthetic polynucleotide

<400> SEQUENCE: 293
gctctggtac tgggtacttt tatctgtccc ctccacccca caggggggcc actaggacag    60
gattggtgac agaaaagccc catccttagg cctcctcctt cctagtctcc tg            112

<210> SEQ ID NO 294
<211> LENGTH: 103
<212> TYPE: DNA
<213> ORGANISM: Artificial Sequence
<220> FEATURE:
<223> OTHER INFORMATION: synthetic polynucleotide

<400> SEQUENCE: 294
gctctggttc tgggtacttt tatctgtccc ctccacccca cagtggggcc actagggaca    60
ggattggtga cagaaaagcc ccatccttag gcctcctcct tcc                      103

<210> SEQ ID NO 295
<211> LENGTH: 108
<212> TYPE: DNA
<213> ORGANISM: Artificial Sequence
<220> FEATURE:
<223> OTHER INFORMATION: synthetic polynucleotide

<400> SEQUENCE: 295
gctctggttc tgggtacttt tatctgtccc ctccacccca cagtggggcc actaggaggg    60
ggacaggatt ggtgacagaa aagccccatc cttaggcctc ctccttcc                 108

<210> SEQ ID NO 296
<211> LENGTH: 59
<212> TYPE: DNA
<213> ORGANISM: Artificial Sequence
<220> FEATURE:
<223> OTHER INFORMATION: synthetic polynucleotide

<400> SEQUENCE: 296
gctctgggga cggacaggat tggtgacaga aaagccccat ccttaggcct cctccttcc     59

<210> SEQ ID NO 297
<211> LENGTH: 102
<212> TYPE: DNA

<213> ORGANISM: Artificial Sequence
<220> FEATURE:
<223> OTHER INFORMATION: synthetic polynucleotide

<400> SEQUENCE: 297

```
gctctggttc tgggtacttt tatctgtccc ctccacccca cagtggggcc actaggacag      60
gattggtgac agaaaagccc catccttagg cctcctcctt cc                        102
```

<210> SEQ ID NO 298
<211> LENGTH: 103
<212> TYPE: DNA
<213> ORGANISM: Artificial Sequence
<220> FEATURE:
<223> OTHER INFORMATION: synthetic polynucleotide

<400> SEQUENCE: 298

```
gctctggttc tgggtacttt tatctgtccc ctccacccca cagtggggcc actagggaca      60
ggattggtga cagaaaagcc ccatccttag gcctcctcct tcc                       103
```

<210> SEQ ID NO 299
<211> LENGTH: 102
<212> TYPE: DNA
<213> ORGANISM: Artificial Sequence
<220> FEATURE:
<223> OTHER INFORMATION: synthetic polynucleotide

<400> SEQUENCE: 299

```
gctctggttc tgggtacttt tatctgtccc ctccacccca cagtggggcc actaggacag      60
gattggtgac agaaaagccc catccttagg cctcctcctt cc                        102
```

<210> SEQ ID NO 300
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 300

Gln Thr Thr Glu Arg Ile Val Ala Ile Gly Thr
1               5                   10

<210> SEQ ID NO 301
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 301

Gln Thr Thr Glu Arg Ile Val Ala Ile Gly Thr
1               5                   10

What is claimed is:

1. A composition comprising a DNA localization component and an effector molecule,
   (a) wherein the DNA localization component comprises at least one guide RNA (gRNA), and
   (b) wherein the effector molecule comprises a fusion protein, wherein the fusion protein comprises (i) an inactivated Cas9 (dCas9) or an inactivated nuclease domain thereof and (ii) Clo051 or a nuclease domain thereof, and wherein the dCas9, or an inactivated nuclease domain, and the Clo051, or nuclease domain thereof, are connected by a Gly-Gly-Gly-Gly-Ser peptide linker.

2. The composition of claim 1, wherein the DNA localization component comprises two guide RNAs (gRNAs), wherein a first gRNA specifically binds to a first strand of a double-stranded DNA target sequence and a second gRNA specifically binds to a second strand of the double-stranded DNA target sequence.

3. The composition of claim 1 or claim 2, wherein the effector molecule comprises a homodimer.

4. The composition of claim 1 or claim 2, wherein the effector molecule comprises a heterodimer.

5. A nucleic acid encoding the effector molecule, or both the DNA localization component and effector molecule of claim 1 or claim 2.

6. A vector comprising the nucleic acid of claim 5.

7. A cell comprising the composition of claim 1 or claim 2.

8. A cell comprising the nucleic acid of claim 5.

9. A cell comprising the vector of claim 6.

10. A composition comprising the nucleic acid of claim 5 further comprising a pharmaceutically-acceptable carrier.

11. A composition comprising the vector of claim 6 and further comprising a pharmaceutically-acceptable carrier.

12. A composition comprising the cell of claim 7.

13. The composition of claim 12, further comprising a pharmaceutically-acceptable carrier.

14. A non-human multicellular organism comprising the composition of claim 1.

15. A non-human multicellular organism comprising the nucleic acid of claim 5.

16. A non-human multicellular organism comprising the vector of claim 6.

17. A non-human multicellular organism comprising the cell of claim 7.

18. A non-human multicellular organism comprising the composition of claim 10.

19. The multicellular organism of claim 14, wherein the multicellular organism is a plant, a non-human animal, or a non-human embryo.

20. A composition comprising the cell of claim 8.

21. A composition comprising the cell of claim 9.

22. A non-human multicellular organism comprising the composition of claim 11.

23. A non-human multicellular organism comprising the composition of claim 12.

24. A non-human multicellular organism comprising the composition of claim 13.

25. The non-human multicellular organism of claim 15, wherein the multicellular organism is a plant, a non-human animal, or a non-human embryo.

26. The non-human multicellular organism of claim 16, wherein the multicellular organism is a plant, a non-human animal, or a non-human embryo.

27. The non-human multicellular organism of claim 17, wherein the multicellular organism is a plant, a non-human animal, or a non-human embryo.

28. The non-human multicellular organism of claim 18, wherein the multicellular organism is a plant, a non-human animal, or a non-human embryo.

* * * * *

UNITED STATES PATENT AND TRADEMARK OFFICE
CERTIFICATE OF CORRECTION

| | | |
|---|---|---|
| PATENT NO. | : 11,473,082 B2 | Page 1 of 1 |
| APPLICATION NO. | : 15/580675 | |
| DATED | : October 18, 2022 | |
| INVENTOR(S) | : Ostertag et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 540 days.

Signed and Sealed this
Twenty-first Day of January, 2025

Coke Morgan Stewart
*Acting Director of the United States Patent and Trademark Office*